(12) United States Patent
Fotakis et al.

(10) Patent No.: US 12,037,399 B2
(45) Date of Patent: Jul. 16, 2024

(54) ANTI-DECTIN-1 ANTIBODIES AND METHODS OF USE THEREOF

(71) Applicant: Dren Bio, Inc., Foster City, CA (US)

(72) Inventors: Panagiotis Fotakis, Foster City, CA (US); Andrew P. Ah Young-Chapon, South San Francisco, CA (US); Nenad Tomasevic, Foster City, CA (US); Ruo Shi Shi, San Mateo, CA (US); Xiaodi Deng, Foster City, CA (US)

(73) Assignee: Dren Bio, Inc., Foster City, CA (US)

( * ) Notice: Subject to any disclaimer, the term of this patent is extended or adjusted under 35 U.S.C. 154(b) by 0 days.

(21) Appl. No.: 17/495,712

(22) Filed: Oct. 6, 2021

(65) Prior Publication Data

US 2022/0127366 A1 Apr. 28, 2022

Related U.S. Application Data

(60) Provisional application No. 63/174,439, filed on Apr. 13, 2021, provisional application No. 63/088,895, filed on Oct. 7, 2020.

(51) Int. Cl.
- *C07K 16/28* (2006.01)
- *A61K 39/00* (2006.01)
- *A61P 35/00* (2006.01)

(52) U.S. Cl.
CPC .......... *C07K 16/2851* (2013.01); *A61P 35/00* (2018.01); *C07K 16/2887* (2013.01); *A61K 2039/505* (2013.01); *C07K 2317/31* (2013.01); *C07K 2317/52* (2013.01); *C07K 2317/56* (2013.01)

(58) Field of Classification Search
CPC ................................................. C07K 16/2851
See application file for complete search history.

(56) References Cited

U.S. PATENT DOCUMENTS

| | | | |
|---|---|---|---|
| 5,731,168 A | 3/1998 | Carter et al. | |
| 5,807,706 A | 9/1998 | Carter et al. | |
| 5,821,333 A | 10/1998 | Carter et al. | |
| 7,642,228 B2 | 1/2010 | Carter et al. | |
| 7,695,936 B2 | 4/2010 | Carter et al. | |
| 8,216,805 B2 | 7/2012 | Carter et al. | |
| 8,679,785 B2 | 3/2014 | Carter et al. | |
| 8,844,834 B1 | 9/2014 | Lyons et al. | |
| 9,527,927 B2 * | 12/2016 | Chowdhury | C07K 16/2863 |
| 2002/0164328 A1 | 11/2002 | Shinikawa et al. | |
| 2003/0115614 A1 | 6/2003 | Kanda et al. | |
| 2003/0157108 A1 | 8/2003 | Presta | |
| 2004/0077842 A1 * | 4/2004 | Himawan | A61P 31/04 530/388.22 |
| 2004/0093621 A1 | 5/2004 | Shitara et al. | |
| 2004/0109865 A1 | 6/2004 | Niwa et al. | |
| 2004/0110282 A1 | 6/2004 | Kanda et al. | |
| 2004/0110704 A1 | 6/2004 | Yamane et al. | |
| 2004/0132140 A1 | 7/2004 | Satoh et al. | |
| 2013/0089553 A1 | 4/2013 | Carter et al. | |
| 2014/0154252 A1 * | 6/2014 | Thompson | C07K 16/2803 424/136.1 |
| 2020/0048371 A1 * | 2/2020 | Mills | C07K 16/2803 |
| 2022/0169737 A1 | 6/2022 | Fotakis et al. | |

FOREIGN PATENT DOCUMENTS

| | | | |
|---|---|---|---|
| AU | 2018204314 A1 | 7/2018 | |
| EP | 3452089 A2 | 3/2019 | |
| WO | WO-9720939 A1 * | 6/1997 | ........... C07K 14/745 |
| WO | WO-2000061739 A1 | 10/2000 | |
| WO | WO-2001029246 A1 | 4/2001 | |
| WO | WO-2003084570 A1 | 10/2003 | |
| WO | WO-2003085119 A1 | 10/2003 | |
| WO | WO-2004056312 A2 | 7/2004 | |
| WO | WO-2005035586 A1 | 4/2005 | |
| WO | WO-2005035778 A1 | 4/2005 | |
| WO | WO-2005053742 A1 | 6/2005 | |
| WO | WO-2006047350 A2 * | 5/2006 | ............. C07K 16/00 |
| WO | WO-2008118587 A2 | 10/2008 | |
| WO | WO-2012129227 A1 | 9/2012 | |
| WO | WO-2013158856 A2 * | 10/2013 | .............. A61P 35/00 |
| WO | WO-2015022420 A1 * | 2/2015 | ......... A61K 38/2235 |
| WO | WO-2016081746 A2 | 5/2016 | |
| WO | WO-2017193032 A2 | 11/2017 | |
| WO | WO-2018140831 A2 | 8/2018 | |
| WO | WO-2018176159 A1 | 10/2018 | |
| WO | WO-2019005641 A1 | 1/2019 | |
| WO | WO-2019032662 A1 | 2/2019 | |
| WO | WO-2020016897 A1 | 1/2020 | |
| WO | WO-2020206354 A1 | 10/2020 | |

(Continued)

OTHER PUBLICATIONS

Bujak, E., et al., Reformatting of scFv antibodies into the scFv-Fc format and their downstream purification. Methods Mol Biol. 2014; 1131:315-34. doi: 10.1007/978-1-62703-992-5_20 (Year: 2014).*

Kontermann RE. Dual targeting strategies with bispecific antibodies. MAbs. Mar.-Apr. 2012;4(2):182-97. doi: 10.4161/mabs.4.2. 19000. Epub Mar. 1, 2012. PMID: 22453100; PMCID: PMC3361654 (Year: 2012).*

Krah, S. et al., Engineering IgG-Like Bispecific Antibodies—An Overview. Antibodies (Basel). Aug. 1, 2018;7(3):28. doi: 10.3390/antib7030028. PMID: 31544880; PMCID: PMC6640676 (Year: 2018).*

Tak W. Mak, Mary E. Saunders, Exploiting Antigen-Antibody Interaction, The Immune Response, 2006 (Year: 2006).*

(Continued)

*Primary Examiner* — Gregory S Emch
*Assistant Examiner* — Ashley H. Gao
(74) *Attorney, Agent, or Firm* — MORRISON & FOERSTER LLP

(57) ABSTRACT

The present disclosure relates to antibodies that bind human Dectin-1, multispecific (e.g., bispecific) binding molecules, and methods of use and production related thereto.

97 Claims, 104 Drawing Sheets

Specification includes a Sequence Listing.

(56) References Cited

FOREIGN PATENT DOCUMENTS

WO    WO-2022077006 A1    4/2022

OTHER PUBLICATIONS

Xu, Y., et al., Production of bispecific antibodies in "knobs-into-holes" using a cell-free expression system. MAbs. 2015;7(1):231-42. doi: 10.4161/19420862.2015.989013. PMID: 25427258; PMCID: PMC4623329 (Year: 2014).*

Chen X, Zaro JL, Shen WC. Fusion protein linkers: property, design and functionality. Adv Drug Deliv Rev. Oct. 2013;65(10):1357-69. doi: 10.1016/j.addr.2012.09.039. Epub Sep. 29, 2012. PMID: 23026637; PMCID: PMC3726540. (Year: 2012).*

Wei, H, et al., Structural basis of a novel heterodimeric Fc for bispecific antibody production. Oncotarget. May 2, 2017;8(31):51037-51049. doi: 10.18632/oncotarget.17558. PMID: 28881627; PMCID: PMC5584228 (Year: 2017).*

Backer et al., (2008). "CD8-dendritic cells preferentially cross-present *Saccharomyces cerevisiae* antigens," European Journal Of Immunology, 38(2):370-380.

Extended European Search Report and Opinion received for European Patent Application No. 20784394.7 dated Dec. 7, 2022, 11 pages.

Goodridge et al., (2011). "Activation of the innate immune receptor Dectin-1 upon formation of a 'phagocytic synapse'", Nature, 472(7344):471-475, 6 pages.

Kennedy et al., (2007). "Dectin-1 promotes fungicidal activity of human neutrophils," European Journal Of Immunology, 37(2):467-478.

Sun et al., (2012). "Dectin-1 is inducible and plays a crucial role in-induced innate immune responses in human bronchial epithelial cells," European Journal Of Clinical Microbiology & Infectious Diseases, 31(10):2755-2764.

Ackerman et al., (2011). "A robust, high-throughput assay to determine the phagocytic activity' of clinical antibody samples," J. Immunol. Methods, 366:8-19, 23 pages.

Arandejelovic et al., (2015). "Phagocytosis of apoptotic cells in homeostasis," Nat Immunol., 16:907-17, 27 pages.

Asano et al., (2018). "CD169 macrophages regulate immune responses toward particulate materials in the circulating fluid," J Biochem, 164(2):77-85.

Beum et al., (2006). "The shaving reaction: rituximab/CD20 complexes are removed from mantle cell lymphoma and chronic lymphocytic leukemia cells by THP-1 monocytes," J. Immunol., 176:2600-2609.

Bondi et al., (2017). "Alzheimer's Disease: Past, Present, and Future," J. Int. Neuropsychol. Soc., 23:818-831, 27 pages.

Brandt et al., (2013). "TLR2 Ligands Induce NF-κB Activation from Endosomal Compartments of Human Monocytes," PLoS One, 11 pages.

Brinkmann et al., (2017). "The making of bispecific antibodies," mAbs, 9(2):182-212.

Byrne et al., (2018). "CRISPR/Cas9 gene editing for the creation of an MGAT1-deficient CHO cell line to control HIV-1 vaccine glycosylation," PLoS Biol., 16:e2005817, 23 pages.

Carmona et al., (2018). "The role of TREM2 in Alzheimer's disease and other neurodegenerative disorders," Lancet Neurol., 17:721-730.

Chen et al., (2013). "Fusion protein linkers: property, design and functionality," Adv. Drug Deliv. Rev., 65:1357-1369, 32 pages.

Deng et al., (2019). "Over-expression of Nectin-4 promotes progression of esophageal cancer and correlates with poor prognosis of the patients," Cancer Cell Int., 19:106, 13 pages.

Dispenzieri et al., (2016). "Immunoglobulin Light Chain Systemic Amyloidosis," Cancer Treat Res, 169:273-318.

Elbein et al., (1990). "Kifunensine, a potent inhibitor of the glycoprotein processing mannosidase I.," J. Biol. Chem., 265:15599-15605.

Fabre-Lafay et al., (2005). "Nectin-4, a new serological breast cancer marker, is a substrate for tumor necrosis factor-a-converting enzyme (TACE)/ADAM-17," J. Biol. Chem., 280:19543-19550.

Fabre-Lafay et al., (2007). "Nectin-4 is a new histological and serological tumor associated marker for breast cancer," BMC Cancer 7:73, 16 pages.

Flannagan et al., (2012). "The cell biology of phagocytosis", Annu. Rev. Pathol., 7:61-98.

Freeman et al., (2014). "Phagocytosis: receptors, signal integration, and the cytoskeleton," Immunological Reviews, 262:193-215.

Gordon, (2016). "Phagocytosis: An Immunobiologic Process," Immunity, 44:463-475.

Gratuze et al., (2018). "New insights into the role of TREM2 in Alzheimer's disease," Mol. Neurodegener., 13:66, 16 pages.

Hansen et al., (2018). "Microglia in Alzheimer's disease," J Cell Biol, 217(2):459-472.

Herre et al., (2004). "Dectin-1 uses novel mechanisms for yeast phagocytosis in macrophages," Blood, 104(13):4038-45.

Hossain et al., (2019). "Use of Dendritic Cell Receptors as Targets for Enhancing Anti-Cancer Immune Responses," Cancers, 11(418), 17 pages.

International Search Report and Written Opinion received for International Patent Application No. PCT/US2020/026721 dated Jun. 29, 2020, 13 pages.

International Search Report and Written Opinion received for International Patent Application No. PCT/US2021/071752 dated Jan. 7, 2022, 22 pages.

Kedashiro et al., (2019). "Nectin-4 cis-interacts with ErbB2 and its trastuzumab-resistant splice variants, enhancing their activation and DNA synthesis," Sci. Rep., 9:18997, 15 pages.

Lock et al., (2004). "Expression of CD33-related siglecs on human mononuclear phagocytes, monocyte-derived dendritic cells and plasmacytoid dendritic cells," Immunobiol, 209:199-207.

Mazor et al., (2015). "Improving target cell specificity using a novel monovalent bispecific IgG design," Mabs, 7:377-389.

Nishiwada et al., (2015). "Nectin-4 expression contributes to tumor proliferation, angiogenesis and patient prognosis in human pancreatic cancer," J. Exp. Clin. Cancer Res., 34:30, 9 pages.

Okazaki et al., (2004). "Fucose depletion from human IgG1 oligosaccharide enhances binding enthalpy and association rate between IgG1 and FcgammaRIIIa," J. Mol. Biol., 336:1239-1249.

Ollier et al., (2019). "Single-step Protein A and Protein G avidity purification methods to support bispecific antibody discovery and development," Mabs, 11:1464-1478, 22 pages.

Patin et al., (2018). "Pattern recognition receptors in fungal immunity," Semin Cell Dev Biol., 89:24-33.

Pearce et al., (1997). "Linear gene fusions of antibody fragments with streptavidin can be linked to biotin labelled secondary molecules to form bispecific reagents," Biochemistry and Molecular Biology International, 42(6):1179-1188.

Rabinovitch, (1995). "Professional and non-professional phagocytes: an introduction," Trends in Cell Biol, 5:85-87.

Ridgway et al., (1996). "Knobs-into-holes' engineering of antibody CH3 domains for heavy chain heterodimerization," Protein Eng., 9:617-621.

Ripka et al., (1986). "Two Chinese hamster ovary glycosylation mutants affected in the conversion of GDP-mannose to GDP-fucose," Arch. Biochem. Biophys., 249:533-545.

Rosales et al., (2017). "Phagocytosis: A Fundamental Process in Immunity," BioMed Research International, 2017:9042851, 18 pages.

Sevigny et al., (2016). "The antibody aducanumab reduces Aβ plaques in Alzheimer's disease," Nature, 537(7618):50-56.

Shatz et al., (2013). "Knobs-into-holes antibody production in mammalian cell lines reveals that asymmetric afucosylation is sufficient for full antibody-dependent cellular cytotoxicity," mAbs, 5(6):872-881.

Spiess et al., (2013). "Bispecific antibodies with natural architecture produced by co-culture of bacteria expressing two distinct half-antibodies," Nature Biotechnology, 31:753-758.

Suenaga et al., (2016). "Involvement of Macrophages in the Pathogenesis of Familial Amyloid Polyneuropathy and Efficacy of Human IPS Cell-Derived Macrophages in Its Treatment," PLoS One, 11:e0163944, 19 pages.

Taylor et al., (2002). "The beta-glucan receptor, dectin-1, is predominantly expressed on the surface of cells of the monocyte/macrophage and neutrophil lineages," J. Immunol., 169:3876-3882.

(56) References Cited

OTHER PUBLICATIONS

Tse et al., (2003). "Differential role of actin, clathrin, and dynamin in Fc gamma receptor-mediated endocytosis and phagocytosis," J Biol Chem., 278:3331-8.
Wall et al., (2012). "AL Amyloid Imaging and Therapy with a Monoclonal Antibody to a Cryptic Epitope on Amyloid Fibrils," PLoS One, 7:e52686, 10 pages.
Wang et al., (2017). "A systemic view of Alzheimer disease—insights from amyloid-β metabolism beyond the brain," Nat. Rev. Neurol., 13:612-623.
Weller et al., (2018). "Current understanding of Alzheimer's disease diagnosis and treatment," F1000Res, 7:F1000 Faculty Rev-1161, 9 pages.
Yamane-Ohnuki et al., (2004). "Establishment of FUT8 knockout Chinese hamster ovary cells: An ideal host cell line for producing completely defucosylated antibodies with enhanced antibody-dependent cellular cytotoxicity," Biotech. Bioeng., 87:614-622.
International Search Report and Written Opinion received for International Patent Application No. PCT/US2023/065290 dated May 18, 2023, 14 pages.

* cited by examiner

| Dectin-1 ab Clone | HEK-Blue hDectin-1a cells EC50 (nM) | HEK-Blue hDectin-1b cells EC50 (nM) | HEK293F hDectin-1a FL EC50 (nM) | Human monocytes EC50 (nM) | Cynomolgus monkey monocytes EC50 (nM) |
|---|---|---|---|---|---|
| 2M24 | 0.4 | 1 | 1.1 | 0.3 | 0.3 |
| 2M08 | 2.6 | >190 | 1.9 | >190 | NA |
| 2M12 | 16.9 | >142 | 2.8 | >142 | NA |
| 2M38 | 4.5 | >96 | 6.1 | >96 | NA |
| 2M49 | >169 | >169 | >169 | >169 | NA |
| 15E2 | 1.2 | 9.3 | 1.4 | 0.6 | 14 |
| 259931 | 0.8 | 0.9 | 1.2 | 0.3 | 16.5 |
| GE2 | 1.9 | 12 | 2.4 | 1.4 | NA |

FIG. 1C

| Dectin-1 antibody Clone | HEK-Blue hDectin-1a cells EC50 (nM) | HEK-Blue hDectin-1b cells EC50 (nM) | HEK293F hDectin-1a FL EC50 (nM) | Human monocytes EC50 (nM) | Competition with natural ligands | TNFa secretion in PBMC (fold change to isotype) | IL6 secretion in PBMC (fold change to isotype) | IFNg secretion in PBMC (fold change to isotype) | Phagocytosis |
|---|---|---|---|---|---|---|---|---|---|
| 2M24 | 0.4 | 1 | 1.1 | 0.3 | NO | 19 | 6.4 | 4.1 | YES |
| 15E2 | 1.2 | 9.3 | 1.4 | 0.6 | YES | 3 | 2.6 | 1.6 | YES |

FIG. 9

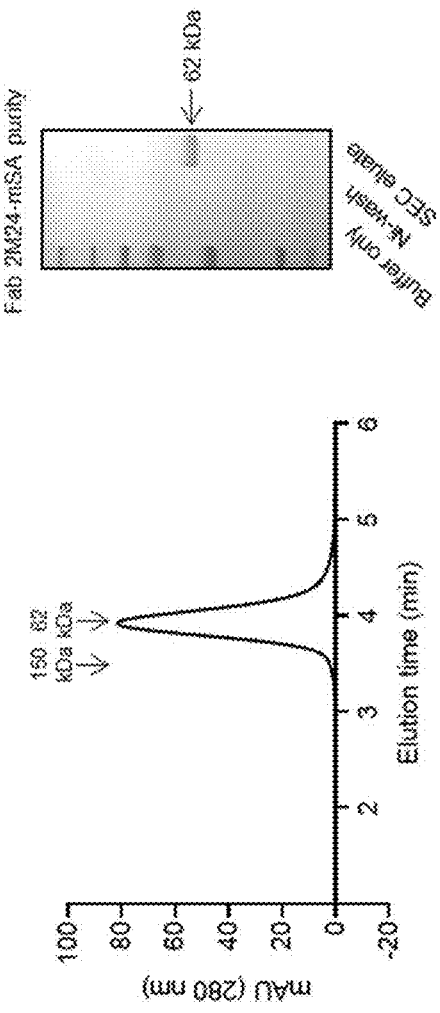
FIG. 20A
FIG. 20B
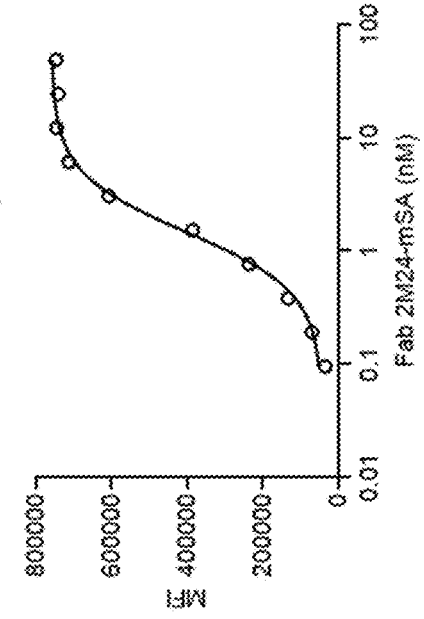
FIG. 20C

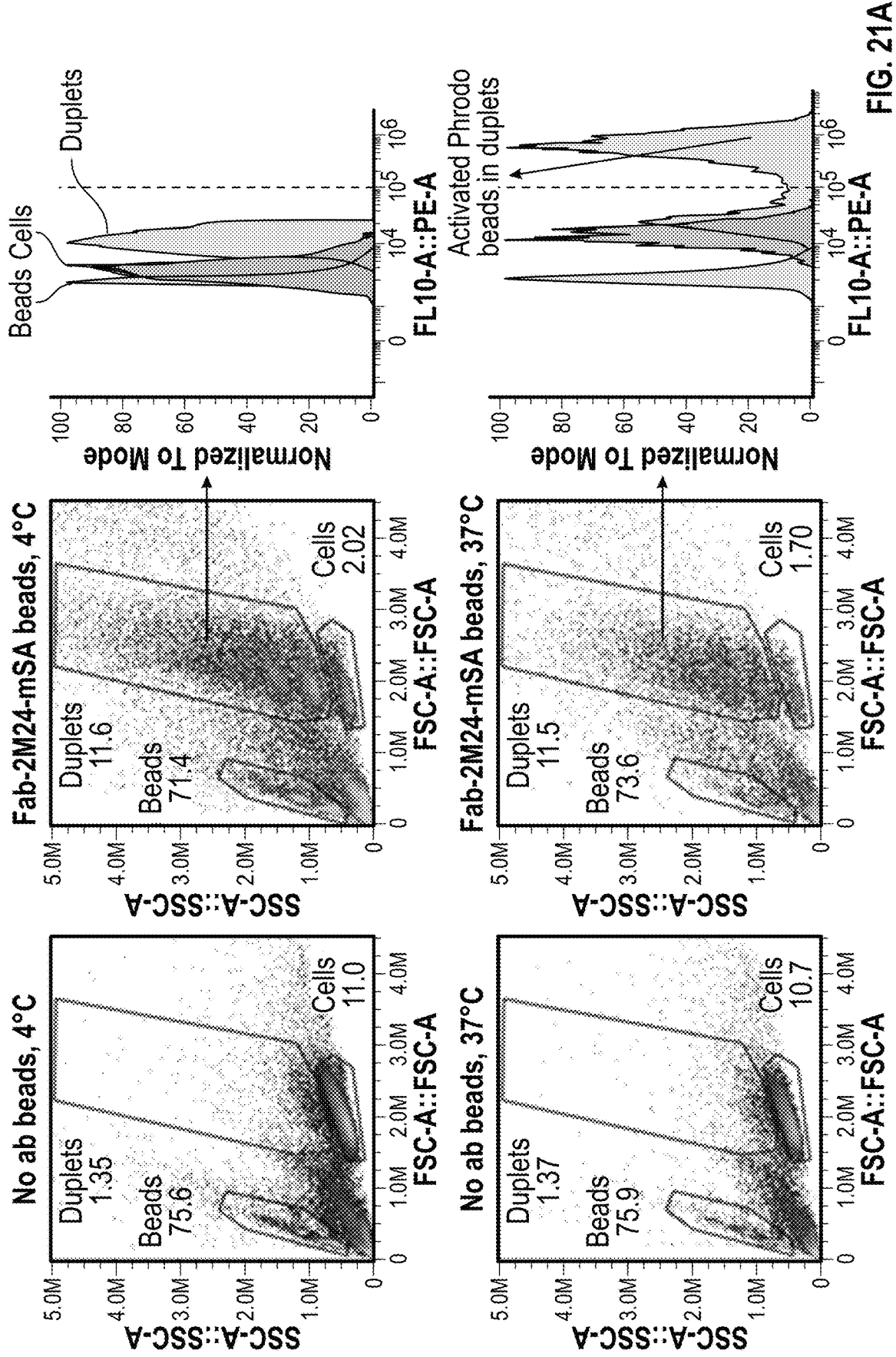

FIG. 28A

SEQUENCE LISTING

```
<160> NUMBER OF SEQ ID NOS: 92

<210> SEQ ID NO 1
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1

Gly Tyr Thr Phe Thr Asp Tyr Tyr
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic Construct

<400> SEQUENCE: 2

Ile Asn Pro Asn Ser Gly Asp Thr
1               5
```

<210> SEQ ID NO 3
<211> LENGTH: 11
<212> TYPE: PRT
<213> ORGANISM: Artificial Sequence
<220> FEATURE:
<223> OTHER INFORMATION: Synthetic Construct

<400> SEQUENCE: 3

Ala Arg Asn Ser Gly Ser Tyr Ser Phe Gly Tyr
1               5                   10

<210> SEQ ID NO 4
<211> LENGTH: 6
<212> TYPE: PRT
<213> ORGANISM: Artificial Sequence
<220> FEATURE:
<223> OTHER INFORMATION: Synthetic Construct

<400> SEQUENCE: 4

Gln Gly Ile Ser Ser Trp
1               5

<210> SEQ ID NO 5
<211> LENGTH: 3
<212> TYPE: PRT
<213> ORGANISM: Artificial Sequence
<220> FEATURE:
<223> OTHER INFORMATION: Synthetic Construct

<400> SEQUENCE: 5

Gly Ala Ser
1

<210> SEQ ID NO 6
<211> LENGTH: 9
<212> TYPE: PRT
<213> ORGANISM: Artificial Sequence
<220> FEATURE:
<223> OTHER INFORMATION: Synthetic Construct

<400> SEQUENCE: 6

Gln Gln Ala Tyr Ser Phe Pro Phe Thr
1               5

<210> SEQ ID NO 7
<211> LENGTH: 118
<212> TYPE: PRT
<213> ORGANISM: Artificial Sequence
<220> FEATURE:
<223> OTHER INFORMATION: Synthetic Construct

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ser Ser Gly Tyr Thr Phe Thr Asp Tyr
            20                  25                  30

Tyr Ile His Trp Val Arg Gln Ala Pro Gly Gln Gly Leu Glu Trp Met
        35                  40                  45

Gly Trp Ile Asn Pro Asn Ser Gly Asp Thr Asn Tyr Ala Gln Lys Phe
    50                  55                  60

Gln Gly Arg Ile Thr Met Thr Arg Asp Thr Ser Ile Ser Thr Ala Tyr
65                  70                  75                  80

Leu Glu Leu Ser Arg Leu Arg Ser Asp Asp Thr Ala Val Phe Tyr Cys

```
                85                  90                  95
Ala Arg Asn Ser Gly Ser Tyr Ser Phe Gly Tyr Trp Gly Gln Gly Thr
                100                 105                 110

Leu Val Thr Val Ser Ser
        115

<210> SEQ ID NO 8
<211> LENGTH: 107
<212> TYPE: PRT
<213> ORGANISM: Artificial Sequence
<220> FEATURE:
<223> OTHER INFORMATION: Synthetic Construct

<400> SEQUENCE: 8

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Phe Gly Ala Ser Ser Leu Gln Ser Gly Val Pro Ser Arg Phe Ser Gly
50                  55                  60

Ser Gly Ser Gly Thr Asp Phe Thr Leu Thr Val Ser Ser Leu Gln Pro
65                  70                  75                  80

Glu Asp Phe Ala Thr Tyr Tyr Cys Gln Gln Ala Tyr Ser Phe Pro Phe
                85                  90                  95

Thr Phe Gly Pro Gly Thr Lys Val Asp Ile Glu
                100                 105

<210> SEQ ID NO 9
<211> LENGTH: 247
<212> TYPE: PRT
<213> ORGANISM: Homo sapiens

<400> SEQUENCE: 9

Met Glu Tyr His Pro Asp Leu Glu Asn Leu Asp Glu Asp Gly Tyr Thr
1               5                   10                  15

Gln Leu His Phe Asp Ser Gln Ser Asn Thr Arg Ile Ala Val Val Ser
            20                  25                  30

Glu Lys Gly Ser Cys Ala Ala Ser Pro Pro Trp Arg Leu Ile Ala Val
        35                  40                  45

Ile Leu Gly Ile Leu Cys Leu Val Ile Leu Val Ile Ala Val Val Leu
50                  55                  60

Gly Thr Met Ala Ile Trp Arg Ser Asn Ser Gly Ser Asn Thr Leu Glu
65                  70                  75                  80

Asn Gly Tyr Phe Leu Ser Arg Asn Lys Glu Asn His Ser Gln Pro Thr
                85                  90                  95

Gln Ser Ser Leu Glu Asp Ser Val Thr Pro Thr Lys Ala Val Lys Thr
                100                 105                 110

Thr Gly Val Leu Ser Ser Pro Cys Pro Pro Asn Trp Ile Ile Tyr Glu
        115                 120                 125

Lys Ser Cys Tyr Leu Phe Ser Met Ser Leu Asn Ser Trp Asp Gly Ser
        130                 135                 140

Lys Arg Gln Cys Trp Gln Leu Gly Ser Asn Leu Leu Lys Ile Asp Ser
145                 150                 155                 160

Ser Asn Glu Leu Gly Phe Ile Val Lys Gln Val Ser Ser Gln Pro Asp
                165                 170                 175
```

Asn Ser Phe Trp Ile Gly Leu Ser Arg Pro Gln Thr Glu Val Pro Trp
            180                 185                 190

Leu Trp Glu Asp Gly Ser Thr Phe Ser Ser Asn Leu Phe Gln Ile Arg
                195                 200                 205

Thr Thr Ala Thr Gln Glu Asn Pro Ser Pro Asn Cys Val Trp Ile His
        210                 215                 220

Val Ser Val Ile Tyr Asp Gln Leu Cys Ser Val Pro Ser Tyr Ser Ile
225                 230                 235                 240

Cys Glu Lys Lys Phe Ser Met
                245

<210> SEQ ID NO 10
<211> LENGTH: 201
<212> TYPE: PRT
<213> ORGANISM: Homo sapiens

<400> SEQUENCE: 10

Met Glu Tyr His Pro Asp Leu Glu Asn Leu Asp Glu Asp Gly Tyr Thr
1               5                   10                  15

Gln Leu His Phe Asp Ser Gln Ser Asn Thr Arg Ile Ala Val Val Ser
            20                  25                  30

Glu Lys Gly Ser Cys Ala Ala Ser Pro Pro Trp Arg Leu Ile Ala Val
        35                  40                  45

Ile Leu Gly Ile Leu Cys Leu Val Ile Leu Val Ile Ala Val Val Leu
    50                  55                  60

Gly Thr Met Gly Val Leu Ser Ser Pro Cys Pro Pro Asn Trp Ile Ile
65                  70                  75                  80

Tyr Glu Lys Ser Cys Tyr Leu Phe Ser Met Ser Leu Asn Ser Trp Asp
                85                  90                  95

Gly Ser Lys Arg Gln Cys Trp Gln Leu Gly Ser Asn Leu Leu Lys Ile
            100                 105                 110

Asp Ser Ser Asn Glu Leu Gly Phe Ile Val Lys Gln Val Ser Ser Gln
        115                 120                 125

Pro Asp Asn Ser Phe Trp Ile Gly Leu Ser Arg Pro Gln Thr Glu Val
    130                 135                 140

Pro Trp Leu Trp Glu Asp Gly Ser Thr Phe Ser Ser Asn Leu Phe Gln
145                 150                 155                 160

Ile Arg Thr Thr Ala Thr Gln Glu Asn Pro Ser Pro Asn Cys Val Trp
                165                 170                 175

Ile His Val Ser Val Ile Tyr Asp Gln Leu Cys Ser Val Pro Ser Tyr
            180                 185                 190

Ser Ile Cys Glu Lys Lys Phe Ser Met
        195                 200

<210> SEQ ID NO 11
<211> LENGTH: 444
<212> TYPE: PRT
<213> ORGANISM: Artificial Sequence
<220> FEATURE:
<223> OTHER INFORMATION: Synthetic Construct

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ser Gly Tyr Thr Phe Thr Asp Tyr
            20                  25                  30

```
Tyr Ile His Trp Val Arg Gln Ala Pro Gly Gln Gly Leu Glu Trp Met
             35                  40                  45

Gly Trp Ile Asn Pro Asn Ser Gly Asp Thr Asn Tyr Ala Gln Lys Phe
 50                  55                  60

Gln Gly Arg Ile Thr Met Thr Arg Asp Thr Ser Ile Ser Thr Ala Tyr
 65                  70                  75                  80

Leu Glu Leu Ser Arg Leu Arg Ser Asp Asp Thr Ala Val Phe Tyr Cys
                 85                  90                  95

Ala Arg Asn Ser Gly Ser Tyr Ser Phe Gly Tyr Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Cys Ser Arg Ser Thr Ser Glu Ser Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Pro Gly
        435                 440
```

```
<210> SEQ ID NO 12
<211> LENGTH: 214
<212> TYPE: PRT
<213> ORGANISM: Artificial Sequence
<220> FEATURE:
<223> OTHER INFORMATION: Synthetic Construct

<400> SEQUENCE: 12

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Phe Gly Ala Ser Ser Leu Gln Ser Gly Val Pro Ser Arg Phe Ser Gly
50                  55                  60

Ser Gly Ser Gly Thr Asp Phe Thr Leu Thr Val Ser Ser Leu Gln Pro
65                  70                  75                  80

Glu Asp Phe Ala Thr Tyr Tyr Cys Gln Gln Ala Tyr Ser Phe Pro Phe
                85                  90                  95

Thr Phe Gly Pro Gly Thr Lys Val Asp Ile Glu Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 13
<211> LENGTH: 12
<212> TYPE: PRT
<213> ORGANISM: Artificial Sequence
<220> FEATURE:
<223> OTHER INFORMATION: Synthetic Construct

<400> SEQUENCE: 13

Gly Gly Gly Ser Gly Gly Gly Ser Gly Gly Gly Ser
1               5                   10

<210> SEQ ID NO 14
<211> LENGTH: 125
<212> TYPE: PRT
<213> ORGANISM: Artificial Sequence
<220> FEATURE:
<223> OTHER INFORMATION: Synthetic Construct

<400> SEQUENCE: 14

Glu Phe Ala Ser Ala Glu Ala Gly Ile Thr Gly Thr Trp Tyr Asn Gln
1               5                   10                  15

His Gly Ser Thr Phe Thr Val Thr Ala Gly Ala Asp Gly Asn Leu Thr
            20                  25                  30
```

-continued

Gly Gln Tyr Glu Asn Arg Ala Gln Gly Thr Gly Cys Gln Asn Ser Pro
            35                  40                  45

Tyr Thr Leu Thr Gly Arg Tyr Asn Gly Thr Lys Leu Glu Trp Arg Val
 50                  55                  60

Glu Trp Asn Asn Ser Thr Glu Asn Cys His Ser Arg Thr Glu Trp Arg
 65                  70                  75                  80

Gly Gln Tyr Gln Gly Gly Ala Glu Ala Arg Ile Asn Thr Gln Trp Asn
                85                  90                  95

Leu Thr Tyr Glu Gly Gly Ser Gly Pro Ala Thr Glu Gln Gly Gln Asp
            100                 105                 110

Thr Phe Thr Lys Val Lys Pro Ser Ala Ala Ser Gly Ser
            115                 120                 125

<210> SEQ ID NO 15
<211> LENGTH: 582
<212> TYPE: PRT
<213> ORGANISM: Artificial Sequence
<220> FEATURE:
<223> OTHER INFORMATION: Synthetic Construct

<400> SEQUENCE: 15

Gln Val Gln Leu Val Gln Ser Gly Ala Glu Val Lys Lys Pro Gly Ala
 1               5                  10                  15

Ser Val Lys Val Ser Cys Lys Ser Ser Gly Tyr Thr Phe Thr Asp Tyr
            20                  25                  30

Tyr Ile His Trp Val Arg Gln Ala Pro Gly Gln Gly Leu Glu Trp Met
            35                  40                  45

Gly Trp Ile Asn Pro Asn Ser Gly Asp Thr Asn Tyr Ala Gln Lys Phe
 50                  55                  60

Gln Gly Arg Ile Thr Met Thr Arg Asp Thr Ser Ile Ser Thr Ala Tyr
 65                  70                  75                  80

Leu Glu Leu Ser Arg Leu Arg Ser Asp Asp Thr Ala Val Phe Tyr Cys
                85                  90                  95

Ala Arg Asn Ser Gly Ser Tyr Ser Phe Gly Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Cys Ser Arg Ser Thr Ser Glu Ser Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
            195                 200                 205

Asn Thr Lys Val Asp Lys Arg Val Glu Ser Lys Tyr Gly Pro Pro Cys
            210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

```
Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Pro Gly Lys Gly Gly Gly
        435                 440                 445

Ser Gly Gly Gly Ser Gly Gly Ser Glu Phe Ala Ser Ala Glu Ala
    450                 455                 460

Gly Ile Thr Gly Thr Trp Tyr Asn Gln His Gly Ser Thr Phe Thr Val
465                 470                 475                 480

Thr Ala Gly Ala Asp Gly Asn Leu Thr Gly Gln Tyr Glu Asn Arg Ala
                485                 490                 495

Gln Gly Thr Gly Cys Gln Asn Ser Pro Tyr Thr Leu Thr Gly Arg Tyr
            500                 505                 510

Asn Gly Thr Lys Leu Glu Trp Arg Val Glu Trp Asn Asn Ser Thr Glu
        515                 520                 525

Asn Cys His Ser Arg Thr Glu Trp Arg Gly Gln Tyr Gln Gly Gly Ala
    530                 535                 540

Glu Ala Arg Ile Asn Thr Gln Trp Asn Leu Thr Tyr Glu Gly Gly Ser
545                 550                 555                 560

Gly Pro Ala Thr Glu Gln Gly Gln Asp Thr Phe Thr Lys Val Lys Pro
                565                 570                 575

Ser Ala Ala Ser Gly Ser
            580

<210> SEQ ID NO 16
<211> LENGTH: 353
<212> TYPE: PRT
<213> ORGANISM: Artificial Sequence
<220> FEATURE:
<223> OTHER INFORMATION: Synthetic Construct

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ser Ser Gly Tyr Thr Phe Thr Asp Tyr
            20                  25                  30

Tyr Ile His Trp Val Arg Gln Ala Pro Gly Gln Gly Leu Glu Trp Met
        35                  40                  45
```

Gly Trp Ile Asn Pro Asn Ser Gly Asp Thr Asn Tyr Ala Gln Lys Phe
            50                  55                  60

Gln Gly Arg Ile Thr Met Thr Arg Asp Thr Ser Ile Ser Thr Ala Tyr
 65                  70                  75                  80

Leu Glu Leu Ser Arg Leu Arg Ser Asp Asp Thr Ala Val Phe Tyr Cys
                 85                  90                  95

Ala Arg Asn Ser Gly Ser Tyr Ser Phe Gly Tyr Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Cys Ser Arg Ser Thr Ser Glu Ser Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Lys Thr Tyr Thr Cys Asn Val Asp His Lys Pro Ser
            195                 200                 205

Asn Thr Lys Val Asp Lys Arg Val Gly Gly Ser Gly Gly Gly Gly Ser
210                 215                 220

Gly Gly Gly Ser Glu Phe Ala Ser Ala Glu Ala Gly Ile Thr Gly Thr
225                 230                 235                 240

Trp Tyr Asn Gln His Gly Ser Thr Phe Thr Val Thr Ala Gly Ala Asp
                245                 250                 255

Gly Asn Leu Thr Gly Gln Tyr Glu Asn Arg Ala Gln Gly Thr Gly Cys
            260                 265                 270

Gln Asn Ser Pro Tyr Thr Leu Thr Gly Arg Tyr Asn Gly Thr Lys Leu
            275                 280                 285

Glu Trp Arg Val Glu Trp Asn Asn Ser Thr Glu Asn Cys His Ser Arg
            290                 295                 300

Thr Glu Trp Arg Gly Gln Tyr Gln Gly Gly Ala Glu Ala Arg Ile Asn
305                 310                 315                 320

Thr Gln Trp Asn Leu Thr Tyr Glu Gly Gly Ser Gly Pro Ala Thr Glu
                325                 330                 335

Gln Gly Gln Asp Thr Phe Thr Lys Val Lys Pro Ser Ala Ala Ser Gly
            340                 345                 350

Ser

<210> SEQ ID NO 17
<211> LENGTH: 365
<212> TYPE: PRT
<213> ORGANISM: Artificial Sequence
<220> FEATURE:
<223> OTHER INFORMATION: Synthetic Construct

<400> SEQUENCE: 17

Gln Val Gln Leu Val Gln Ser Gly Ala Glu Val Lys Lys Pro Gly Ala
 1               5                  10                  15

Ser Val Lys Val Ser Cys Lys Ser Ser Gly Tyr Thr Phe Thr Asp Tyr
                20                  25                  30

Tyr Ile His Trp Val Arg Gln Ala Pro Gly Gln Gly Leu Glu Trp Met
            35                  40                  45

Gly Trp Ile Asn Pro Asn Ser Gly Asp Thr Asn Tyr Ala Gln Lys Phe
        50                  55                  60

Gln Gly Arg Ile Thr Met Thr Arg Asp Thr Ser Ile Ser Thr Ala Tyr
 65                  70                  75                  80

Leu Glu Leu Ser Arg Leu Arg Ser Asp Asp Thr Ala Val Phe Tyr Cys
                 85                  90                  95

Ala Arg Asn Ser Gly Ser Tyr Ser Phe Gly Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Gly Gly Ser Gly Gly Gly Gly Ser
    210                 215                 220

Gly Gly Gly Ser Glu Phe Ala Ser Ala Glu Ala Gly Ile Thr Gly Thr
225                 230                 235                 240

Trp Tyr Asn Gln His Gly Ser Thr Phe Thr Val Thr Ala Gly Ala Asp
                245                 250                 255

Gly Asn Leu Thr Gly Gln Tyr Glu Asn Arg Ala Gln Gly Thr Gly Cys
            260                 265                 270

Gln Asn Ser Pro Tyr Thr Leu Thr Gly Arg Tyr Asn Gly Thr Lys Leu
        275                 280                 285

Glu Trp Arg Val Glu Trp Asn Asn Ser Thr Glu Asn Cys His Ser Arg
    290                 295                 300

Thr Glu Trp Arg Gly Gln Tyr Gln Gly Gly Ala Glu Ala Arg Ile Asn
305                 310                 315                 320

Thr Gln Trp Asn Leu Thr Tyr Glu Gly Gly Ser Gly Pro Ala Thr Glu
                325                 330                 335

Gln Gly Gln Asp Thr Phe Thr Lys Val Lys Pro Ser Ala Ala Ser Gly
            340                 345                 350

Ser Ala Ala Ala Gly Ala Ser His His His His His
        355                 360                 365

<210> SEQ ID NO 18
<211> LENGTH: 368
<212> TYPE: PRT
<213> ORGANISM: Artificial Sequence
<220> FEATURE:
<223> OTHER INFORMATION: Synthetic Construct

<400> SEQUENCE: 18

Gln Trp Gln Leu Gln Gln Ser Gly Ala Glu Leu Ala Arg Pro Gly Ala
1               5                   10                  15

Ser Trp Lys Met Ser Cys Lys Ala Ser Gly Tyr Thr Phe Thr Thr Tyr
                20                  25                  30

Thr Met His Trp Trp Lys Gln Arg Pro Gly Gln Gly Leu Glu Trp Ile
            35                  40                  45

```
Gly Tyr Ile Asn Pro Ser Ser Gly Tyr Thr Asn Tyr Asn Gln Lys Phe
        50                  55                  60

Lys Asp Lys Ala Thr Leu Thr Ala Asp Lys Ser Ser Thr Ala Ser
 65                  70                  75                  80

Met Gln Leu Ser Ser Leu Thr Ser Glu Asp Ser Ala Trp Tyr Tyr Cys
                 85                  90                  95

Ala Arg Glu Arg Ala Val Leu Val Pro Tyr Ala Met Asp Tyr Trp Gly
            100                 105                 110

Gln Gly Thr Ser Val Thr Val Ser Ala Ser Thr Lys Gly Pro Ser
            115                 120                 125

Val Phe Pro Leu Ala Pro Cys Ser Arg Ser Thr Ser Glu Ser Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Leu Gly Thr Lys Thr Tyr Thr Cys Asn Val Asp His
            195                 200                 205

Lys Pro Ser Asn Thr Lys Val Asp Lys Arg Val Gly Gly Ser Gly
210                 215                 220

Gly Gly Ser Gly Gly Gly Ser Glu Phe Ala Ser Ala Glu Ala Gly Ile
225                 230                 235                 240

Thr Gly Thr Trp Tyr Asn Gln His Gly Ser Thr Phe Thr Val Thr Ala
                245                 250                 255

Gly Ala Asp Gly Asn Leu Thr Gly Gln Tyr Glu Asn Arg Ala Gln Gly
            260                 265                 270

Thr Gly Cys Gln Asn Ser Pro Tyr Thr Leu Thr Gly Arg Tyr Asn Gly
            275                 280                 285

Thr Lys Leu Glu Trp Arg Val Glu Trp Asn Asn Ser Thr Glu Asn Cys
290                 295                 300

His Ser Arg Thr Glu Trp Arg Gly Gln Tyr Gln Gly Gly Ala Glu Ala
305                 310                 315                 320

Arg Ile Asn Thr Gln Trp Asn Leu Thr Tyr Glu Gly Gly Ser Gly Pro
                325                 330                 335

Ala Thr Glu Gln Gly Gln Asp Thr Phe Thr Lys Val Lys Pro Ser Ala
            340                 345                 350

Ala Ser Gly Ser Ala Ala Ala Gly Ala Ser His His His His His
            355                 360                 365
```

<210> SEQ ID NO 19
<211> LENGTH: 213
<212> TYPE: PRT
<213> ORGANISM: Artificial Sequence
<220> FEATURE:
<223> OTHER INFORMATION: Synthetic Construct

<400> SEQUENCE: 19

```
Gln Ile Val Leu Thr Gln Ser Pro Ala Val Met Ser Ala Ser Pro Gly
 1               5                  10                  15

Glu Lys Trp Thr Ile Thr Cys Thr Ala Ser Ser Ser Leu Ser Tyr Met
                20                  25                  30

His Trp Phe Gln Gln Lys Pro Gly Thr Ser Pro Lys Leu Trp Leu Tyr
            35                  40                  45
```

-continued

```
Ser Thr Ser Ile Leu Ala Ser Gly Val Pro Thr Arg Phe Ser Gly Ser
 50                  55                  60

Gly Ser Gly Thr Ser Tyr Ser Leu Thr Ile Ser Arg Met Glu Ala Glu
 65                  70                  75                  80

Asp Ala Ala Thr Tyr Tyr Cys Gln Gln Arg Ser Ser Ser Pro Phe Thr
                 85                  90                  95

Phe Gly Ser Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
210

<210> SEQ ID NO 20
<211> LENGTH: 248
<212> TYPE: PRT
<213> ORGANISM: Artificial Sequence
<220> FEATURE:
<223> OTHER INFORMATION: Synthetic Construct

<400> SEQUENCE: 20

Gln Val Gln Leu Gln Gln Pro Gly Ala Glu Leu Val Lys Pro Gly Ala
 1               5                  10                  15

Ser Val Lys Met Ser Cys Lys Ala Ser Gly Tyr Thr Phe Thr Ser Tyr
                 20                  25                  30

Asn Met His Trp Val Lys Gln Thr Pro Gly Arg Gly Leu Glu Trp Ile
             35                  40                  45

Gly Ala Ile Tyr Pro Gly Asn Gly Asp Thr Ser Tyr Asn Gln Lys Phe
         50                  55                  60

Lys Gly Lys Ala Thr Leu Thr Ala Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190
```

```
Pro Ser Ser Ser Leu Gly Thr Lys Thr Tyr Thr Cys Asn Val Asp His
        195                 200                 205

Lys Pro Ser Asn Thr Lys Val Asp Lys Arg Val Ala Ala Ala Gly Ala
    210                 215                 220

Ser His His His His His Gly Ser Gly Leu Asn Asp Ile Phe Glu
225                 230                 235                 240

Ala Gln Lys Ile Glu Trp His Glu
            245

<210> SEQ ID NO 21
<211> LENGTH: 213
<212> TYPE: PRT
<213> ORGANISM: Artificial Sequence
<220> FEATURE:
<223> OTHER INFORMATION: Synthetic Construct

<400> SEQUENCE: 21

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 22
<211> LENGTH: 247
<212> TYPE: PRT
<213> ORGANISM: Artificial Sequence
<220> FEATURE:
<223> OTHER INFORMATION: Synthetic Construct

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30
```

```
Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Ala Ala Ala Gly Ala Ser
210                 215                 220

His His His His His Gly Ser Gly Leu Asn Asp Ile Phe Glu Ala
225                 230                 235                 240

Gln Lys Ile Glu Trp His Glu
                245

<210> SEQ ID NO 23
<211> LENGTH: 214
<212> TYPE: PRT
<213> ORGANISM: Artificial Sequence
<220> FEATURE:
<223> OTHER INFORMATION: Synthetic Construct

<400> SEQUENCE: 23

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Asn Thr Ala
             20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140
```

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 24
<211> LENGTH: 121
<212> TYPE: PRT
<213> ORGANISM: Artificial Sequence
<220> FEATURE:
<223> OTHER INFORMATION: Synthetic Construct

<400> SEQUENCE: 24

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala
        115                 120

<210> SEQ ID NO 25
<211> LENGTH: 106
<212> TYPE: PRT
<213> ORGANISM: Artificial Sequence
<220> FEATURE:
<223> OTHER INFORMATION: Synthetic Construct

<400> SEQUENCE: 25

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys

<210> SEQ ID NO 26
<211> LENGTH: 5
<212> TYPE: PRT
<213> ORGANISM: Artificial Sequence
<220> FEATURE:
<223> OTHER INFORMATION: Synthetic Construct

<400> SEQUENCE: 26

Gly Gly Gly Gly Ser
1               5

<210> SEQ ID NO 27
<211> LENGTH: 15
<212> TYPE: PRT
<213> ORGANISM: Artificial Sequence
<220> FEATURE:
<223> OTHER INFORMATION: Synthetic Construct

<400> SEQUENCE: 27

Gly Gly Gly Gly Ser Gly Gly Gly Gly Ser Gly Gly Gly Gly Ser
1               5                   10                  15

<210> SEQ ID NO 28
<211> LENGTH: 20
<212> TYPE: PRT
<213> ORGANISM: Artificial Sequence
<220> FEATURE:
<223> OTHER INFORMATION: Synthetic Construct

<400> SEQUENCE: 28

Gly Gly Gly Gly Ser Gly Gly Gly Gly Ser Gly Gly Gly Gly Ser Gly
1               5                   10                  15

Gly Gly Gly Ser
            20

<210> SEQ ID NO 29
<211> LENGTH: 14
<212> TYPE: PRT
<213> ORGANISM: Artificial Sequence
<220> FEATURE:
<223> OTHER INFORMATION: Synthetic Construct

<400> SEQUENCE: 29

Glu Pro Lys Arg Ser Asp Lys Thr His Thr Cys Pro Pro Cys
1               5                   10

<210> SEQ ID NO 30
<211> LENGTH: 9
<212> TYPE: PRT
<213> ORGANISM: Artificial Sequence
<220> FEATURE:
<223> OTHER INFORMATION: Synthetic Construct

<400> SEQUENCE: 30

Ser Ala Thr His Thr Cys Pro Pro Cys
1               5

<210> SEQ ID NO 31
<211> LENGTH: 476
<212> TYPE: PRT
<213> ORGANISM: Artificial Sequence
<220> FEATURE:
<223> OTHER INFORMATION: Synthetic Construct

<400> SEQUENCE: 31

```
Gln Val Gln Leu Val Gln Ser Gly Ala Glu Lys Lys Pro Gly Ala
  1               5                  10                  15

Ser Val Lys Val Ser Cys Lys Ser Ser Gly Tyr Thr Phe Thr Asp Tyr
             20                  25                  30

Tyr Ile His Trp Val Arg Gln Ala Pro Gly Gln Gly Leu Glu Trp Met
             35                  40                  45

Gly Trp Ile Asn Pro Asn Ser Gly Asp Thr Asn Tyr Ala Gln Lys Phe
 50                  55                  60

Gln Gly Arg Ile Thr Met Thr Arg Asp Thr Ser Ile Ser Thr Ala Tyr
 65                  70                  75                  80

Leu Glu Leu Ser Arg Leu Arg Ser Asp Asp Thr Ala Val Phe Tyr Cys
                 85                  90                  95

Ala Arg Asn Ser Gly Ser Tyr Ser Phe Gly Tyr Trp Gly Gln Gly Thr
                100                 105                 110

Leu Val Thr Val Ser Ser Gly Gly Gly Ser Gly Gly Gly Gly Ser
            115                 120                 125

Gly Gly Gly Gly Ser Gly Gly Gly Ser Asp Ile Gln Met Thr Gln
        130                 135                 140

Ser Pro Ser Ser Val Ser Ala Ser Val Gly Asp Arg Val Thr Ile Thr
145                 150                 155                 160

Cys Arg Ala Ser Gln Gly Ile Ser Ser Trp Leu Ala Trp Tyr Gln Gln
                165                 170                 175

Lys Pro Gly Lys Ala Pro Lys Leu Leu Ile Phe Gly Ala Ser Ser Leu
                180                 185                 190

Gln Ser Gly Val Pro Ser Arg Phe Ser Gly Ser Gly Ser Gly Thr Asp
                195                 200                 205

Phe Thr Leu Thr Val Ser Ser Leu Gln Pro Glu Asp Phe Ala Thr Tyr
210                 215                 220

Tyr Cys Gln Gln Ala Tyr Ser Phe Pro Phe Thr Phe Gly Pro Gly Thr
225                 230                 235                 240

Lys Val Asp Ile Glu Glu Pro Lys Arg Ser Asp Lys Thr His Thr Cys
                245                 250                 255

Pro Pro Cys Pro Ala Pro Glu Leu Leu Gly Gly Pro Ser Val Phe Leu
                260                 265                 270

Phe Pro Pro Lys Pro Lys Asp Thr Leu Met Ile Ser Arg Thr Pro Glu
            275                 280                 285

Val Thr Cys Val Val Val Asp Val Ser His Glu Asp Pro Glu Val Lys
        290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
                325                 330                 335

Thr Val Leu His Gln Asp Trp Leu Asn Gly Lys Glu Tyr Lys Cys Lys
                340                 345                 350

Val Ser Asn Lys Ala Leu Pro Ala Pro Ile Glu Lys Thr Ile Ser Lys
            355                 360                 365

Ala Lys Gly Gln Pro Arg Glu Pro Gln Val Tyr Thr Leu Pro Pro Ser
        370                 375                 380

Arg Glu Glu Met Thr Lys Asn Gln Val Ser Leu Trp Cys Leu Val Lys
385                 390                 395                 400

Gly Phe Tyr Pro Ser Asp Ile Ala Val Glu Trp Glu Ser Asn Gly Gln
                405                 410                 415
```

```
Pro Glu Asn Asn Tyr Lys Thr Thr Pro Pro Val Leu Asp Ser Asp Gly
            420                 425                 430

Ser Phe Phe Leu Tyr Ser Lys Leu Thr Val Asp Lys Ser Arg Trp Gln
        435                 440                 445

Gln Gly Asn Val Phe Ser Cys Ser Val Met His Glu Ala Leu His Asn
    450                 455                 460

His Tyr Thr Gln Lys Ser Leu Ser Leu Ser Pro Gly
465                 470                 475

<210> SEQ ID NO 32
<211> LENGTH: 450
<212> TYPE: PRT
<213> ORGANISM: Artificial Sequence
<220> FEATURE:
<223> OTHER INFORMATION: Synthetic Construct

<400> SEQUENCE: 32

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300
```

```
Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Ser Cys Ala Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn Arg Phe Thr Gln Lys Ser Leu Ser Leu Ser
            435                 440                 445

Pro Gly
    450

<210> SEQ ID NO 33
<211> LENGTH: 213
<212> TYPE: PRT
<213> ORGANISM: Artificial Sequence
<220> FEATURE:
<223> OTHER INFORMATION: Synthetic Construct

<400> SEQUENCE: 33

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205
```

Asn Arg Gly Glu Cys
    210

<210> SEQ ID NO 34
<211> LENGTH: 120
<212> TYPE: PRT
<213> ORGANISM: Artificial Sequence
<220> FEATURE:
<223> OTHER INFORMATION: Synthetic Construct

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 35
<211> LENGTH: 107
<212> TYPE: PRT
<213> ORGANISM: Artificial Sequence
<220> FEATURE:
<223> OTHER INFORMATION: Synthetic Construct

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 36
<211> LENGTH: 120
<212> TYPE: PRT
<213> ORGANISM: Artificial Sequence
<220> FEATURE:
<223> OTHER INFORMATION: Synthetic Construct

<400> SEQUENCE: 36

Gln Val Thr Leu Arg Glu Ser Gly Pro Ala Leu Val Lys Pro Thr Gln

-continued

```
                1               5                  10                 15
        Thr Leu Thr Leu Thr Cys Thr Phe Ser Gly Phe Ser Leu Ser Thr Ser
                        20                  25                 30
        Gly Met Ser Val Gly Trp Ile Arg Gln Pro Pro Gly Lys Ala Leu Glu
                        35                  40                 45
        Trp Leu Ala Asp Ile Trp Trp Asp Asp Lys Lys Asp Tyr Asn Pro Ser
                        50                  55                 60
        Leu Lys Ser Arg Leu Thr Ile Ser Lys Asp Thr Ser Ala Asn Gln Val
        65                      70                  75                 80
        Val Leu Lys Val Thr Asn Met Asp Pro Ala Asp Thr Ala Thr Tyr Tyr
                        85                  90                 95
        Cys Ala Arg Ser Met Ile Thr Asn Trp Tyr Phe Asp Val Trp Gly Ala
                        100                 105                110
        Gly Thr Thr Val Thr Val Ser Ser
                        115                 120
```

<210> SEQ ID NO 37
<211> LENGTH: 106
<212> TYPE: PRT
<213> ORGANISM: Artificial Sequence
<220> FEATURE:
<223> OTHER INFORMATION: Synthetic Construct

<400> SEQUENCE: 37

```
        Asp Ile Gln Met Thr Gln Ser Pro Ser Thr Leu Ser Ala Ser Val Gly
        1               5                  10                 15
        Asp Arg Val Thr Ile Thr Cys Lys Cys Gln Leu Ser Val Gly Tyr Met
                        20                  25                 30
        His Trp Tyr Gln Gln Lys Pro Gly Lys Ala Pro Lys Leu Leu Ile Tyr
                        35                  40                 45
        Asp Thr Ser Lys Leu Ala Ser Gly Val Pro Ser Arg Phe Ser Gly Ser
                        50                  55                 60
        Gly Ser Gly Thr Ala Phe Thr Leu Thr Ile Ser Ser Leu Gln Pro Asp
        65                      70                  75                 80
        Asp Phe Ala Thr Tyr Tyr Cys Phe Gln Gly Ser Gly Tyr Pro Phe Thr
                        85                  90                 95
        Phe Gly Gly Gly Thr Lys Leu Glu Ile Lys
                        100                 105
```

<210> SEQ ID NO 38
<211> LENGTH: 122
<212> TYPE: PRT
<213> ORGANISM: Artificial Sequence
<220> FEATURE:
<223> OTHER INFORMATION: Synthetic Construct

<400> SEQUENCE: 38

```
        Glu Val Gln Leu Val Glu Ser Gly Gly Gly Leu Val Gln Pro Gly Gly
        1               5                  10                 15
        Ser Leu Arg Leu Ser Cys Ala Ala Ser Gly Phe Thr Phe Ser Val Tyr
                        20                  25                 30
        Tyr Met Asn Trp Val Arg Gln Ala Pro Gly Lys Gly Leu Glu Trp Val
                        35                  40                 45
        Ser Asp Ile Asn Asn Glu Gly Gly Thr Thr Tyr Tyr Ala Asp Ser Val
                        50                  55                 60
        Lys Gly Arg Phe Thr Ile Ser Arg Asp Asn Ser Lys Asn Ser Leu Tyr
        65                      70                  75                 80
```

-continued

```
Leu Gln Met Asn Ser Leu Arg Ala Glu Asp Thr Ala Val Tyr Tyr Cys
                 85                  90                  95

Ala Arg Asp Ala Gly Tyr Ser Asn His Val Pro Ile Phe Asp Ser Trp
            100                 105                 110

Gly Gln Gly Thr Leu Val Thr Val Ser Ser
        115                 120
```

<210> SEQ ID NO 39
<211> LENGTH: 110
<212> TYPE: PRT
<213> ORGANISM: Artificial Sequence
<220> FEATURE:
<223> OTHER INFORMATION: Synthetic Construct

<400> SEQUENCE: 39

```
Gln Ala Val Val Thr Gln Glu Pro Ser Leu Thr Val Ser Pro Gly Gly
1               5                   10                  15

Thr Val Thr Leu Thr Cys Gly Leu Lys Ser Gly Ser Val Thr Ser Asp
            20                  25                  30

Asn Phe Pro Thr Trp Tyr Gln Gln Thr Pro Gly Gln Ala Pro Arg Leu
        35                  40                  45

Leu Ile Tyr Asn Thr Asn Thr Arg His Ser Gly Val Pro Asp Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ala Glu Tyr Phe Cys Ala Leu Phe Ile Ser Asn
                85                  90                  95

Pro Ser Val Glu Phe Gly Gly Gly Thr Gln Leu Thr Val Leu
            100                 105                 110
```

<210> SEQ ID NO 40
<211> LENGTH: 117
<212> TYPE: PRT
<213> ORGANISM: Artificial Sequence
<220> FEATURE:
<223> OTHER INFORMATION: Synthetic Construct

<400> SEQUENCE: 40

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asn Met Asn Trp Val Arg Gln Ala Pro Gly Lys Gly Leu Glu Trp Val
        35                  40                  45

Ser Tyr Ile Ser Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Ser
65                  70                  75                  80

Leu Gln Met Asn Ser Leu Arg Asp Glu Asp Thr Ala Val Tyr Tyr Cys
                85                  90                  95

Ala Arg Ala Tyr Tyr Tyr Gly Met Asp Val Trp Gly Gln Gly Thr Thr
            100                 105                 110

Val Thr Val Ser Ser
        115
```

<210> SEQ ID NO 41
<211> LENGTH: 107
<212> TYPE: PRT
<213> ORGANISM: Artificial Sequence

```
<220> FEATURE:
<223> OTHER INFORMATION: Synthetic Construct

<400> SEQUENCE: 41

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Gly Trp
            20                  25                  30

Leu Ala Trp Tyr Gln Gln Lys Pro Gly Lys Ala Pro Lys Phe Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Pro
                85                  90                  95

Thr Phe Gly Gly Gly Thr Lys Val Glu Ile Lys
            100                 105

<210> SEQ ID NO 42
<211> LENGTH: 121
<212> TYPE: PRT
<213> ORGANISM: Artificial Sequence
<220> FEATURE:
<223> OTHER INFORMATION: Synthetic Construct

<400> SEQUENCE: 42

Gln Val Gln Leu Gln Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Tyr Thr Gly Glu Pro Thr Tyr Thr Asp Asp Phe
    50                  55                  60

Lys Gly Arg Phe Ala Phe Ser Leu Asp Thr Ser Val Ser Thr Ala Tyr
65                  70                  75                  80

Leu Gln Ile Ser Ser Leu Lys Ala Asp Asp Thr Ala Val Tyr Phe Cys
                85                  90                  95

Ala Arg Gly Gly Phe Gly Ser Ser Tyr Trp Tyr Phe Asp Val Trp Gly
            100                 105                 110

Gln Gly Ser Leu Val Thr Val Ser Ser
        115                 120

<210> SEQ ID NO 43
<211> LENGTH: 107
<212> TYPE: PRT
<213> ORGANISM: Artificial Sequence
<220> FEATURE:
<223> OTHER INFORMATION: Synthetic Construct

<400> SEQUENCE: 43

Asp Ile Gln Leu Thr Gln Ser Pro Ser Ser Leu Ser Ala Ser Val Gly
1               5                   10                  15

Asp Arg Val Ser Ile Thr Cys Lys Ala Ser Gln Asp Val Ser Ile Ala
            20                  25                  30

Val Ala Trp Tyr Gln Gln Lys Pro Gly Lys Ala Pro Lys Leu Leu Ile
        35                  40                  45
```

Tyr Ser Ala Ser Tyr Arg Tyr Thr Gly Val Pro Asp Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Val Tyr Tyr Cys Gln Gln His Tyr Ile Thr Pro Leu
                 85                  90                  95

Thr Phe Gly Ala Gly Thr Lys Val Glu Ile Lys
                100                 105

<210> SEQ ID NO 44
<211> LENGTH: 111
<212> TYPE: PRT
<213> ORGANISM: Artificial Sequence
<220> FEATURE:
<223> OTHER INFORMATION: Synthetic Construct

<400> SEQUENCE: 44

Gln Val Gln Leu Lys Glu Ser Gly Pro Gly Leu Val Ala Pro Ser Gln
 1               5                  10                  15

Ser Leu Ser Ile Thr Cys Thr Val Ser Gly Phe Ser Leu Ser Ser Tyr
                 20                  25                  30

Gly Val Ser Trp Val Arg Gln Pro Pro Gly Lys Gly Leu Glu Trp Leu
             35                  40                  45

Gly Val Ile Trp Gly Asp Gly Ser Thr Asn Tyr Lys Pro Asn Leu Met
 50                  55                  60

Ser Arg Leu Ser Ile Ser Lys Asp Ile Ser Lys Ser Gln Val Leu Phe
 65                  70                  75                  80

Lys Leu Asn Ser Leu Gln Thr Asp Asp Thr Ala Thr Tyr Tyr Cys Val
                 85                  90                  95

Thr Leu Asp Tyr Trp Gly Gln Gly Thr Ser Val Thr Val Ser Ser
                100                 105                 110

<210> SEQ ID NO 45
<211> LENGTH: 112
<212> TYPE: PRT
<213> ORGANISM: Artificial Sequence
<220> FEATURE:
<223> OTHER INFORMATION: Synthetic Construct

<400> SEQUENCE: 45

Asp Val Val Met Thr Gln Thr Pro Leu Ser Leu Pro Val Ser Leu Gly
 1               5                  10                  15

Asp Gln Ala Ser Ile Ser Cys Arg Ser Ser Gln Ser Leu Val His Arg
                 20                  25                  30

Asn Gly Asn Thr Tyr Leu His Trp Tyr Leu Gln Lys Pro Gly Gln Ser
             35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Leu Tyr Phe Cys Phe Gln Thr
                 85                  90                  95

Thr Tyr Val Pro Asn Thr Phe Gly Gly Gly Thr Lys Leu Glu Ile Lys
                100                 105                 110

<210> SEQ ID NO 46
<211> LENGTH: 119
<212> TYPE: PRT
<213> ORGANISM: Artificial Sequence
<220> FEATURE:
<223> OTHER INFORMATION: Synthetic Construct

<400> SEQUENCE: 46

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 47
<211> LENGTH: 112
<212> TYPE: PRT
<213> ORGANISM: Artificial Sequence
<220> FEATURE:
<223> OTHER INFORMATION: Synthetic Construct

<400> SEQUENCE: 47

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110

<210> SEQ ID NO 48
<211> LENGTH: 124
<212> TYPE: PRT
<213> ORGANISM: Artificial Sequence
<220> FEATURE:
<223> OTHER INFORMATION: Synthetic Construct

<400> SEQUENCE: 48

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ala Phe Ser Ser Tyr
            20                  25                  30

Gly Met His Trp Val Arg Gln Ala Pro Gly Lys Gly Leu Glu Trp Val
        35                  40                  45

Ala Val Ile Trp Phe Asp Gly Thr Lys Lys Tyr Tyr Thr Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Thr Leu Arg Ala Glu Asp Thr Ala Val Tyr Tyr Cys
                 85                  90                  95

Ala Arg Asp Arg Gly Ile Gly Ala Arg Arg Gly Pro Tyr Tyr Met Asp
                100                 105                 110

Val Trp Gly Lys Gly Thr Thr Val Thr Val Ser Ser
            115                 120

<210> SEQ ID NO 49
<211> LENGTH: 107
<212> TYPE: PRT
<213> ORGANISM: Artificial Sequence
<220> FEATURE:
<223> OTHER INFORMATION: Synthetic Construct

<400> SEQUENCE: 49

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ser Ser Tyr
                 20                  25                  30

Leu Asn Trp Tyr Gln Gln Lys Pro Gly Lys Ala Pro Lys Leu Leu Ile
             35                  40                  45

Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Leu
                 85                  90                  95

Thr Phe Gly Gly Gly Thr Lys Val Glu Ile Lys
                100                 105

<210> SEQ ID NO 50
<211> LENGTH: 124
<212> TYPE: PRT
<213> ORGANISM: Artificial Sequence
<220> FEATURE:
<223> OTHER INFORMATION: Synthetic Construct

<400> SEQUENCE: 50

Glu Val Gln Leu Val Glu Ser Gly Gly Gly Leu Val Gln Pro Gly Gly
  1               5                  10                  15

Ser Leu Arg Leu Ser Cys Ser Ala Ser Gly Phe Thr Phe Ser Ser Phe
                 20                  25                  30

Gly Met His Trp Val Arg Gln Ala Pro Gly Lys Gly Leu Glu Trp Val
             35                  40                  45

Ala Tyr Ile Ser Ser Gly Ser Ser Thr Ile Tyr Gly Asp Thr Val
         50                  55                  60

Lys Gly Arg Phe Thr Ile Ser Arg Asp Asn Ala Lys Asn Ser Leu Phe
 65                  70                  75                  80

Leu Gln Met Ser Ser Leu Arg Ala Glu Asp Thr Ala Val Tyr Tyr Cys
                 85                  90                  95

Ala Arg Glu Gly Gly Tyr Tyr Tyr Gly Arg Ser Tyr Tyr Thr Met Asp
                100                 105                 110

Tyr Trp Gly Gln Gly Thr Thr Val Thr Val Ser Ser
            115                 120

-continued

```
<210> SEQ ID NO 51
<211> LENGTH: 112
<212> TYPE: PRT
<213> ORGANISM: Artificial Sequence
<220> FEATURE:
<223> OTHER INFORMATION: Synthetic Construct

<400> SEQUENCE: 51
```

Asp Val Val Met Thr Gln Ser Pro Leu Ser Leu Pro Val Thr Pro Gly
1               5                   10                  15

Ala Pro Ala Ser Ile Ser Cys Arg Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Ile Tyr Tyr Cys Phe Gln Gly
                85                  90                  95

Ser His Val Pro Pro Thr Phe Gly Pro Gly Thr Lys Leu Glu Ile Lys
            100                 105                 110

```
<210> SEQ ID NO 52
<211> LENGTH: 119
<212> TYPE: PRT
<213> ORGANISM: Artificial Sequence
<220> FEATURE:
<223> OTHER INFORMATION: Synthetic Construct

<400> SEQUENCE: 52
```

Glu Val Gln Leu Val Glu Ser Gly Gly Arg Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Tyr Trp Ile Arg Gln Ala Pro Gly Lys Gly Leu Glu Trp Val
        35                  40                  45

Ala Arg Ile Arg Ser Lys Ser Asn Asn Tyr Ala Ile Tyr Tyr Ala Asp
    50                  55                  60

Ser Val Lys Asp Arg Phe Thr Ile Phe Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Pro Tyr Ser Asp Ser Phe Ala Tyr Trp Gly Gln Gly
            100                 105                 110

Thr Leu Val Thr Val Ser Ala
        115

```
<210> SEQ ID NO 53
<211> LENGTH: 112
<212> TYPE: PRT
<213> ORGANISM: Artificial Sequence
<220> FEATURE:
<223> OTHER INFORMATION: Synthetic Construct

<400> SEQUENCE: 53
```

Asp Val Val Met Thr Gln Thr Pro Leu Ser Leu Pro Val Ser Leu Gly
1               5                   10                  15

```
Asp Gln Ala Ser Ile Ser Cys Arg Ser Ser Gln Ser Leu Val His Ser
                20                  25                  30

Thr Gly Asn Thr Tyr Leu His Trp Tyr Leu Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Phe Thr Phe Gly Gly Gly Thr Lys Leu Glu Ile Lys
                100                 105                 110
```

<210> SEQ ID NO 54
<211> LENGTH: 119
<212> TYPE: PRT
<213> ORGANISM: Artificial Sequence
<220> FEATURE:
<223> OTHER INFORMATION: Synthetic Construct

<400> SEQUENCE: 54

```
Glu Val Gln Leu Val Glu Ser Gly Gly Arg Leu Val Gln Pro Lys Gly
1               5                   10                  15

Ser Leu Lys Leu Ser Cys Ala Ala Ser Gly Phe Thr Phe Asn Thr Tyr
                20                  25                  30

Ala Met Tyr Trp Ile Arg Gln Ala Pro Gly Lys Gly Leu Glu Trp Val
        35                  40                  45

Ala Arg Ile Arg Ser Lys Ser Asn Asn Tyr Ala Ile Tyr Tyr Ala Asp
    50                  55                  60

Ser Val Lys Asp Arg Phe Thr Ile Phe Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Pro Tyr Ser Asp Ser Phe Ala Tyr Trp Gly Gln Gly
                100                 105                 110

Thr Leu Val Thr Val Ser Ala
        115
```

<210> SEQ ID NO 55
<211> LENGTH: 112
<212> TYPE: PRT
<213> ORGANISM: Artificial Sequence
<220> FEATURE:
<223> OTHER INFORMATION: Synthetic Construct

<400> SEQUENCE: 55

```
Asp Val Val Met Thr Gln Thr Pro Leu Ser Leu Pro Val Ser Leu Gly
1               5                   10                  15

Asp Gln Ala Ser Ile Ser Cys Arg Ser Ser Leu Ser Leu Val His Ser
                20                  25                  30

Thr Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Phe Cys Ser Gln Ser
                85                  90                  95
```

```
Thr His Val Pro Phe Thr Phe Gly Gly Gly Thr Lys Leu Glu Ile Lys
                100                 105                 110
```

<210> SEQ ID NO 56
<211> LENGTH: 121
<212> TYPE: PRT
<213> ORGANISM: Artificial Sequence
<220> FEATURE:
<223> OTHER INFORMATION: Synthetic Construct

<400> SEQUENCE: 56

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Lys Thr Gly Glu Pro Thr Tyr Ala Glu Glu Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Lys Glu Asp Thr Ala Thr Tyr Phe Cys
                85                  90                  95

Gly Arg Gly Gly Tyr Gly Ser Ser Tyr Trp Tyr Phe Asp Val Trp Gly
            100                 105                 110

Ala Gly Thr Thr Val Thr Val Ser Ser
        115                 120
```

<210> SEQ ID NO 57
<211> LENGTH: 107
<212> TYPE: PRT
<213> ORGANISM: Artificial Sequence
<220> FEATURE:
<223> OTHER INFORMATION: Synthetic Construct

<400> SEQUENCE: 57

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Ile Ala
            20                  25                  30

Val Ala Trp Tyr Gln Gln Lys Pro Gly Gln Ser Pro Lys Val Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Arg Val Gln Ala
65                  70                  75                  80

Glu Asp Leu Ala Val Tyr Tyr Cys Gln Gln His Tyr Ile Thr Pro Leu
                85                  90                  95

Thr Phe Gly Ala Gly Thr Lys Leu Glu Leu Lys
            100                 105
```

<210> SEQ ID NO 58
<211> LENGTH: 116
<212> TYPE: PRT
<213> ORGANISM: Artificial Sequence
<220> FEATURE:
<223> OTHER INFORMATION: Synthetic Construct

<400> SEQUENCE: 58

```
Gln Val Gln Leu Gln Gln Ser Gly Pro Glu Leu Val Arg Pro Gly Thr
1               5                   10                  15

Ser Val Arg Ile Ser Cys Lys Ala Ser Gly Tyr Thr Phe Thr Ile Tyr
            20                  25                  30

Trp Leu Gly Trp Val Lys Gln Arg Pro Gly His Gly Leu Glu Trp Ile
        35                  40                  45

Gly Asn Ile Phe Pro Gly Ser Ala Tyr Ile Asn Tyr Asn Glu Lys Phe
    50                  55                  60

Lys Gly Lys Ala Thr Leu Thr Ala Asp Thr Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Glu Gly Ser Asn Ser Gly Tyr Trp Gly Gln Gly Thr Thr Leu
            100                 105                 110

Thr Val Ser Ser
            115
```

<210> SEQ ID NO 59
<211> LENGTH: 113
<212> TYPE: PRT
<213> ORGANISM: Artificial Sequence
<220> FEATURE:
<223> OTHER INFORMATION: Synthetic Construct
<400> SEQUENCE: 59

```
Asp Ile Val Met Thr Gln Ser Pro Ser Ser Leu Ser Val Ser Ala Gly
1               5                   10                  15

Glu Lys Val Thr Met Thr Cys Lys Ser Ser Gln Ser Leu Leu Asn Ser
            20                  25                  30

Gly Asn Gln Gln Asn Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Asn Ser Val Gln Ala Glu Asp Leu Ala Val Tyr Tyr Cys Gln Ser
                85                  90                  95

Asp His Ile Tyr Pro Tyr Thr Phe Gly Gly Gly Thr Lys Leu Glu Ile
            100                 105                 110

Lys
```

<210> SEQ ID NO 60
<211> LENGTH: 116
<212> TYPE: PRT
<213> ORGANISM: Artificial Sequence
<220> FEATURE:
<223> OTHER INFORMATION: Synthetic Construct
<400> SEQUENCE: 60

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Ser Thr Asp Tyr Asn Ala Ala Phe Ile
    50                  55                  60
```

```
Ser Arg Leu Ser Ile Ser Lys Asp Thr Ser Lys Ser Gln Val Phe
 65                  70                  75                  80

Lys Met Asn Ser Leu Gln Ala Asp Thr Ala Ile Tyr Tyr Cys Ala
                 85                  90                  95

Arg Glu Leu Ile His Ala Met Asp Asn Trp Gly Gln Gly Thr Ser Val
                100                 105                 110

Thr Val Ser Ser
        115
```

<210> SEQ ID NO 61
<211> LENGTH: 106
<212> TYPE: PRT
<213> ORGANISM: Artificial Sequence
<220> FEATURE:
<223> OTHER INFORMATION: Synthetic Construct

<400> SEQUENCE: 61

```
Asp Ile Gln Met Thr Gln Ser Pro Ala Ser Leu Ser Val Ser Val Gly
 1               5                  10                  15

Glu Thr Val Thr Ile Thr Cys Arg Ala Ser Glu Asn Ile Tyr Ser Asn
                 20                  25                  30

Leu Ala Trp Tyr Gln Gln Lys Gln Gly Asn Ser Pro Gln Leu Leu Val
             35                  40                  45

Phe Ala Ala Thr Asn Leu Ala Asp Gly Val Pro Ser Arg Phe Ser Gly
 50                  55                  60

Ser Gly Ser Gly Thr Gln Tyr Ser Leu Lys Ile Asn Ser Leu Gln Ser
 65                  70                  75                  80

Glu Asp Phe Gly Thr Tyr Tyr Cys Gln His Phe Trp Gly Thr Pro Thr
                 85                  90                  95

Phe Gly Gly Gly Thr Lys Leu Glu Ile Lys
                100                 105
```

<210> SEQ ID NO 62
<211> LENGTH: 119
<212> TYPE: PRT
<213> ORGANISM: Artificial Sequence
<220> FEATURE:
<223> OTHER INFORMATION: Synthetic Construct

<400> SEQUENCE: 62

```
Gln Val Gln Leu Lys Gln Ser Gly Pro Gly Leu Val Gln Pro Ser Gln
 1               5                  10                  15

Ser Leu Ser Ile Thr Cys Thr Val Ser Gly Phe Ser Leu Thr Asn Tyr
                 20                  25                  30

Gly Val His Trp Val Arg Gln Ser Pro Gly Lys Gly Leu Glu Trp Leu
             35                  40                  45

Gly Val Ile Trp Ser Gly Gly Asn Thr Asp Tyr Asn Thr Pro Phe Thr
 50                  55                  60

Ser Arg Leu Ser Ile Asn Lys Asp Asn Ser Lys Ser Gln Val Phe Phe
 65                  70                  75                  80

Lys Met Asn Ser Leu Gln Ser Asn Asp Thr Ala Ile Tyr Tyr Cys Ala
                 85                  90                  95

Arg Ala Leu Thr Tyr Tyr Asp Tyr Glu Phe Ala Tyr Trp Gly Gln Gly
                100                 105                 110

Thr Leu Val Thr Val Ser Ala
        115
```

<210> SEQ ID NO 63

```
<211> LENGTH: 107
<212> TYPE: PRT
<213> ORGANISM: Artificial Sequence
<220> FEATURE:
<223> OTHER INFORMATION: Synthetic Construct

<400> SEQUENCE: 63

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys
            100                 105

<210> SEQ ID NO 64
<211> LENGTH: 121
<212> TYPE: PRT
<213> ORGANISM: Artificial Sequence
<220> FEATURE:
<223> OTHER INFORMATION: Synthetic Construct

<400> SEQUENCE: 64

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asp Tyr Asn Pro Ser
    50                  55                  60

Leu Lys Ser Arg Val Thr Met Ser Val Asp Thr Ser Lys Asn Gln Phe
65                  70                  75                  80

Ser Leu Lys Val Asn Ser Val Thr Ala Ala Asp Thr Ala Val Tyr Tyr
                85                  90                  95

Cys Ala Arg Val Ser Ile Phe Gly Val Gly Thr Phe Asp Tyr Trp Gly
            100                 105                 110

Gln Gly Thr Leu Val Thr Val Ser Ser
        115                 120

<210> SEQ ID NO 65
<211> LENGTH: 107
<212> TYPE: PRT
<213> ORGANISM: Artificial Sequence
<220> FEATURE:
<223> OTHER INFORMATION: Synthetic Construct

<400> SEQUENCE: 65

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30
```

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys His Gln Tyr Gly Ser Thr Pro Leu
                 85                  90                  95

Thr Phe Gly Gly Gly Thr Lys Ala Glu Ile Lys
            100                 105

<210> SEQ ID NO 66
<211> LENGTH: 119
<212> TYPE: PRT
<213> ORGANISM: Artificial Sequence
<220> FEATURE:
<223> OTHER INFORMATION: Synthetic Construct

<400> SEQUENCE: 66

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Ile Ser Ser Tyr
             20                  25                  30

Gly Val His Trp Ile Arg Gln Pro Pro Gly Lys Gly Leu Glu Trp Ile
             35                  40                  45

Gly Val Ile Trp Thr Gly Gly Ser Thr Asp Tyr Asn Ser Ala Leu Met
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Asp Gly Asp Tyr Asp Arg Tyr Thr Met Asp Tyr Trp Gly Gln Gly
            100                 105                 110

Thr Leu Val Thr Val Ser Ser
        115

<210> SEQ ID NO 67
<211> LENGTH: 111
<212> TYPE: PRT
<213> ORGANISM: Artificial Sequence
<220> FEATURE:
<223> OTHER INFORMATION: Synthetic Construct

<400> SEQUENCE: 67

Asp Ile Val Met Thr Gln Ser Pro Asp Ser Leu Ala Val Ser Leu Gly
 1               5                  10                  15

Glu Arg Ala Thr Ile Asn Cys Arg Ala Ser Lys Ser Val Ser Thr Ser
             20                  25                  30

Gly Tyr Ser Tyr Met His Trp Tyr Gln Gln Lys Pro Gly Gln Pro Pro
             35                  40                  45

Lys Leu Leu Ile Tyr Leu Ala Ser Asn Leu Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln His Ser Arg
                 85                  90                  95

Glu Leu Pro Tyr Thr Phe Gly Gln Gly Thr Lys Leu Glu Ile Lys
            100                 105                 110

<210> SEQ ID NO 68
<211> LENGTH: 118
<212> TYPE: PRT
<213> ORGANISM: Artificial Sequence
<220> FEATURE:
<223> OTHER INFORMATION: Synthetic Construct

<400> SEQUENCE: 68

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Glu Trp Met
        35                  40                  45

Gly Trp Ile Asn Thr Tyr Thr Gly Glu Pro Thr Tyr Ala Asp Asp Phe
    50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Ile Gly Asp Ser Ser Pro Ser Asp Tyr Trp Gly Gln Gly Thr
            100                 105                 110

Leu Val Thr Val Ser Ser
        115

<210> SEQ ID NO 69
<211> LENGTH: 107
<212> TYPE: PRT
<213> ORGANISM: Artificial Sequence
<220> FEATURE:
<223> OTHER INFORMATION: Synthetic Construct

<400> SEQUENCE: 69

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Ser Val Ser Asn Asp
            20                  25                  30

Val Val Trp Tyr Gln Gln Lys Pro Gly Gln Ala Pro Arg Leu Leu Ile
        35                  40                  45

Tyr Tyr Ala Ser Asn Arg Tyr Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Asp Tyr Thr Ser Pro Trp
                85                  90                  95

Thr Phe Gly Gln Gly Thr Lys Leu Glu Ile Lys
            100                 105

<210> SEQ ID NO 70
<211> LENGTH: 118
<212> TYPE: PRT
<213> ORGANISM: Artificial Sequence
<220> FEATURE:
<223> OTHER INFORMATION: Synthetic Construct

<400> SEQUENCE: 70

Gln Val Gln Leu Gln Glu Ser Gly Pro Gly Leu Val Lys Pro Ser Glu
1               5                   10                  15

```
Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Val Tyr Tyr Ser Gly Thr Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Ser Ile Ala Val Thr Gly Phe Tyr Phe Asp Tyr Trp Gly Gln Gly Thr
                100                 105                 110

Leu Val Thr Val Ser Ser
            115
```

```
<210> SEQ ID NO 71
<211> LENGTH: 108
<212> TYPE: PRT
<213> ORGANISM: Artificial Sequence
<220> FEATURE:
<223> OTHER INFORMATION: Synthetic Construct

<400> SEQUENCE: 71
```

```
Glu Ile Val Leu Thr Gln Ser Pro Gly Thr Leu Ser Leu Ser Pro Gly
1               5                   10                  15

Glu Arg Val Thr Leu Ser Cys Arg Ala Ser Gln Arg Val Asn Asn Asn
            20                  25                  30

Tyr Leu Ala Trp Tyr Gln Gln Arg Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp Arg Ser Pro
                85                  90                  95

Leu Thr Phe Gly Gly Gly Thr Lys Leu Glu Ile Lys
                100                 105
```

```
<210> SEQ ID NO 72
<211> LENGTH: 119
<212> TYPE: PRT
<213> ORGANISM: Artificial Sequence
<220> FEATURE:
<223> OTHER INFORMATION: Synthetic Construct

<400> SEQUENCE: 72
```

```
Gln Val Gln Leu Gln Gln Ser Gly Pro Glu Leu Glu Lys Pro Gly Ala
1               5                   10                  15

Ser Val Lys Ile Ser Cys Lys Ala Ser Gly Tyr Ser Phe Thr Gly Tyr
            20                  25                  30

Thr Met Asn Trp Val Lys Gln Ser His Gly Lys Ser Leu Glu Trp Ile
        35                  40                  45

Gly Leu Ile Thr Pro Tyr Asn Gly Ala Ser Ser Tyr Asn Gln Lys Phe
    50                  55                  60

Arg Gly Lys Ala Thr Leu Thr Val Asp Lys Ser Ser Ser Thr Ala Tyr
65                  70                  75                  80

Met Asp Leu Leu Ser Leu Thr Ser Glu Asp Ser Ala Val Tyr Phe Cys
                85                  90                  95
```

```
Ala Arg Gly Gly Tyr Asp Gly Arg Gly Phe Asp Tyr Trp Gly Ser Gly
            100                 105                 110

Thr Pro Val Thr Val Ser Ser
        115

<210> SEQ ID NO 73
<211> LENGTH: 106
<212> TYPE: PRT
<213> ORGANISM: Artificial Sequence
<220> FEATURE:
<223> OTHER INFORMATION: Synthetic Construct

<400> SEQUENCE: 73

Asp Ile Glu Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

His Trp Tyr Gln Gln Lys Ser Gly Thr Ser Pro Lys Arg Trp Ile Tyr
            35                  40                  45

Asp Thr Ser Lys Leu Ala Ser Gly Val Pro Gly Arg Phe Ser Gly Ser
        50                  55                  60

Gly Ser Gly Asn Ser Tyr Ser Leu Thr Ile Ser Ser Val Glu Ala Glu
65                  70                  75                  80

Asp Asp Ala Thr Tyr Tyr Cys Gln Gln Trp Ser Lys His Pro Leu Thr
                85                  90                  95

Phe Gly Ser Gly Thr Lys Val Glu Ile Lys
            100                 105

<210> SEQ ID NO 74
<211> LENGTH: 116
<212> TYPE: PRT
<213> ORGANISM: Artificial Sequence
<220> FEATURE:
<223> OTHER INFORMATION: Synthetic Construct

<400> SEQUENCE: 74

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Ile Thr Asp Ser
            20                  25                  30

Asn Ile His Trp Val Arg Gln Ala Pro Gly Gln Ser Leu Glu Trp Ile
            35                  40                  45

Gly Tyr Ile Tyr Pro Tyr Asn Gly Gly Thr Asp Tyr Asn Gln Lys Phe
        50                  55                  60

Lys Asn Arg Ala Thr Leu Thr Val Asp Asn Pro Thr Asn Thr Ala Tyr
65                  70                  75                  80

Met Glu Leu Ser Ser Leu Arg Ser Glu Asp Thr Ala Phe Tyr Tyr Cys
                85                  90                  95

Val Asn Gly Asn Pro Trp Leu Ala Tyr Trp Gly Gln Gly Thr Leu Val
            100                 105                 110

Thr Val Ser Ser
        115

<210> SEQ ID NO 75
<211> LENGTH: 111
<212> TYPE: PRT
<213> ORGANISM: Artificial Sequence
<220> FEATURE:
<223> OTHER INFORMATION: Synthetic Construct
```

<400> SEQUENCE: 75

Asp Ile Gln Leu Thr Gln Ser Pro Ser Thr Leu Ser Ala Ser Val Gly
1               5                   10                  15

Asp Arg Val Thr Ile Thr Cys Arg Ala Ser Glu Ser Leu Asp Asn Tyr
            20                  25                  30

Gly Ile Arg Phe Leu Thr Trp Phe Gln Gln Lys Pro Gly Lys Ala Pro
        35                  40                  45

Lys Leu Leu Met Tyr Ala Ala Ser Asn Gln Gly Ser Gly Val Pro Ser
    50                  55                  60

Arg Phe Ser Gly Ser Gly Ser Gly Thr Glu Phe Thr Leu Thr Ile Ser
65                  70                  75                  80

Ser Leu Gln Pro Asp Asp Phe Ala Thr Tyr Tyr Cys Gln Gln Thr Lys
                85                  90                  95

Glu Val Pro Trp Ser Phe Gly Gln Gly Thr Lys Val Glu Val Lys
            100                 105                 110

<210> SEQ ID NO 76
<211> LENGTH: 125
<212> TYPE: PRT
<213> ORGANISM: Artificial Sequence
<220> FEATURE:
<223> OTHER INFORMATION: Synthetic Construct

<400> SEQUENCE: 76

Glu Val Gln Leu Val Glu Ser Gly Gly Arg Leu Val Gln Pro Lys Gly
1               5                   10                  15

Ser Leu Lys Leu Ser Cys Ala Ala Ser Gly Phe Ala Phe Asn Thr Tyr
            20                  25                  30

Ala Leu Tyr Trp Ile Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Ala Arg Phe Tyr Tyr Ser Asp Tyr Gly Tyr Ala Met
            100                 105                 110

Asp Tyr Trp Gly Gln Gly Thr Ser Val Thr Val Ser Ser
        115                 120                 125

<210> SEQ ID NO 77
<211> LENGTH: 112
<212> TYPE: PRT
<213> ORGANISM: Artificial Sequence
<220> FEATURE:
<223> OTHER INFORMATION: Synthetic Construct

<400> SEQUENCE: 77

Asp Ile Val Met Thr Gln Ala Ala Pro Ser Val Pro Val Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

```
Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Leu Thr Phe Gly Ala Gly Thr Lys Leu Glu Leu Lys
            100                 105                 110

<210> SEQ ID NO 78
<211> LENGTH: 118
<212> TYPE: PRT
<213> ORGANISM: Artificial Sequence
<220> FEATURE:
<223> OTHER INFORMATION: Synthetic Construct

<400> SEQUENCE: 78

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser
            115

<210> SEQ ID NO 79
<211> LENGTH: 108
<212> TYPE: PRT
<213> ORGANISM: Artificial Sequence
<220> FEATURE:
<223> OTHER INFORMATION: Synthetic Construct

<400> SEQUENCE: 79

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 80
<211> LENGTH: 119
<212> TYPE: PRT
```

<213> ORGANISM: Artificial Sequence
<220> FEATURE:
<223> OTHER INFORMATION: Synthetic Construct

<400> SEQUENCE: 80

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Ser Tyr
            20                  25                  30

Trp Leu His Trp Val Arg Gln Ala Pro Gly Lys Gly Leu Glu Trp Val
        35                  40                  45

Gly Met Ile Asp Pro Ser Asn Ser Asp Thr Arg Phe Asn Pro Asn Phe
    50                  55                  60

Lys Asp Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Thr Tyr Arg Ser Tyr Val Thr Pro Leu Asp Tyr Trp Gly Gln Gly
            100                 105                 110

Thr Leu Val Thr Val Ser Ser
        115

<210> SEQ ID NO 81
<211> LENGTH: 113
<212> TYPE: PRT
<213> ORGANISM: Artificial Sequence
<220> FEATURE:
<223> OTHER INFORMATION: Synthetic Construct

<400> SEQUENCE: 81

Asp Ile Gln Met Thr Gln Ser Pro Ser Ser Leu Ser Ala Ser Val Gly
1               5                   10                  15

Asp Arg Val Thr Ile Thr Cys Lys Ser Gln Ser Leu Leu Tyr Thr
            20                  25                  30

Ser Ser Gln Lys Asn Tyr Leu Ala Trp Tyr Gln Gln Lys Pro Gly Lys
        35                  40                  45

Ala Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Phe Ala Thr Tyr Tyr Cys Gln Gln
                85                  90                  95

Tyr Tyr Ala Tyr Pro Trp Thr Phe Gly Gln Gly Thr Lys Val Glu Ile
            100                 105                 110

Lys

<210> SEQ ID NO 82
<211> LENGTH: 120
<212> TYPE: PRT
<213> ORGANISM: Artificial Sequence
<220> FEATURE:
<223> OTHER INFORMATION: Synthetic Construct

<400> SEQUENCE: 82

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Ile Glu Asp Tyr
            20                  25                  30

Tyr Met His Trp Val Arg Gln Ala Pro Gly Gln Gly Leu Glu Trp Met
                35                  40                  45

Gly Trp Ile Asp Pro Glu Asn Gly Asp Thr Glu Tyr Ala Pro Thr Phe
 50                  55                  60

Gln Gly Arg Val Thr Met Thr Arg Asp Thr Ser Ile Asn Thr Ala Tyr
65                  70                  75                  80

Met Glu Leu Ser Arg Leu Arg Ser Asp Thr Ala Val Tyr Tyr Cys
                85                  90                  95

Ala Arg His Asp Ala His Tyr Gly Thr Trp Phe Ala Tyr Trp Gly Gln
                100                 105                 110

Gly Thr Leu Val Thr Val Ser Ser
            115                 120

<210> SEQ ID NO 83
<211> LENGTH: 112
<212> TYPE: PRT
<213> ORGANISM: Artificial Sequence
<220> FEATURE:
<223> OTHER INFORMATION: Synthetic Construct

<400> SEQUENCE: 83

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Ile Arg Asn
                20                  25                  30

Asp Gly Asn Thr Tyr Leu Glu Trp Tyr Gln Gln Arg Pro Gly Gln Ser
            35                  40                  45

Pro Arg Arg Leu Ile Tyr Arg Val Ser Asn Arg Phe Ser Gly Val Pro
 50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
                100                 105                 110

<210> SEQ ID NO 84
<211> LENGTH: 116
<212> TYPE: PRT
<213> ORGANISM: Artificial Sequence
<220> FEATURE:
<223> OTHER INFORMATION: Synthetic Construct

<400> SEQUENCE: 84

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ala Phe Thr Ala Tyr
                20                  25                  30

Asn Ile His Trp Val Arg Gln Ala Pro Gly Gln Gly Leu Glu Trp Met
            35                  40                  45

Gly Ser Phe Asp Pro Tyr Asp Gly Ser Ser Tyr Asn Gln Lys Phe
 50                  55                  60

Lys Asp Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala Arg Gly Trp Tyr Tyr Phe Asp Tyr Trp Gly His Gly Thr Leu Val
                100                 105                 110

Thr Val Ser Ser
        115

<210> SEQ ID NO 85
<211> LENGTH: 107
<212> TYPE: PRT
<213> ORGANISM: Artificial Sequence
<220> FEATURE:
<223> OTHER INFORMATION: Synthetic Construct

<400> SEQUENCE: 85

Asp Ile Val Met Thr Gln Thr Pro Leu Ser Leu Pro Val Thr Pro Gly
1               5                   10                  15

Glu Pro Ala Ser Ile Ser Cys Arg Ala Ser Lys Ser Ile Ser Lys Tyr
            20                  25                  30

Leu Ala Trp Tyr Gln Gln Lys Pro Gly Gln Ala Pro Arg Leu Leu Ile
        35                  40                  45

Tyr Ser Gly Ser Thr Leu Gln Ser Gly Ile Pro Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Gln Gln His Asp Glu Ser Pro Tyr
                85                  90                  95

Thr Phe Gly Glu Gly Thr Lys Val Glu Ile Lys
            100                 105

<210> SEQ ID NO 86
<211> LENGTH: 122
<212> TYPE: PRT
<213> ORGANISM: Artificial Sequence
<220> FEATURE:
<223> OTHER INFORMATION: Synthetic Construct

<400> SEQUENCE: 86

Gln Val Gln Leu Val Gln Ser Gly Ala Glu Val Lys Lys Pro Gly Ser
1               5                   10                  15

Ser Val Lys Val Ser Cys Lys Ala Ser Gly Phe Thr Phe Ala Thr Tyr
            20                  25                  30

Asn Met His Trp Val Arg Gln Ala Pro Gly Gln Gly Leu Glu Trp Met
        35                  40                  45

Gly Tyr Ile Tyr Pro Gly Asp Gly Asn Ala Asn Tyr Asn Gln Gln Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Phe Asp Tyr Asp Gly Tyr Tyr Phe Asp Ser Trp
            100                 105                 110

Gly Gln Gly Thr Leu Val Thr Val Ser Ser
        115                 120

<210> SEQ ID NO 87
<211> LENGTH: 107
<212> TYPE: PRT
<213> ORGANISM: Artificial Sequence
<220> FEATURE:
<223> OTHER INFORMATION: Synthetic Construct

<400> SEQUENCE: 87

-continued

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Ala Pro Lys Leu Leu Ile
        35                  40                  45

His Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Gly Ala Pro Leu
                85                  90                  95

Thr Phe Gly Gln Gly Thr Lys Leu Glu Ile Lys
            100                 105
```

<210> SEQ ID NO 88
<211> LENGTH: 4
<212> TYPE: PRT
<213> ORGANISM: Artificial Sequence
<220> FEATURE:
<223> OTHER INFORMATION: Synthetic Construct

<400> SEQUENCE: 88

```
Asp Tyr Tyr Ile
1
```

<210> SEQ ID NO 89
<211> LENGTH: 17
<212> TYPE: PRT
<213> ORGANISM: Artificial Sequence
<220> FEATURE:
<223> OTHER INFORMATION: Synthetic Construct

<400> SEQUENCE: 89

```
Trp Ile Asn Pro Asn Ser Gly Asp Thr Asn Tyr Ala Gln Lys Phe Gln
1               5                   10                  15

Gly
```

<210> SEQ ID NO 90
<211> LENGTH: 9
<212> TYPE: PRT
<213> ORGANISM: Artificial Sequence
<220> FEATURE:
<223> OTHER INFORMATION: Synthetic Construct

<400> SEQUENCE: 90

```
Asn Ser Gly Ser Tyr Ser Phe Gly Tyr
1               5
```

<210> SEQ ID NO 91
<211> LENGTH: 11
<212> TYPE: PRT
<213> ORGANISM: Artificial Sequence
<220> FEATURE:
<223> OTHER INFORMATION: Synthetic Construct

<400> SEQUENCE: 91

```
Arg Ala Ser Gln Gly Ile Ser Ser Trp Leu Ala
1               5                   10
```

<210> SEQ ID NO 92
<211> LENGTH: 7
<212> TYPE: PRT

```
<213> ORGANISM: Artificial Sequence
<220> FEATURE:
<223> OTHER INFORMATION: Synthetic Construct

<400> SEQUENCE: 92

Gly Ala Ser Ser Leu Gln Ser
1               5
```

ANTI-DECTIN-1 ANTIBODIES AND METHODS OF USE THEREOF

CROSS-REFERENCE TO RELATED APPLICATIONS

This application claims priority to U.S. Provisional Application Ser. No. 63/088,895, filed Oct. 7, 2020, and 63/174,439, filed Apr. 13, 2021, the disclosures of each of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name 186542000400SEQLIST.TXT, date recorded: Oct. 6, 2021, size: 108,547 bytes).

FIELD

The present disclosure relates to antibodies that bind human Dectin-1, multispecific (e.g., bispecific) binding molecules, and methods of use and production related thereto.

BACKGROUND

Phagocytosis is a major mechanism used to remove pathogens and cell debris. Professional phagocytes, such as monocytes, macrophages, dendritic cells, and granulocytes, specifically recognize and engulf host or foreign agents that are aberrant or cause disease. The engulfed material is destroyed through the endo-lysosomal pathway in the phagocytes. Moreover, dendritic cells and macrophages can present antigens to the cells of the adaptive immune system to further promote the elimination of the disease-causing agents.

Dectin-1 is a C-type lectin receptor that recognizes beta-glucans and promotes anti-fungal phagocytic activities. It is expressed on phagocytes and has been clearly shown to be sufficient for activating phagocytosis. Dectin-1 can be exploited for antibody-targeted phagocytosis and elimination of disease-causing agents.

It would be beneficial to develop targeted removal and degradation of accumulated disease-causing agents without boosting overall phagocytosis. This disclosure provides a solution for the problems and describes other advantages.

All references cited herein, including patent applications, patent publications, and scientific literature, are herein incorporated by reference in their entirety, as if each individual reference were specifically and individually indicated to be incorporated by reference.

BRIEF SUMMARY

The present disclosure relates to antibodies that bind human Dectin-1, multispecific (e.g., bispecific) binding molecules, and methods of use and production related thereto. Described herein are methods of targeted phagocytosis to remove disease-causing agents, including host cells/host cell products, microbes or their products, etc., upon administration of multispecific (e.g., bispecific) binding molecules comprising a Dectin-1 binding arm and a second arm that specifically binds to the agent. The multispecific (e.g., bispecific) binding molecules allow the phagocyte to engage the target agent and form a synapse between it and promote clustering of Dectin-1 on the phagocyte. This stimulates phagocytosis of the target agent and at the same time cytokine secretion via the Dectin-1/Syk/NfkB pathway by the phagocyte. Moreover, antigens from the engulfed material are presented on the surface of dendritic cells/macrophages to boost an adaptive immune response against the disease-causing agent. Overall, it is thought that the Dectin-1 agonistic, multispecific (e.g., bispecific) binding molecules promote immune stimulation, targeted phagocytosis, and neo-antigen presentation/activation of the adaptive immune system to eliminate the disease-causing agent.

As such, the present disclosure describes, inter alia, the generation and functional characterization of an agonistic anti-human Dectin-1 antibody that exhibits high affinity binding to Dectin-1 and can promote immune stimulation. Further described is the generation of bispecific antibody formats including the anti-human Dectin-1 antibody with antibodies targeting antigens on disease-causing agents, with data supporting target engagement, immune stimulation, phagocytosis, and antigen presentation.

In some embodiments, provided herein is an antibody or antigen-binding fragment thereof that binds to human Dectin-1, wherein the antibody or fragment comprises a heavy chain variable (VH) domain and a light chain variable (VL) domain, wherein the VH domain comprises a CDR-H1 comprising the sequence GYTFTDYY (SEQ ID NO:1), a CDR-H2 comprising the sequence INPNSGDT (SEQ ID NO:2), and a CDR-H3 comprising the sequence ARNSGSYSFGY (SEQ ID NO:3), and wherein the VL domain comprises a CDR-L1 comprising the sequence QGISSW (SEQ ID NO:4), a CDR-L2 comprising the sequence GAS (SEQ ID NO:5), and a CDR-L3 comprising the sequence QQAYSFPFT (SEQ ID NO:6). In some embodiments, provided herein is an antibody or antigen-binding fragment thereof that binds to human Dectin-1, wherein the antibody or fragment comprises a heavy chain variable (VH) domain and a light chain variable (VL) domain, wherein the VH domain comprises a CDR-H1, CDR-H2, and CDR-H3 from the VH domain sequence QVQLVQSGAEVKKPGASVKVSCKSSGYTFTDYYIHWVRQAPGQGLEWMGWINPNSGD TNYAQKFQGRITMTRDTSISTAYLELSRLRSDDTAVFYCARNSGSYSFGYWGQGTLVTV SS (SEQ ID NO:7), and wherein the VL domain comprises a CDR-L1, CDR-L2, and CDR-L3 from the VL domain sequence DIQMTQSPSSVSASVGDRVTITCRASQGISSWLAWYQQKPGKAPKLLIF-GASSLQSGVPS RFSGSGSGTDFTLTVSSLQPEDFATYYCQQAYSFPFTFGPGTKVDIE (SEQ ID NO:8). In some embodiments, provided herein is an antibody or antigen-binding fragment thereof that binds to human Dectin-1, wherein the antibody or fragment comprises a heavy chain variable (VH) domain and a light chain variable (VL) domain, wherein the VH domain comprises a CDR-H1 comprising the sequence DYYI (SEQ ID NO:88), a CDR-H2 comprising the sequence WINPNSGDTNYAQKFQG (SEQ ID NO:89), and a CDR-H3 comprising the sequence NSGSYSFGY (SEQ ID NO:90), and wherein the VL domain comprises a CDR-L1 comprising the sequence RASQGISSWLA (SEQ ID NO:91), a CDR-L2 comprising the sequence GASSLQS (SEQ ID NO:92), and a CDR-L3 comprising the sequence QQAYSFPFT (SEQ ID NO:6). In some embodiments, the VH domain comprises a sequence with at least 90%, at least 91%, at least 92%, at least 93%, at least 94%, at least 95%, at least 96%, at least 97%, at least 98%, or at least 99% identity to the amino acid sequence QVQLVQSGAEVKKPGASVKVSCK-SSGYTFTDYYIHWVRQAPGQGLEWMGWINPNSGD TNYAQKFQGRITMTRDTSIS- TAYLELSRLRSDDTAVFYCARNSGSYSFGYWGQGTLVTV SS (SEQ ID NO:7); and/or the VL domain comprises a sequence with at least 90%, at least 91%, at least 92%, at least 93%, at least 94%, at least 95%, at least 96%, at least 97%, at least 98%, or at least 99% identity to the amino acid sequence DIQMTQSPSSVSASVGDRVTITCRASQGISS-WLAWYQQKPGKAPKLLIFGASSLQSGVPS RFSGSGSGTDFTLTVSSLQPEDFATYYCQQAY-SFPFTFGPGTKVDIE (SEQ ID NO:8). In some embodiments, the VH domain comprises the sequence QVQLVQS-GAEVKKPGASVKVSCKSSGYTFTDYYIHWVRQAPG QGLEWMGWINPNSGD TNYAQKFQGRITMTRDTSIS-TAYLELSRLRSDDTAVFYCARNSGSYS-FGYWGQGTLVTV SS (SEQ ID NO:7); and/or the VL domain comprises the sequence DIQMTQSPSSVSASVGDRVTITCRASQGISS-WLAWYQQKPGKAPKLLIFGASSLQSGVPS RFSGSGSGTDFTLTVSSLQPEDFATYYCQQAY-SFPFTFGPGTKVDIE (SEQ ID NO:8). In some embodiments, provided herein is an antibody or antigen-binding fragment thereof that binds to human Dectin-1, wherein the antibody or fragment binds to human Dectin-1 expressed on the surface of a cell with an EC50 of less than 2 nM, less than 1 nM, or less than 0.5 nM. In some embodiments, provided herein is an antibody or antigen-binding fragment thereof that binds to human Dectin-1, wherein the antibody or fragment is capable of binding human or cynomolgus Dectin-1. In some embodiments, provided herein is an antibody or antigen-binding fragment thereof that binds to human Dectin-1, wherein the antibody or fragment does not compete (e.g., for binding to human Dectin-1) with a native ligand of Dectin-1, e.g., human Dectin-1. In some embodiments, the antibody or fragment competes for binding to human Dectin-1 with a reference antibody that comprises: (a) a heavy chain variable (VH) domain comprising a CDR-H1 comprising the sequence GYTFTDYY (SEQ ID NO:1), a CDR-H2 comprising the sequence INPNSGDT (SEQ ID NO:2), and a CDR-H3 comprising the sequence ARNSGSYSFGY (SEQ ID NO:3), and a light chain variable (VL) domain comprising a CDR-L1 comprising the sequence QGISSW (SEQ ID NO:4), a CDR-L2 comprising the sequence GAS (SEQ ID NO:5), and a CDR-L3 comprising the sequence QQAYSFPFT (SEQ ID NO:6); (b) a heavy chain variable (VH) domain comprising a CDR-H1 comprising the sequence DYYI (SEQ ID NO:88), a CDR-H2 comprising the sequence WINPNSGDTNYAQKFQG (SEQ ID NO:89), and a CDR-H3 comprising the sequence NSGSYSFGY (SEQ ID NO:90), and a light chain variable (VL) domain comprising a CDR-L1 comprising the sequence RASQGISSWLA (SEQ ID NO:91), a CDR-L2 comprising the sequence GASSLQS (SEQ ID NO:92), and a CDR-L3 comprising the sequence QQAYSFPFT (SEQ ID NO:6); or (c) a heavy chain variable (VH) domain comprising the sequence QVQLVQSGAEVKKPGASVKVSCK-SSGYTFTDYYIHWVRQAPGQGLEWMGWINPNSGD TNYAQKFQGRITMTRDTSISTAYLELSRLRSDD-TAVFYCARNSGSYSFGYWGQGTLVTV SS (SEQ ID NO:7) and a light chain variable (VL) domain comprising the sequence DIQMTQSPSSVSASVGDRVTITCRASQ-GISSWLAWYQQKPGKAPKLLIFGASSLQSGVPS RFSGSGSGTDFTLTVSSLQPEDFATYYCQQAY-SFPFTFGPGTKVDIE (SEQ ID NO:8). In some embodiments, the antibody or fragment is a human, humanized, or chimeric antibody or fragment. In some embodiments, the antibody or fragment binds to human Dectin-1 expressed on the surface of a macrophage, monocyte, dendritic cell, and/or granulocyte. In some embodiments, the antigen-binding antibody fragment is a Fab, Fab', F(ab')2, Fv, Fab'-SH, F(ab')2, single chain antibody, NANOBODY® single domain antibody, or scFv fragment. In some embodiments, the antibody further comprises an Fc region. In some embodiments, the antibody or fragment is a multispecific antibody or fragment. In some embodiments, the antibody or fragment is a bispecific antibody, fragment, or diabody comprising a first antigen binding domain comprising the VH and VL domains that bind to human Dectin-1 and a second antigen binding domain that binds to a target of interest or comprising a first antigen binding domain that binds to a target of interest and a second antigen binding domain comprising the VH and VL domains that bind to human Dectin-1. In some embodiments, the bispecific antibody comprises a first antibody arm comprising a single chain variable fragment (scFv) comprising the VH and VL domains that bind to human Dectin-1 and a first Fc region, and a second antibody arm comprising an antibody heavy chain that comprises the VH domain of the second antigen binding domain in association with an antibody light chain that comprises the VL domain of the second antigen binding domain and a second Fc region connected to the VH domain of the second antigen binding domain. In some embodiments, the second antigen-binding domain binds to CD20 and comprises a VH domain comprising the sequence of SEQ ID NO:24 and a VL domain comprising the sequence of SEQ ID NO:25. In some embodiments, the second antigen-binding domain binds to Trop-2 and comprises a VH domain comprising the sequence of SEQ ID NO:42 and a VL domain comprising the sequence of SEQ ID NO:43. In some embodiments, the second antigen-binding domain binds to light chain amyloid and comprises a VH domain comprising the sequence of SEQ ID NO:44 and a VL domain comprising the sequence of SEQ ID NO:45. In some embodiments, the first Fc region comprises one or more knob-forming mutations, and the second Fc region comprises one or more cognate hole-forming mutations, or wherein the second Fc region comprises one or more knob-forming mutations, and the first Fc region comprises one or more cognate hole-forming mutations. In some embodiments, the first Fc region comprises a T366W substitution, and the second Fc region comprises T366S, L368A, and Y407V substitutions, according to EU numbering. In some embodiments, the first antibody arm comprises a first linker between the VH and VL domains, and a second linker between the VL domain and the first Fc region. In some embodiments, the first linker comprises one or more repeats of the sequence GGGGS (SEQ ID NO:26). In some embodiments, the first linker comprises the sequence GGGGSGGGGSGGGGS (SEQ ID NO:27) or GGGGSGGGGSGGGGSGGGGS (SEQ ID NO:28). In some embodiments, the second linker comprises the sequence EPKRSDKTHTCPPC (SEQ ID NO:29) or SATHTCPPC (SEQ ID NO:30). In some embodiments, the bispecific antibody comprises a first IgG antibody comprising the first antigen binding domain covalently linked to a second IgG antibody comprising the second antigen binding domain. In some embodiments, the bispecific antibody comprises a first antibody arm comprising a first antibody heavy chain that comprises the VH domain of the first antigen binding domain and a first Fc region and a second antibody arm comprising a second antibody heavy chain that comprises the VH domain of the second antigen binding domain and a second Fc region, wherein the first Fc region comprises one or more knob-forming mutations, and the second Fc region comprises one or more cognate hole-forming mutations. In some embodiments, the first Fc region comprises a T366W substitution, and the second Fc region comprises T366S, L368A, and Y407V substitutions, according to EU numbering. In some embodiments, the bispecific antibody comprises a first antibody arm comprising a first antibody heavy chain that comprises the VH domain of the first antigen binding domain and a first Fc region and a second antibody arm comprising a second antibody heavy chain that comprises the VH domain of the second antigen binding domain and a second Fc region, wherein the first Fc region comprises one or more hole-forming mutations, and the second Fc region comprises one or more cognate knob-forming mutations. In some embodiments, the first Fc region comprises T366S, L368A, and Y407V substitutions, and the second Fc region comprises a T366W substitution, according to EU numbering. In some embodiments, the bispecific antibody comprises a first IgG antibody comprising the first antigen binding domain coupled to biotin or an avidin-binding derivative thereof, and a second IgG antibody comprising the second antigen binding domain coupled to avidin, streptavidin, neutravidin, or a biotin-binding derivative thereof, wherein the biotin or avidin-binding derivative thereof is bound to the avidin, streptavidin, neutravidin, or biotin-binding derivative thereof. In some embodiments, the bispecific antibody comprises a first IgG antibody comprising the first antigen binding domain coupled to avidin, streptavidin, neutravidin, or a biotin-binding derivative thereof, and a second IgG antibody comprising the second antigen binding domain coupled to biotin or an avidin-binding derivative thereof, wherein the biotin or avidin-binding derivative thereof is bound to the avidin, streptavidin, neutravidin, or biotin-binding derivative thereof. In some embodiments, the target of interest is a disease-causing agent. In some embodiments, the disease-causing agent is a bacterial cell, fungal cell, virus, senescent cell, tumor cell, protein aggregate (e.g., amyloid beta, or lambda or kappa light chain amyloids), LDL particle, mast cell, eosinophil, ILC2 cell, or inflammatory immune cell. In some embodiments, the target of interest is an antigen expressed on the surface of the bacterial cell, fungal cell, senescent cell, tumor cell, mast cell, eosinophil, ILC2 cell, or inflammatory immune cell. In some embodiments, the target of interest is a surface antigen of the virus. In some embodiments, the target of interest is an antigen expressed on the surface of a cancer cell. In some embodiments, the target of interest is CD70, HER2, DLL3, NECTIN-4, TROP-2, Mesothelin, LIV-1, C-MET, FOLR1, CD20, CCR8, CD33, or EGFR. In some embodiments, the target of interest is CD20; the second antigen-binding domain comprises a heavy chain variable (VH) domain and a light chain variable (VL) domain; and the VH domain of the second antigen-binding domain comprises the sequence QVQLQQPGAELVKPGASVKMSCKASGYTFTSYNMHWVKQTPGRGLEWIGAIYPGNGD TSYNQKFKGKATLTADKSSSTAYMQLSSLTSEDSAVYYCARSTYYGGDWYF NVWGAG TTVTVSA (SEQ ID NO:24) and/or the VL domain of the second antigen-binding domain comprises the sequence QIVLSQSPAILSASPGEKVTMTCRASSSVSYIHWFQQKPGSSPKPWIYATSNLASGVPVRF SGSGSGTSYSLTISRVEAEDAATYYCQQWTSNPPTFGGGTKLEIK (SEQ ID NO:25). In some embodiments, the antibody comprises two antibody heavy chains, and wherein each of the antibody heavy chains comprises an amino acid substitution at one or more of positions 234, 235, and 237, according to EU numbering. In some embodiments, each of the antibody heavy chains comprises L234A, L235E, and G237A substitutions, according to EU numbering. In some embodiments, the antibody comprises two antibody heavy chains, and wherein only one of the antibody heavy chains comprises H435R and Y436F substitutions, according to EU numbering. In some embodiments, the antibody comprises two arms, and only one of the antibody arms comprises a heavy chain comprising F126C and C220V substitutions and a light chain comprising S121C and C214V substitutions, according to EU numbering. In some embodiments, the bispecific antibody comprises a first and a second antibody heavy chain, wherein the VH domain of the first antibody heavy chain forms an antigen binding domain with the VL domain of the first antibody light chain, wherein the VH domain of the second antibody heavy chain forms an antigen binding domain with the VL domain of the second antibody light chain, wherein the first antibody heavy chain comprises F126C, C220V, and T366W substitutions, wherein the first antibody light chain comprises S121C and C214V substitutions, and wherein the second antibody heavy chain comprises T366S, L368A, Y407V, H435R, and Y436F substitutions, according to EU numbering. In some embodiments, the first and second antibody heavy chains further comprise L234A, L235E, and G237A substitutions, according to EU numbering. In some embodiments, the first and second antibody heavy chains comprise human IgG1 Fc domains. In some embodiments, the antibody comprises a first and a second antibody heavy chain, wherein at least one or two of the first and second antibody heavy chains is/are non-fucosylated. In some embodiments, the antibody may be produced in a cell line having an alpha1,6-fucosyltransferase (Fut8) or alpha-1,3-mannosyl-glycoprotein 2-beta-N-acetylglucosaminyltranferase (MGAT1) knockout. In some embodiments, the antibody may be produced in a cell line overexpressing β1,4-N-acetylglucosaminyltransferase III (GnT-III). In further embodiments, the cell line additionally overexpresses Golgi μ-mannosidase II (ManII). In some embodiments, the antibody may be produced in a cell line treated with an inhibitor of mannosidase I, e.g., kifunensine.

In some embodiments, provided herein is a multispecific binding molecule, comprising: (a) a first antibody or antigen-binding fragment thereof comprising a first antigen-binding domain, wherein the first antigen-binding domain binds to human Dectin-1; and (b) a second antibody or antigen-binding fragment thereof comprising a second antigen-binding domain, wherein the second antigen binding domain binds to a target of interest. In some embodiments, the target of interest is a disease-causing agent. In some embodiments, the disease-causing agent is a bacterial cell, fungal cell, virus, senescent cell, tumor cell, protein aggregate (e.g., amyloid beta, or lambda or kappa light chain amyloids), LDL particle, mast cell, eosinophil, ILC2 cell, or inflammatory immune cell. In some embodiments, the target of interest is an antigen expressed on the surface of the bacterial cell, fungal cell, senescent cell, tumor cell, mast cell, eosinophil, ILC2 cell, or inflammatory immune cell. In some embodiments, the target of interest is a surface antigen of the virus. In some embodiments, the target of interest is CD70, HER2, DLL3, NECTIN-4, TROP-2, Mesothelin, LIV-1, C-MET, FOLR1, CD20, CCR8, CD33, or EGFR. In some embodiments, the first antigen-binding domain comprises a heavy chain variable (VH) domain and a light chain variable (VL) domain, wherein the VH domain comprises a CDR-H1 comprising the sequence GYTFTDYY (SEQ ID NO:1), a CDR-H2 comprising the sequence INPNSGDT (SEQ ID NO:2), and a CDR-H3 comprising the sequence ARNSGSYSFGY (SEQ ID NO:3), and wherein the VL domain comprises a CDR-L1 comprising the sequence QGISSW (SEQ ID NO:4), a CDR-L2 comprising the sequence GAS (SEQ ID NO:5), and a CDR-L3 comprising the sequence QQAYSFPFT (SEQ ID NO:6). In some embodiments, the first antigen-binding domain comprises a heavy chain variable (VH) domain and a light chain variable (VL) domain, wherein the VH domain comprises a CDR-H1, CDR-H2, and CDR-H3 from the VH domain sequence QVQLVQSGAEVKKPGASVKVSCK-SSGYTFTDYYIHWVRQAPGQGLEWMGWINPNSGD TNYAQKFQGRITMTRDTSISTAYLELSRLRSDD-TAVFYCARNSGSYSFGYWGQGTLVTV SS (SEQ ID NO:7), and wherein the VL domain comprises a CDR-L1, CDR-L2, and CDR-L3 from the VL domain sequence DIQMTQSPSSVSASVGDRVTITCRASQGISS-WLAWYQQKPGKAPKLLIFGASSLQSGVPS RFSGSGSGTDFTLTVSSLQPEDFATYYCQQAY-SFPFTFGPGTKVDIE (SEQ ID NO:8). In some embodiments, the VH domain comprises a sequence with at least 90%, at least 91%, at least 92%, at least 93%, at least 94%, at least 95%, at least 96%, at least 97%, at least 98%, or at least 99% identity to the amino acid sequence QVQLVQS-GAEVKKPGASVKVSCK-SSGYTFTDYYIHWVRQAPGQGLEWMGWINPNSGD TNYAQKFQGRITMTRDTSISTAYLELSRLRSDD-TAVFYCARNSGSYSFGYWGQGTLVTV SS (SEQ ID NO:7); and/or the VL domain comprises a sequence with at least 90%, at least 91%, at least 92%, at least 93%, at least 94%, at least 95%, at least 96%, at least 97%, at least 98%, or at least 99% identity to the amino acid sequence DIQMTQSPSSVSASVGDRVTITCRASQGISS-WLAWYQQKPGKAPKLLIFGASSLQSGVPS RFSGSGSGTDFTLTVSSLQPEDFATYYCQQAY-SFPFTFGPGTKVDIE (SEQ ID NO:8). In some embodiments, the VH domain comprises the sequence QVQLVQS-GAEVKKPGASVKVSCKSSGYTFTDYYIHWVRQAP GQGLEWMGWINPNSGD TNYAQKFQGRITMTRDT-SISTAYLELSRLRSDDTAVFYCARNSGSYS-FGYWGQGTLVTV SS (SEQ ID NO:7); and/or wherein the VL domain comprises the sequence DIQMTQSPSSVSASVGDRVTITCRASQGISS-WLAWYQQKPGKAPKLLIFGASSLQSGVPS RFSGSGSGTDFTLTVSSLQPEDFATYYCQQAY-SFPFTFGPGTKVDIE (SEQ ID NO:8). In some embodiments, the first antigen-binding domain: binds to human Dectin-1 expressed on the surface of a macrophage, monocyte, dendritic cell, or granulocyte; binds to human Dectin-1 expressed on the surface of a cell with an EC50 of less than 2 nM; is capable of binding human or cynomolgus Dectin-1; and/or does not compete with a native ligand of human Dectin-1. In some embodiments, the second antigen-binding domain binds to CD20 and comprises a VH domain comprising the sequence of SEQ ID NO:24 and a VL domain comprising the sequence of SEQ ID NO:25. In some embodiments, the second antigen-binding domain binds to Trop-2 and comprises a VH domain comprising the sequence of SEQ ID NO:42 and a VL domain comprising the sequence of SEQ ID NO:43. In some embodiments, the second antigen-binding domain binds to light chain amyloid and comprises a VH domain comprising the sequence of SEQ ID NO:44 and a VL domain comprising the sequence of SEQ ID NO:45. In some embodiments, one or both of the first and second antibodies or fragments are human or humanized antibodies or fragments. In some embodiments, one or both of the first and second antibodies or fragments are Fab, Fab', F(ab')2, Fv, Fab'-SH, F(ab')2, single chain antibodies, NANOBODY® single domain antibodies, or scFv fragments. In some embodiments, one or both of the first and second antibodies or fragments further comprise an Fc domain. In some embodiments, the first antibody or fragment is a Fab fragment, and wherein the second antibody or fragment is a full-length antibody, e.g., that comprises an antibody heavy chain and an antibody light chain. In some embodiments, the first and the second antibodies or fragments are both full-length antibodies, e.g., that each comprise an antibody heavy chain and an antibody light chain. In some embodiments, the multispecific binding molecule comprises a first antibody arm comprising a single chain variable fragment (scFv) comprising the VH and VL domains that bind to human Dectin-1 and a first Fc region, and a second antibody arm comprising an antibody heavy chain that comprises the VH domain of the second antigen binding domain in association with an antibody light chain that comprises the VL domain of the second antigen binding domain and a second Fc region connected to the VH domain of the second antigen binding domain. In some embodiments, the first Fc region comprises one or more knob-forming mutations, and the second Fc region comprises one or more cognate hole-forming mutations, or wherein the second Fc region comprises one or more knob-forming mutations, and the first Fc region comprises one or more cognate hole-forming mutations. In some embodiments, the first Fc region comprises a T366W substitution, and the second Fc region comprises T366S, L368A, and Y407V substitutions, according to EU numbering. In some embodiments, the first antibody arm comprises a first linker between the VH and VL domains, and a second linker between the VL domain and the first Fc region. In some embodiments, the first linker comprises one or more repeats of the sequence GGGGS (SEQ ID NO:26). In some embodiments, the first linker comprises the sequence GGGGSGGGGSGGGGS (SEQ ID NO:27) or GGGGSGGGGSGGGGSGGGGS (SEQ ID NO:28). In some embodiments, the second linker comprises the sequence EPKRSDKTHTCPPC (SEQ ID NO:29) or SATH-TCPPC (SEQ ID NO:30). In some embodiments, the first antibody or fragment is coupled to avidin, streptavidin, neutravidin, or a biotin-binding derivative thereof, and the second antibody or fragment is coupled to biotin or an avidin-binding derivative thereof; or wherein the second antibody or fragment is coupled to avidin, streptavidin, neutravidin, or a biotin-binding derivative thereof, and the first antibody or fragment is coupled to biotin or an avidin-binding derivative thereof; and wherein the first antibody or fragment is bound to the second antibody or fragment via an interaction between the avidin, streptavidin, neutravidin, or biotin-binding derivative thereof and the biotin or avidin-binding derivative thereof. In some embodiments, the first antibody or fragment is a Fab fragment coupled to monomeric streptavidin (mSA), and wherein the second antibody or fragment is a biotinylated antibody that comprises an antibody heavy chain and an antibody light chain. In some embodiments, the first antibody or fragment is a full-length antibody coupled to monomeric streptavidin (mSA), and wherein the second antibody or fragment is a biotinylated full-length antibody. In some embodiments, the multispecific binding molecule comprises a first IgG antibody comprising the first antigen binding domain covalently linked to a second IgG antibody comprising the second antigen binding domain. In some embodiments, the multispecific binding molecule comprises a first antibody arm comprising a first antibody heavy chain that comprises the VH domain of the first antigen binding domain and a first Fc region and a first antibody light chain comprising the VL domain of the first antigen binding domain, and a second antibody arm comprising a second antibody heavy chain that comprises the VH domain of the second antigen binding domain and a second Fc region and a second antibody light chain comprising the VL domain of the second antigen binding domain, wherein the first Fc region comprises one or more knob-forming mutations, and the second Fc region comprises one or more cognate hole-forming mutations. In some embodiments, the first Fc region comprises a T366W substitution, and wherein the second Fc region comprises T366S, L368A, and Y407V substitutions, according to EU numbering. In some embodiments, the multispecific binding molecule comprises a first antibody arm comprising the VH domain of the first antigen binding domain and a first Fc region and a second antibody arm comprising the VH domain of the second antigen binding domain and a second Fc region, wherein the first Fc region comprises one or more hole-forming mutations, and the second Fc region comprises one or more cognate knob-forming mutations. In some embodiments, the first Fc region comprises T366S, L368A, and Y407V substitutions, and wherein the second Fc region comprises a T366W substitution, according to EU numbering. In some embodiments, the multispecific binding molecule comprises two antibody Fc regions, and wherein each of the antibody heavy chains comprises an amino acid substitution at one or more of positions 234, 235, and 237, according to EU numbering. In some embodiments, each of the antibody Fc regions comprises L234A, L235E, and G237A substitutions, according to EU numbering. In some embodiments, the multispecific binding molecule comprises two antibody heavy chains, and wherein only one of the antibody heavy chains comprises H435R and Y436F substitutions, according to EU numbering. In some embodiments, only one of the antibody arms comprises a heavy chain comprising F126C and C220V substitutions and a light chain comprising S121C and C214V substitutions, according to EU numbering. In some embodiments, the multispecific binding molecule comprises a first antibody heavy chain and a first antibody light chain and a second antibody heavy chain and a second antibody light chain, wherein the VH domain of the first antibody heavy chain forms a first antigen binding domain with the VL domain of the first antibody light chain, wherein the VH domain of the second antibody heavy chain forms a second antigen binding domain with the VL domain of the second antibody light chain, wherein the first antibody heavy chain comprises F126C, C220V, and T366W substitutions, wherein the first antibody light chain comprises S121C and C214V substitutions, and wherein the second antibody heavy chain comprises T366S, L368A, Y407V, H435R, and Y436F substitutions, according to EU numbering. In some embodiments, the first and second antibody heavy chains further comprise L234A, L235E, and G237A substitutions, according to EU numbering. In some embodiments, the first and second antibody heavy chains comprise human IgG1 Fc domains. In some embodiments, at least one or two of the heavy chains of the antibody is non-fucosylated. In some embodiments, the antibody may be produced in a cell line having an alpha1,6-fucosyltransferase (Fut8) or alpha-1,3-mannosyl-glycoprotein 2-beta-N-acetylglucosaminyltranferase (MGAT1) knockout. In some embodiments, the antibody may be produced in a cell line overexpressing β1,4-N-acetylglucosaminyltransferase III (GnT-III). In further embodiments, the cell line additionally overexpresses Golgi μ-mannosidase II (ManII). In some embodiments, the antibody may be produced in a cell line treated with an inhibitor of mannosidase I, e.g., kifunensine.

In some embodiments, provided herein is a multispecific binding molecule, comprising: (a) a first antibody or antigen-binding fragment thereof comprising a first antigen-binding domain, wherein the first antigen-binding domain binds to a first target of interest; and (b) a second antibody or antigen-binding fragment thereof comprising a second antigen-binding domain, wherein the second antigen binding domain binds to a second target of interest; wherein: (i) the first antibody or fragment is coupled to avidin, streptavidin, neutravidin, or a biotin-binding derivative thereof, and the second antibody or fragment is coupled to biotin or an avidin-binding derivative thereof; or (ii) the second antibody or fragment is coupled to avidin, streptavidin, neutravidin, or a biotin-binding derivative thereof, and the first antibody or fragment is coupled to biotin or an avidin-binding derivative thereof; and wherein the first antibody or fragment is bound to the second antibody or fragment via an interaction between the avidin, streptavidin, neutravidin, or biotin-binding derivative thereof and the biotin or avidin-binding derivative thereof. In some embodiments, the first target of interest is human Dectin-1. In some embodiments, the first antigen-binding domain comprises a heavy chain variable (VH) domain and a light chain variable (VL) domain, wherein the VH domain comprises a CDR-H1 comprising the sequence GYTFTDYY (SEQ ID NO:1), a CDR-H2 comprising the sequence INPNSGDT (SEQ ID NO:2), and a CDR-H3 comprising the sequence ARNSGSYSFGY (SEQ ID NO:3), and wherein the VL domain comprises a CDR-L1 comprising the sequence QGISSW (SEQ ID NO:4), a CDR-L2 comprising the sequence GAS (SEQ ID NO:5), and a CDR-L3 comprising the sequence QQAYSFPFT (SEQ ID NO:6). In some embodiments, the first antigen-binding domain comprises a heavy chain variable (VH) domain and a light chain variable (VL) domain, wherein the VH domain comprises a CDR-H1, CDR-H2, and CDR-H3 from the VH domain sequence QVQLVQSGAEVKKPGASVKVSCK-SSGYTFTDYYIHWVRQAPGQGLEWMGWINPNSGD TNYAQKFQGRITMTRDTSISTAYLELSRLRSDD-TAVFYCARNSGSYSFGYWGQGTLVTV SS (SEQ ID NO:7), and wherein the VL domain comprises a CDR-L1, CDR-L2, and CDR-L3 from the VL domain sequence DIQMTQSPSSVSASVGDRVTITCRASQGISS-WLAWYQQKPGKAPKLLIFGASSLQSGVPS RFSGSGSGTDFTLTVSSLQPEDFATYYCQQAY-SFPFTFGPGTKVDIE (SEQ ID NO:8). In some embodiments, the first antigen-binding domain comprises a heavy chain variable (VH) domain and a light chain variable (VL) domain, wherein the VH domain comprises a CDR-H1 comprising the sequence DYYI (SEQ ID NO:88), a CDR-H2 comprising the sequence WINPNSGDTNYAQKFQG (SEQ ID NO:89), and a CDR-H3 comprising the sequence NSGSYSFGY (SEQ ID NO:90), and wherein the VL domain comprises a CDR-L1 comprising the sequence RASQGISSWLA (SEQ ID NO:91), a CDR-L2 comprising the sequence GASSLQS (SEQ ID NO:92), and a CDR-L3 comprising the sequence QQAYSFPFT (SEQ ID NO:6). In some embodiments, the VH domain comprises a sequence with at least 90%, at least 91%, at least 92%, at least 93%, at least 94%, at least 95%, at least 96%, at least 97%, at least 98%, or at least 99% identity to the amino acid sequence QVQLVQSGAEVKKPGASVKVSCK-SSGYTFTDYYIHWVRQAPGQGLEWMGWINPNSGD TNYAQKFQGRITMTRDTSISTAYLELSRLRSDD-TAVFYCARNSGSYSFGYWGQGTLVTV SS (SEQ ID NO:7); and/or the VL domain comprises a sequence with at least 90%, at least 91%, at least 92%, at least 93%, at least 94%, at least 95%, at least 96%, at least 97%, at least 98%, or at least 99% identity to the amino acid sequence DIQMTQSPSSVSASVGDRVTITCRASQGISS-WLAWYQQKPGKAPKLLIFGASSLQSGVPS RFSGSGSGTDFTLTVSSLQPEDFATYYCQQAY-SFPFTFGPGTKVDIE (SEQ ID NO:8). In some embodiments, the VH domain comprises the sequence QVQLVQS-GAEVKKPGASVKVSCKSSGYTFTDYYIHWVRQAP GQGLEWMGWINPNSGD TNYAQKFQGRITMTRDT-SISTAYLELSRLRSDDTAVFYCARNSGSYS-FGYWGQGTLVTV SS (SEQ ID NO:7); and/or wherein the VL domain comprises the sequence DIQMTQSPSSVSASVGDRVTITCRASQGISS-WLAWYQQKPGKAPKLLIFGASSLQSGVPS RFSGSGSGTDFTLTVSSLQPEDFATYYCQQAY-SFPFTFGPGTKVDIE (SEQ ID NO:8). In some embodiments, provided herein is a multispecific binding molecule, comprising a first polypeptide chain comprising the sequence QVQLVQSGAEVKKPGASVKVSCK-SSGYTFTDYYIHWVRQAPGQGLEWMGWINPNSGD TNYAQKFQGRITMTRDTSISTAYLELSRLRSDD-TAVFYCARNSGSYSFGYWGQGTLVTV SSGGGGSGGGGSGGGGSGGGGSDIQMTQSPSSVSA SVGDRVTITCRASQGISSWLAWYQ QKPGKAPKLLIF-GASSLQSGVPSRFSGSGSGTDFTLTVSSLQPEDFA-TYYCQQAYSFPFTF GPGTKVDIEEPKRSDKTH-TCPPCPAPELLGGPSVFLFPPKPKDTLMISRTPEVTC VVVDVS HEDPEVKFNWYVDGVEVHNAKTKPRE-EQYNSTYRVVSVLTVLHQDWLNGKEYKCKVS NKA-LPAPIEKTISKAKGQPREPQVYTLPPSREEMT-KNQVSLWCLVKGFYPSDIAVEWESN GQPENNYKTTPPVLDSDGSFFLYSK-LTVDKSRWQQGNVFSCSVMHEALHNHYTQKSLS LSPG (SEQ ID NO:31), a second polypeptide chain comprising the sequence QVQLQQPGAELVKP-GASVKMSCKASGYTFTSYNMHWVKQTPGRGLEWI-GAIYPGNGD TSYNQKFKGKATLTADKSSSTAYMQLSSLTSED-SAVYYCARSTYYGGDWYFNVWGAG TTVTVSAASTKGPSVFPLAPSSKSTSGGTAAL-GCLVKDYFPEPVTVSWNSGALTSGVHTF PAVLQSSG-LYS-LSSVVTVPSSSLGTQTYICNVNHKPSNTKVDKKVEP KSCDKTHTCPPCP APELLGGPSVFLFPPKPKDTLMIS-RTPEVTCVVVDVSHEDPEVKFNWYVDGVEVHNAKT KPREEQYN-STYRVVSVLTVLHQDWLNGKEYKCKVSNKALPA-PIEKTISKAKGQPREPQV YTLPPSREEMTKNQVSLS-CAVKGFYPSDIAVEWESNGQPENNYKTTPPVLDSD GSFFLVS KLTVDKSRWQQGNVFSCSVMHEALHNRFTQKSLSL-SPG (SEQ ID NO:32), and a third polypeptide chain comprising the sequence QIVLSQSPAILSASPGEKVTMT-CRASSSVSYIHWFQQKPGSSPKPWIYATSNLASGVPV RF SGSGSGTSYSLTISRVEAE-DAATYYCQQWTSNPPTFGGGTKLEIKRTVAAPSVFI FPPSDE QLKSGTASVVCLLNNFYPREAKVQWKVD-NALQSGNSQESVTEQDSKDSTYSLSSTLTS KADYEKHKVYACEVTHQGLSSPVTKSFNRGEC (SEQ ID NO:33). In some embodiments, provided herein is a multispecific binding molecule comprising a first arm comprising a first antigen-binding domain and a second arm comprising a second antigen-binding domain; wherein the first antigen-binding domain binds to human Dectin-1 and the second antigen-binding domain binds to a target of interest; and wherein the first arm comprises a polypeptide chain comprising the sequence QVQLVQSGAEVKKP-GASVKVSCKSSGYTFTDYYIHWVRQAPGQ-GLEWMGWINPNSGD TNYAQKFQGRITMTRDTSIS-TAYLELSRLRSDDTAVFYCARNSGSYSFGYWGQGT LVTV SSGGGGSGGGGSGGGGSGGGGSDIQMTQSPSSVSA SVGDRVTITCRASQGISSWLAWYQ QKPGKAPKLLIF-GASSLQSGVPSRFSGSGSGTDFTLTVSSLQPEDFA-TYYCQQAYSFPFTF GPGTKVDIEEPKRSDKTH-TCPPCPAPELLGGPSVFLFPPKPKDTLMISRTPEVTC VVVDVS HEDPEVKFNWYVDGVEVHNAKTKPRE-EQYNSTYRVVSVLTVLHQDWLNGKEYKCKVS NKA-LPAPIEKTISKAKGQPREPQVYTLPPSREEMT-KNQVSLWCLVKGFYPSDIAVEWESN GQPENNYKTTPPVLDSDGSFFLYSK-LTVDKSRWQQGNVFSCSVMHEALHNHYTQKSLS LSPG (SEQ ID NO:31). In some embodiments, the first antigen-binding domain binds to human Dectin-1 expressed on the surface of a macrophage, monocyte, dendritic cell, or granulocyte. In some embodiments, one or both of the first and second antibodies or fragments are human or humanized antibodies or fragments. In some embodiments, one or both of the first and second antibodies or fragments are Fab, Fab', F(ab')2, Fv, Fab'-SH, F(ab')2, single chain antibodies, NANOBODY® single domain antibodies, or scFv fragments. In some embodiments, one or both of the first and second antibodies or fragments further comprise an Fc domain. In some embodiments, the first antibody or fragment is a Fab fragment, and wherein the second antibody comprises an antibody heavy chain and an antibody light chain. In some embodiments, the first antibody or fragment is a Fab fragment coupled to monomeric streptavidin (mSA), and wherein the second antibody is a biotinylated antibody that comprises an antibody heavy chain and an antibody light chain. In some embodiments, the first antibody or fragment is a full-length antibody coupled to monomeric streptavidin (mSA), and wherein the second antibody is a biotinylated antibody that comprises an antibody heavy chain and an antibody light chain. In some embodiments, the second target of interest is a disease-causing agent. In some embodiments, the disease-causing agent is a bacterial cell, fungal cell, virus, senescent cell, tumor cell, protein aggregate (e.g., amyloid beta, or lambda or kappa light chain amyloids), LDL particle, mast cell, eosinophil, ILC2 cell, or inflammatory immune cell. In some embodiments, the target of interest is an antigen expressed on the surface of the bacterial cell, fungal cell, senescent cell, tumor cell, mast cell, eosinophil, ILC2 cell, or inflammatory immune cell. In some embodiments, the target of interest is a surface antigen of the virus. In some embodiments, the target of interest is an antigen expressed on the surface of a cancer cell. In some embodiments, the target of interest is CD70, HER2, DLL3, NECTIN-4, TROP-2, Mesothelin, LIV-1, C-MET, FOLR1, CD20, CCR8, CD33, or EGFR. In some embodiments, the target of interest is CD20; the second antigen-binding domain comprises a heavy chain variable (VH) domain and a light chain variable (VL) domain; and the VH domain of the second antigen-binding domain comprises the sequence QVQLQQPGAEL-VKPGASVKMSCKASGYTFTSYNMHWVKQTPGR-GLEWIGAIYPGNGD TSYNQKFKGKATLTADKSSSTAYMQLSSLTSED-SAVYYCARSTYYGGDWYFNVWGAG TTVTVSA (SEQ ID NO:24) and/or the VL domain of the second antigen-binding domain comprises the sequence QIVLSQ-SPAILSASPGEKVTMT-CRASSSVSYIHWFQQKPGSSPKPWIYATSN-LASGVPVRF SGSGSGTSYSLTISRVEAE-DAATYYCQQWTSNPPTFGGGTKLEIK (SEQ ID NO:25). In some embodiments, the second antigen-binding domain binds to Trop-2 and comprises a VH domain comprising the sequence of SEQ ID NO:42 and a VL domain comprising the sequence of SEQ ID NO:43. In some embodiments, the second antigen-binding domain binds to light chain amyloid and comprises a VH domain comprising the sequence of SEQ ID NO:44 and a VL domain comprising the sequence of SEQ ID NO:45.

In some embodiments, provided herein is a polynucleotide encoding the antibody or multispecific binding molecule of any one of the above embodiments. In some embodiments, provided herein is a vector (e.g., an expression vector) comprising the polynucleotide of any one of the above embodiments. In some embodiments, provided herein is a host cell (e.g., an isolated host cell or cell line) comprising the polynucleotide or vector of any one of the above embodiments. In some embodiments, provided herein is a method of producing an antibody or multispecific binding molecule, comprising culturing the host cell of any one of the above embodiments under conditions suitable for production of the antibody or multispecific binding molecule. In some embodiments, the method further comprises recovering the antibody or multispecific binding molecule. In some embodiments, provided herein is a pharmaceutical composition comprising the antibody or multispecific binding molecule of any one of the above embodiments and a pharmaceutically acceptable carrier.

In some embodiments, provided herein is a method of generating a multispecific binding molecule, comprising: (a) providing a first antibody or antigen-binding fragment thereof comprising a first antigen-binding domain, wherein the first antigen-binding domain binds to a first target of interest; (b) providing a second antibody or antigen-binding fragment thereof comprising a second antigen-binding domain, wherein the second antigen binding domain binds to a second target of interest; wherein: (i) the first antibody or fragment is coupled to avidin, streptavidin, neutravidin, or a biotin-binding derivative thereof, and the second antibody or fragment is coupled to biotin or an avidin-binding derivative thereof; or (ii) the second antibody or fragment is coupled to avidin, streptavidin, neutravidin, or a biotin-binding derivative thereof, and the first antibody or fragment is coupled to biotin or an avidin-binding derivative thereof; and (c) contacting the first antibody or fragment with the second antibody or fragment under conditions suitable for binding between the first antibody or fragment and the second antibody or fragment via an interaction between the avidin, streptavidin, neutravidin, or biotin-binding derivative thereof and the biotin or avidin-binding derivative thereof, thereby generating a multispecific binding molecule. In some embodiments, provided herein is a method of identifying a multispecific binding molecule that binds a first and a second target of interest, comprising: (a) providing a first antibody or antigen-binding fragment thereof comprising a first antigen-binding domain, wherein the first antigen-binding domain binds to a first target of interest; (b) providing a second antibody or antigen-binding fragment thereof comprising a second antigen-binding domain, wherein the second antigen binding domain binds to a second target of interest; wherein: (i) the first antibody or fragment is coupled to avidin, streptavidin, neutravidin, or a biotin-binding derivative thereof, and the second antibody or fragment is coupled to biotin or an avidin-binding derivative thereof; or (ii) the second antibody or fragment is coupled to avidin, streptavidin, neutravidin, or a biotin-binding derivative thereof, and the first antibody or fragment is coupled to biotin or an avidin-binding derivative thereof; (c) contacting the first antibody or fragment with the second antibody or fragment under conditions suitable for binding between the first antibody or fragment and the second antibody or fragment via an interaction between the avidin, streptavidin, neutravidin, or biotin-binding derivative thereof and the biotin or avidin-binding derivative thereof, thereby generating a multispecific binding molecule; and (d) measuring binding between the multispecific binding molecule and at least one of the first and the second target of interest. In some embodiments, the first target of interest is human Dectin-1. In some embodiments, the first antigen-binding domain comprises a heavy chain variable (VH) domain and a light chain variable (VL) domain, wherein the VH domain comprises a CDR-H1 comprising the sequence GYTFTDYY (SEQ ID NO:1), a CDR-H2 comprising the sequence INPNSGDT (SEQ ID NO:2), and a CDR-H3 comprising the sequence ARNSGSYSFGY (SEQ ID NO:3), and wherein the VL domain comprises a CDR-L1 comprising the sequence QGISSW (SEQ ID NO:4), a CDR-L2 comprising the sequence GAS (SEQ ID NO:5), and a CDR-L3 comprising the sequence QQAYSFPFT (SEQ ID NO:6). In some embodiments, the first antigen-binding domain comprises a heavy chain variable (VH) domain and a light chain variable (VL) domain, wherein the VH domain comprises a CDR-H1, CDR-H2, and CDR-H3 from the VH domain sequence TNYAQKFQGRITMTRDTSISTAYLELSRLRSDD-TAVFYCARNSGSYSFGYWGQGTLVTV SS (SEQ ID NO:7), and wherein the VL domain comprises a CDR-L1, CDR-L2, and CDR-L3 from the VL domain sequence DIQMTQSPSSVSASVGDRVTITCRASQGISS-WLAWYQQKPGKAPKLLIFGASSLQSGVPS RFSGSGSGTDFTLTVSSLQPEDFATYYCQQAY-SFPFTFGPGTKVDIE (SEQ ID NO:8). In some embodiments, the first antigen-binding domain comprises a heavy chain variable (VH) domain and a light chain variable (VL) domain, wherein the VH domain comprises a CDR-H1 comprising the sequence DYYI (SEQ ID NO:88), a CDR-H2 comprising the sequence WINPNSGDTNYAQKFQG (SEQ ID NO:89), and a CDR-H3 comprising the sequence NSGSYSFGY (SEQ ID NO:90), and wherein the VL domain comprises a CDR-L1 comprising the sequence RASQGISSWLA (SEQ ID NO:91), a CDR-L2 comprising the sequence GASSLQS (SEQ ID NO:92), and a CDR-L3 comprising the sequence QQAYSFPFT (SEQ ID NO:6). In some embodiments, the VH domain comprises a sequence with at least 90%, at least 91%, at least 92%, at least 93%, at least 94%, at least 95%, at least 96%, at least 97%, at least 98%, or at least 99% identity to the amino acid sequence QVQLVQSGAEVKKPGASVKVSCK-SSGYTFTDYYIHWVRQAPGQGLEWMGWINPNSGD TNYAQKFQGRITMTRDTSISTAYLELSRLRSDD-TAVFYCARNSGSYSFGYWGQGTLVTV SS (SEQ ID NO:7); and/or the VL domain comprises a sequence with at least 90%, at least 91%, at least 92%, at least 93%, at least 94%, at least 95%, at least 96%, at least 97%, at least 98%, or at least 99% identity to the amino acid sequence DIQMTQSPSSVSASVGDRVTITCRASQGISS-WLAWYQQKPGKAPKLLIFGASSLQSGVPS RFSGSGSGTDFTLTVSSLQPEDFATYYCQQAY-SFPFTFGPGTKVDIE (SEQ ID NO:8). In some embodiments, the VH domain comprises the sequence QVQLVQS-GAEVKKPGASVKVSCKSSGYTFTDYYIHWVRQAPG QGLEWMGWINPNSGD TNYAQKFQGRITMTRDTSIS-TAYLELSRLRSDDTAVFYCARNSGSYS-FGYWGQGTLVTV SS (SEQ ID NO:7); and/or wherein the VL domain comprises the sequence DIQMTQSPSSVSASVGDRVTITCRASQGISS-WLAWYQQKPGKAPKLLIFGASSLQSGVPS RFSGSGSGTDFTLTVSSLQPEDFATYYCQQAY-SFPFTFGPGTKVDIE (SEQ ID NO:8). In some embodiments, the first antigen-binding domain binds to human Dectin-1 expressed on the surface of a macrophage, monocyte, dendritic cell, or granulocyte. In some embodiments, one or both of the first and second antibodies or fragments are human or humanized antibodies or fragments. In some embodiments, one or both of the first and second antibodies or fragments are Fab, Fab', F(ab')2, Fv, Fab'-SH, F(ab')2, single chain antibodies, NANOBODY® single domain antibodies, or scFv fragments. In some embodiments, one or both of the first and second antibodies or fragments further comprise an Fc domain. In some embodiments, the first antibody or fragment is a Fab fragment, and wherein the second antibody or fragment is a full-length antibody, e.g., that comprises an antibody heavy chain and an antibody light chain. In some embodiments, the first and the second antibodies or fragments are both full-length antibodies, e.g., that each comprise an antibody heavy chain and an antibody light chain. In some embodiments, the first antibody or fragment is a Fab fragment coupled to monomeric streptavidin (mSA), and wherein the second antibody is a biotinylated antibody that comprises an antibody heavy chain and an antibody light chain. In some embodiments, the first antibody or fragment is a full-length antibody coupled to monomeric streptavidin (mSA), and wherein the second antibody or fragment is a biotinylated full-length antibody. In some embodiments, the second target of interest is a disease-causing agent. In some embodiments, the disease-causing agent is a bacterial cell, fungal cell, virus, senescent cell, tumor cell, protein aggregate (e.g., amyloid beta, or lambda or kappa light chain amyloids), LDL particle, mast cell, eosinophil, ILC2 cell, or inflammatory immune cell. In some embodiments, the target of interest is an antigen expressed on the surface of the bacterial cell, fungal cell, senescent cell, tumor cell, mast cell, eosinophil, ILC2 cell, or inflammatory immune cell. In some embodiments, the target of interest is a surface antigen of the virus. In some embodiments, the target of interest is an antigen expressed on the surface of a cancer cell. In some embodiments, the target of interest is CD70, HER2, DLL3, NECTIN-4, TROP-2, Mesothelin, LIV-1, C-MET, FOLR1, CD20, CCR8, CD33, or EGFR. In some embodiments, the target of interest is CD20, the second antigen-binding domain comprises a heavy chain variable (VH) domain and a light chain variable (VL) domain, and the VH domain of the second antigen-binding domain comprises the sequence QVQLQQPGAEL-VKPGASVKMSCKASGYTFTSYNMHWVKQTPGR-GLEWIGAIYPGNGD TSYNQKFKGKATLTADKSSSTAYMQLSSLTSED-SAVYYCARSTYYGGDWYFNVWGAG TTVTVSA (SEQ ID NO:24) and/or the VL domain of the second antigen-binding domain comprises the sequence QIVLSQ-SPAILSASPGEKVTMT-CRASSSVSYIHWFQQKPGSSPKPWIYATSN-LASGVPVRF SGSGSGTSYSLTISRVEAE-DAATYYCQQWTSNPPTFGGGTKLEIK (SEQ ID NO:25). In some embodiments, the antibody comprises two antibody Fc regions, and wherein each of the antibody Fc regions comprises an amino acid substitution at one or more of positions 234, 235, and 237, according to EU numbering. In some embodiments, each of the antibody heavy chains comprises L234A, L235E, and G237A substitutions, according to EU numbering. In some embodiments, the antibody comprises two antibody heavy chains, and wherein only one of the antibody heavy chains comprises H435R and Y436F substitutions, according to EU numbering. In some embodiments, only one of the antibody arms comprises a heavy chain comprising F126C and C220V substitutions and a light chain comprising S121C and C214V substitutions, according to EU numbering. In some embodiments, the bispecific antibody comprises two antibody heavy chains and two antibody light chains, wherein the VH domain of the first antibody heavy chain forms an antigen binding domain with the VL domain of the first antibody light chain, wherein the VH domain of the second antibody heavy chain forms an antigen binding domain with the VL domain of the second antibody light chain, wherein the first antibody heavy chain comprises F126C, C220V, and T366W substitutions, wherein the first antibody light chain comprises S121C and C214V substitutions, and wherein the second antibody heavy chain comprises T366S, L368A, Y407V, H435R, and Y436F substitutions, according to EU numbering. In some embodiments, the first and second antibody heavy chains further comprise L234A, L235E, and G237A substitutions, according to EU numbering. In some embodiments, the first and second antibody heavy chains comprise human IgG1 Fc domains. In some embodiments, at least one or two of the heavy chains of the antibody is non-fucosylated. In some embodiments, the antibody may be produced in a cell line having an alpha1,6-fucosyltransferase (Fut8) or alpha-1,3-mannosyl-glycoprotein 2-beta-N-acetylglucosaminyltransferase (MGAT1) knockout. In some embodiments, the antibody may be produced in a cell line overexpressing β1,4-N-acetylglucosaminyltransferase III (GnT-III). In further embodiments, the cell line additionally overexpresses Golgi μ-mannosidase II (ManII). In some embodiments, the antibody may be produced in a cell line treated with an inhibitor of mannosidase I, e.g., kifunensine.

In some embodiments, provided herein is a method of treating a disease or disorder, comprising administering an effective amount of the antibody, multispecific binding molecule, or composition of any one of the above embodiments to an individual in need thereof. In some embodiments, the first target of interest is human Dectin-1, and wherein the second target of interest is a disease-causing agent. In some embodiments, the disease-causing agent is a bacterial cell, fungal cell, virus, senescent cell, tumor cell, protein aggregate (e.g., amyloid beta, or lambda or kappa light chain amyloids), LDL particle, mast cell, eosinophil, ILC2 cell, or inflammatory immune cell. In some embodiments, the target of interest is an antigen expressed on the surface of the bacterial cell, fungal cell, senescent cell, tumor cell, mast cell, eosinophil, ILC2 cell, or inflammatory immune cell. In some embodiments, the target of interest is a surface antigen of the virus. In some embodiments, the disease or disorder is cancer, a bacterial infection, a fungal infection, a viral infection, a mast cell disease or disorder, systemic mastocytosis, amyloidosis (e.g., light chain amyloidosis or Alzheimer's disease), or an aging-related disease or disorder. In some embodiments, the target of interest is CD70, HER2, DLL3, NECTIN-4, TROP-2, Mesothelin, LIV-1, C-MET, FOLR1, CD20, CCR8, CD33, or EGFR. In some embodiments, the individual is a human.

In some embodiments, provided herein is a method of treating cancer, comprising administering an effective amount of a composition comprising a multispecific binding molecule to an individual in need thereof, wherein the multispecific binding molecule comprises: (a) a first antibody or antigen-binding fragment thereof comprising a first antigen-binding domain, wherein the first antigen-binding domain binds to human Dectin-1; and (b) a second antibody or antigen-binding fragment thereof comprising a second antigen-binding domain, wherein the second antigen binding domain binds to CD70, HER2, DLL3, NECTIN-4, TROP-2, Mesothelin, LIV-1, C-MET, FOLR1, CD20, CCR8, CD33, or EGFR. In some embodiments, the second antigen binding domain binds to human CD70, human HER2, human DLL3, human NECTIN-4, human TROP-2, human Mesothelin, human LIV-1, human C-MET, human FOLR1, human CD20, human CCR8, human CD33, or human EGFR, e.g., as expressed on the surface of a cancer cell. In some embodiments, the first antigen-binding domain comprises a heavy chain variable (VH) domain and a light chain variable (VL) domain, wherein the VH domain comprises a CDR-H1 comprising the sequence GYTFTDYY (SEQ ID NO:1), a CDR-H2 comprising the sequence INPNSGDT (SEQ ID NO:2), and a CDR-H3 comprising the sequence ARNSGSYSFGY (SEQ ID NO:3), and wherein the VL domain comprises a CDR-L1 comprising the sequence QGISSW (SEQ ID NO:4), a CDR-L2 comprising the sequence GAS (SEQ ID NO:5), and a CDR-L3 comprising the sequence QQAYSFPFT (SEQ ID NO:6). In some embodiments, the first antigen-binding domain comprises a heavy chain variable (VH) domain and a light chain variable (VL) domain, wherein the VH domain comprises a CDR-H1, CDR-H2, and CDR-H3 from the VH domain sequence QVQLVQSGAEVKKPGASVKVSCKSSGYTFTDYYIHWVRQAPGQGLEWMGWINPNSGDTNYAQKFQGRITMTRDTSISTAYLELSRLRSDDTAVFYCARNSGSYSFGYWGQGTLVTV SS (SEQ ID NO:7), and wherein the VL domain comprises a CDR-L1, CDR-L2, and CDR-L3 from the VL domain sequence DIQMTQSPSSVSASVGDRVTITCRASQGISSWLAWYQQKPGKAPKLLIFGASSLQSGVPSRFSGSGSGTDFTLTVSSLQPEDFATYYCQQAYSFPFTFGPGTKVDIE (SEQ ID NO:8). In some embodiments, the first antigen-binding domain comprises a heavy chain variable (VH) domain and a light chain variable (VL) domain, wherein the VH domain comprises a CDR-H1 comprising the sequence DYYI (SEQ ID NO:88), a CDR-H2 comprising the sequence WINPNSGDTNYAQKFQG (SEQ ID NO:89), and a CDR-H3 comprising the sequence NSGSYSFGY (SEQ ID NO:90), and wherein the VL domain comprises a CDR-L1 comprising the sequence RASQGISSWLA (SEQ ID NO:91), a CDR-L2 comprising the sequence GASSLQS (SEQ ID NO:92), and a CDR-L3 comprising the sequence QQAYSFPFT (SEQ ID NO:6). In some embodiments, the VH domain comprises a sequence with at least 90%, at least 91%, at least 92%, at least 93%, at least 94%, at least 95%, at least 96%, at least 97%, at least 98%, or at least 99% identity to the amino acid sequence QVQLVQSGAEVKKPGASVKVSCKSSGYTFTDYYIHWVRQAPGQGLEWMGWINPNSGDTNYAQKFQGRITMTRDTSISTAYLELSRLRSDDTAVFYCARNSGSYSFGYWGQGTLVTV SS (SEQ ID NO:7); and/or the VL domain comprises a sequence with at least 90%, at least 91%, at least 92%, at least 93%, at least 94%, at least 95%, at least 96%, at least 97%, at least 98%, or at least 99% identity to the amino acid sequence DIQMTQSPSSVSASVGDRVTITCRASQGISSWLAWYQQKPGKAPKLLIFGASSLQSGVPSRFSGSGSGTDFTLTVSSLQPEDFATYYCQQAYSFPFTFGPGTKVDIE (SEQ ID NO:8). In some embodiments, the VH domain of the first antigen-binding domain comprises the sequence QVQLVQSGAEVKKPGASVKVSCKSSGYTFTDYYIHWVRQAPGQGLEWMGWINPNSGD TNYAQKFQGRITMTRDTSISTAYLELSRLRSDDTAVFYCARNSGSYSFGYWGQGTLVTV SS (SEQ ID NO:7); and/or wherein the VL domain of the first antigen-binding domain comprises the sequence DIQMTQSPSSVSASVGDRVTITCRASQGISSWLAWYQQKPGKAPKLLIFGASSLQSGVPSRFSGSGSGTDFTLTVSSLQPEDFATYYCQQAYSFPFTFGPGTKVDIE (SEQ ID NO:8). In some embodiments, the second antigen binding domain binds to CD20; wherein the second antigen-binding domain comprises a heavy chain variable (VH) domain and a light chain variable (VL) domain; and wherein the VH domain of the second antigen-binding domain comprises the sequence QVQLQQPGAELVKPGASVKMSCKASGYTFTSYNMHWVKQTPGRGLEWIGAIYPGNGD TSYNQKFKGKATLTADKSSSTAYMQLSSLTSEDSAVYYCARSTYYGGDWYFNVWGAG TTVTVSA (SEQ ID NO:24) and/or wherein the VL domain of the second antigen-binding domain comprises the sequence QIVLSQSPAILSASPGEKVTMTCRASSSVSYIHWFQQKPGSSPKPWIYATSNLASGVPVRF SGSGSGTSYSLTISRVEAEDAATYYCQQWTSNPPTFGGGTKLEIK (SEQ ID NO:25). In some embodiments, the multispecific binding molecule comprises a first antibody arm comprising the first antigen binding domain and a first Fc region and a second antibody arm comprising the second antigen binding domain and a second Fc region, wherein the first Fc region comprises one or more knob-forming mutations, and the second Fc region comprises one or more cognate hole-forming mutations. In some embodiments, the first Fc region comprises a T366W substitution, and the second Fc region comprises T366S, L368A, and Y407V substitutions, according to EU numbering. In some embodiments, the multispecific binding molecule comprises a first antibody arm comprising the first antigen binding domain and a first Fc region and a second antibody arm comprising the second antigen binding domain and a second Fc region, wherein the first Fc region comprises one or more hole-forming mutations, and the second Fc region comprises one or more cognate knob-forming mutations. In some embodiments, the first Fc region comprises T366S, L368A, and Y407V substitutions, and the second Fc region comprises a T366W substitution, according to EU numbering. In some embodiments, the antibody comprises two antibody Fc regions, and wherein each of the antibody Fc regions comprises an amino acid substitution at one or more of positions 234, 235, and 237, according to EU numbering. In some embodiments, each of the antibody heavy chains comprises L234A, L235E, and G237A substitutions, according to EU numbering. In some embodiments, the antibody comprises two antibody heavy chains, and wherein only one of the antibody heavy chains comprises H435R and Y436F substitutions, according to EU numbering. In some embodiments, only one of the antibody arms comprises a heavy chain comprising F126C and C220V substitutions and a light chain comprising S121C and C214V substitutions, according to EU numbering. In some embodiments, the bispecific antibody comprises two antibody heavy chains and two antibody light chains, wherein the VH domain of the first antibody heavy chain forms an antigen binding domain with the VL domain of the first antibody light chain, wherein the VH domain of the second antibody heavy chain forms an antigen binding domain with the VL domain of the second antibody light chain, wherein the first antibody heavy chain comprises F126C, C220V, and T366W substitutions, wherein the first antibody light chain comprises S121C and C214V substitutions, and wherein the second antibody heavy chain comprises T366S, L368A, Y407V, H435R, and Y436F substitutions, according to EU numbering. In some embodiments, the first and second antibody heavy chains further comprise L234A, L235E, and G237A substitutions, according to EU numbering. In some embodiments, the first and second antibody heavy chains comprise human IgG1 Fc domains. In some embodiments (e.g., wherein the second antigen binding domain binds to CD20), the antibody comprises three polypeptide chains: a first polypeptide chain comprising the sequence QVQLVQSGAEVKKPGASVKVSCK-SSGYTFTDYYIHWVRQAPGQGLEWMGWINPNSGD TNYAQKFQGRITMTRDTSISTAYLELSRLRSDD-TAVFYCARNSGSYSFGYWGQGTLVTV SSGGGGSGGGGSGGGGSGGGGSDIQMTQSPSSVSAS VGDRVTITCRASQGISSWLAWYQ QKPGKAPKLLIF-GASSLQSGVPSRFSGSGSGTDFTLTVSSLQPEDFA-TYYCQQAYSFPFTF GPGTKVDIEEPKRSDKTH-TCPPCPAPELLGGPSVFLFPPKPKDTLMISRTPEVTCV VVDVS HEDPEVKFNWYVDGVEVHNAKTKPRE-EQYNSTYRVVSVLTVLHQDWLNGKEYKCKVS NKA-LPAPIEKTISKAKGQPREPQVYTLPPSREEMT-KNQVSLWCLVKGFYPSDIAVEWESN GQPENNYKTTPPVLDSDGSFFLYSK-LTVDKSRWQQGNVFSCSVMHEALHNHYTQKSLS LSPG (SEQ ID NO:31), a second polypeptide chain comprising the sequence QVQLQQPGAELVKP-GASVKMSCKASGYTFTSYNMHWVKQTPGRGLEWI-GAIYPGNGD TSYNQKFKGKATLTADKSSSTAYMQLSSLTSED-SAVYYCARSTYYGGDWYFNVWGAG TTVTVSAASTKGPSVFPLAPSSKSTSGGTAAL-GCLVKDYFPEPVTVSWNSGALTSGVHTF PAVLQSSG-LYS-LSSVVTVPSSSLGTQTYICNVNHKPSNTKVDKKVEP KSCDKTHTCPPCP APELLGGPSVFLFPPKPKDTLMIS-RTPEVTCVVVDVSHEDPEVKFNWYVDGVEVHNAKT KPREEQYN-STYRVVSVLTVLHQDWLNGKEYKCKVSNKALPA-PIEKTISKAKGQPREPQV YTLPPSREEMTKNQVSLS-CAVKGFYPSDIAVEWESNGQPENNYKTTPPVLDSD GSFFLVS KLTVDKSRWQQGNVFSCSVMHEALHNRFTQKSLSL-SPG (SEQ ID NO:32), and a third polypeptide chain comprising the sequence QIVLSQSPAILSASPGEKVTMT-CRASSSVSYIHWFQQKPGSSPKPWIYATSNLASGVP VRF SGSGSGTSYSLTISRVEAE-DAATYYCQQWTSNPPTFGGGTKLEIKRTVAAPSVFI FPPSDE QLKSGTASVVCLLNNFYPREAKVQWKVD-NALQSGNSQESVTEQDSKDSTYSLSSTLTS KADYEKHKVYACEVTHQGLSSPVTKSFNRGEC (SEQ ID NO:33). In some embodiments, at least one or two of the heavy chains of the antibody is non-fucosylated. In some embodiments, the antibody may be produced in a cell line having an alpha1,6-fucosyltransferase (Fut8) or alpha-1,3-mannosyl-glycoprotein 2-beta-N-acetylglucosaminyltranferase (MGAT1) knockout. In some embodiments, the antibody may be produced in a cell line overexpressing β1,4-N-acetylglucosaminyltransferase III (GnT-III). In further embodiments, the cell line additionally overexpresses Golgi μ-mannosidase II (ManII). In some embodiments, the antibody may be produced in a cell line treated with an inhibitor of mannosidase I, e.g., kifunensine. In some embodiments, the individual is a human.

In some embodiments, provided herein is a kit or article of manufacture comprising the antibody, multispecific binding molecule, or composition of any one of the above embodiments and instructions for using the antibody, multispecific binding molecule, or composition according to the method of any one of the above embodiments.

It is to be understood that one, some, or all of the properties of the various embodiments described herein may be combined to form other embodiments of the present disclosure. These and other aspects of the present disclosure will become apparent to one of skill in the art. These and other embodiments of the present disclosure are further described by the detailed description that follows.

BRIEF DESCRIPTION OF THE DRAWINGS

FIGS. 1A-1C show the binding analysis of the anti-human Dectin-1 antibody (clone 2M24) in human and monkey monocytes derived from peripheral blood mononuclear cells (PBMC) by flow cytometry. Single, live and CD14+ cells were gated to identify monocytes. The cells were incubated with 2M24 anti-Dectin-1 primary antibody or a mIgG1 isotype control antibody, followed by incubation with a fluorescent anti-mouse secondary antibody. The primary antibodies were used in a serial dose titration. FIG. 1A shows the binding analysis for anti-human Dectin-1 clone 2M24 in human monocytes. FIG. 1B shows the binding analysis for anti-human Dectin-1 clone 2M24 antibody in cynomolgus monocytes. FIG. 1C depicts a comparison of binding to human monocytes, HEK cells overexpressing human Dectin-1 and cynomolgus monocytes between the 2M24 clone and other Dectin-1 antibodies identified from the ATX-Gx Alloy transgenic mice immunization as well as commercial anti-Dectin-1 antibodies. Anti-human Dectin-1 clone 2M24 antibody demonstrated high affinity to both human and cynomolgus monkey Dectin-1 expressed in monocytes, and exhibited superior affinity as compared to other anti-Dectin-1 antibodies, including commercial antibodies.

FIG. 2A shows the phagocytosis of beads over 2.5 hours in HEK-Blue hDectin-1a cells (top) and representative images of pHrodo positive cells at 2.5 hours of phagocytosis (bottom). FIG. 2B shows the phagocytosis of beads over 4 hours in human monocytes (top), as well as representative images of pHrodo positive cells at 2.5 hours of phagocytosis (bottom). In the representative images, engulfed beads fluoresce brightly in phagosomes.

FIG. 3A shows the binding analysis of the fully human 2M24 anti-Dectin-1 antibody to HEK cells, while FIG. 3B shows the binding to primary human monocytes. The primary antibodies were used in a serial dose titration followed by a fluorescent secondary antibody against the primary antibody. The fully human 2M24 anti-Dectin-1 hIgG4 antibody bound with high affinity to Dectin-1 expressing cells.

FIG. 5A shows the results for a secreted alkaline phosphatase assay performed using immobilized fully human 2M24 anti-Dectin-1 antibody. The fully human 2M24 (hIgG4) anti-Dectin-1 antibody or an isotype control antibody were immobilized overnight in U-bottomed polypropylene microtiter plates at quantities ranging from 0.1-10 μg per well, followed by culture of HEK-Blue hDectin-1a cells for 22 hours and evaluation of alkaline phosphatase secretion at OD 630 nm in the supernatant. FIG. 5B shows the results for a secreted alkaline phosphatase assay performed using bead-conjugated fully human 2M24 anti-Dectin-1 antibody. Biotin beads of 3, 10 and 16.5 μm in size were conjugated to streptavidin 2M24 (hIgG4) anti-Dectin-1 antibody. Antibody-conjugated beads were mixed with HEK-Blue hDectin-1a cells for 22 hours, and the supernatant was evaluated for alkaline phosphatase secretion at OD 630 nm. Bars represent mean±s.d.; n=2 replicates. The 2M24 (hIgG4) anti-Dectin-1 antibody induced alkaline phosphatase secretion in HEK-Blue hDectin-1a cells both in an immobilized form and conjugated to beads.

FIG. 6A shows the results for primary human monocytes stimulated with soluble 15E2 anti-Dectin-1 antibody, while FIG. 6B shows the results for stimulated primary human macrophages. Soluble 15E2 anti-Dectin-1 antibody did not induce cytokine secretion in primary human monocytes and macrophages.

FIG. 7A shows the cytokine secretion by human monocytes following stimulation with immobilized anti-Dectin-1 antibodies, while FIG. 7B shows the cytokine secretion by cultured human PBMCs after stimulation. Bars represent mean±s.d.; n=2 replicates. The 2M24 anti-Dectin-1 antibody induced cytokine secretion in both primary human monocytes and PBMCs and exhibited superior immune stimulation to the 15E2 Dectin-1 agonistic antibody

FIG. 9 depicts a summary of the functional characterization of the 2M24 and 15E2 anti-Dectin-1 antibodies.

FIG. 10A depicts the differential labeling of antibodies with MTA or FOL reagents FIG. 10B depicts the covalent crosslinking of antibodies via specific MTA-FOL interactions.

FIG. 12A shows an SDS-PAGE analysis of covalently conjugated antibody pairs (2M24/anti-hCD20, 2M24/anti-hCD70, and isotype controls) under non-reducing and reducing conditions. FIG. 12B shows a flow cytometry-based characterization of bispecific (2M24/anti-hCD70 or isotype control) binding to Dectin-1-expressing HEK293 cells (top left) and two renal carcinoma cell lines—A498 (top right) and 786-0 (bottom left). FIG. 12B also depicts the EC50 concentration (nM) based on a non-linear regression fitting (bottom right). Anti-Dectin-1/ anti-hCD70 bispecific binds Dectin-1- or CD70-expressing cells with an affinity of 1.8 nM or 12.34 nM, respectively.

Figure 13:
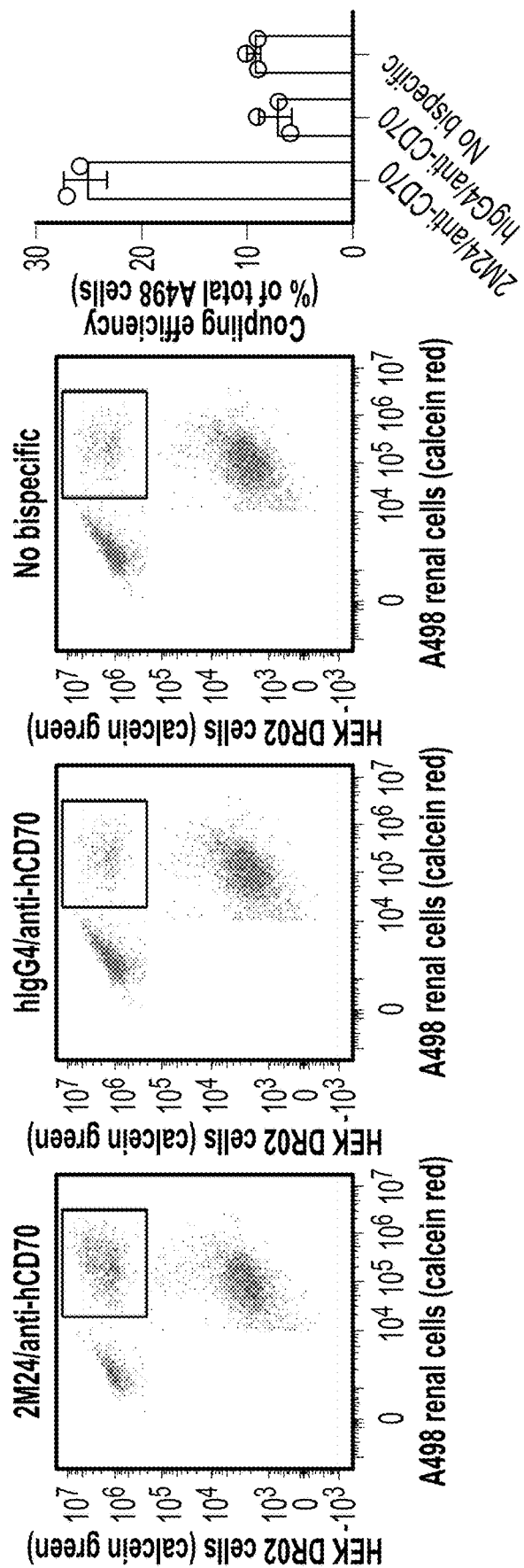
Figure 14A:
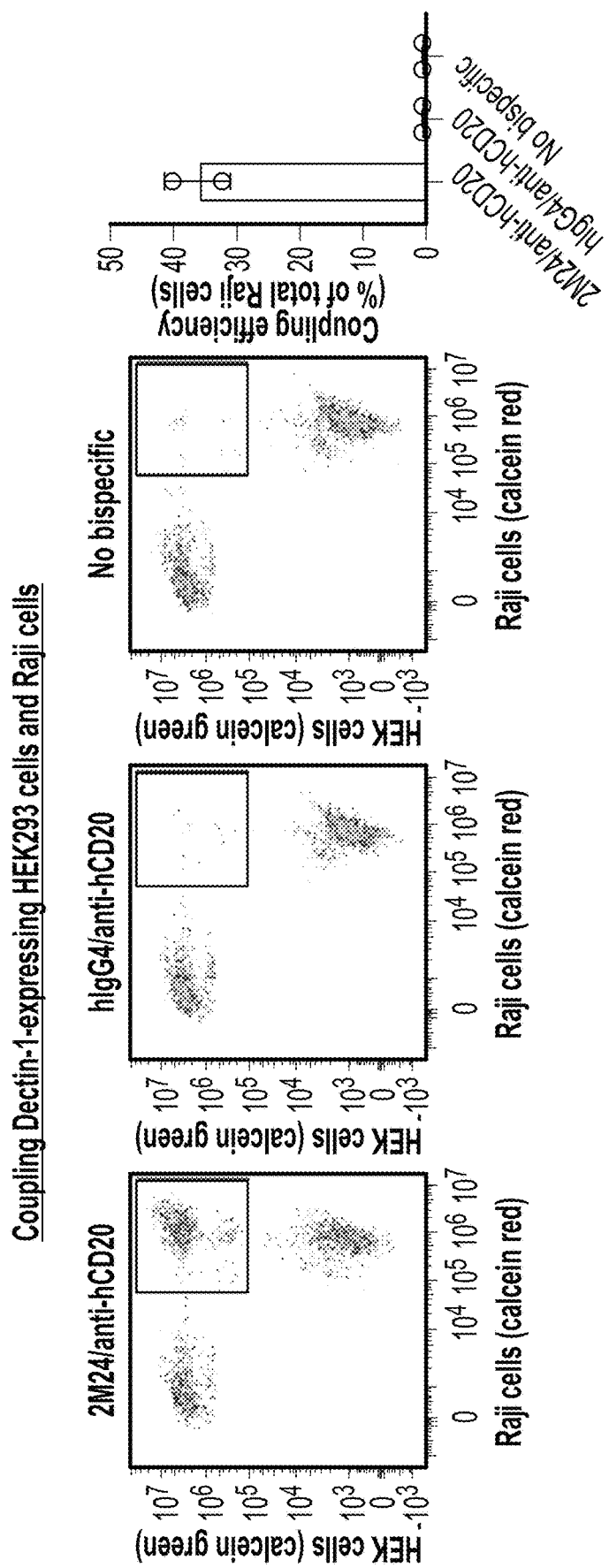
Figure 14B:
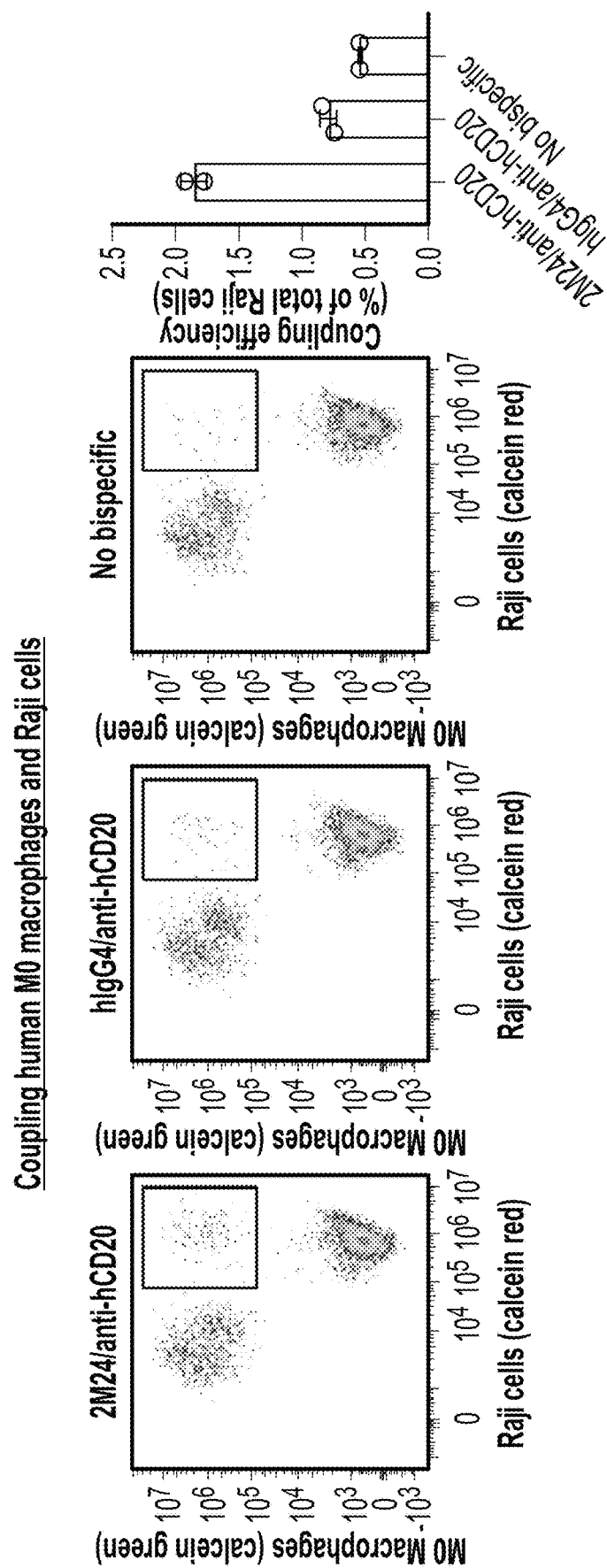

FIG. 13 shows coupling of Dectin-1-expressing HEK293 cell line and A498 renal carcinoma cell line induced by 2M24/anti-hCD70 bispecific. Shown are a flow cytometry analysis of co-cultures of HEK293 cells (labeled with calcein green) and A498 cells (labeled with calcein red) in the presence of 2M24/anti-hCD70 bispecific or isotype control (left). Coupling of HEK293 and A498 cells is indicated by a double-positive signal (green+red+, square box). Also shown is coupling efficiency, which is quantified as the percentage of total target cells (A498) that forms doublets with HEK293 cells (right). Bars represent mean±s.d.; n=3 replicates. The 2M24/anti-hCD70 bispecific antibody induced coupling of Dectin-1-expressing HEK293 cell line and A498 renal carcinoma cell line FIGS. 14A-14B shows the coupling of Dectin-1-expressing cells and B cells induced by anti-Dectin-1/anti-hCD20 bispecific antibody. FIG. 14A shows the coupling of Dectin-1-expressing HEK293 cells and B cells induced by anti-Dectin-1/anti-hCD20 bispecific antibody. Shown are a flow cytometry analysis of co-cultures of HEK293 cells (labeled with calcein green) and Raji cells (labeled with calcein red) in the presence of 2M24/anti-hCD70 bispecific or isotype control (left). Coupling of HEK293 and Raji cells is indicated by a double-positive signal (green+red+; square box). Also shown is the coupling efficiency, which is quantified as the percentage of total target cells (Raji) that forms doublets with HEK293 cells (right). Bars represent mean±s.d.; n=2 replicates. FIG. 14B shows the results of similar experiments performed to assess the coupling of human MO macrophages and Raji cells induced by anti-Dectin-1/anti-hCD20 bispecific. Bars represent mean±s.d.; n=2 replicates. The 2M24/anti-hCD20 bispecific induced coupling of Dectin-1-expressing cells and CDC20-positive B cells (Raji cells).

Figure 15:
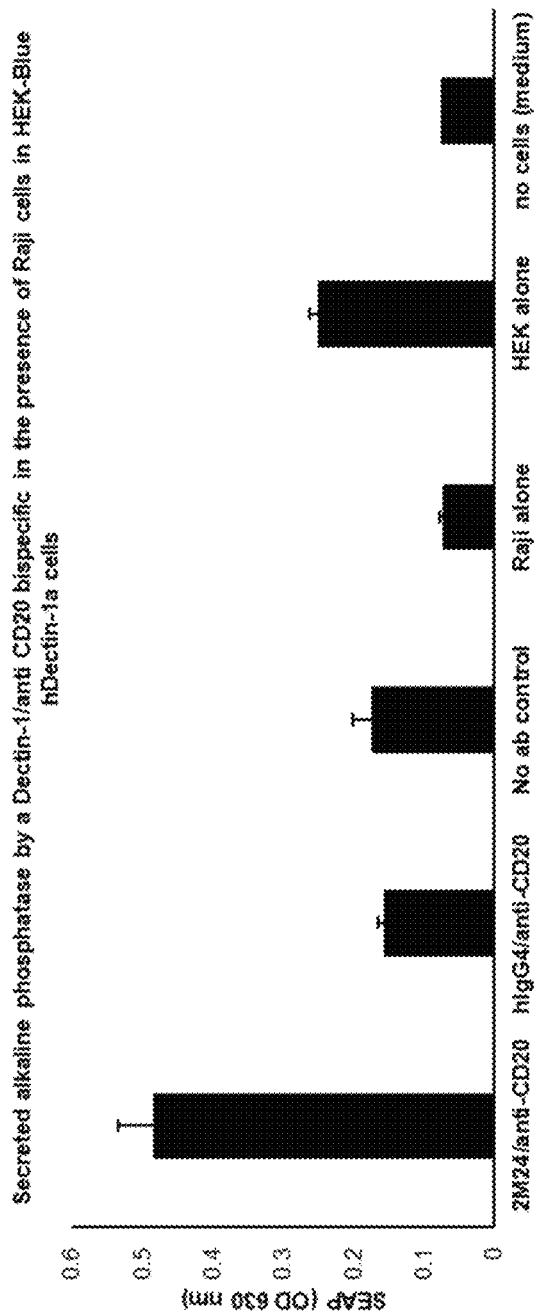

FIG. 15 shows the results of a secreted alkaline phosphatase reporter assay by Dectin-1 in HEK-Blue hDectin-1a cells using an anti-Dectin-1/anti-CD20 bispecific in the presence of Raji cells. A 2M24 (hIgG4)/a-CD20 bispecific antibody was incubated with Raji cells, after which it was washed twice to remove unbound bispecific antibody. The Raji cells were then mixed with HEK-Blue hDectin-1a cells at a ratio of 200.000 Raji cells to 100.000 HEK cells for 22 hours. Secreted alkaline phosphatase was evaluated at OD 630 nm in the supernatant. Bars represent mean±s.d.; n=2 replicates. Raji cells coated with an anti-Dectin-1/anti CD20 bispecific induced alkaline phosphatase secretion in HEK-Blue hDectin-1a cells.

Figure 16:
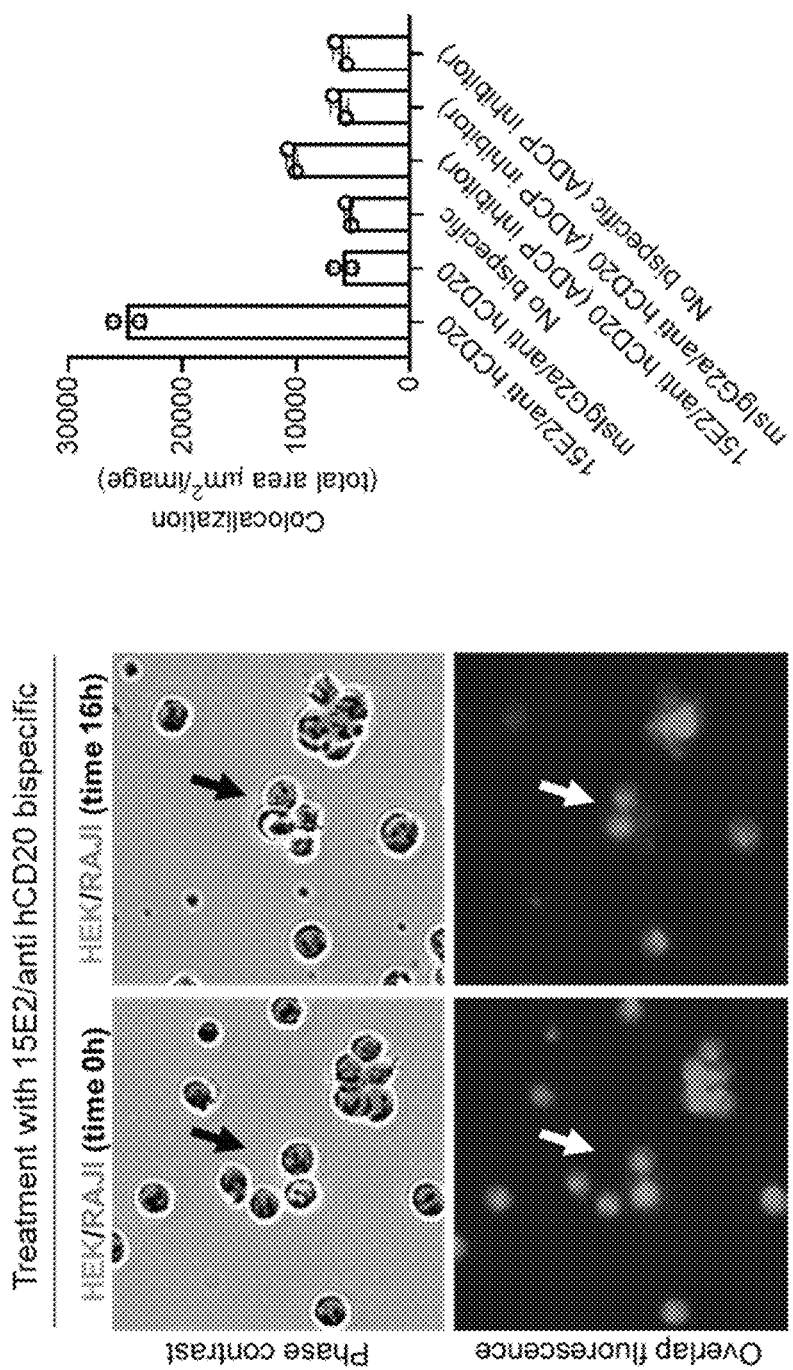

FIG. 16 shows the induction of Raji cell phagocytosis by Dectin-1-expressing HEK 293 cells by anti-Dectin-1/anti-hCD20 bispecific antibodies. Representative Incucyte images illustrating phagocytosis of Raji cells by HEK cells (arrowhead) at 16 h versus 0 h are shown (left). Co-localization is indicated by yellow fluorescence. Reduction in calcein red signal of Raji cells at 16 h indicates phagocytosis-mediated cell death. Quantification of overlap or co-localization of HEK (calcein green) and Raji (calcein red) in different treatment groups are shown (right). Pre-incubation of HEK cells with ADCP inhibitor Latrunculin A blocks phagocytosis mediated by 15E2/anti-hCD20 bispecific antibody. (n=2 replicates).

Figure 17:
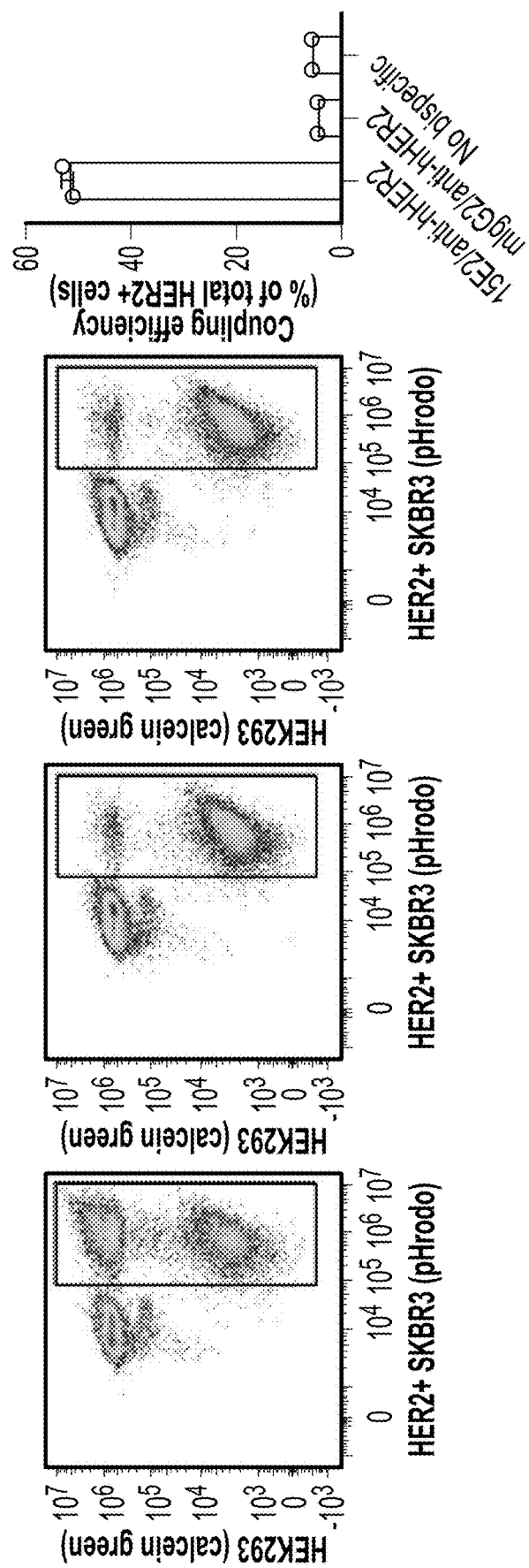

FIG. 17 shows coupling of Dectin-1- and HER2-expressing cells induced by anti-Dectin-1/anti-hHER2 bispecific antibodies. Shown are a flow cytometry analysis of co-cultures of Dectin-1-expressing HEK 293 cells (labeled with calcein green) and HER2-expressing SKBR3 cells (labeled with pHrodo red) in the presence of 15E2/anti-hHER2 bispecific or isotype control (left). Coupling of HEK 293 and SKBR3 cells is indicated by a double-positive signal (green+red+; square box). Also shown is the coupling efficiency, which is quantified as the percentage of total target cells (SKBR3) that forms doublets with the Dectin-1 expressing cells (right). Bars represent mean±s.d.; n=2 replicates. Anti-Dectin-1/anti-hHER2 bispecific induces coupling of Dectin-1- and HER2-positive cancer cells.

Figure 18:
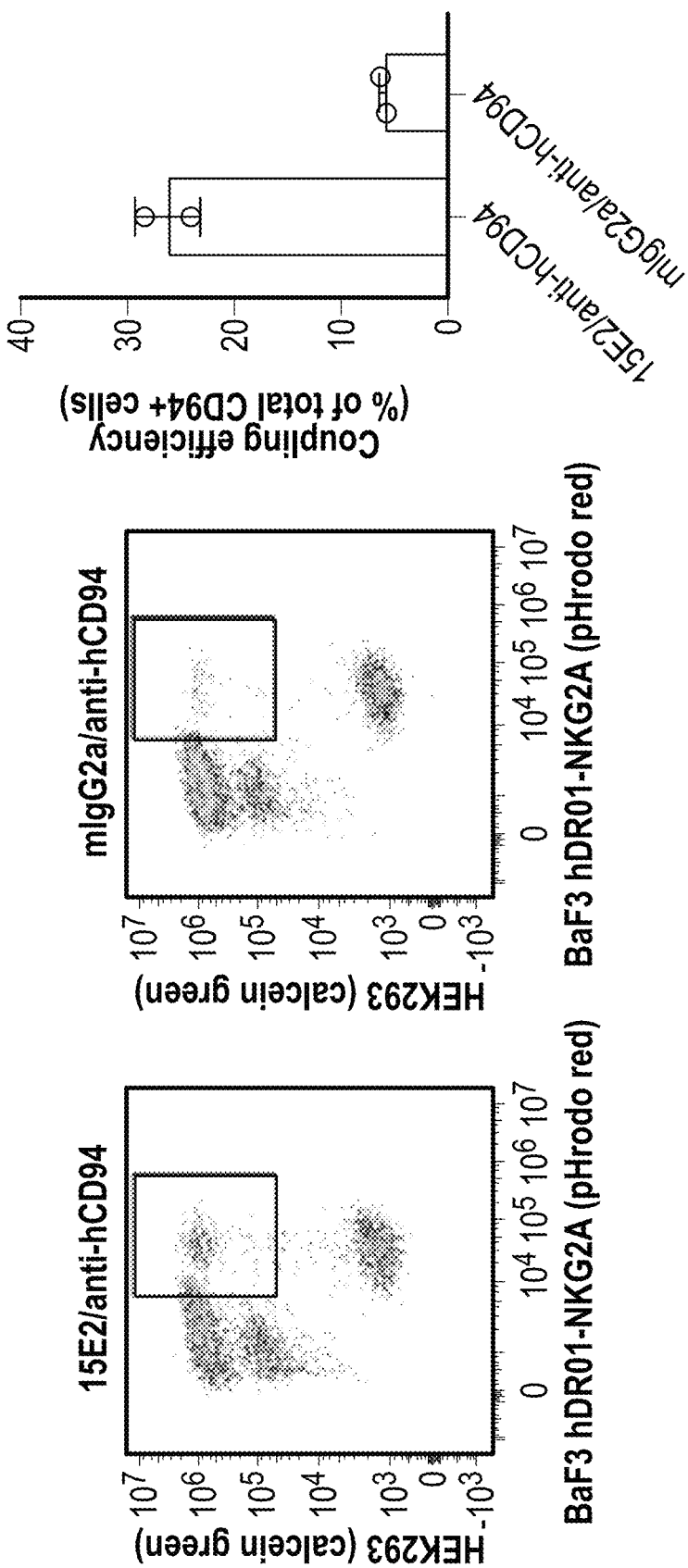

FIG. 18 shows coupling of Dectin-1-expressing HEK293 cells and CD94-expressing BaF3 cells induced by anti-Dectin-1/anti-hCD94 bispecific induces. Shown are a flow cytometry analysis of co-cultures of HEK293 cells (labeled with calcein green) and BaF3 cells (labeled with pHrodo red) in the presence of 2M24/anti-hCD94 bispecific or isotype control (left). Coupling of HEK293 and BaF3 cells is indicated by a double-positive signal (green+red+; square box). Also shown is the coupling efficiency, which is quantified as the percentage of total target cells (BaF3) that forms doublets with HEK293 cells (right). Bars represent mean±s.d.; n=2 replicates. Anti-Dectin-1/anti-hCD94 bispecific induced coupling of Dectin-1- and CD94-expressing cells.

Figure 19A:
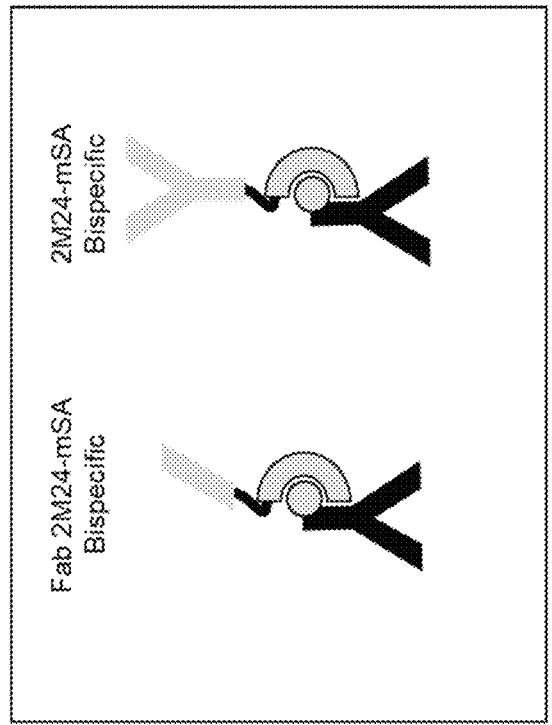
Figure 19B:
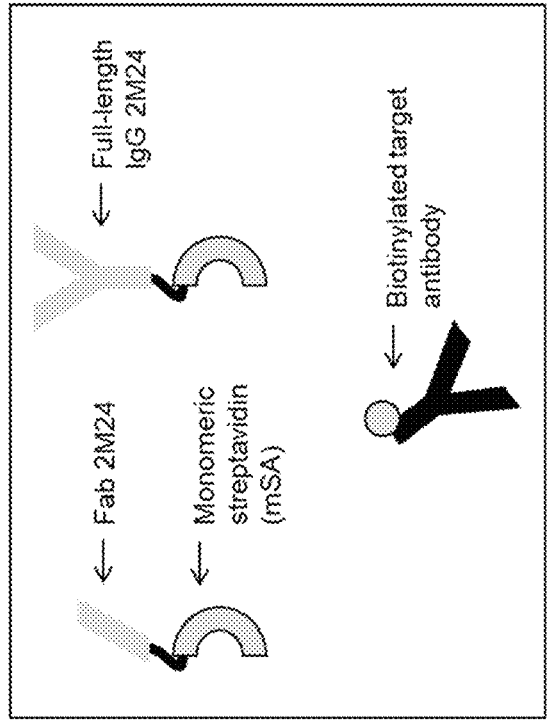

FIGS. 19A-19B show a schematic illustration of Fab 2M24-mSA or full length 2M24-mSA bound to a biotinylated target antibody. FIG. 19A shows chimeric fusions of monomeric Streptavidin (mSA) and Fab 2M24 or full length 2M24. mSA is genetically fused to either Fab 2M24 or full length 2M24. FIG. 19B shows the coupling of Fab 2M24-mSA or 2M24-mSA to biotinylated target antibodies. The chimeric fusions are incubated with biotinylated target antibodies to generate a bispecific comprising a Dectin-1-binding arm and a second arm binding a target receptor or protein of interest.

FIGS. 20A-20C show the biochemical and functional characterization of Fab 2M24-mSA fusion protein. FIG. 20A shows an HPLC characterization of recombinant Fab 2M24-mSA. FIG. 20B shows an SDS-PAGE analysis of purified Fab 2M24-mSA under reducing conditions. FIG. 20C shows a flow cytometry characterization of Fab 2M24-mSA binding to HEK 293 cells stably overexpressing human Dectin-1 ($EC_{50}$=1.45 nM). Fab 2M24 fusion to monomeric streptavidin binds to Dectin-1-expressing cells with an affinity of 1.45 nM.

Figure 21B:
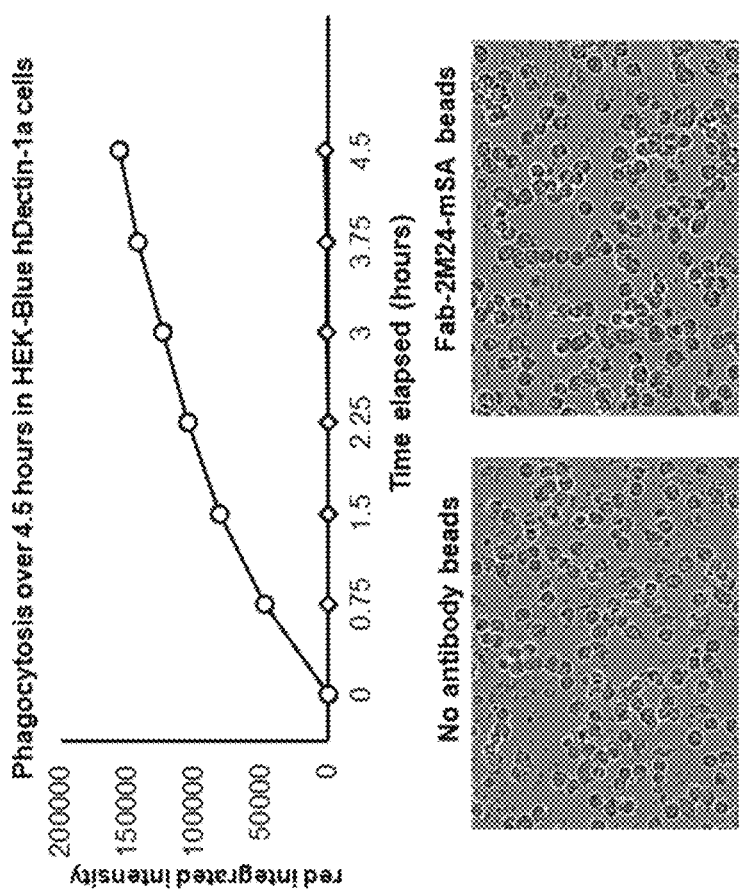

FIGS. 21A-21B shows the phagocytosis of pHrodo-labeled polystyrene biotin beads conjugated with a Fab-2M24 anti-Dectin-1 antibody tagged with monomeric streptavidin (Fab-2M24-mSA). FIG. 21A shows duplet formation of HEK-Blue hDectin-1a cells with Fab-2M24-mSA conjugated to biotin beads and phagocytosis of the beads, assessed by flow cytometry. FIG. 21B shows the phagocytosis of phrodo biotin beads (~3 μm) conjugated to Fab-2M24-mSA assessed by IncuCyte live imaging (top), as well as representative images of pHrodo positive cells at 3 hours of phagocytosis (engulfed beads fluoresce brightly red in phagosomes) vs. no bead controls (bottom). Fab 2M24-mSA fusion induced binding and phagocytosis of beads by Dectin-1-expressing HEK 293 cells.

Figure 22A:
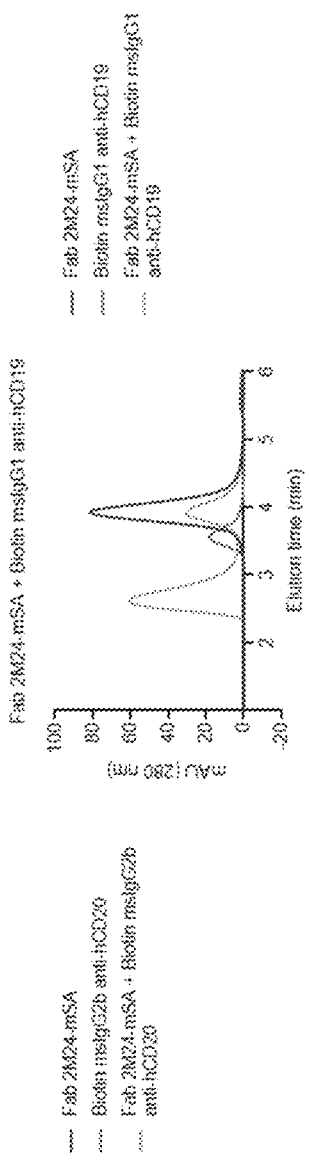
Figure 22B:
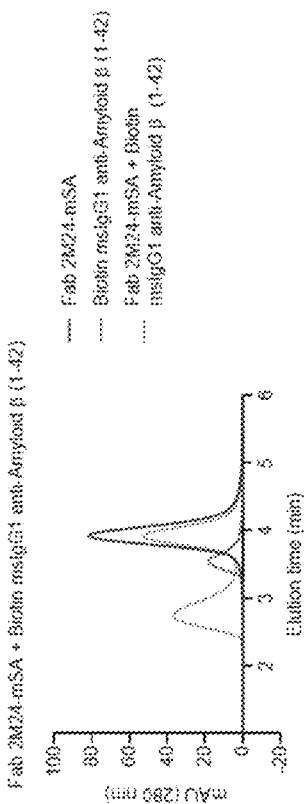
Figure 22C:
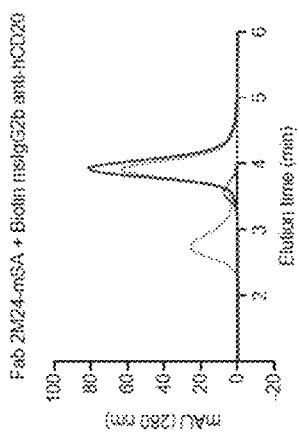
Figure 22D:
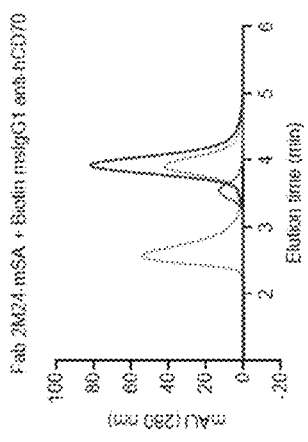

FIGS. 22A-22D show bispecific complexes comprising Fab 2M24-mSA and target biotinylated antibodies. Depicted are the HPLC analyses of Fab 2M24-mSA in complex with biotinylated anti-hCD20 (FIG. 22A), biotinylated anti-hCD19 (FIG. 22B), biotinylated anti-hCD70 (FIG. 22C), or biotinylated anti-Amyloid β 1-42 (FIG. 22D). Each panel contains superposition of A280 traces including Fab 2M24-mSA alone, target biotinylated antibody alone, and Fab 2M24-mSA in complex with biotinylated target antibody.

Figure 23:
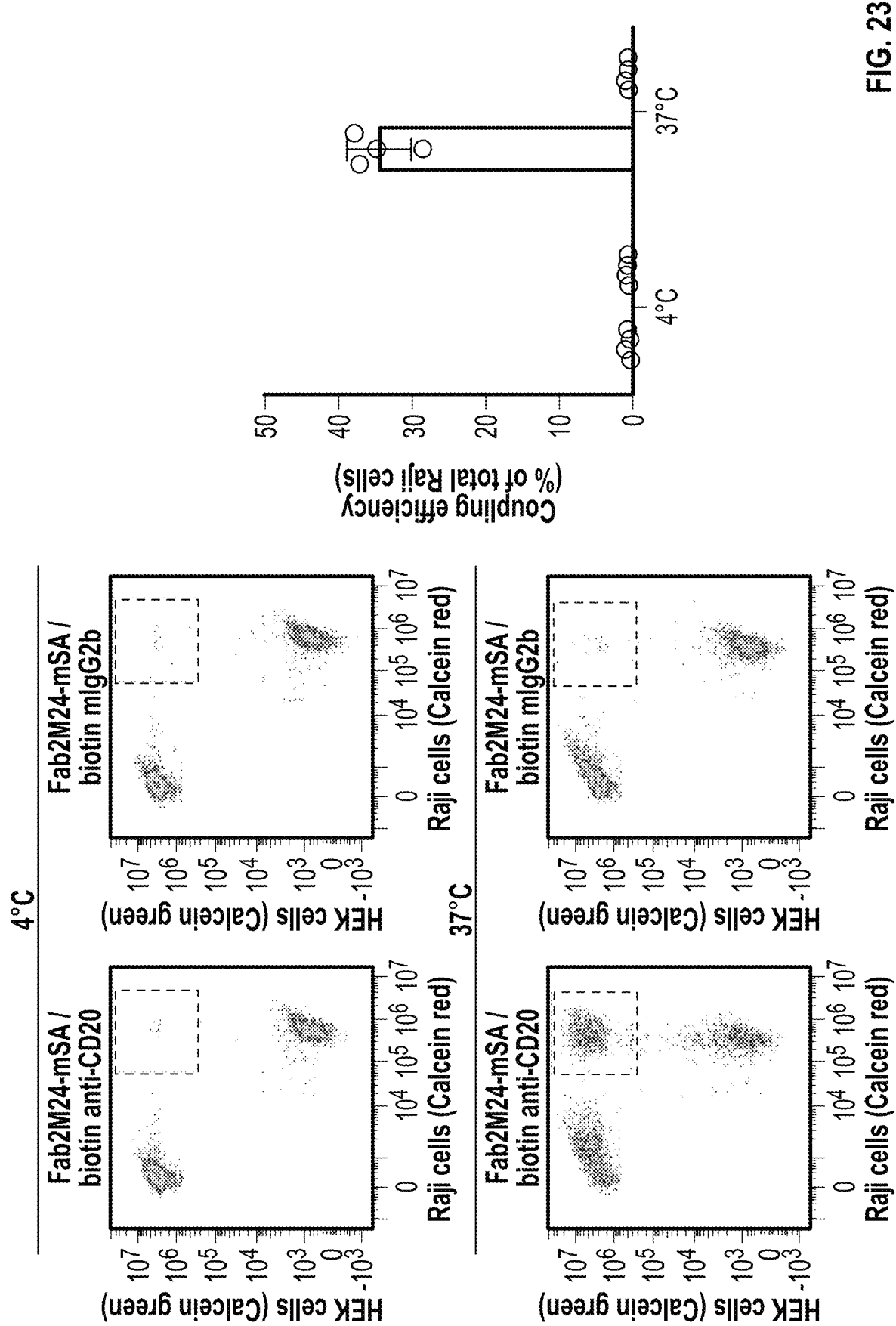

FIG. 23 shows coupling of Dectin-1-expressing HEK293 cells and CD20-expressing Raji cells induced by Fab 2M24-mSA/biotin anti-hCD20 bispecific antibodies. Shown are the flow cytometry analysis of co-cultures of HEK293 (labeled with calcein green) and Raji (labeled with calcein red) in the presence of Fab 2M24-mSA/biotin anti-hCD20 bispecific or isotype bispecific control (left). Co-cultures were incubated at 4° C. or 37° C. Coupling of HEK293 and Raji cells is indicated by a double-positive signal (green+red+; dotted-square). Also shown is the coupling efficiency, which is quantified as the percentage of total target cell (Raji) that forms doublets (right). Bars represent mean±s.d.; n=4 replicates. Fab 2M24-mSA/biotin anti-hCD20 bispecific induced coupling of Dectin-1-expressing HEK293 cells and Raji cells.

Figure 24:
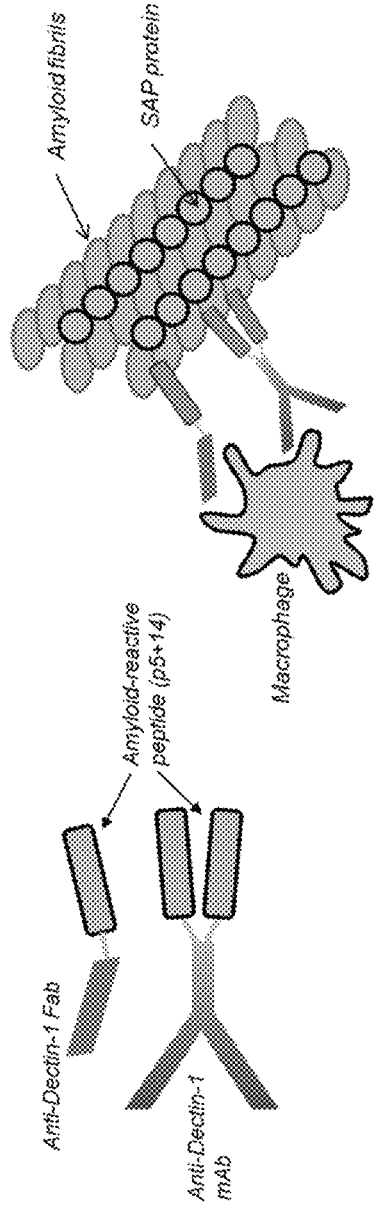
Figure 24:
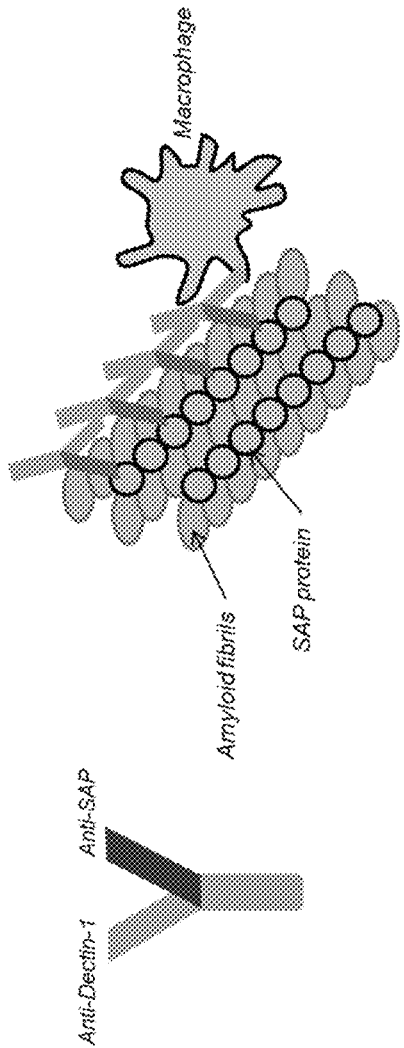

FIG. 24 is a schematic of targeted phagocytosis of amyloid deposits in amyloidosis using Dectin-1 agonistic bispecific antibodies.

Figures 25A, 25B:
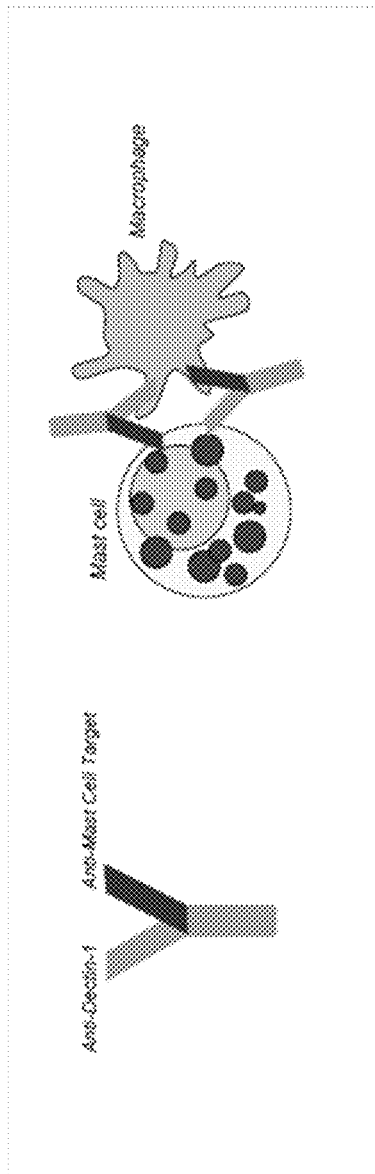

FIGS. 25A-25B show strategies for targeted depletion of mast cells using Dectin-1 agonistic bispecific antibodies. FIG. 25A is a schematic of depletion of mast cells by Dectin-1 agonistic bispecific antibodies. FIG. 25B shows a list of potential targets for mast cell depletion.

Figure 26:
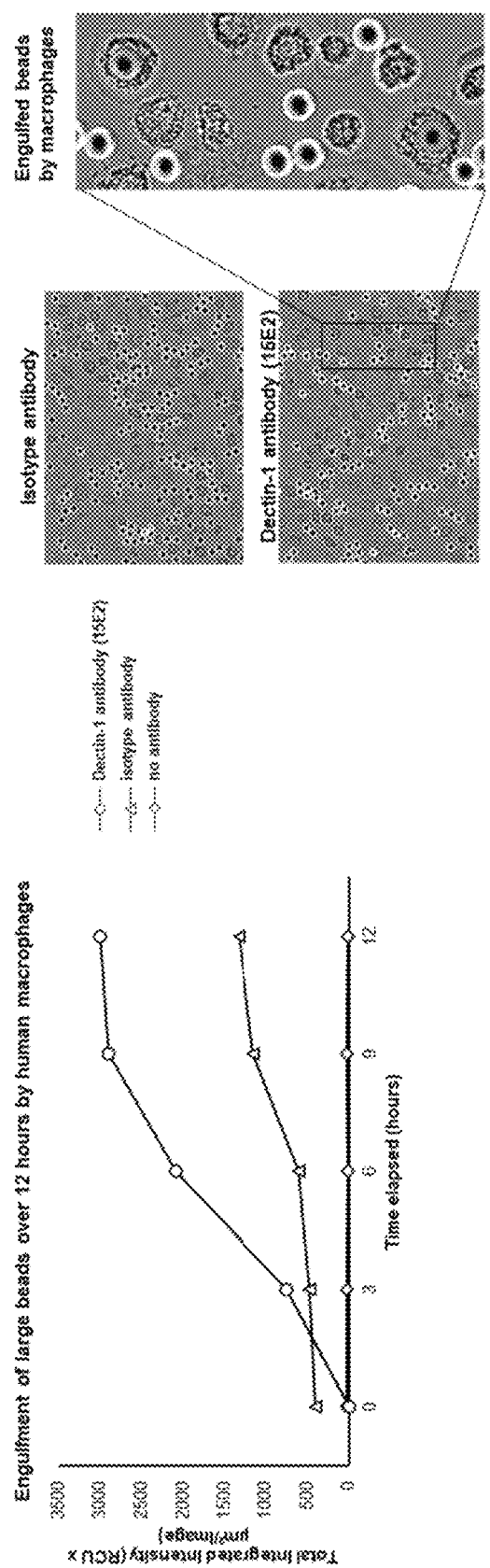

FIG. 26 shows the phagocytosis of large (~16.2 μm) phrodo-labelled beads by human dendritic cells. FIG. 26 shows the quantification of phagocytosis of beads over 12 hours (left), and representative images of pHrodo positive cells at 3 hours of phagocytosis (engulfed beads fluoresce brightly red in phagosomes; right). Dectin-1 antibody promoted the directed phagocytosis of beads in cultured monocyte-derived dendritic cells.

Figure 27:
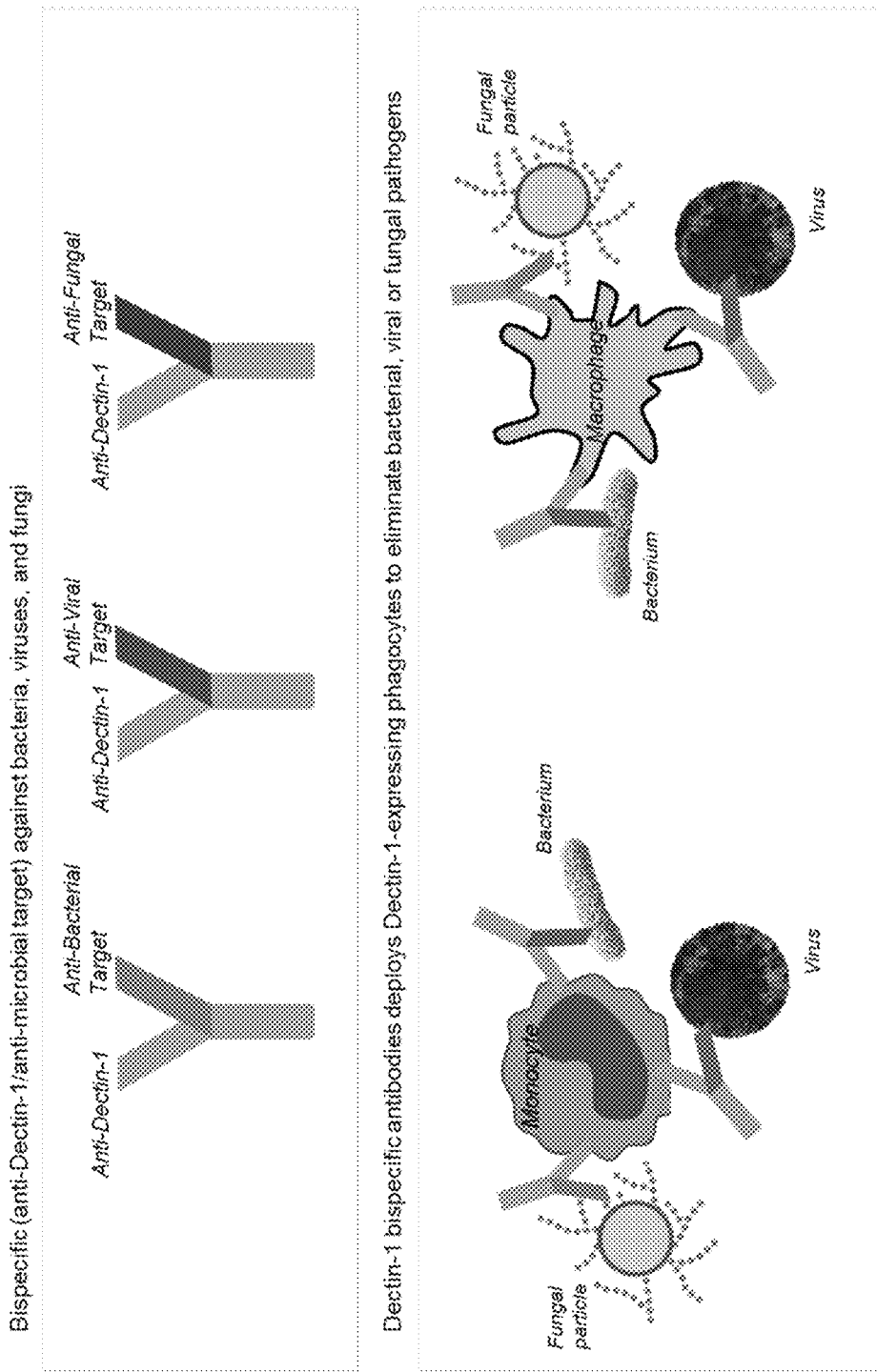

FIG. 27 is a schematic of targeted depletion of microbes by Dectin-1 agonistic bispecific antibodies. Bispecific antibodies with a Dectin-1-binding arm and a microbial agent-binding arm are generated to target bacteria, viruses or fungi (top). The Dectin-1 bispecific antibodies deploy Dectin-1-expressing phagocytes to eliminate bacterial, viral or fungal pathogens (bottom).

Figure 28A:
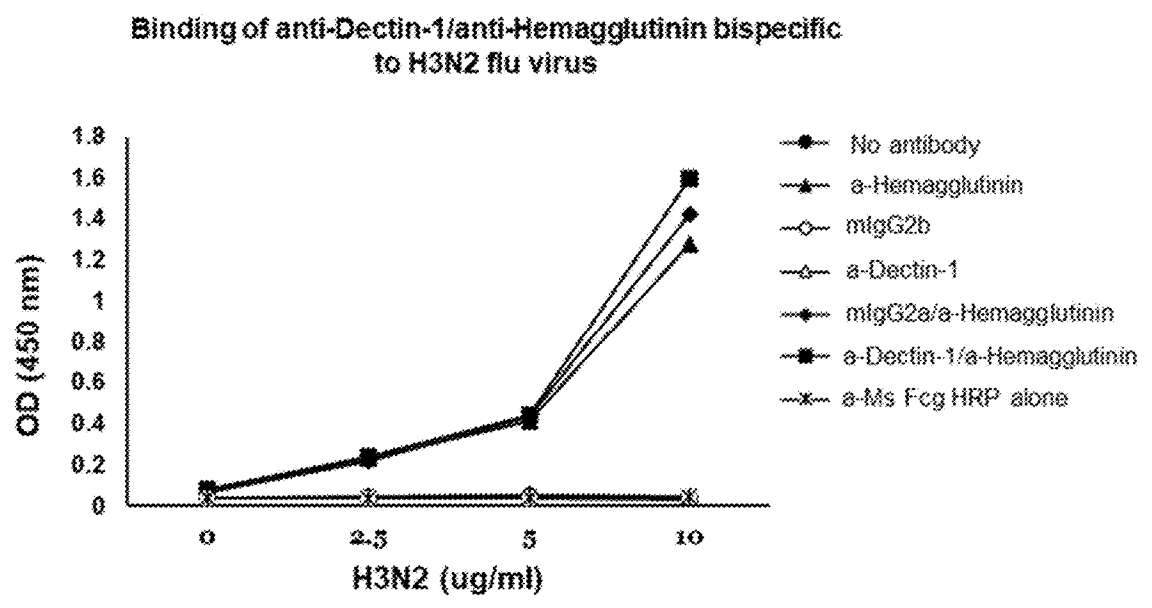
Figure 28B:
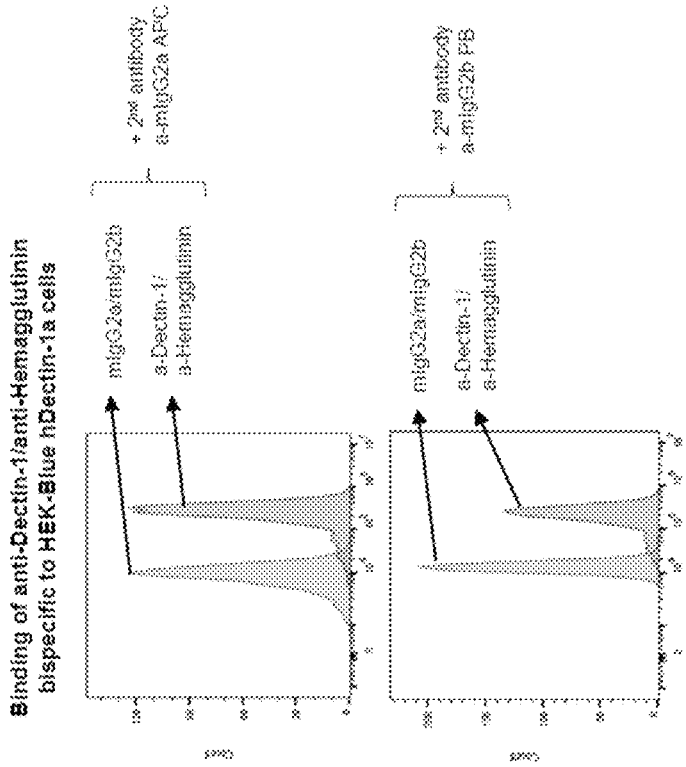

FIGS. 28A-28B show binding of bispecific antibodies comprised of Dectin-1 antibody (15E2 clone) conjugated to anti-H3N2 Hemagglutinin antibody (12CA5 clone) to the H3N2 flu virus and to Dectin-1-expressing cells. FIG. 28A shows the binding analysis of an anti-Dectin-1/anti-Hemagglutinin bispecific antibody to the H3N2 flu virus as assessed by ELISA. 96 well microtiter plates were coated with the H3N2 flu viral particles followed by incubation of single antibodies, bispecific antibodies and isotype controls. After extensive washing, the primary antibodies were detected with a secondary anti-mouse FcgR HRP antibody. FIG. 28B shows the binding analysis of an anti-Dectin-1/anti-Hemagglutinin bispecific antibody to HEK cells expressing Dectin-1 by flow cytometry. HEK cells were incubated with the primary antibodies followed by detection with a secondary fluorescent antibody against the anti-Dectin-1 antibody (anti-mIgG2a APC) or the Hemagglutinin antibody (anti-mIgG2b PB). The anti-Dectin-1/anti-Hemagglutinin bispecific antibody bound efficiently to both the H3N2 flu virus and to HEK cells expressing Dectin-1.

Figure 29A:
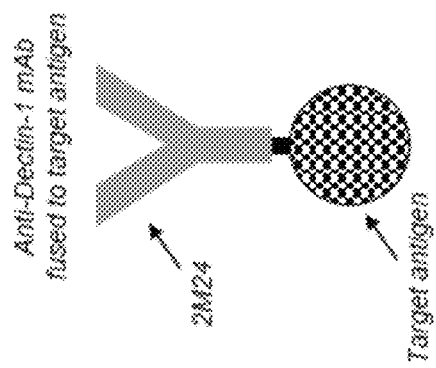
Figure 29B:
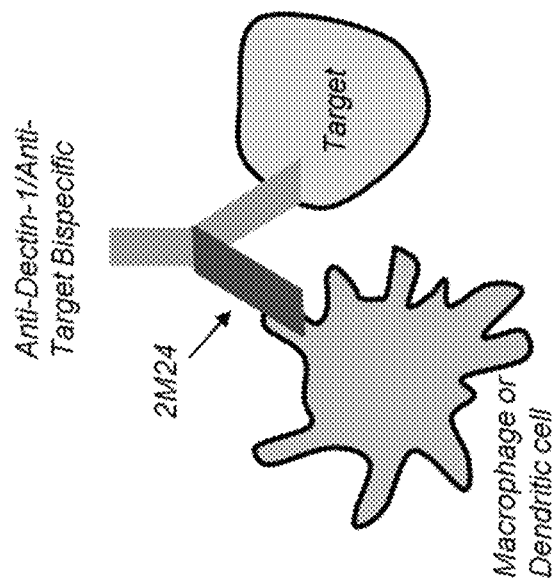

FIGS. 29A-29B show schematic diagrams using anti-Dectin-1 antibodies to deliver antigens for vaccine development, using anti-Dectin-1 antibodies fused to target antigens for delivery to APCs (FIG. 29A), or anti-Dectin-1 bispecific antibodies for targeted delivery of disease-causing agents (e.g., cells, microbes, proteins, etc.) to APCs (FIG. 29B).

Figure 30:
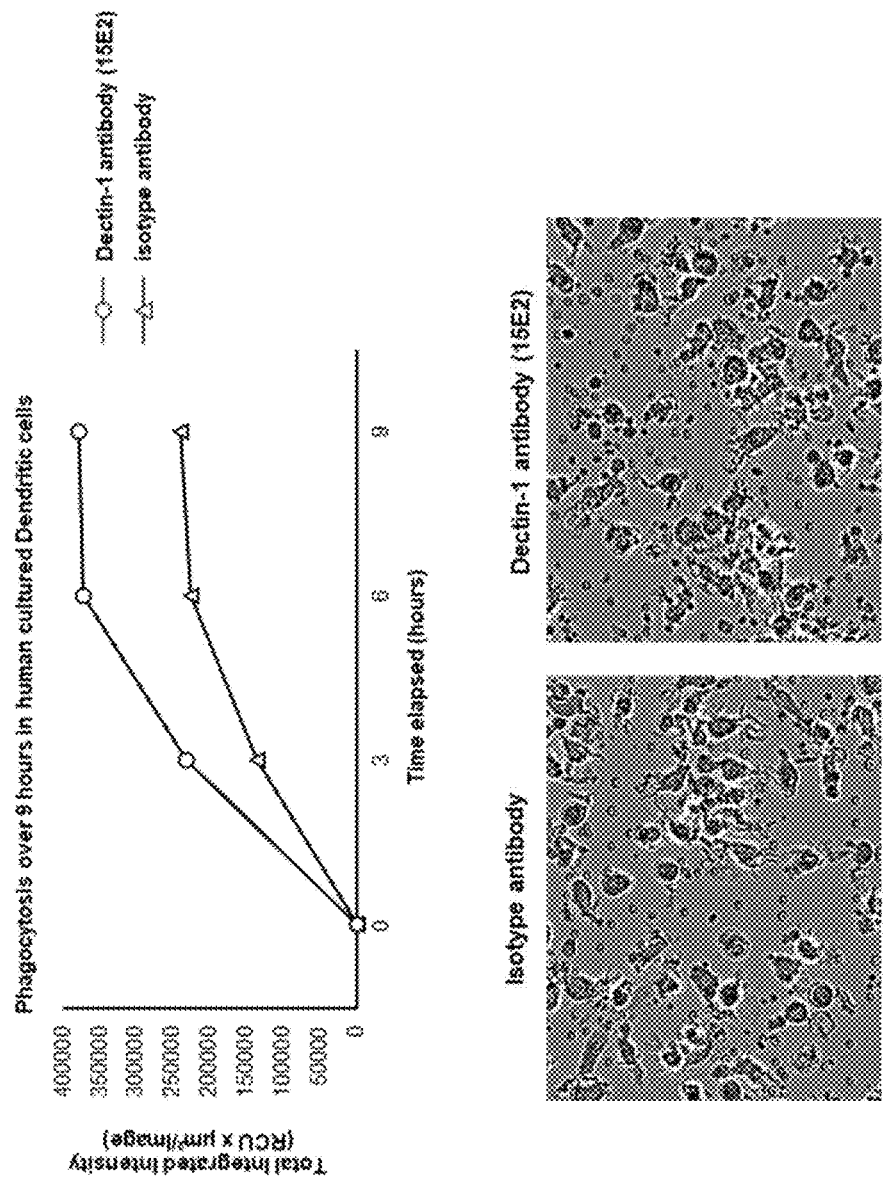

FIG. 30 shows the phagocytosis of pHrodo-labeled polystyrene anti-mouse Fc IgG beads (~3.4 μm) conjugated with Dectin-1 antibody (15E2) or isotype control antibody by human dendritic cells. Polystyrene anti-mouse Fc IgG beads were labeled with a pH-sensitive fluorescent dye (pHrodo Red) and conjugated with a Dectin-1 antibody or isotype control. The beads were then incubated with cultured monocyte-derived dendritic cells at a ratio of 1:3 (cells:beads). Bead phagocytosis was monitored by IncuCyte live cell imaging. Phagocytosis was quantified using the IncuCyte analysis software and expressed as total integrated intensity (total sum fluorescent intensity) of red objects (pHrodo) in the image. FIG. 30 shows the quantification of phagocytosis of beads over 9 hours (top) and representative images of pHrodo positive cells at 3 hours of phagocytosis (engulfed beads fluoresce brightly red in phagosomes; bottom).

Figure 31A:
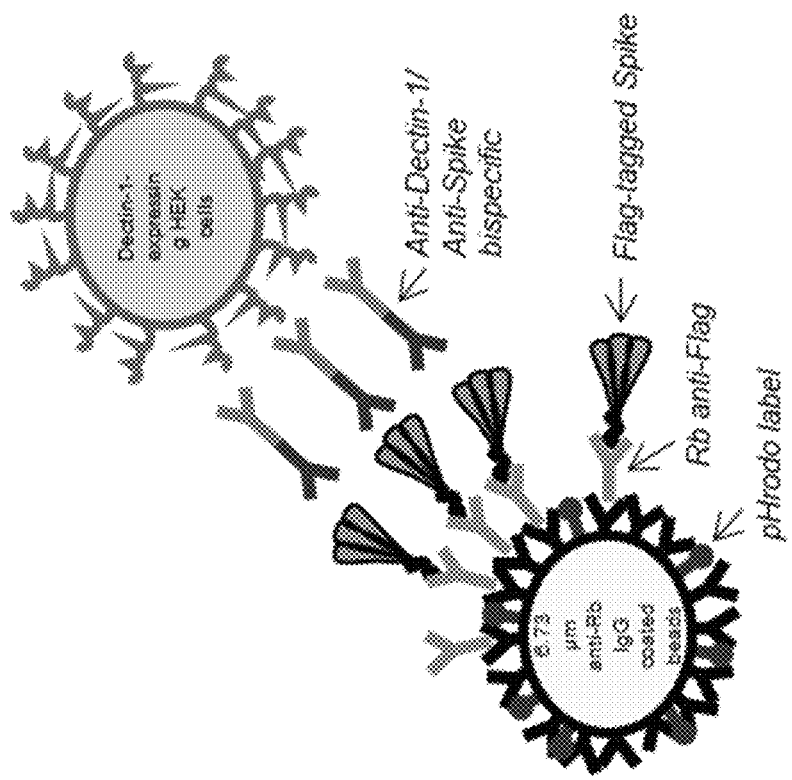
Figure 31B:
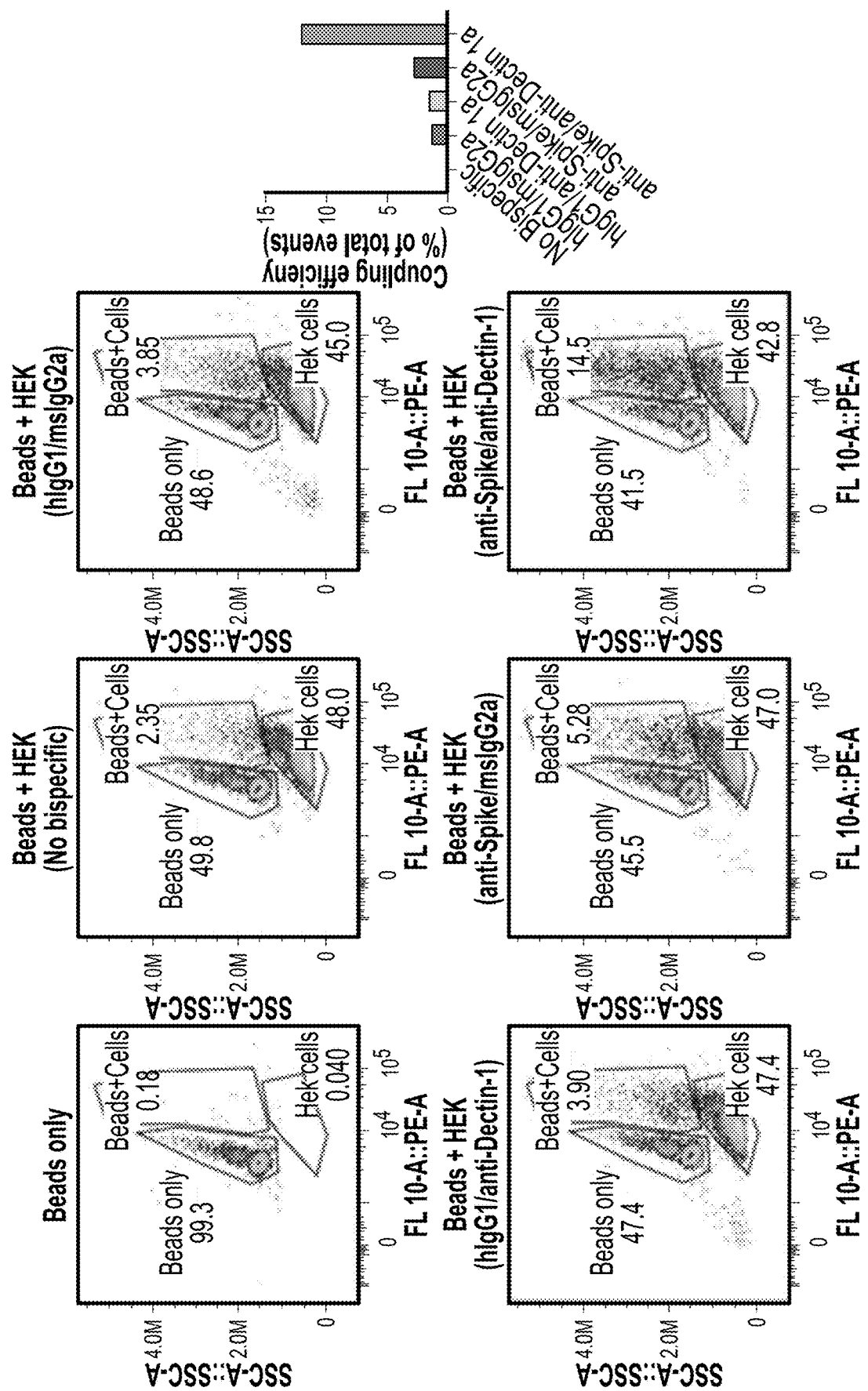
Figure 31C:
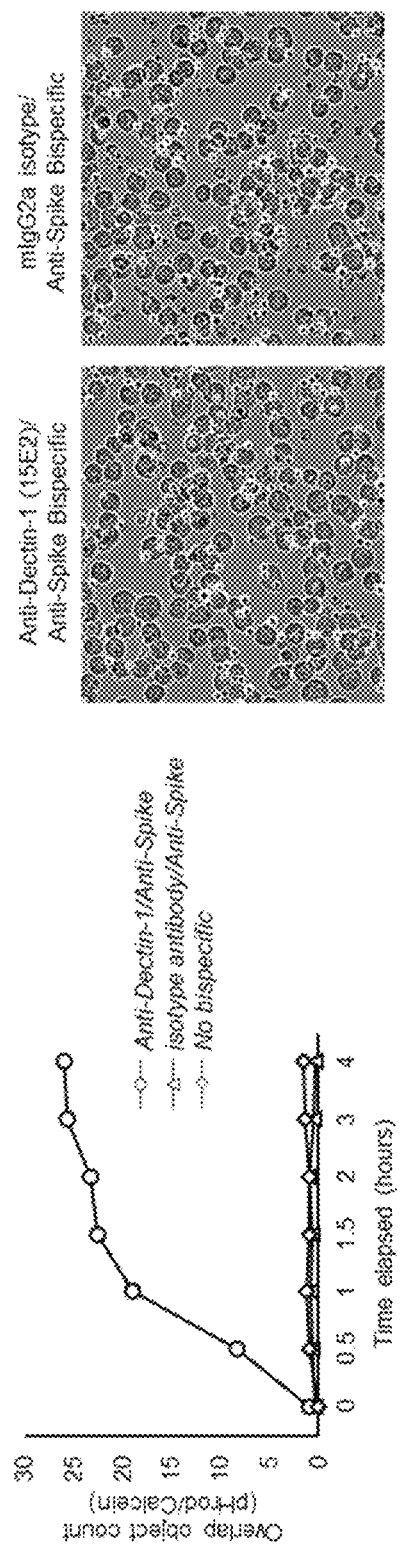

FIGS. 31A-31C show the phagocytosis of SARS-CoV-2 Spike protein-coated beads by Dectin-1-expressing HEK 293 cells. FIG. 31A is a schematic illustration of the experiment. Beads coated with the Spike protein from SARS-CoV-2 are coupled to Dectin-1-expressing HEK 293 cells by an anti-Dectin-1 bispecific antibody comprising a Dectin-1 protein binding arm and a Spike protein binding arm. FIG. 31B shows a flow cytometry characterization of effector (HEK 293 cells) and target (Spike-coated beads) engagement by the bispecific and isotype controls (panel A), as well as a quantification of coupling efficiency based on doublet population (panel B). FIG. 31C shows the phagocytosis of SARS-CoV-2 Spike protein-coated beads by HEK 293 cells in a co-culture experiment. Phagocytosis of pHrodo-labeled beads was monitored by the change in pHrodo fluorescence as a result of acidic pH in phagosomes. FIG. 31C shows quantification of phagocytosis (left), which was quantified by the Incucyte analysis software and expressed as overlap of red object count (pHrodo) to calcein-positive cells, as well as representative images of pHrodo-positive cells at 2 hours of phagocytosis (engulfed beads fluoresce brightly red in phagosomes; right).

Figure 32A:
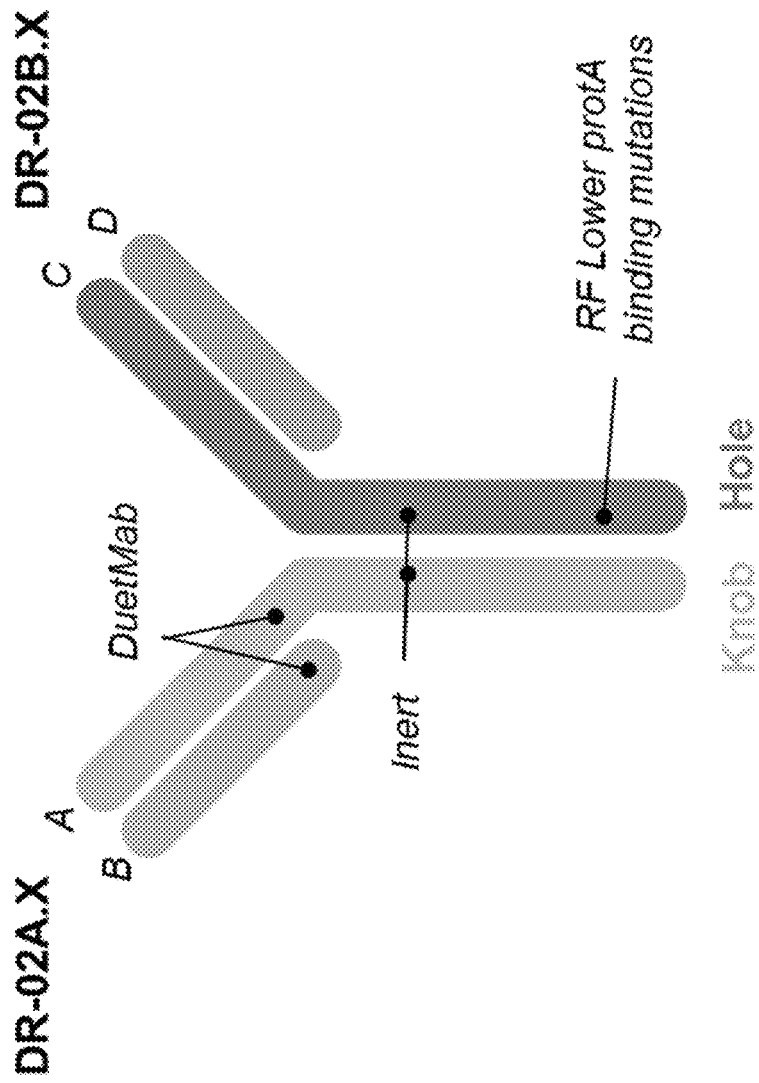
Figure 32B:
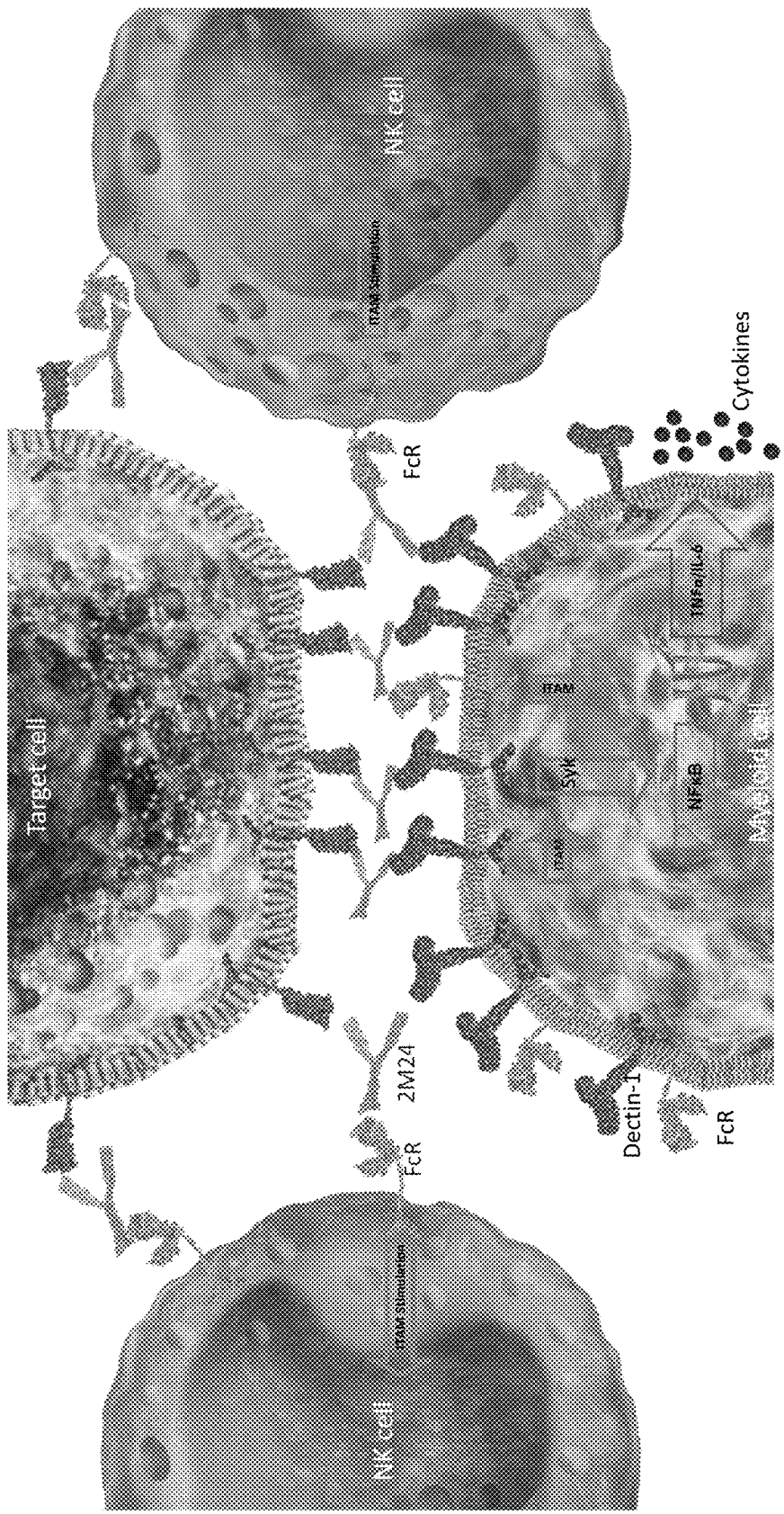

FIGS. 32A & 32B show a bispecific antibody design for human bispecific antibodies (e.g., human IgG1 bispecific antibodies) targeting Dectin-1 and a disease target or antigen. FIG. 32A provides a diagram of the design. One arm (2M24A.X) with VH domain A and VL domain B targets human Dectin-1, while the other arm (2M24B.X) with VH domain C and VL domain D targets a disease target or antigen. FIG. 32B provides a diagram of an exemplary mechanism of action for an anti-Dectin-1 bispecific antibody with an active Fc domain, which targets hDectin-1 (via the first arm) on myeloid cells, an antigen on a target cell/disease-causing agent (via the second arm), and Fc receptors on myeloid and NK cells, eliciting robust immune stimulation and phagocytosis.

Figure 33A:
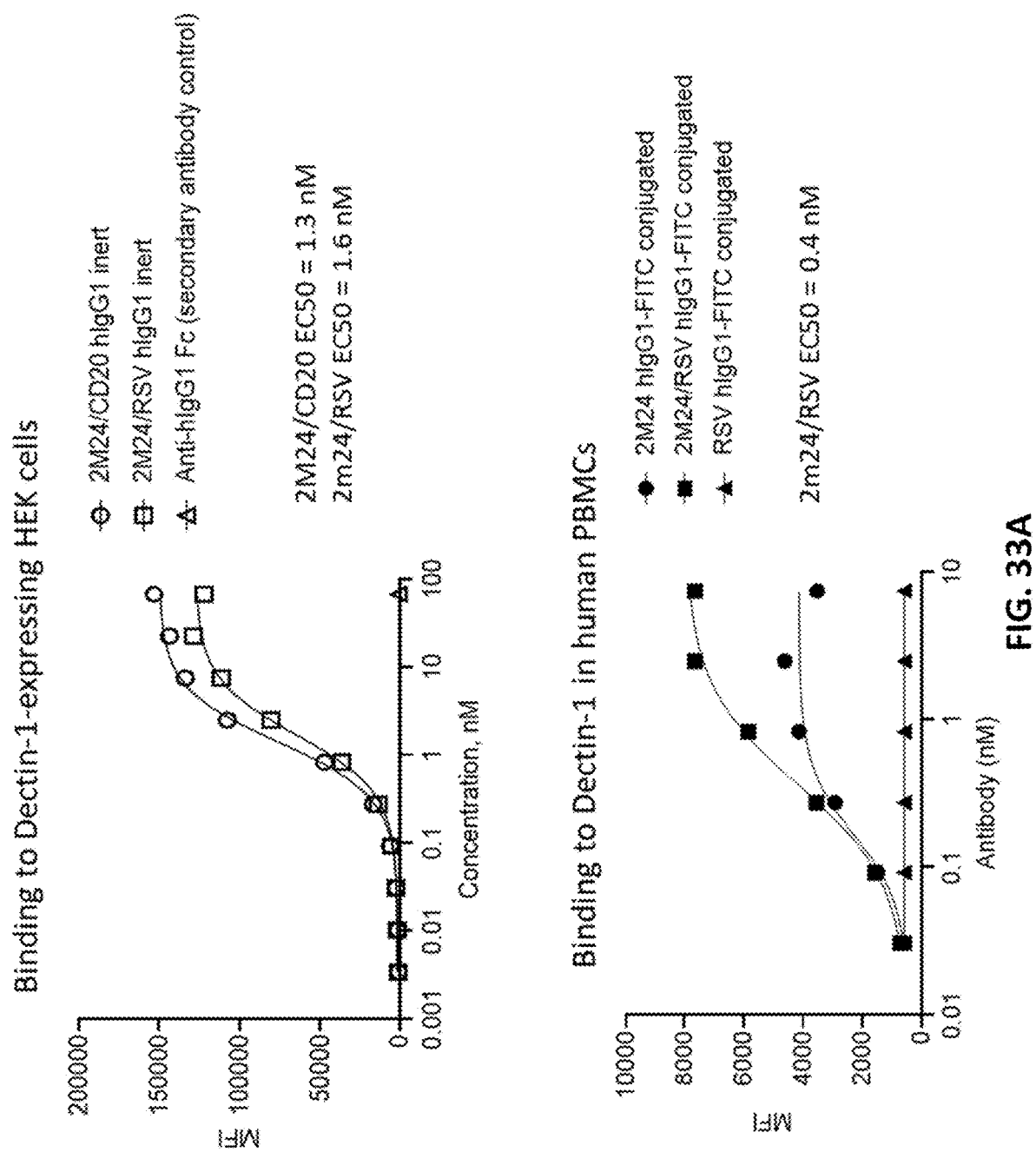
Figure 33B:
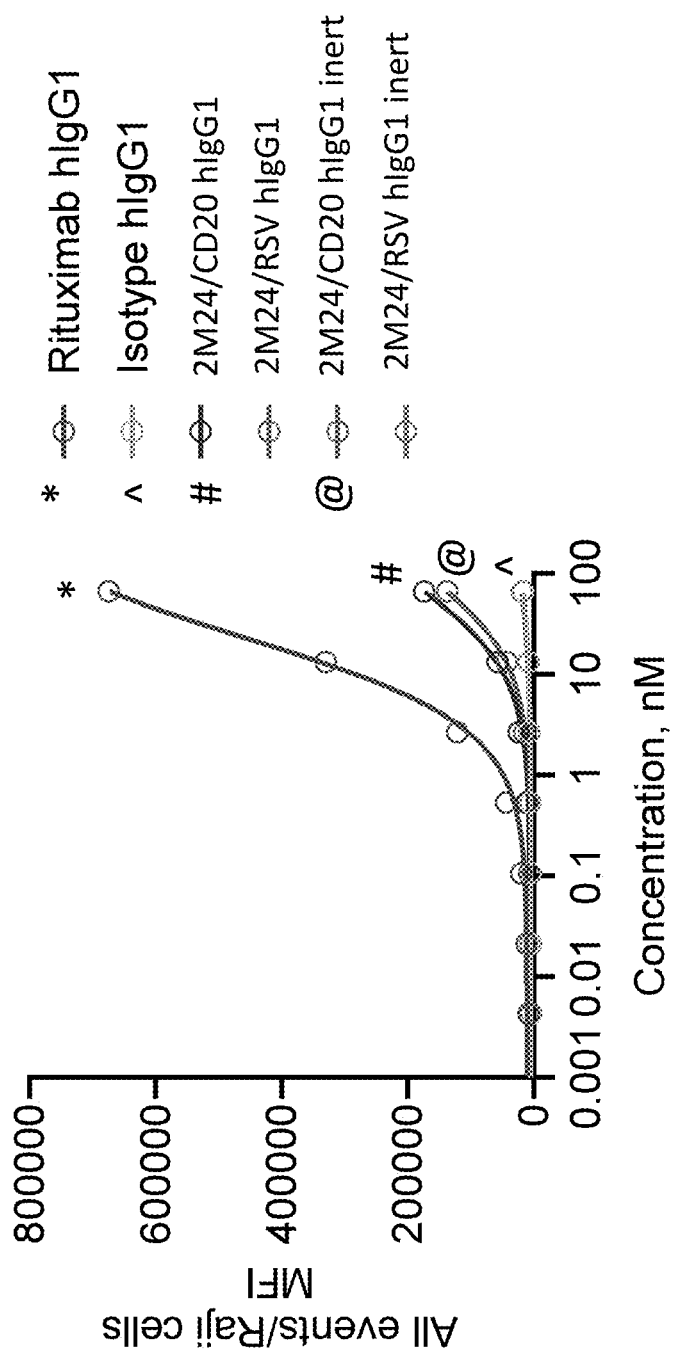

FIGS. 33A & 33B show that a bispecific antibody with one arm targeting hDectin-1 and the other arm targeting hCD20 (using the variable domains of rituximab) binds to cells expressing human Dectin-1 or human CD20. FIG. 33A (top panel) shows binding of the bispecific antibody targeting hDectin-1 and hCD20 (2M24/CD20), or a bispecific antibody targeting hDectin-1 and RSV (2M24/RSV), to HEK293 cells stably expressing human Dectin-1, as assessed by flow cytometry. FIG. 33A (bottom panel) shows binding of the bispecific antibody 2M24/RSV hIgG1-FITC conjugated and 2M24 bivalent hIgG1-FITC conjugated to PBMCs, as assessed by flow cytometry. FIG. 33B shows binding of rituximab (human IgG1), 2M24/CD20 with active human IgG1 Fc, 2M24/CD20 with inert human IgG1 Fc, 2M24/RSV with active human IgG1 Fc, or 2M24/RSV with inert human IgG1 Fc to CD20-expressing B cell lymphoma Raji cell line.

Figure 34A:
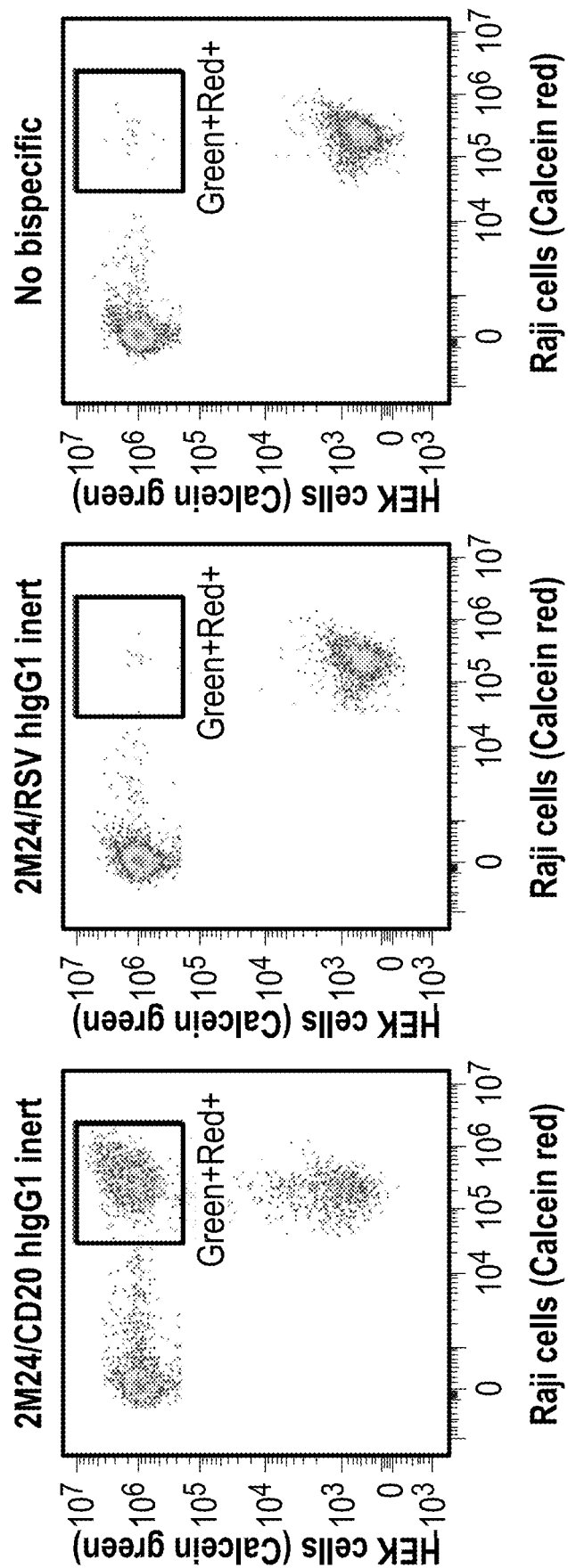
Figure 34B:
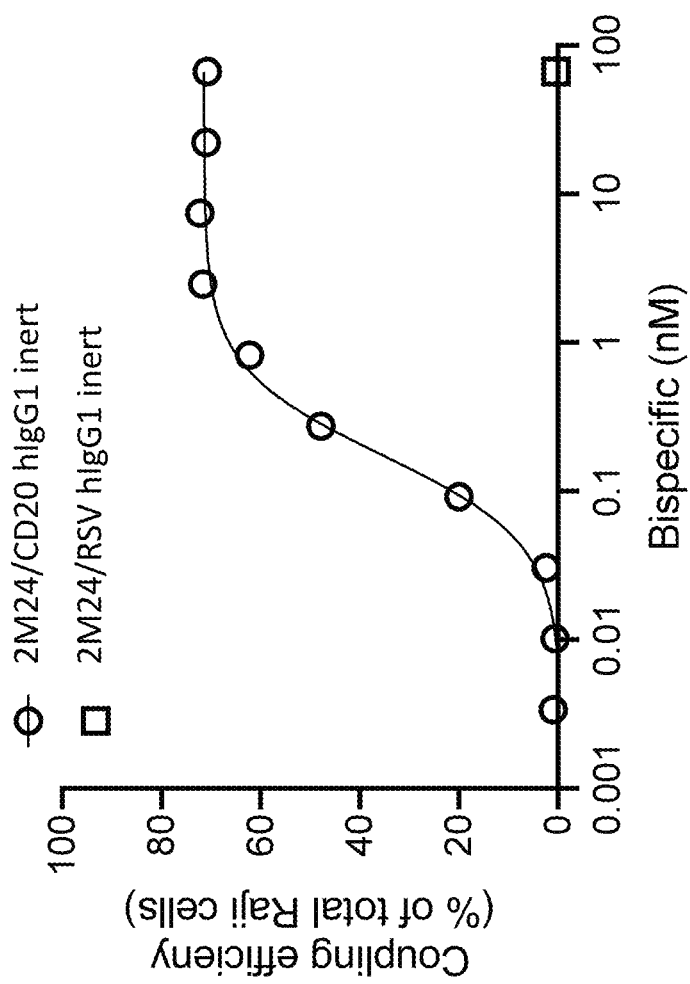

FIGS. 34A & 34B show that bispecific antibody targeting hDectin-1 and hCD20 (2M24/CD20) induces coupling of Dectin-1- and CD20-expressing cells. FIG. 34A: To assess coupling of Dectin-1-expressing HEK293 cells (effector) and CD20-expressing Raji cells (target), cells were differentially labeled with calcein green (effector) or calcein red (target) dyes. Labeled cells were co-cultured and treated with hIgG1 inert 2M24/CD20 or 2M24/RSV (control) bispecific antibody to induce effector:target coupling. Successful coupling of effector:target cells is indicated by the double-positive staining (Calcein green+, calcein red+, square box). FIG. 34B: Dose-titration of bispecifics in co-cultures of effector:target cells. Coupling efficiency is quantified as the percentage of total target cells that binds or couples to effector cells.

Figure 35A:
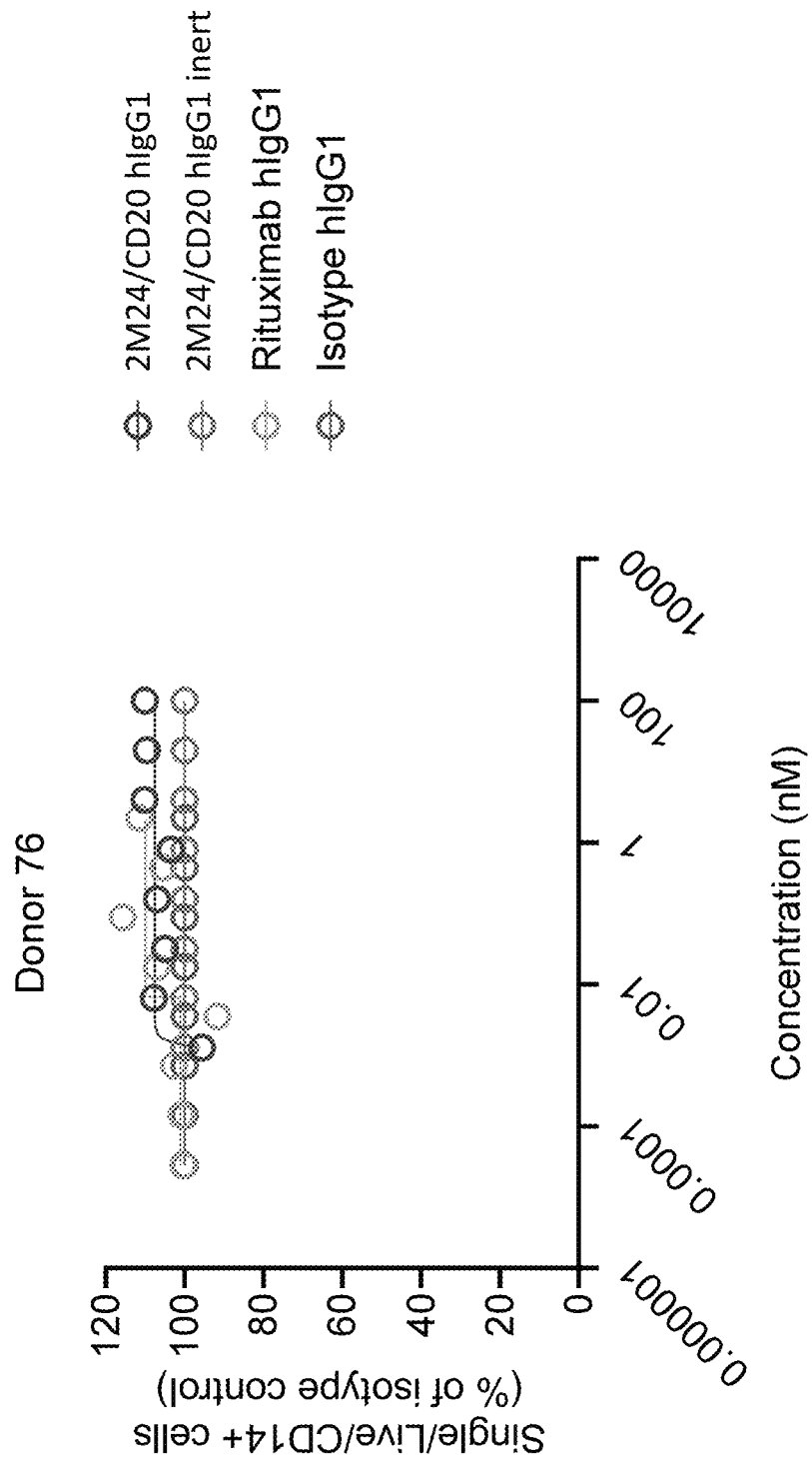
Figure 35B:
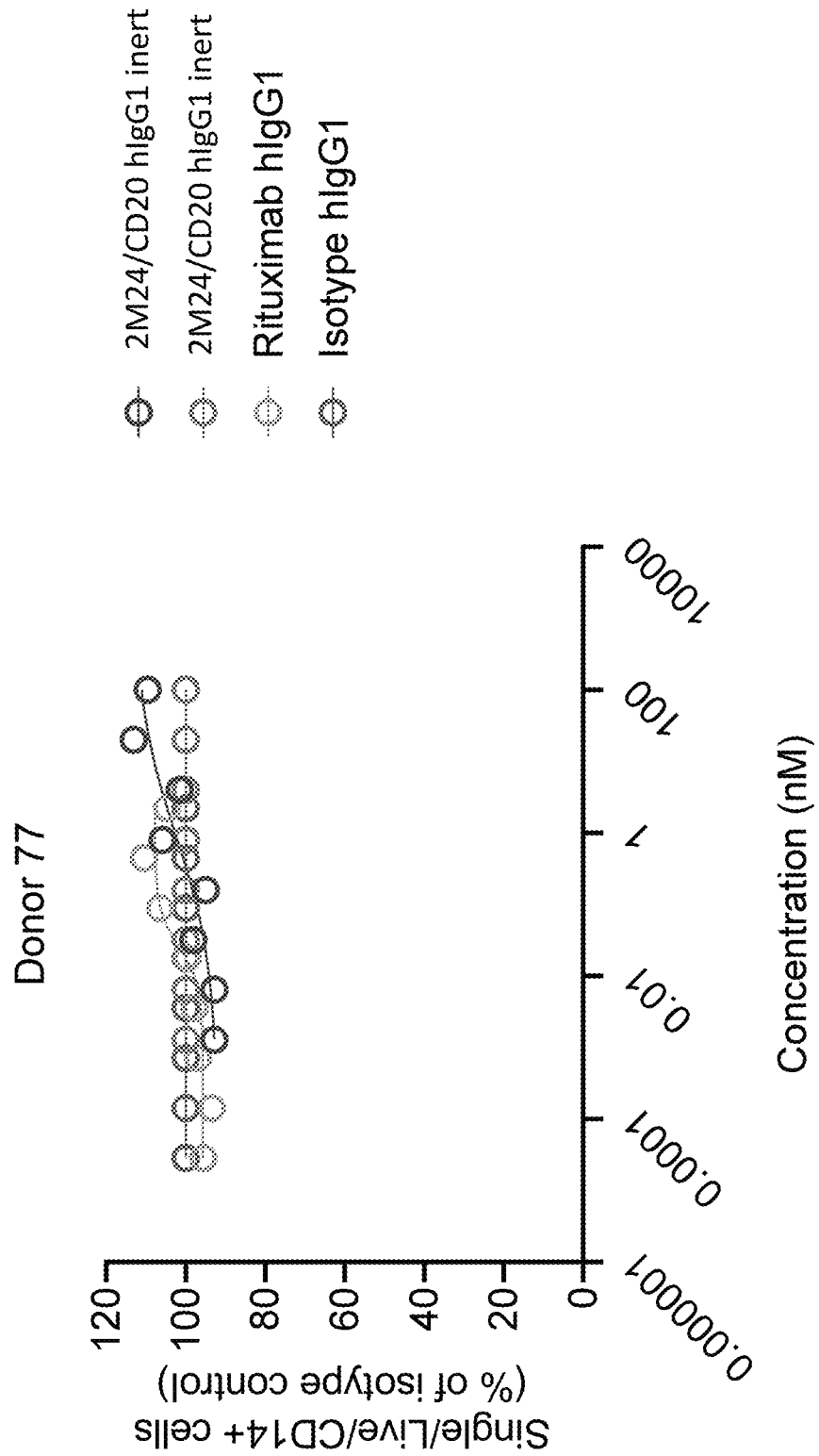

FIGS. 35A & 35B show that bispecific antibody targeting hDectin-1 and hCD20 (2M24/CD20) with an active hIgG1 Fc does not induce monocyte depletion by antibody dependent-cellular cytotoxicity (ADCC) or antibody-dependent cellular phagocytosis (ADCP). PBMCs from two healthy donors—donor 76 (FIG. 35A) and donor 77 (FIG. 35B) were treated with increasing concentrations of 2M24/CD20 bispecific antibody (hIgG1 active or inert isotypes) and rituximab for 24 h, and subsequently analyzed by flow cytometry to quantify the levels of live, CD14+ monocytes remaining (as a % of isotype controls).

Figure 36A:
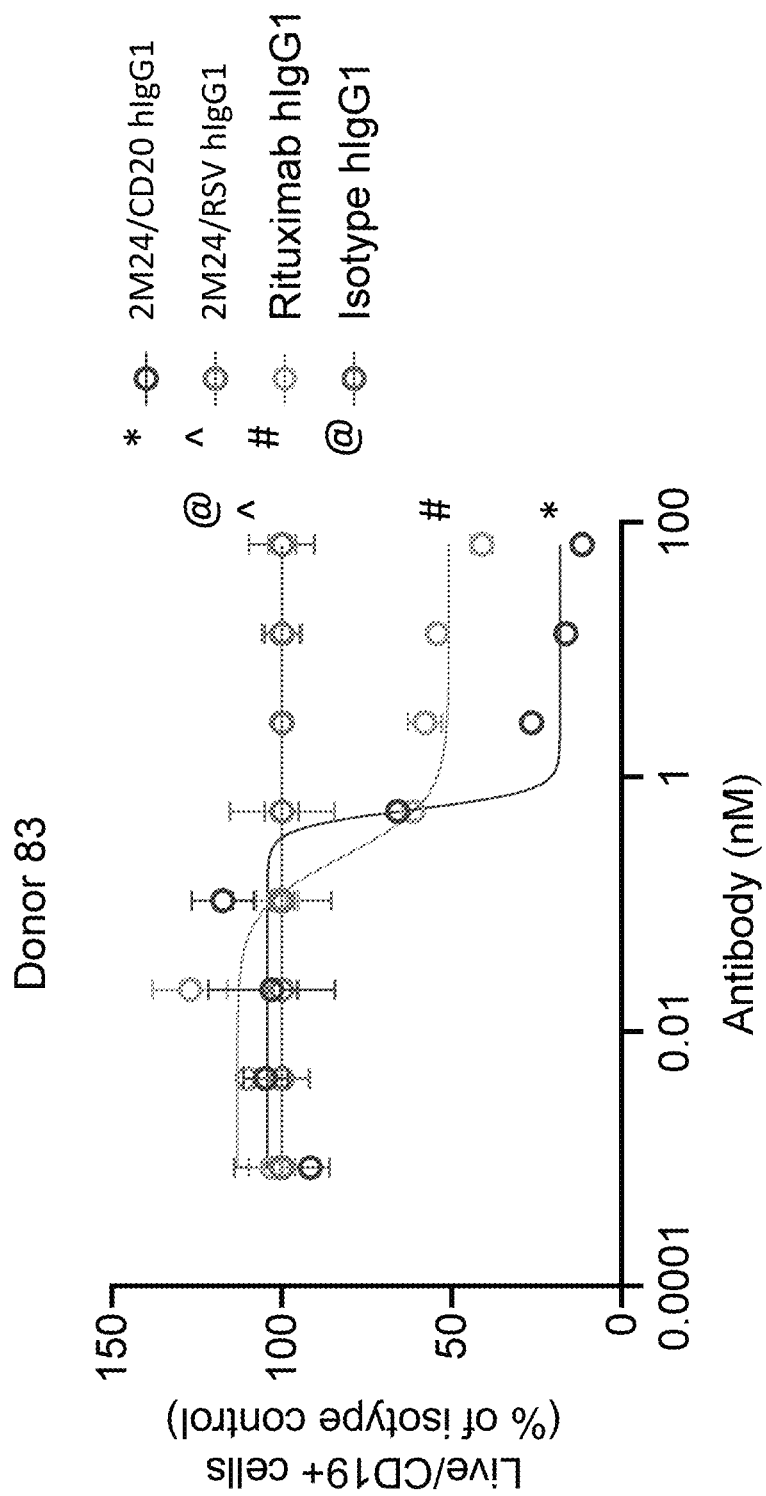
Figure 36B:
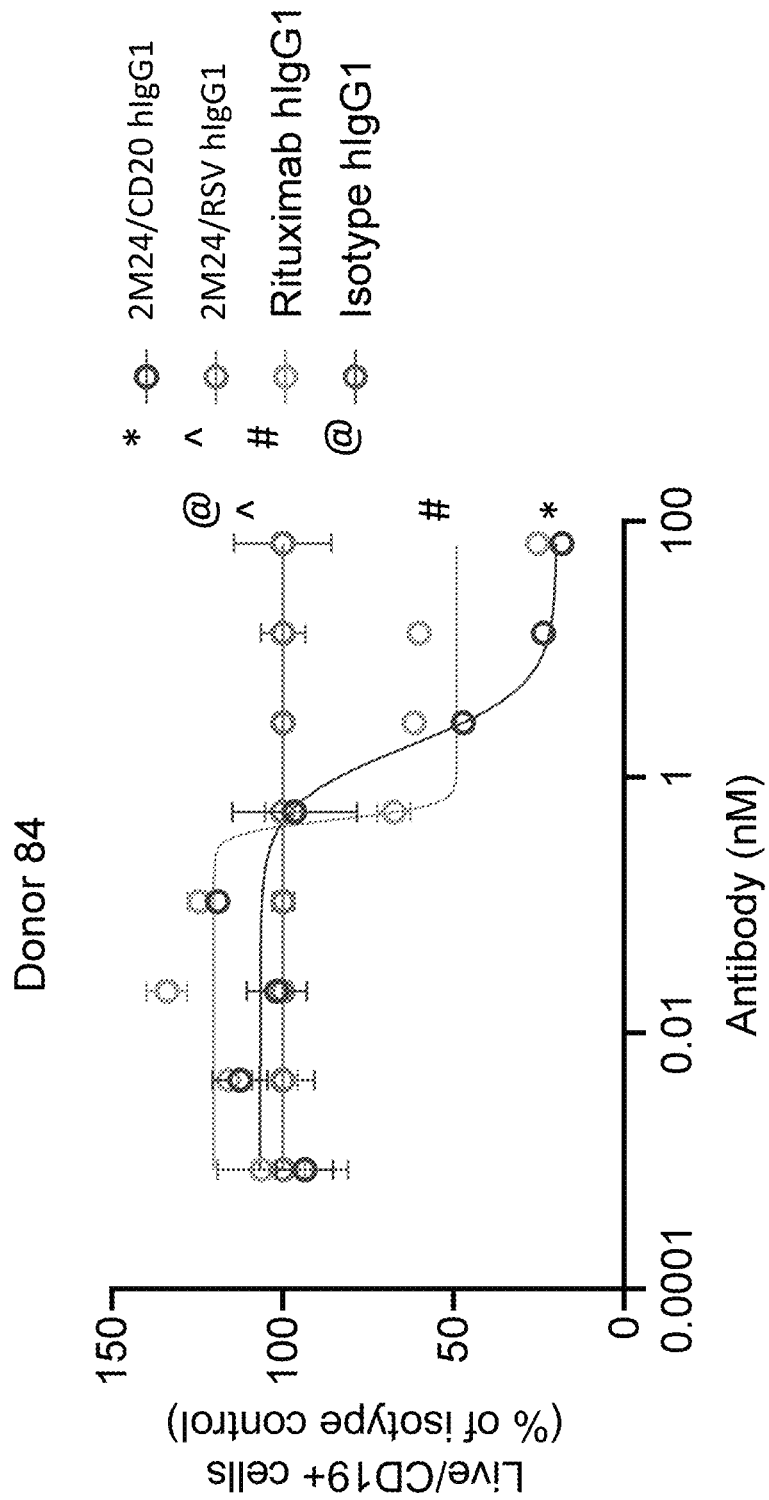

FIGS. 36A & 36B show that bispecific antibody targeting hDectin-1 and hCD20 (2M24/CD20) with an active hIgG1 Fc elicits superior B cell depletion compared to Rituximab. PBMCs from two healthy donors—donors 83 (FIG. 36A) and 84 (FIG. 36B)—were treated with increasing concentrations of the indicated antibodies for 24 h, and subsequently analyzed by flow cytometry to quantify the levels of remaining live, CD19+ B cells (reported as a % of B cells in isotype control-treated PBMCs).

Figure 37A:
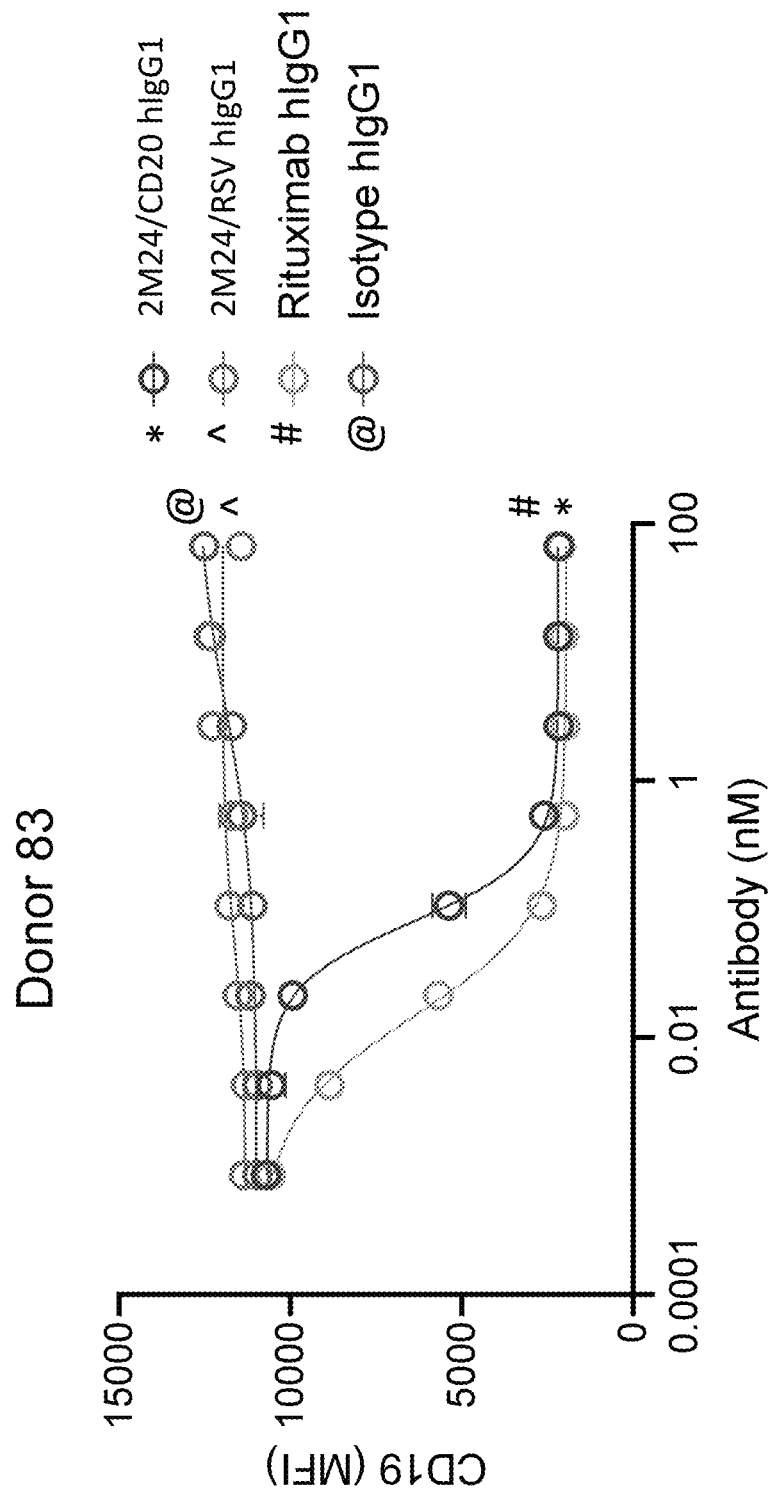
Figure 37B:
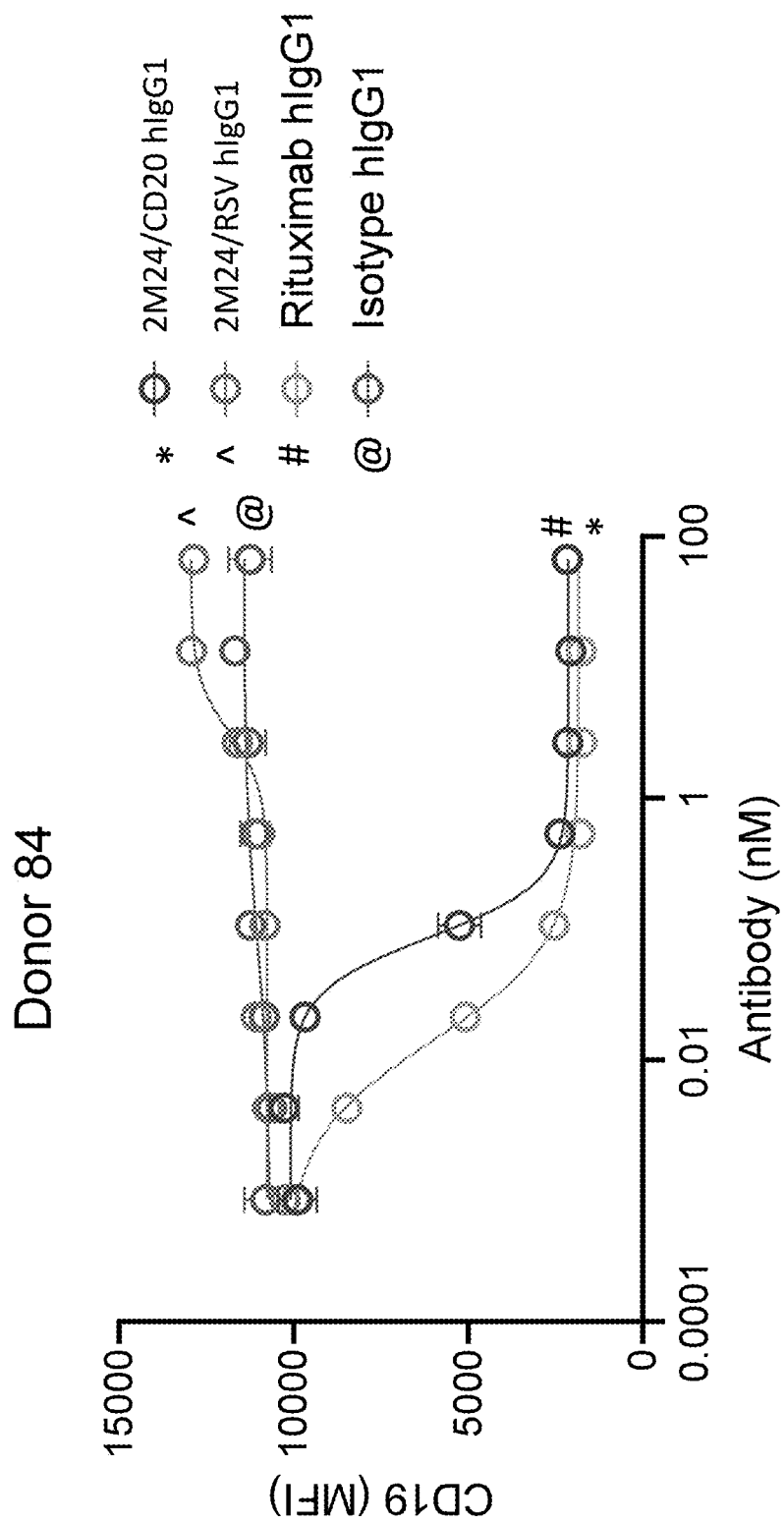

FIGS. 37A & 37B show that Rituximab induces higher B cell shaving (CD19 downregulation) compared to 2M24/CD20 active IgG1 bispecific antibody. Expression of CD19+ on B cells from two healthy donors—donor 83 (FIG. 37A) and donor 84 (FIG. 37B)—was quantified by flow cytometry following a 24-hour incubation with increasing concentration of 2M24/CD20 hIgG1 (active isotype) bispecific antibody, Rituximab, or isotype controls. The mean fluorescent intensity (MFI) for CD19 staining using anti-CD19 (BV605 conjugated) was used to evaluate the effect of 2M24/CD20 bispecific and Rituximab on CD19 expression on B cells. EC50 values were calculated based on non-linear regression analysis.

Figure 38:
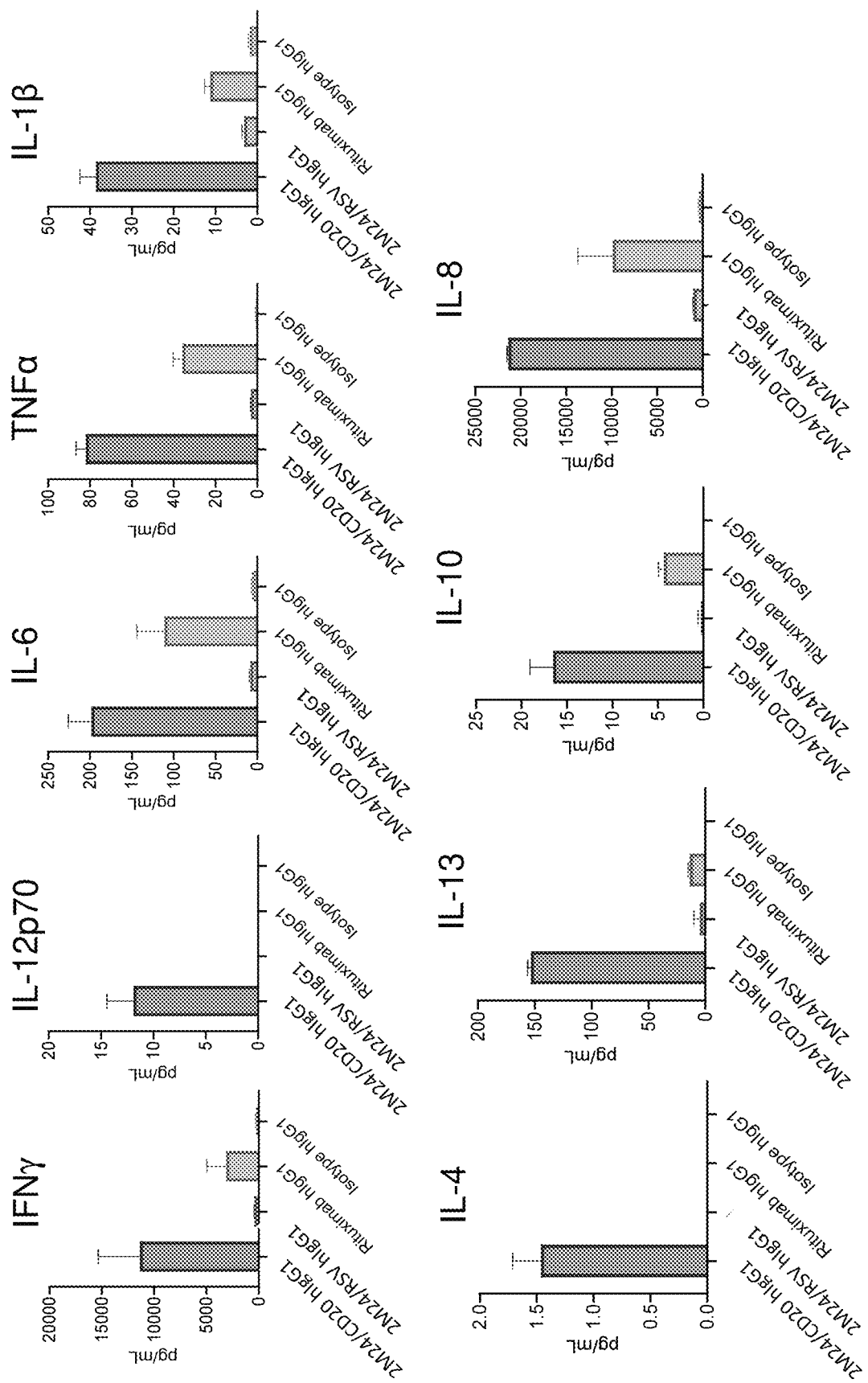

FIG. 38 shows differential cytokine release induced by 2M24/CD20 active IgG1 bispecific antibody as compared to rituximab. ELISA-based (mesoscale discovery) quantification of cytokines was undertaken in supernatants isolated from healthy donor PBMCs treated with 2M24/CD20 active hIgG1 bispecific, Rituximab, or isotype controls. PBMCs were stimulated with antibodies overnight, and supernatants were subsequently analyzed by MSD. Cytokines tested were IFN$\gamma$, IL-12p70, IL-6, TNF$\alpha$, IL-1$\beta$, IL-4, IL-13, IL-10, and IL-8. Each plot shows cytokine secretion (in pg/mL) as a function of antibody used for treatment (from left to right: 2M24/CD20 hIgG1 bispecific, 2M24/RSV hIgG1 bispecific, rituximab hIgG1, and isotype control hIgG1).

Figure 39A:
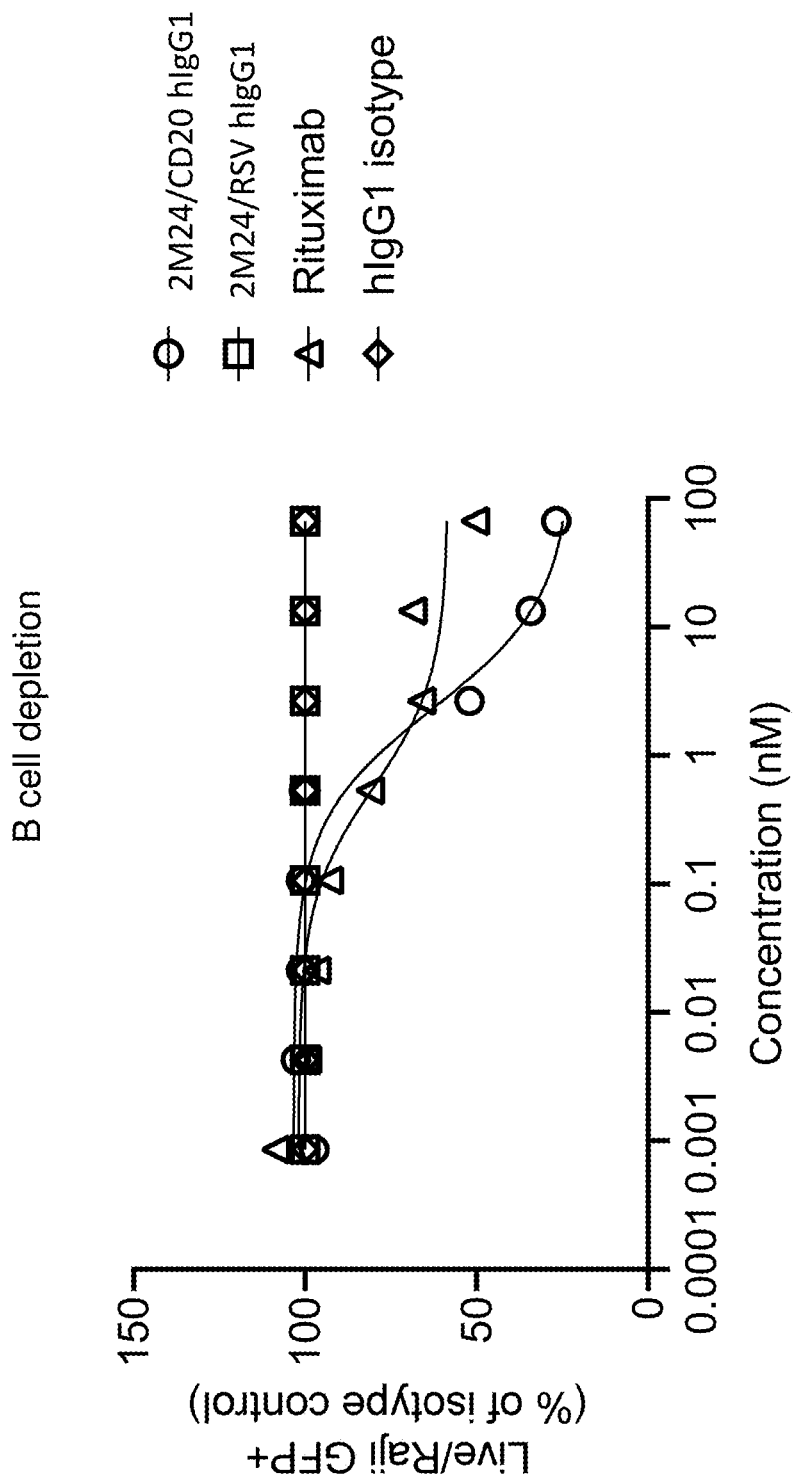
Figure 39B:
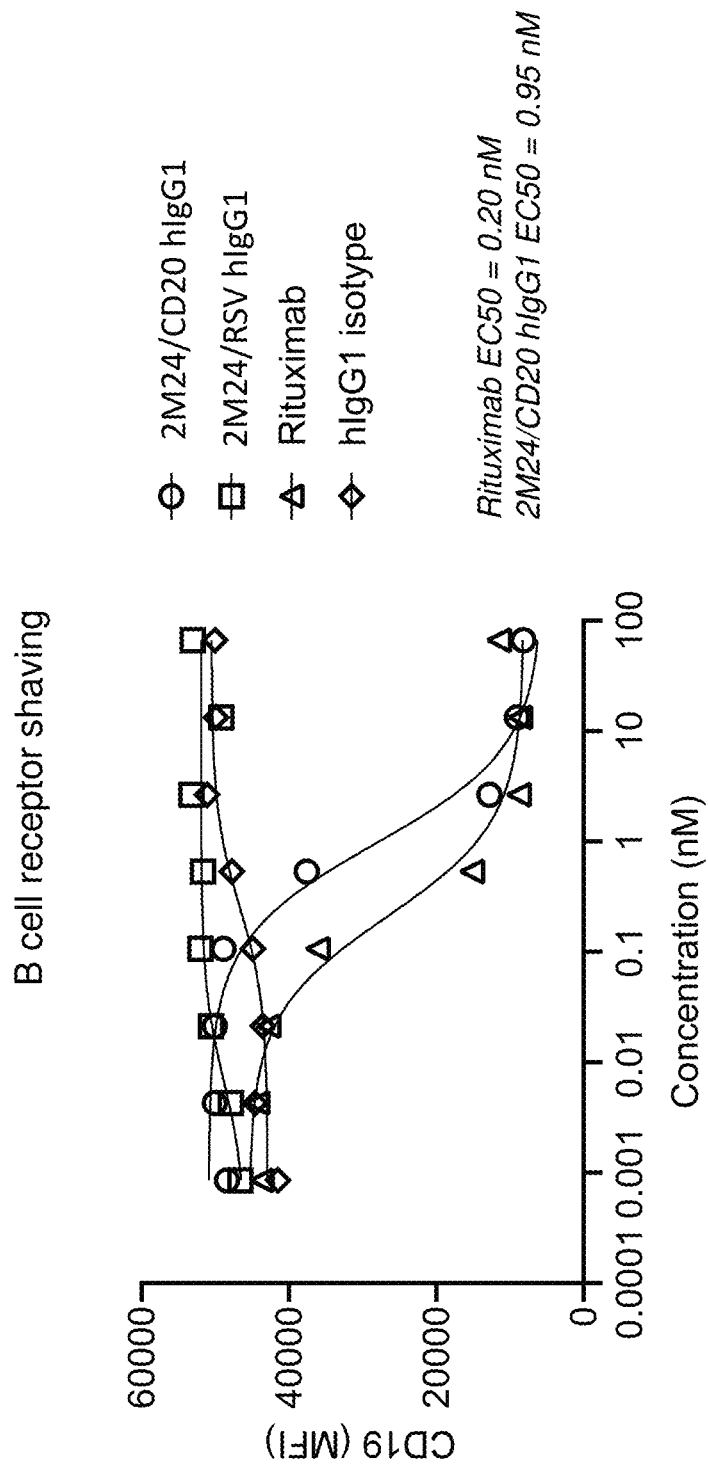

FIGS. 39A & 39B show that 2M24/CD20 hIgG1 (active isotype) bispecific antibody induces superior B-cell depletion and lower CD19 shaving compared to Rituximab in co-cultures of human macrophages and GFP-expressing Raji B cells. FIG. 39A: Flow cytometry analysis of co-cultures of human macrophages and Raji-GFP cells (3:1 ratio) in the presence of 2M24/CD20 hIgG1 (active isotype) bispecific, 2M24/RSV control, fucosylated Rituximab or isotype hIgG1 control. Co-cultures were incubated at 37° C. for 24 hours and then stained with a PE a-CD206 Ab to label macrophages and a BV-605 a-CD19 antibody to label Raji cells. The number of the remaining live/Raji-GFP+ cells was assessed in the end of the experiment. The primary antibodies were used in a serial dose titration. FIG. 39B: Assessment of CD19 on Raji-GFP cells after 24 hours. B-cell receptor shaving is shown as the reduction in the CD19 MFI in the presence of a-Dectin-1/a-hCD20 bispecific or Rituximab.

Figure 40A:
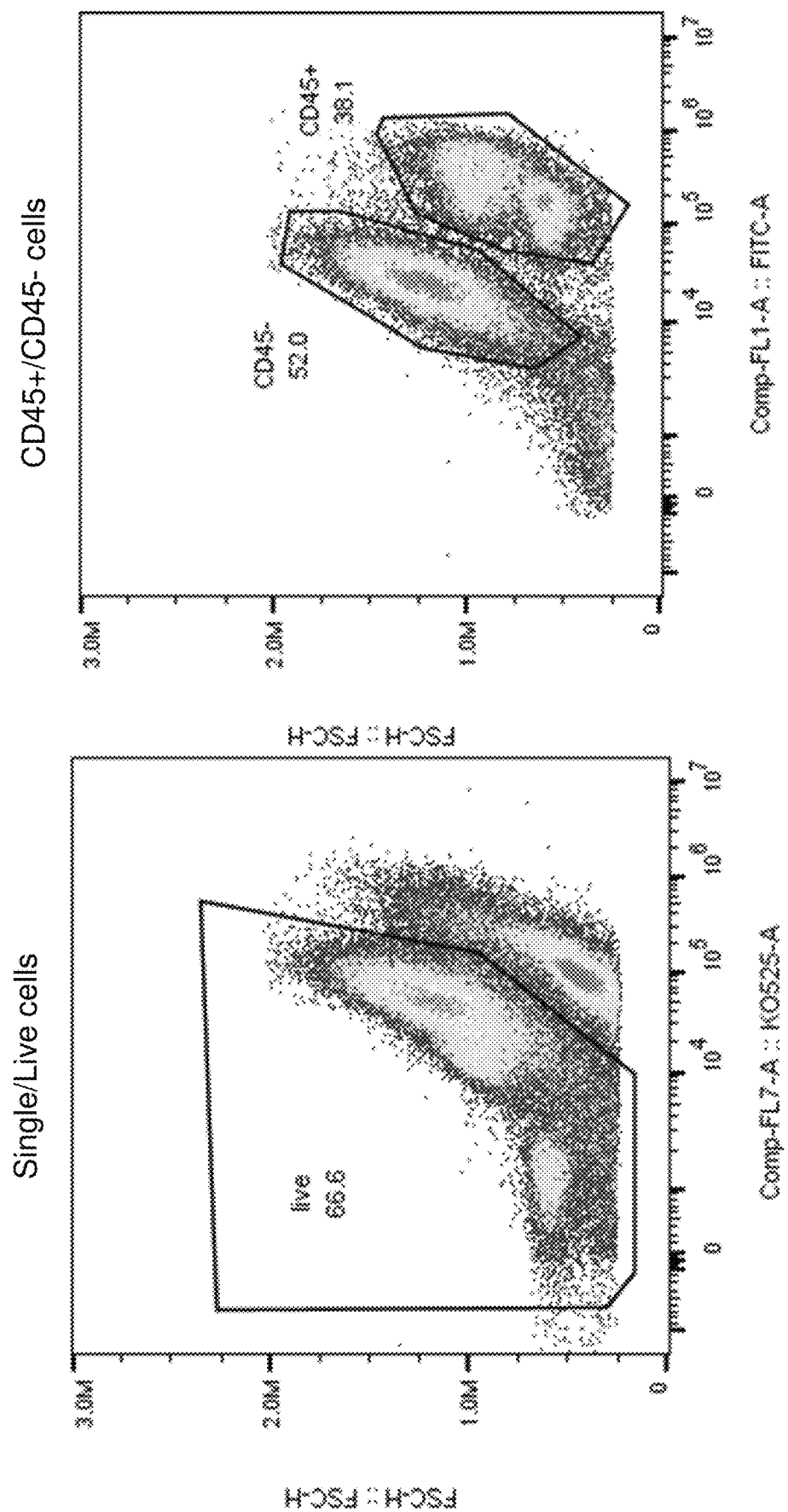
Figure 40B:
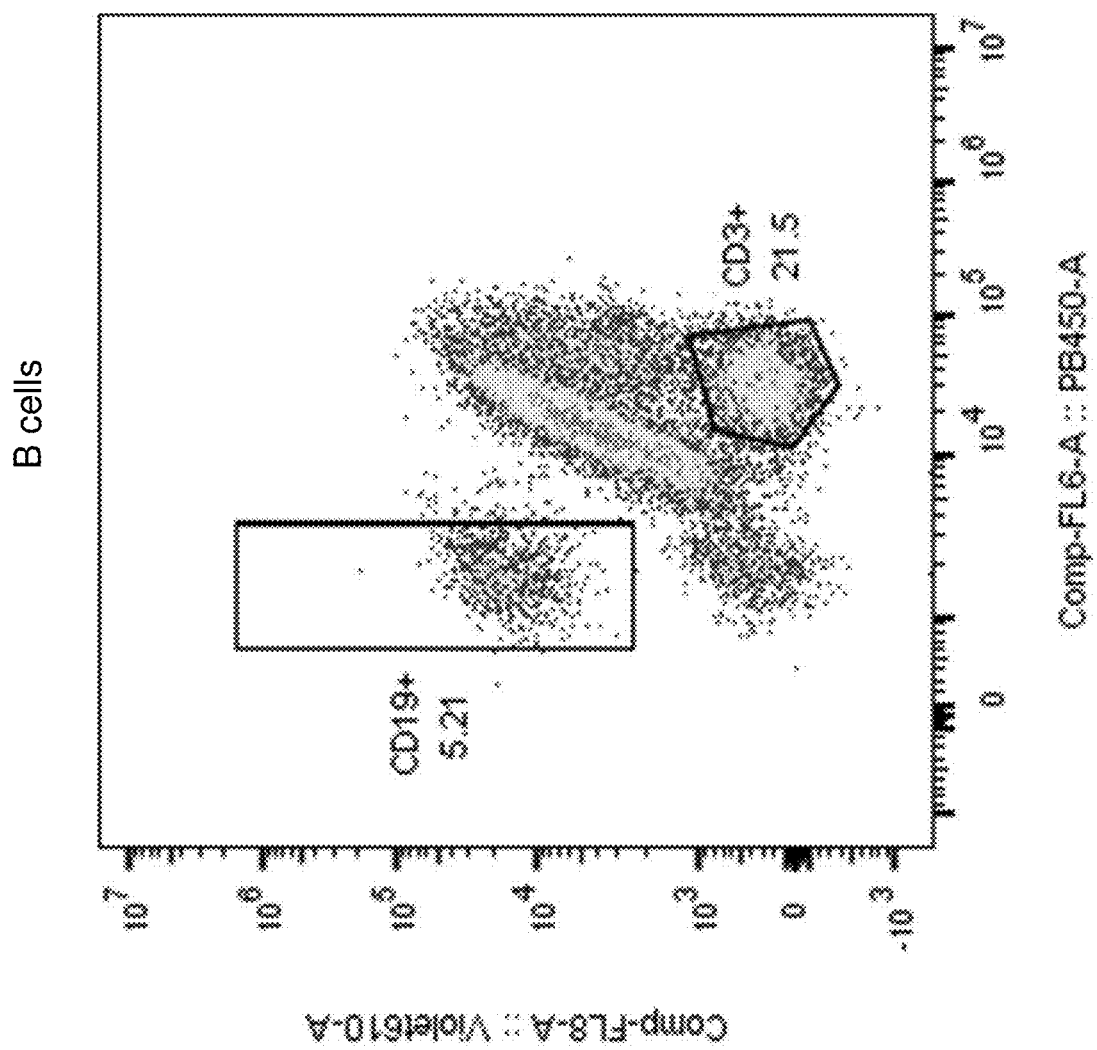
Figure 40C:
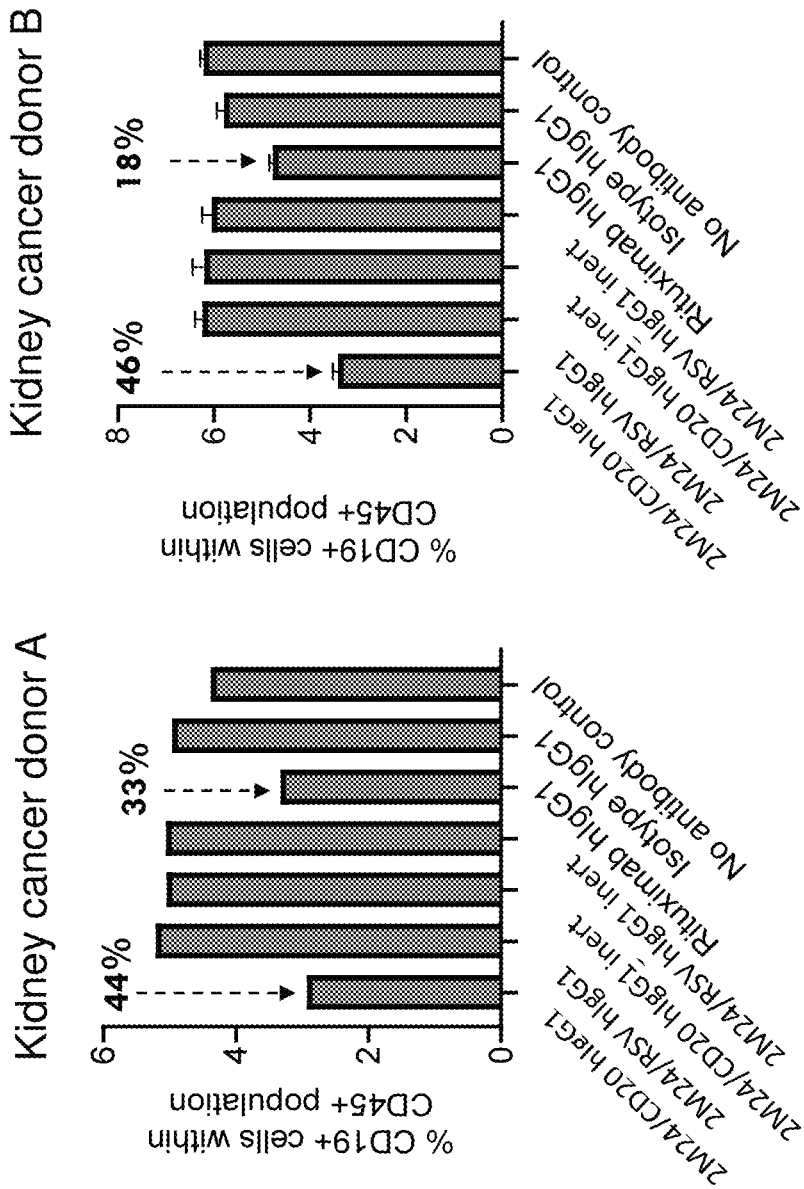

FIGS. 40A-40C show that 2M24/CD20 active IgG1 bispecific antibody induces superior tissue B cell depletion as compared to Rituximab in single cell suspension of kidney cancer biopsies. Single cell suspensions from two Kidney cancer tissue biopsies were analyzed by flow cytometry in the presence of 2M24/CD20 hIgG1 (active or inert) bispecific antibody, 2M24/RSV hIgG1 controls, fucosylated Rituximab, and respective isotype controls. Kidney cancer tissue biopsies were dissociated to single cell suspensions and treated with primary antibodies (2 µg/ml) for 24 hours at 37° C. Immune cell populations were analyzed by flow cytometry. Cells were initially gated for live cells, further separated into CD45+ cells (immune cells) and CD45– cells (non-immune cells), and then CD19+ (B cells) and CD3+ (T Cells) cells were identified within the CD45+ population (FIGS. 40A & 40B). The number of the remaining B cells was assessed by an anti-CD19 antibody and expressed as percentage of the CD45+ immune cell population (FIG. 40C).

Figures 41A, 41B, 41C:
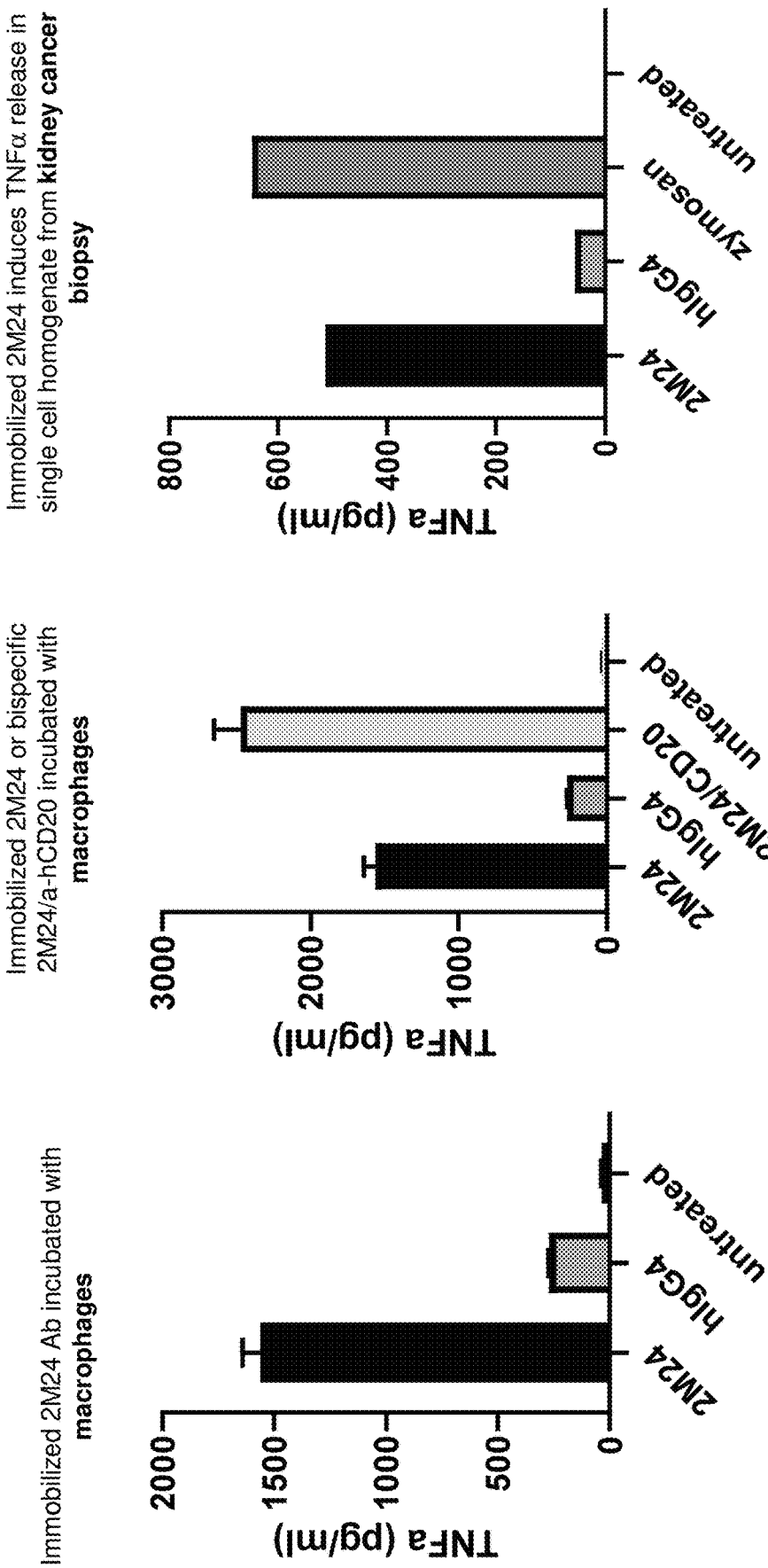

FIGS. 41A-41C show that Anti-Dectin 1 antibody (clone 2M24) induces Dectin 1-clustering and TNF$\alpha$ secretion from human macrophages. Cytokine secretion by cultured macrophages and single cell suspension of kidney cancer biopsies stimulated with immobilized anti-Dectin-1 antibody (clone 2M24) or 2M24/CD20 bispecific antibody was tested. The anti-Dectin-1 antibody (clone 2M24), isotype control or the 2M24/CD20 bispecific antibody were immobilized overnight in U-bottomed polypropylene microtiter plates at 10 ug per well, followed by culture of human monocyte-derived macrophages (FIGS. 41A & 41B) or single cell suspension from kidney cancer biopsy (FIG. 41C). The cells were cultured for 24 hours and evaluation of TNF$\alpha$ secretion in the supernatant was assessed by ELISA. As a positive control, cells were stimulated with zymosan.

Figure 42:
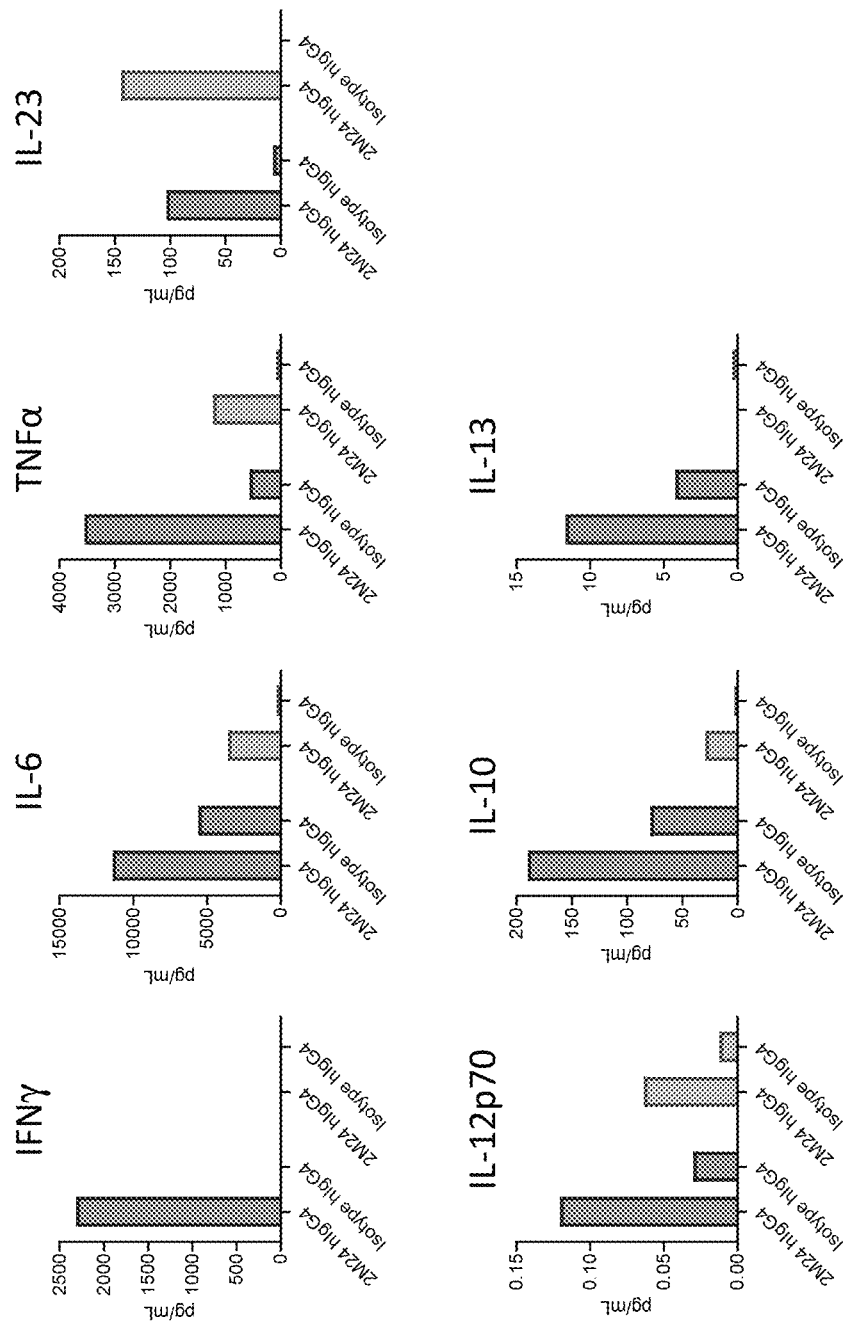

FIG. 42 shows that immobilized anti-Dectin 1 antibody (clone 2M24) promotes immune stimulation in single cell suspension of kidney cancer biopsies. Single-cell suspensions from kidney cancer biopsies were treated with immobilized anti-Dectin-1 antibody (clone 2M24) or isotype control hIgG4 antibody for 24 h. Supernatants were analyzed by ELISA for the release of various cytokines, including IFN$\gamma$, IL-6, TNF$\alpha$, IL-23, IL-12p70, IL-10, and IL-13. Each plot shows amount of cytokine (pg/mL) as a function of antibody treatment. Shown are results from treatment with anti-Dectin-1 antibody (clone 2M24) or isotype control hIgG4 antibody using kidney cancer donor 3 (left) or donor 4 (right).

Figure 43:
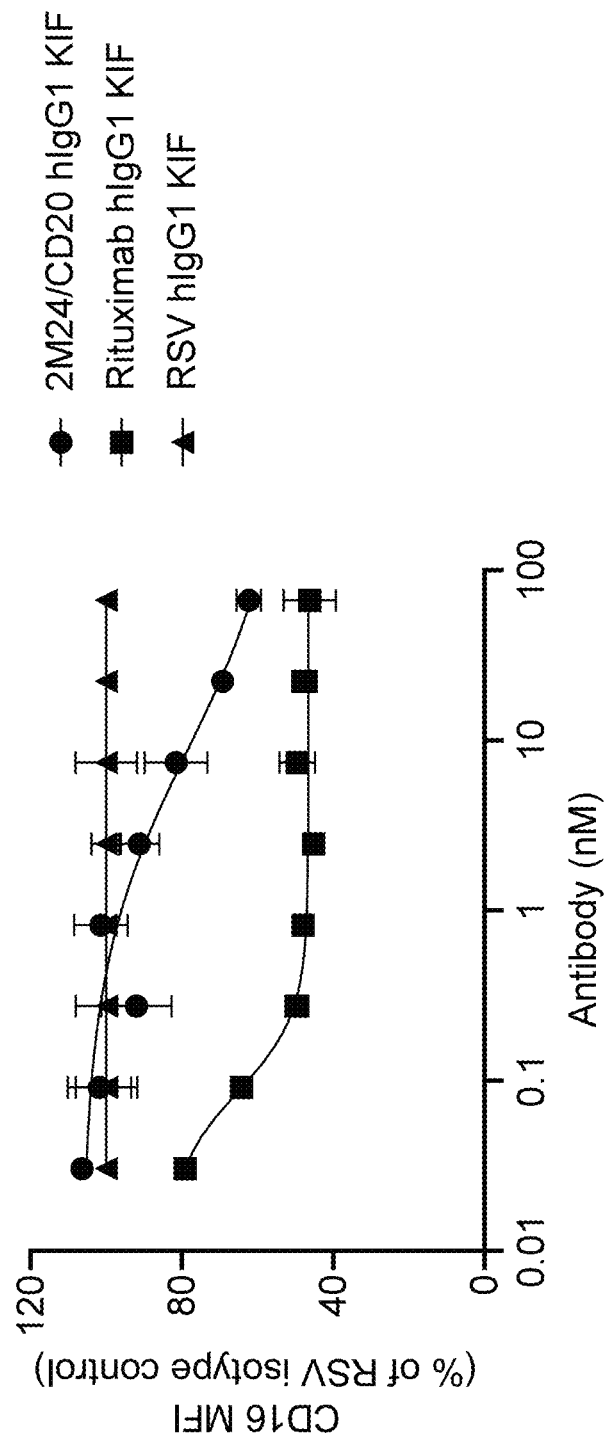

FIG. 43 shows the effect of 2M24/CD20 bispecific antibody on CD16 expression in human NK cells, as compared to rituximab or isotype control (RSV). Results indicate that CD16 antigen levels on NK cells are better maintained in PBMCs treated with the 2M24/CD20 bispecific compared to rituximab.

Figure 44:
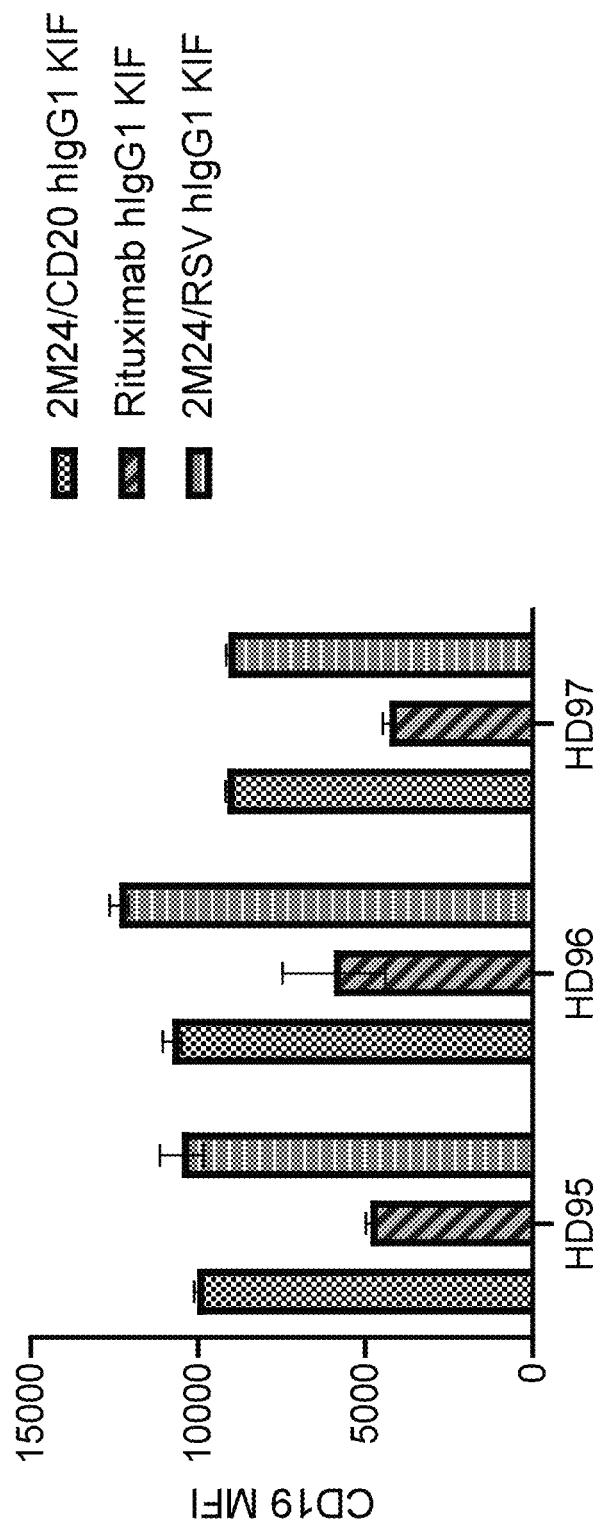

FIG. 44 shows the effect of 2M24/CD20 bispecific antibody on CD19 expression in human B cells, as compared to rituximab or isotype control (2M24/RSV bispecific). Results indicate that CD19 antigen levels are better maintained on B cells treated with the 2M24/CD20 bispecific compared to rituximab.

Figure 45:
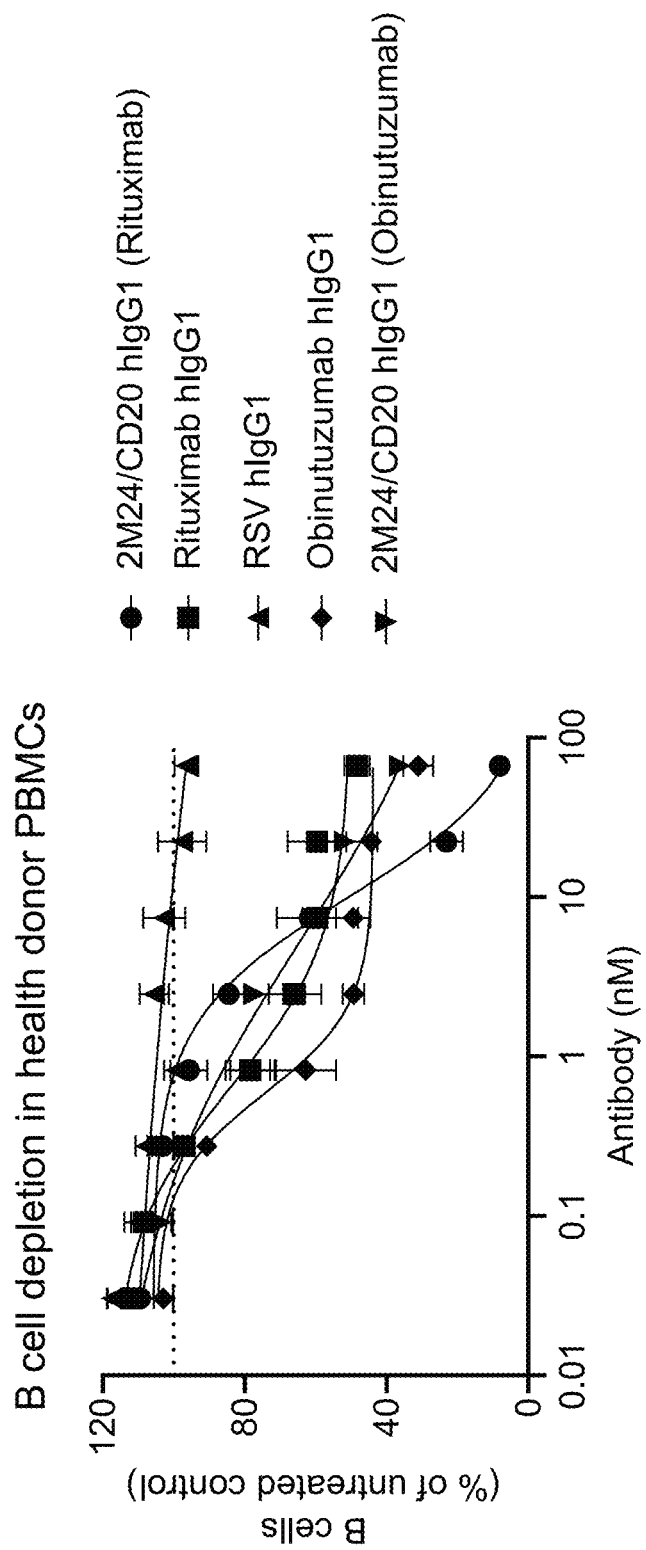

FIG. 45 shows depletion of human B cells by 2M24/CD20 bispecific antibody derived from rituximab or 2M24/CD20 bispecific antibody derived from obinutuzumab. Results indicate that the 2M24/CD20 bispecific derived from the rituximab arm is better at depleting B cells compared to the bispecific derived from obinutuzumab.

Figure 46:
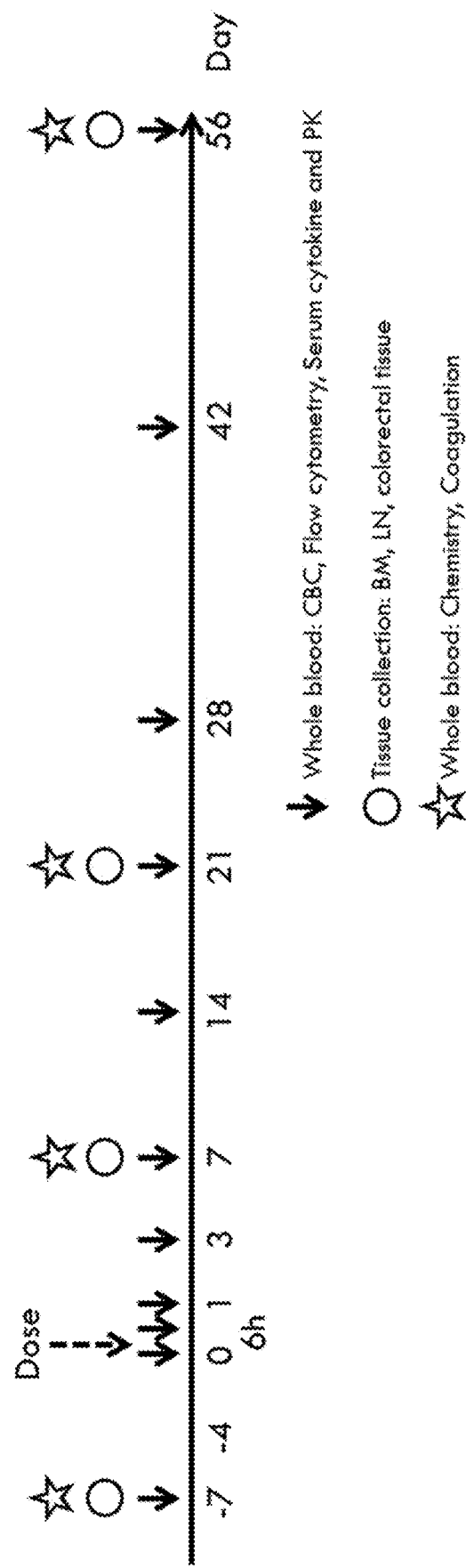

FIG. 46 shows the design of an exploratory study on safety and efficacy of 2M24/CD20 bispecific antibody in non-human primates.

Figure 47:
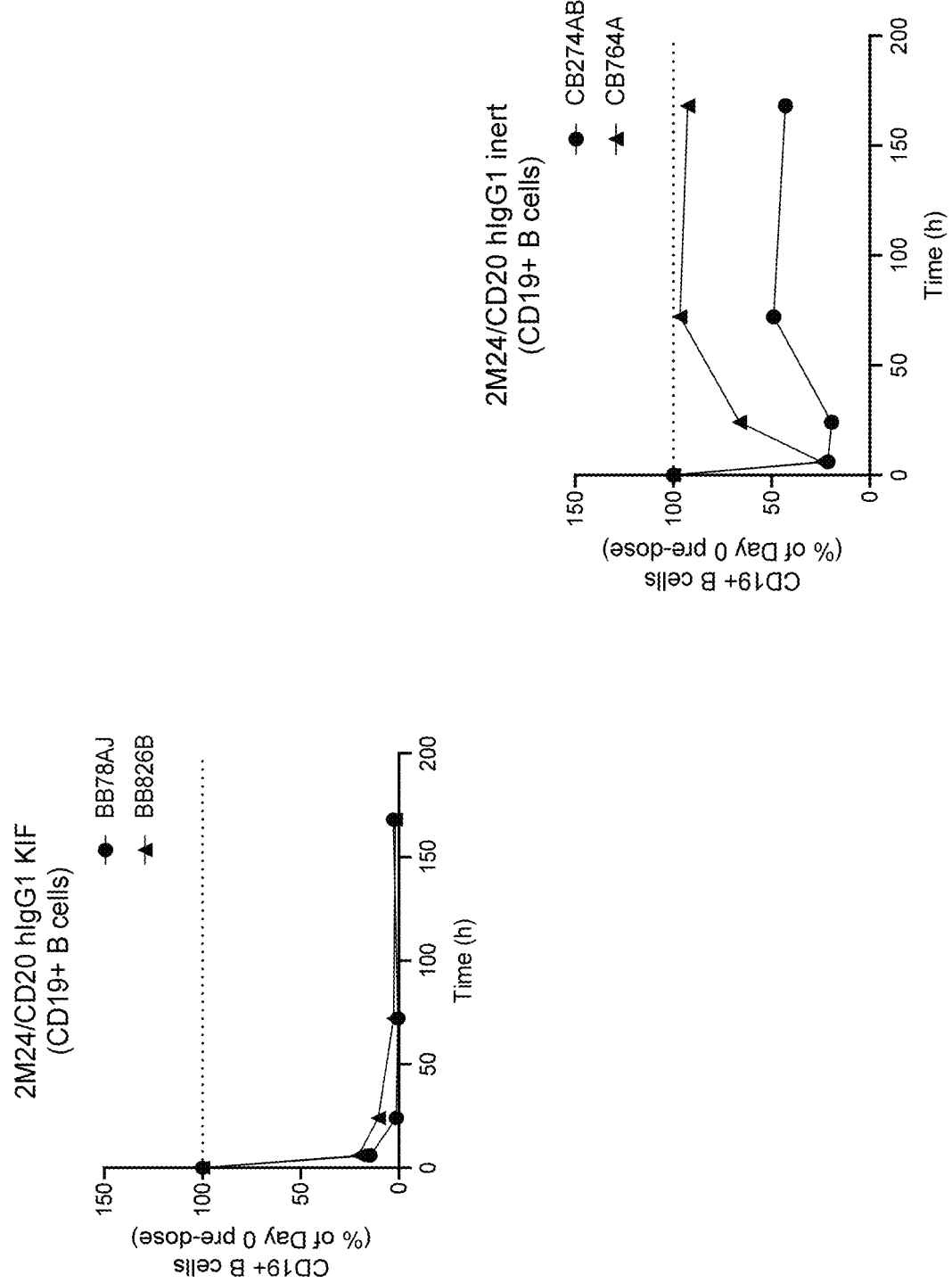
Figure 48:
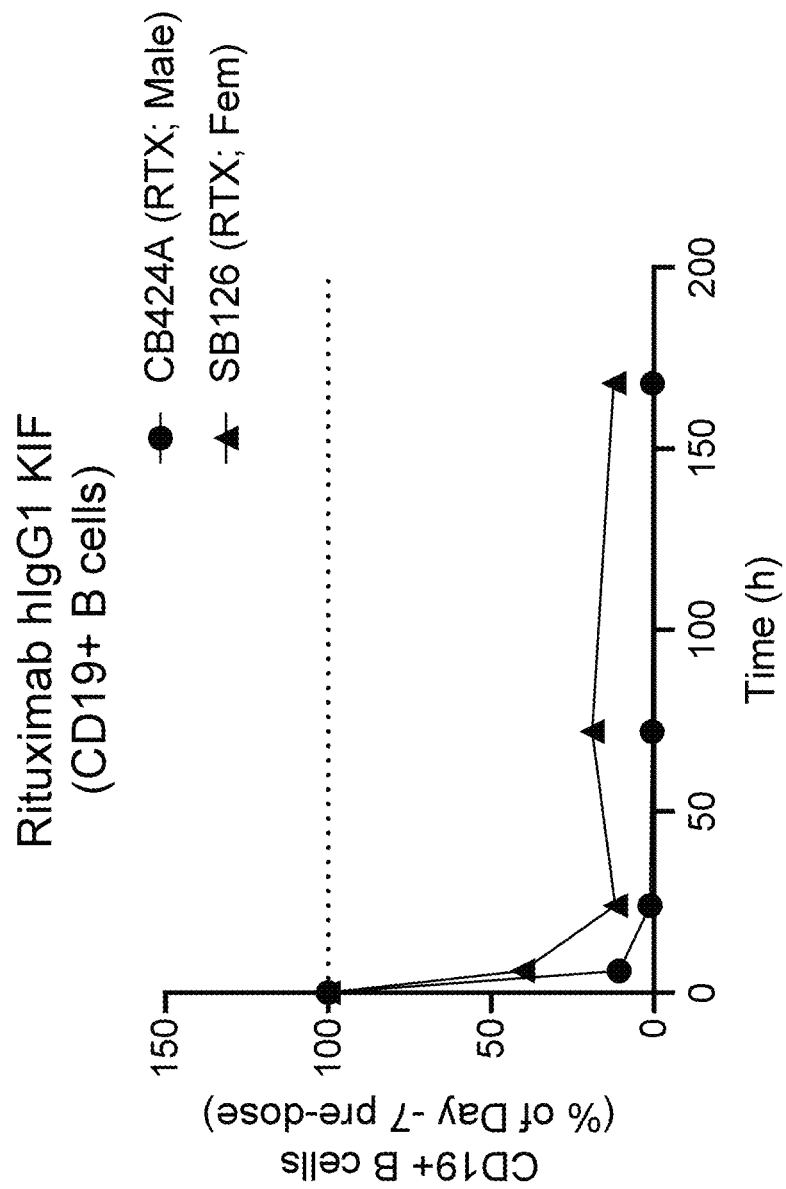

FIGS. 47 & 48 show depletion of circulating B cells in cynomolgus monkeys by 2M24/CD20 hIgG1 bispecific antibody generated in cells treated with kifunensine (KIF). FIG. 47: B cell depletion in monkeys treated with 5 mg/kg 2M24/CD20 hIgG1 KIF (upper) or 2M24/CD20 hIgG1 inert (lower). FIG. 48: B cell depletion in monkeys treated with 5 mg/kg rituximab hIgG1 KIF.

Figure 49A:
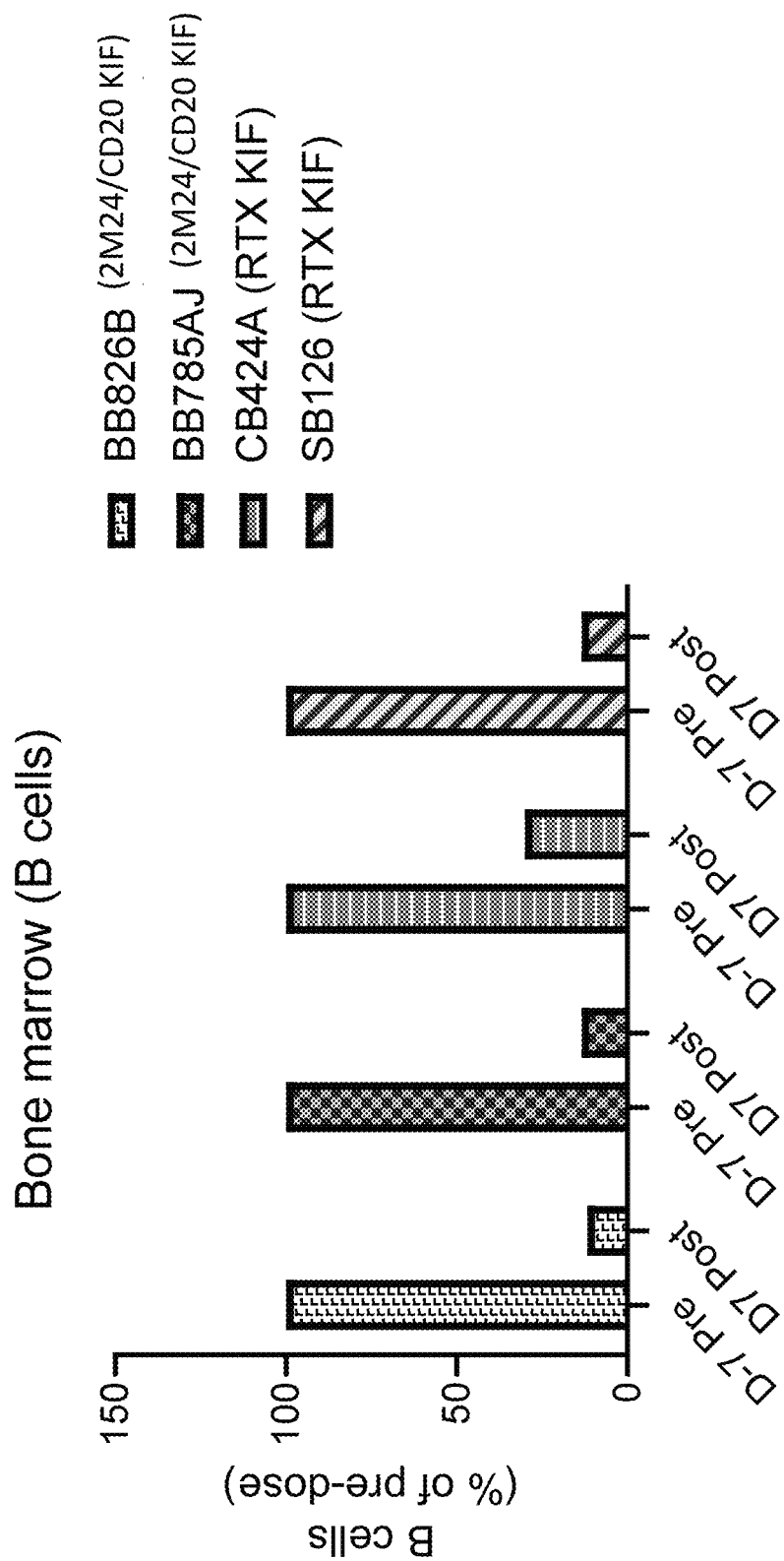
Figure 49B:
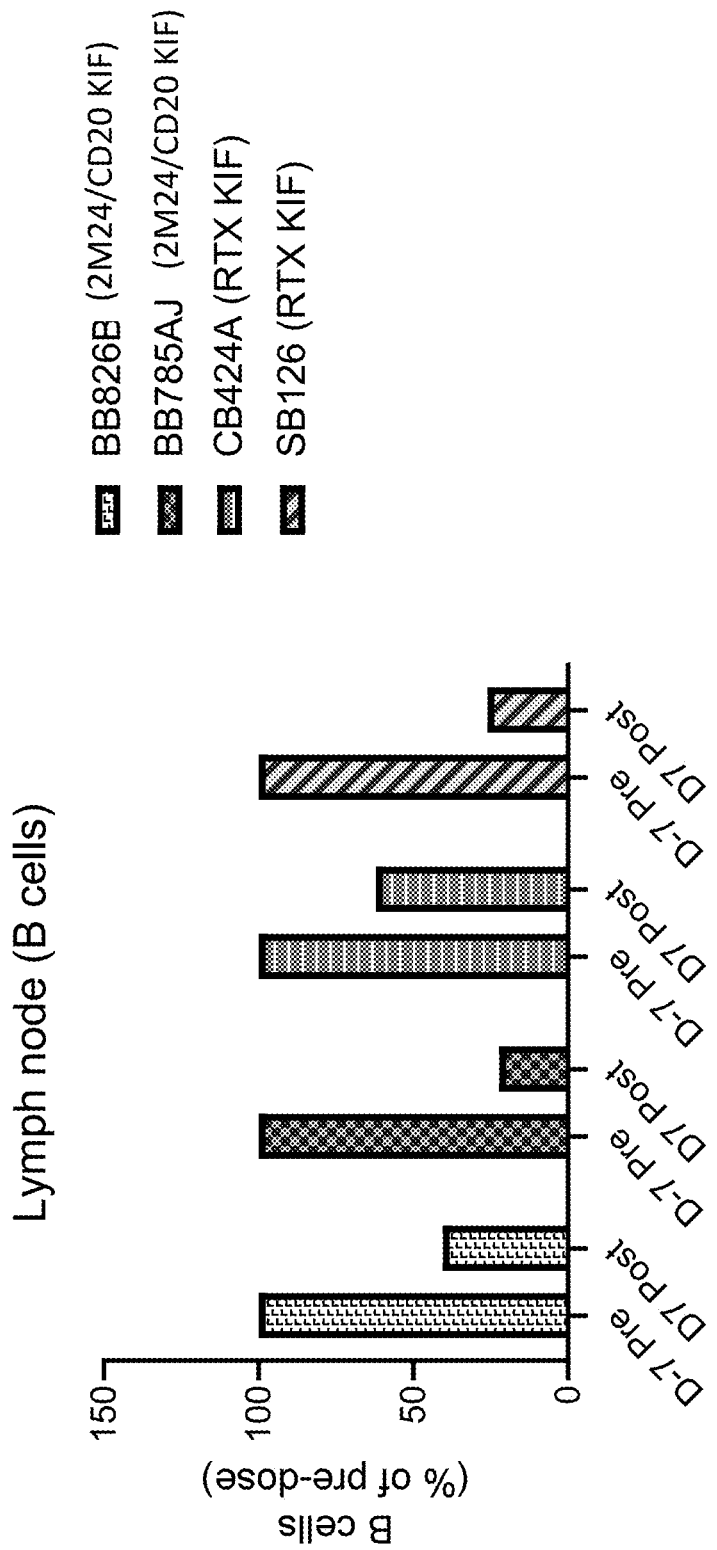

FIGS. 49A & 49B show depletion of tissue-resident B cells in cynomolgus monkeys by 2M24/CD20 hIgG1 bispecific antibody generated in cells treated with kifunensine (KIF). FIG. 49A: B cell depletion in bone marrow of monkeys treated with 5 mg/kg 2M24/CD20 hIgG1 KIF or rituximab hIgG1 KIF. FIG. 49B: B cell depletion in lymph nodes of monkeys treated with 5 mg/kg 2M24/CD20 hIgG1 KIF or rituximab hIgG1 KIF.

Figure 50:
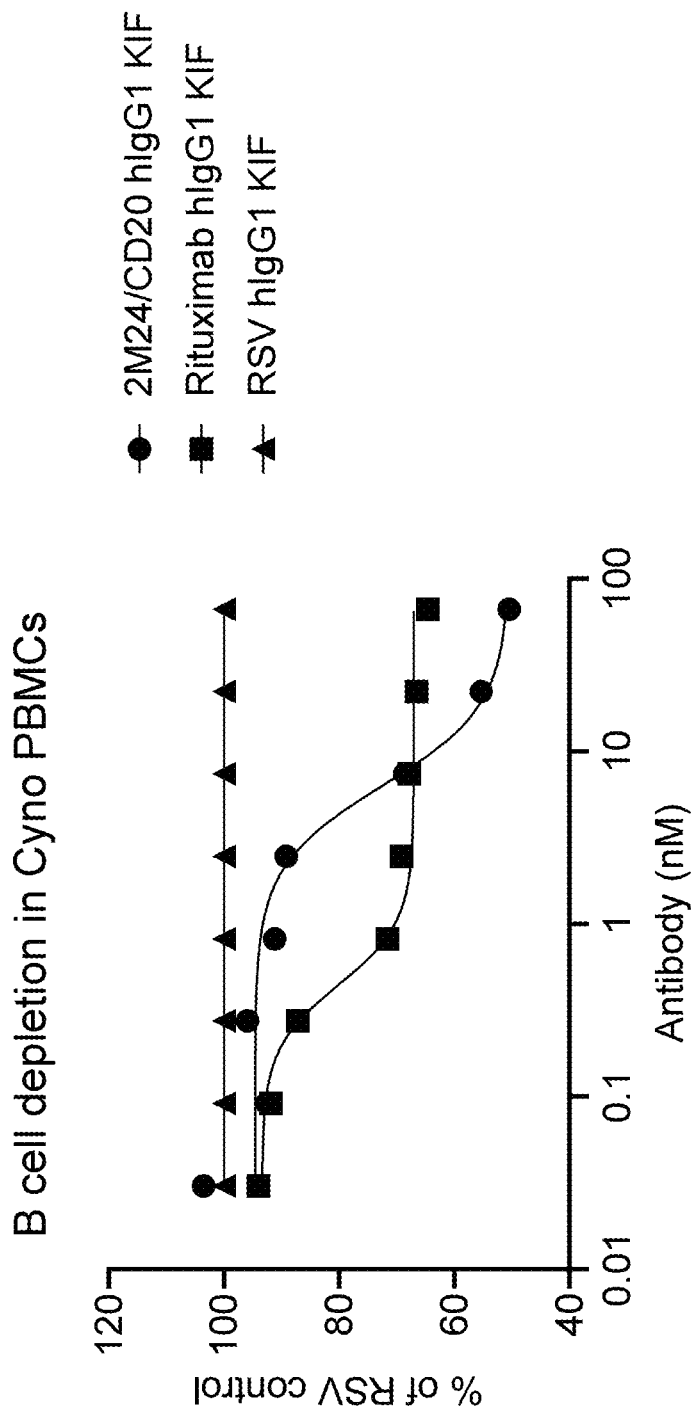

FIG. 50 shows depletion of B cells from cynomolgus monkey PBMCs ex vivo.

Figure 51:
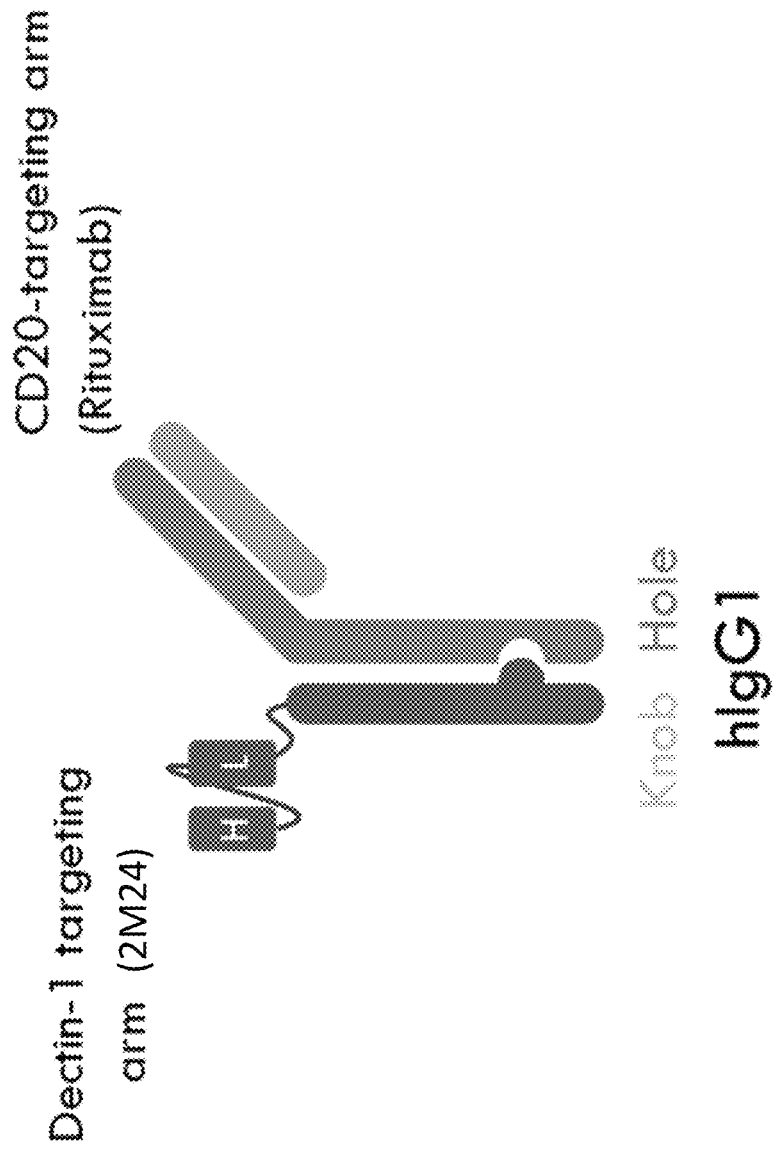

FIG. 51 shows the format of a bispecific molecule that uses knobs-into-holes technology to pair an anti-CD20 conventional half-antibody with an anti-Dectin-1 single chain variable fragment (scFv) Fc fusion arm (2M24 scFv/CD20). H: 2M24 VH domain; L: 2M24 VL domain.

Figure 52A:
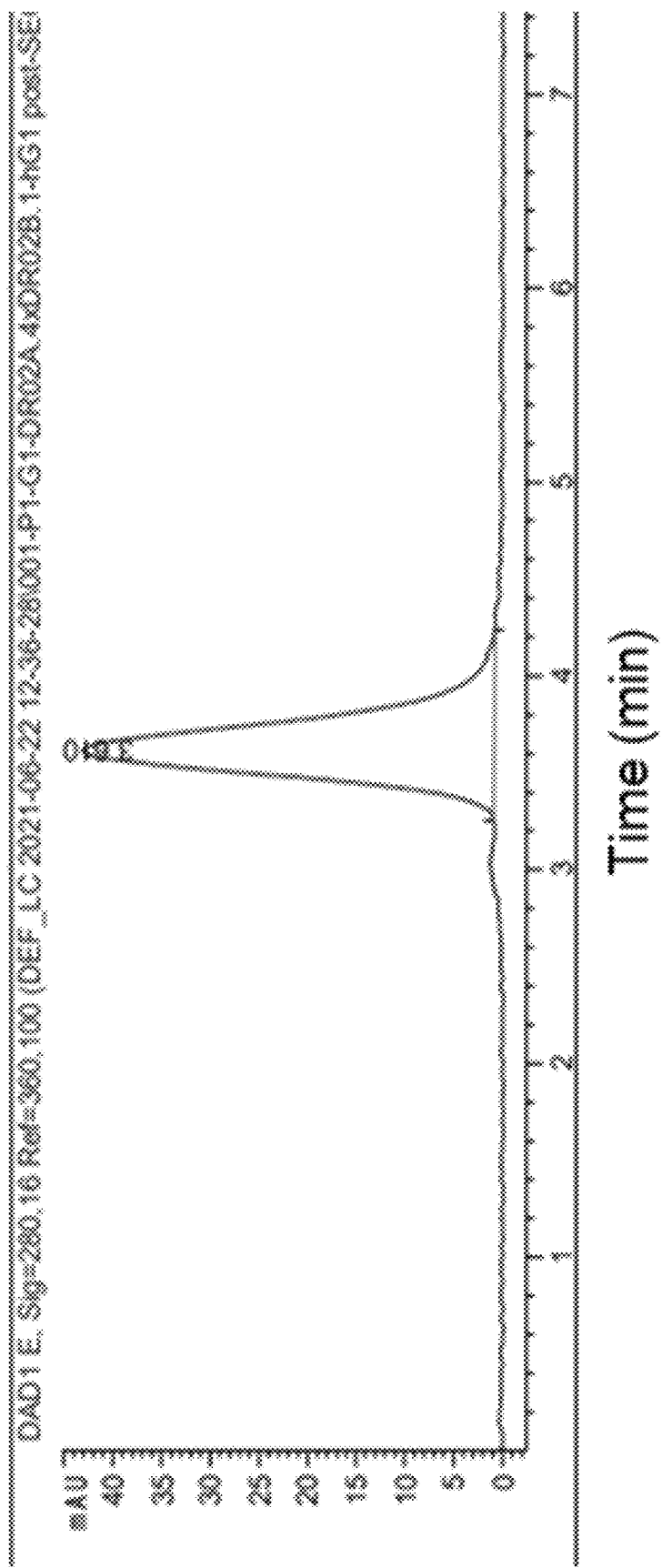
Figure 52B:
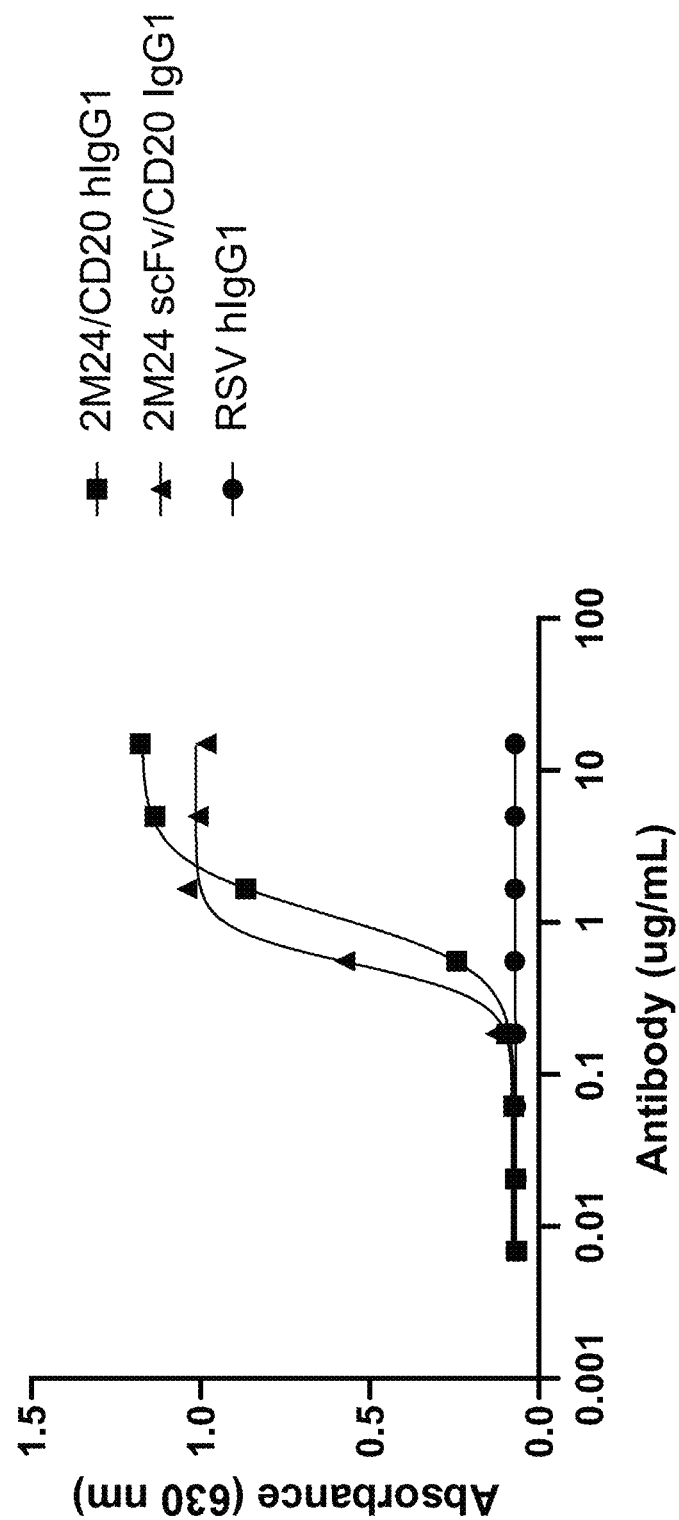
Figure 52C:
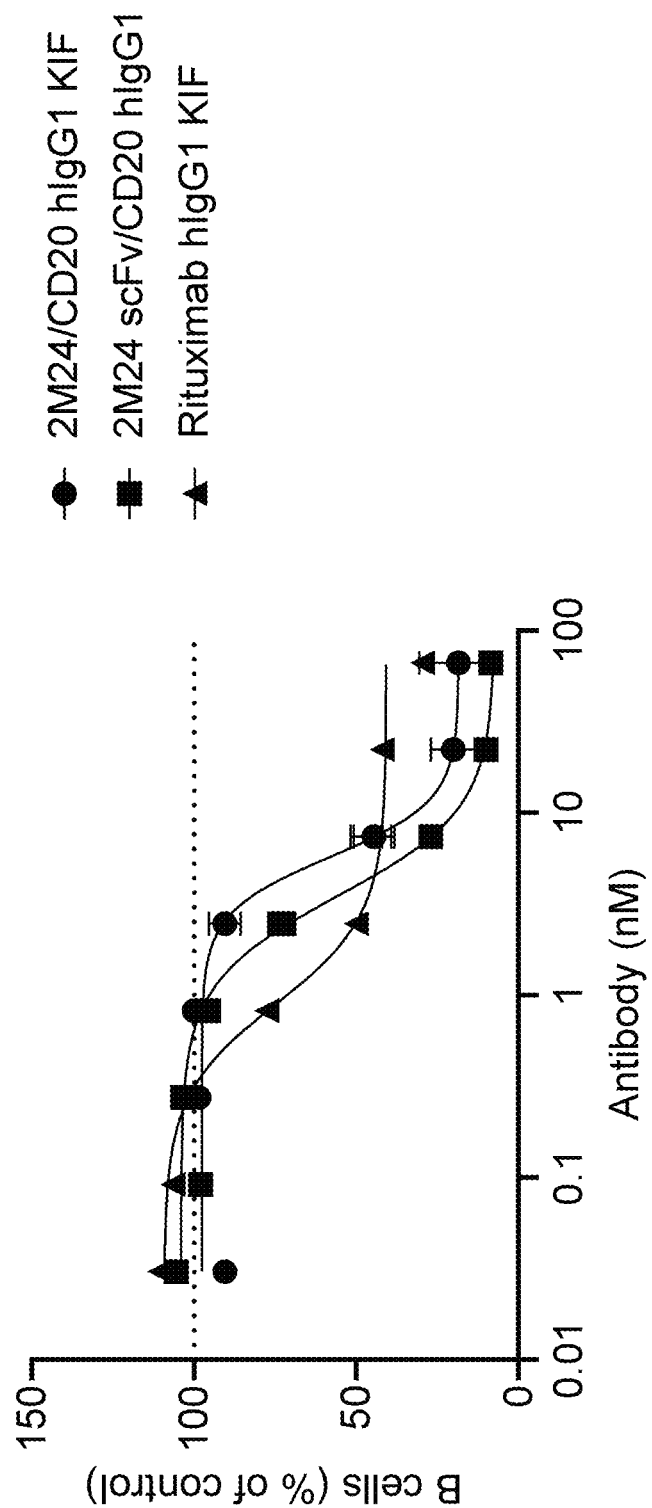

FIGS. 52A-52C show purification and functional characterization of the 2M24/CD20 bispecific antibody. FIG. 52A shows purification of the molecule by size exclusion chromatography (SEC). FIG. 52B shows that purified bispecific antibody promoted targeted immune stimulation, as assessed in an NFκB reporter assay. FIG. 52C shows human B cell depletion by the 2M24 scFv/CD20 bispecific antibody.

Figure 53A:
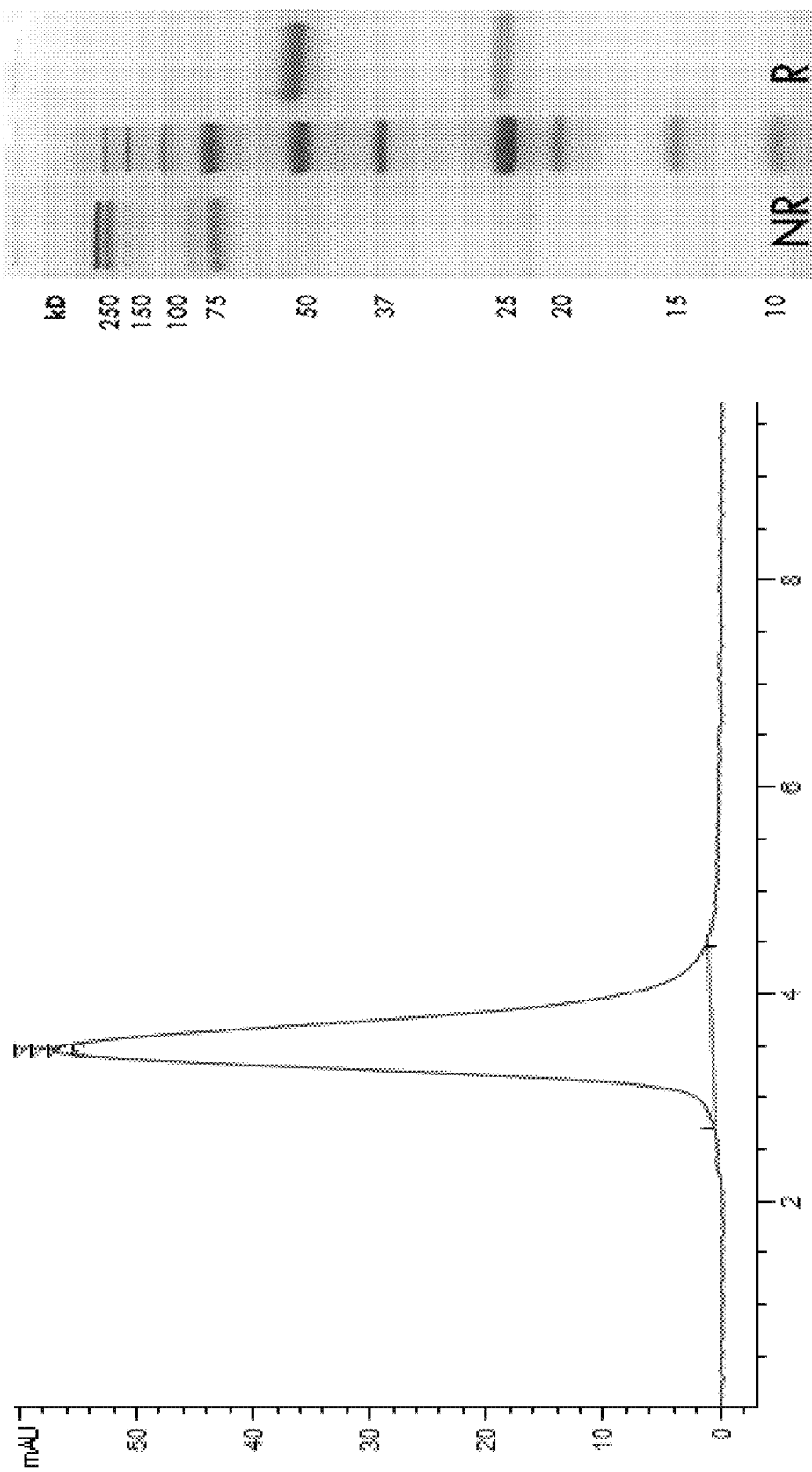
Figure 53B:
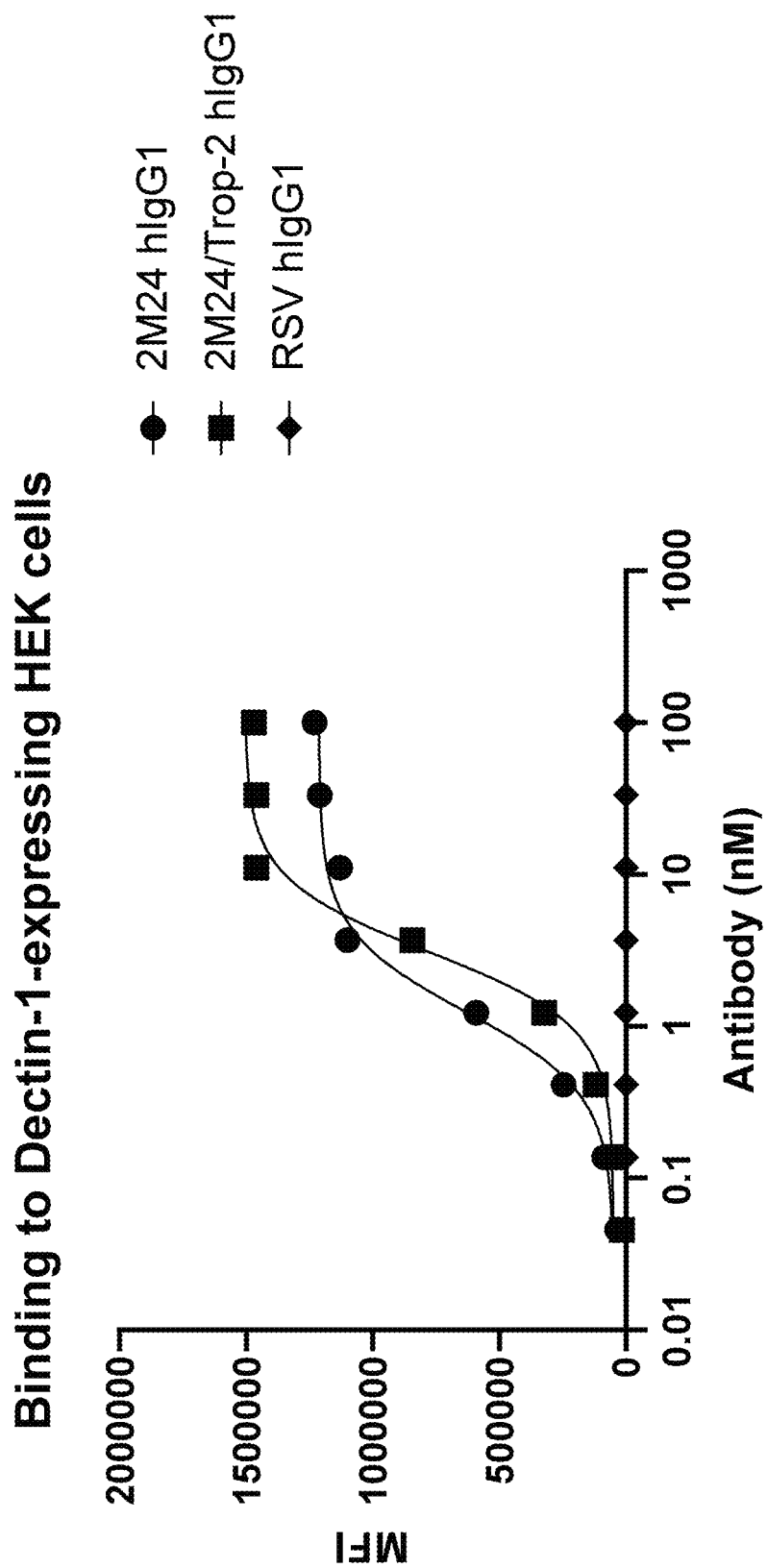
Figure 53C:
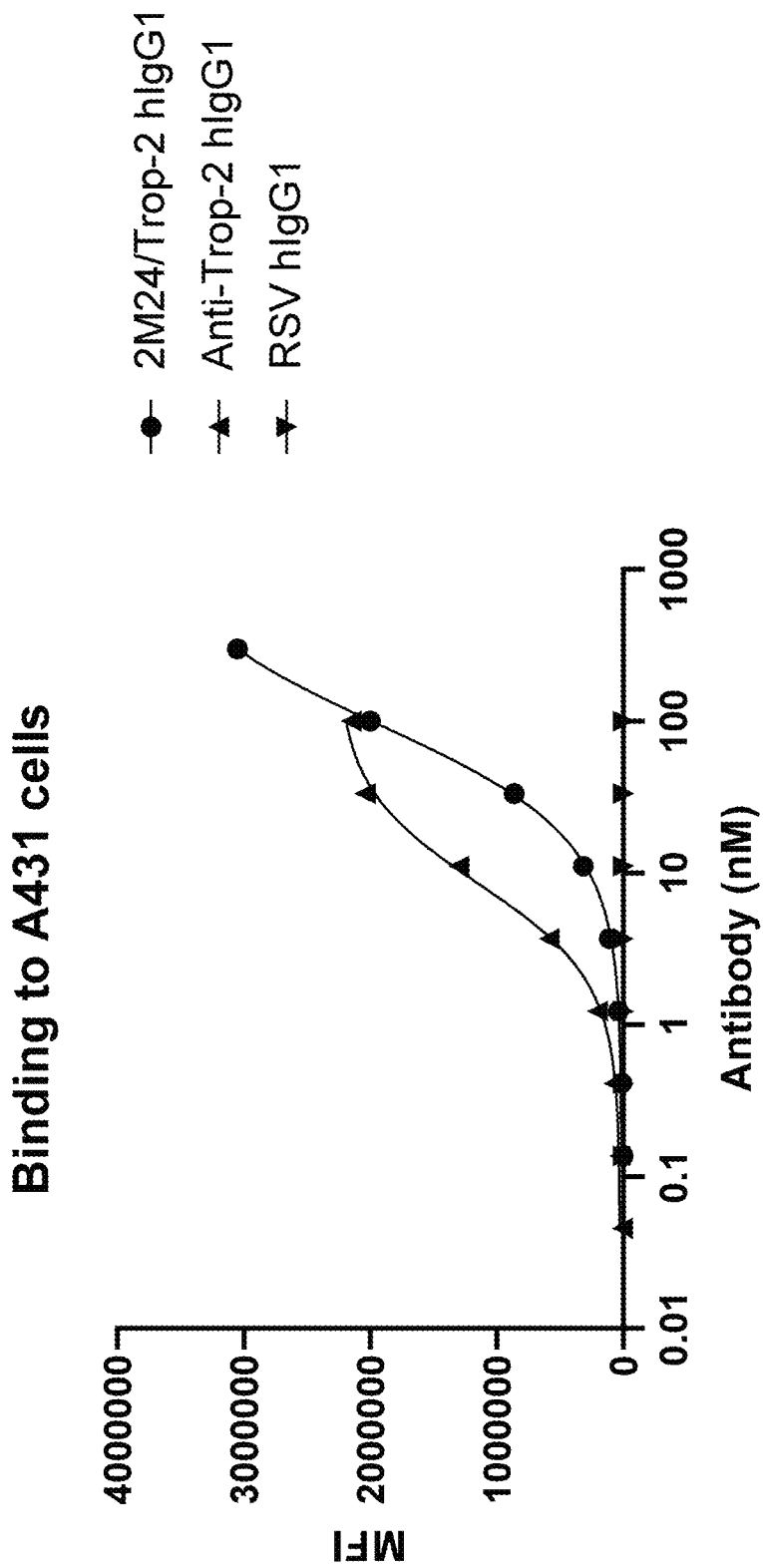

FIGS. 53A-53C show development and characterization of an anti-Dectin-1 (2M24)/anti-Trop-2 bispecific antibody. FIG. 53A shows the purification of 2M24/Trop-2 bispecific antibody by SEC (left). Purified antibody was analyzed by SDS-PAGE under non-reducing (NR) or reducing (R) conditions (right). FIGS. 53B & 53C show high affinity binding of the molecule to Dectin-1-expressing HEK cells (FIG. 53B) and moderate affinity binding to the Trop-2 expressing A431 cancer cell line (FIG. 53C).

Figure 54:
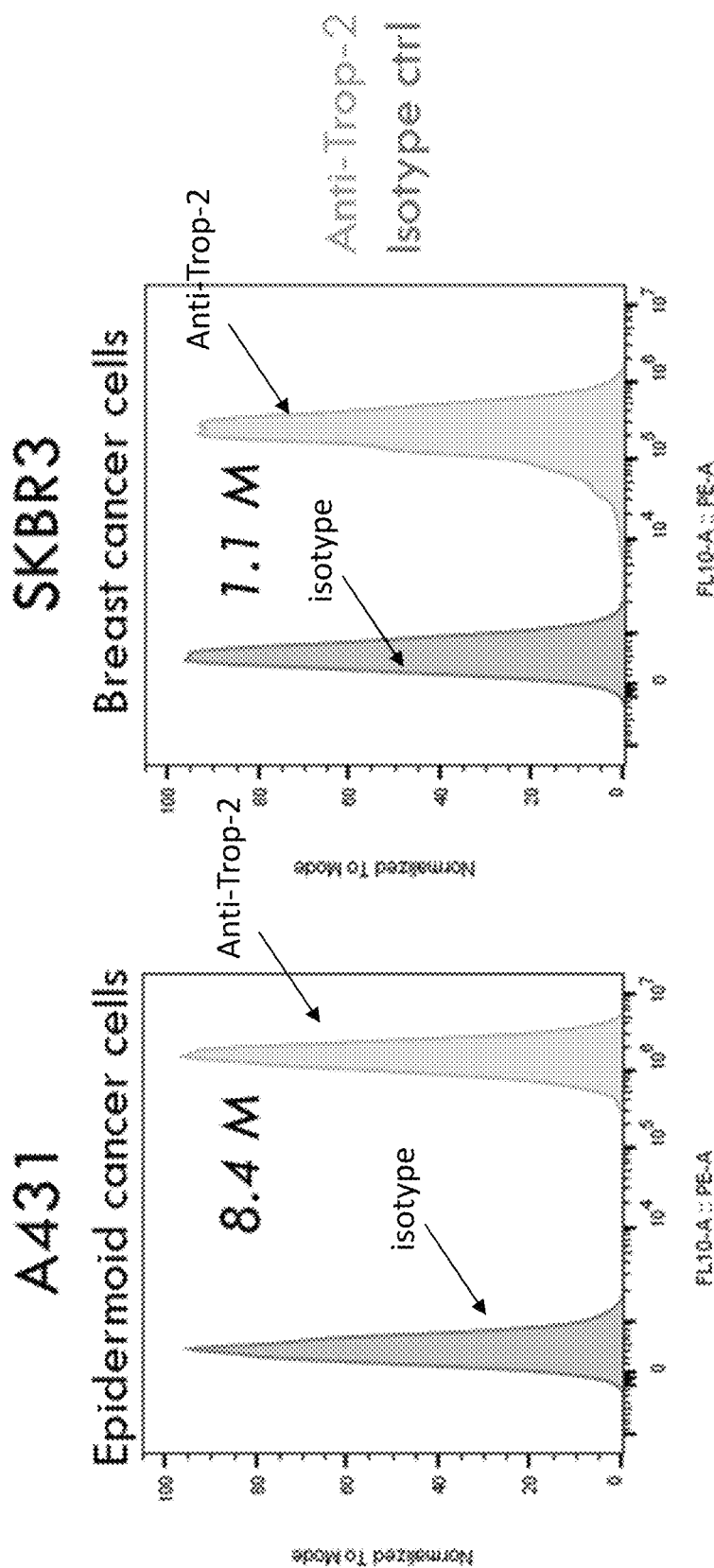

FIG. 54 shows Trop-2 expression levels on cancer cells.

Figure 55A:
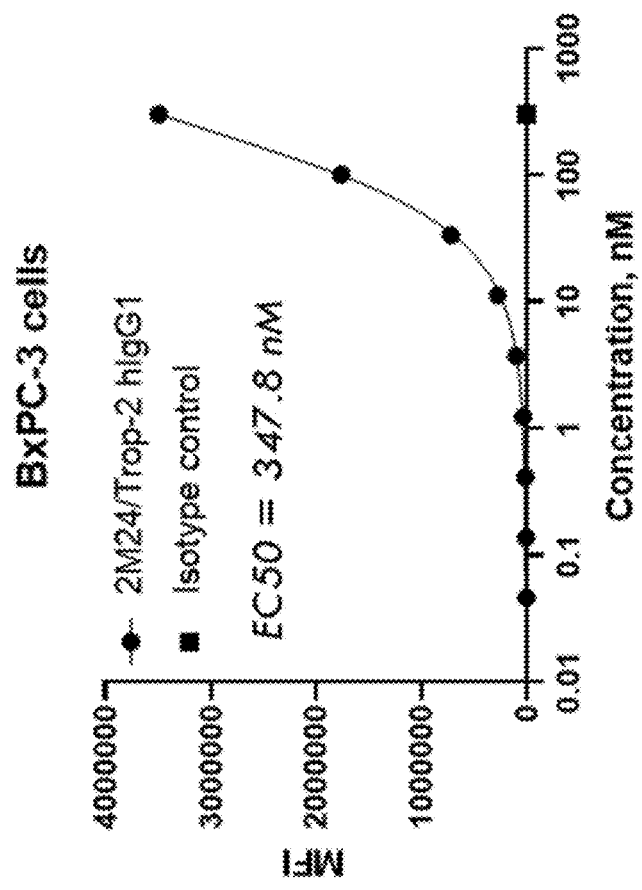
Figure 55B:
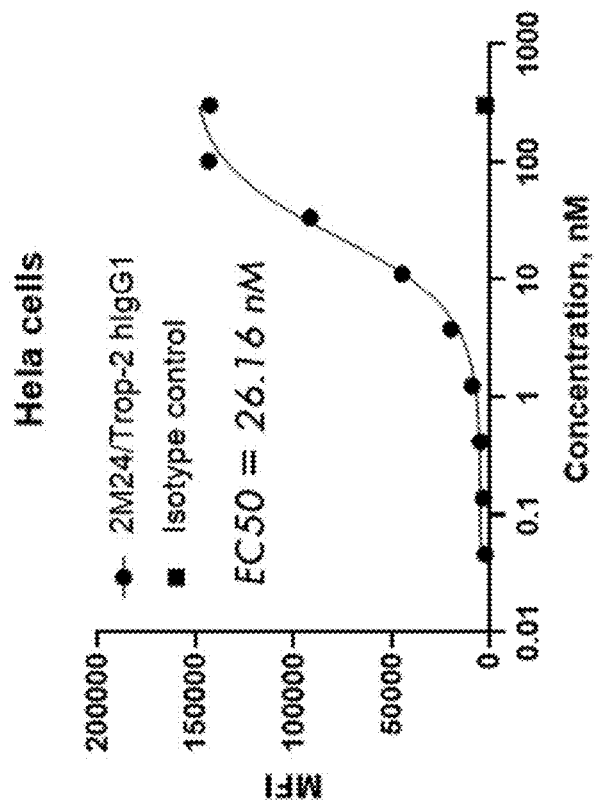
Figure 55C:
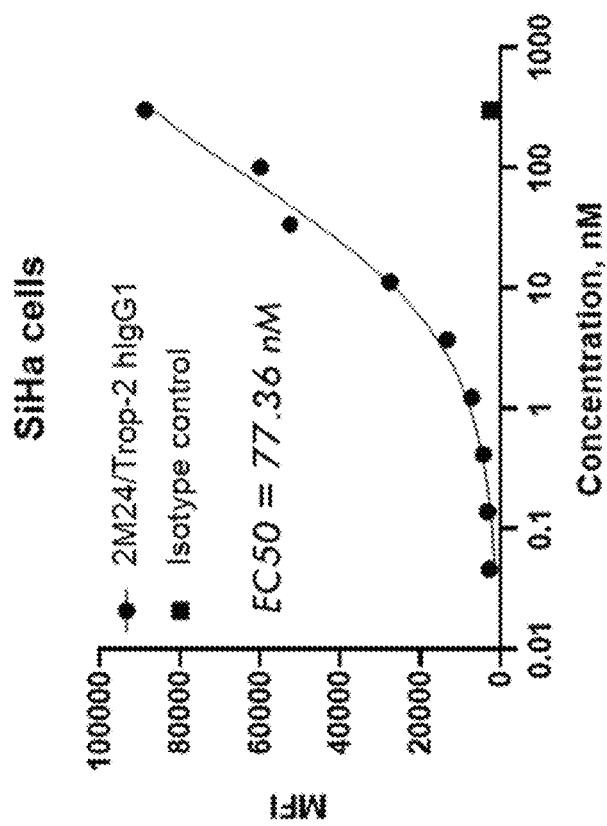
Figure 55D:
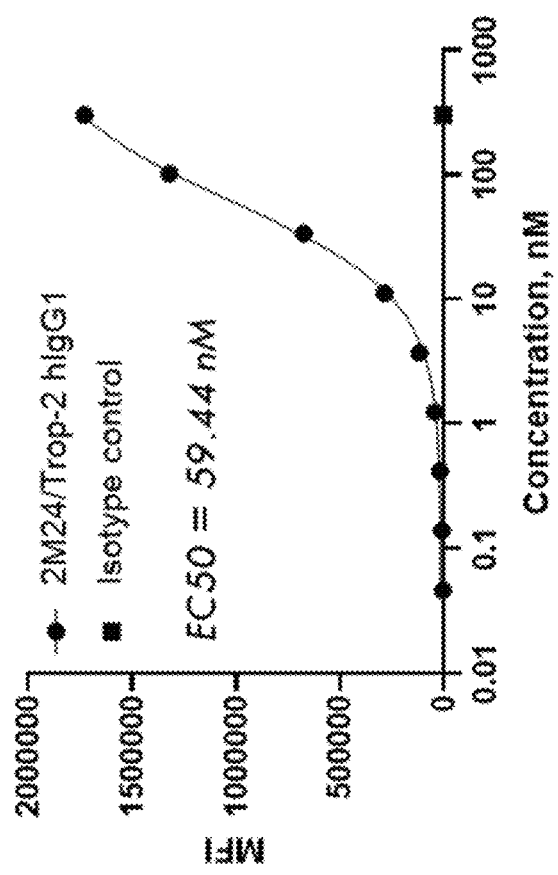

FIGS. 55A-55D show binding of 2M24/Trop-2 bispecific antibody to Trop-2-expressing cell lines HeLa (FIG. 55A), BxPC-3 (FIG. 55B), SiHa (FIG. 55C), and Capan-2 (FIG. 55D). Binding EC50, as determined using four-parameter logistic (4PL) non-linear regression, is shown for each cell line.

Figure 56A:
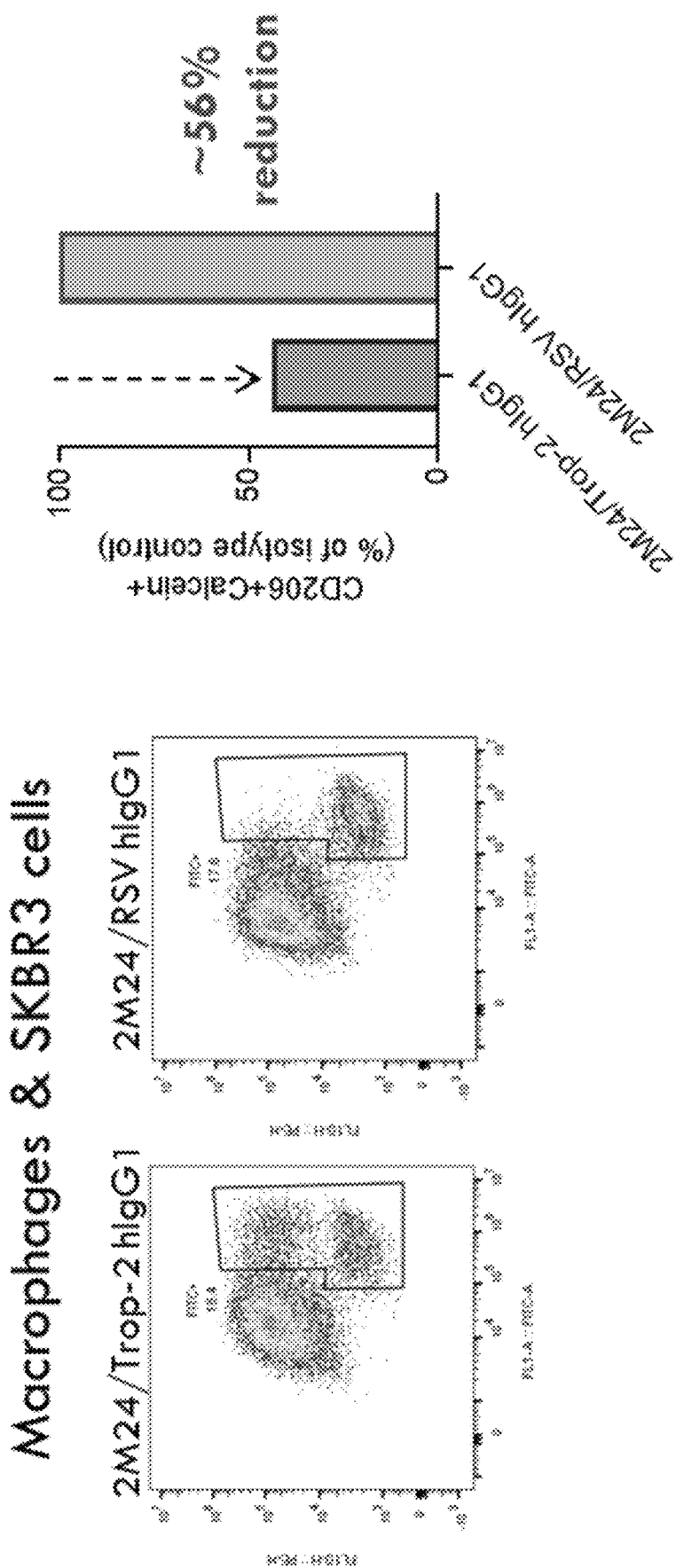
Figure 56B:
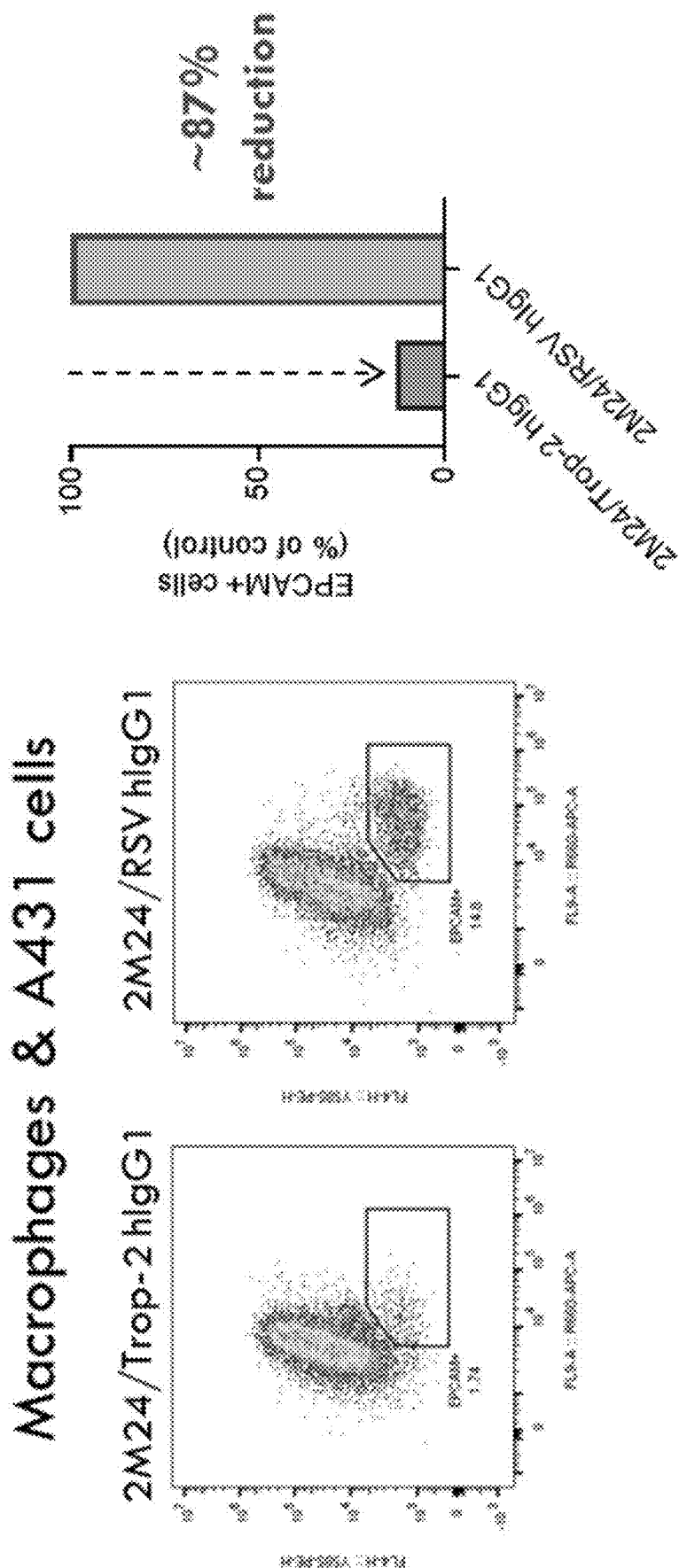

FIGS. 56A & 56B show depletion of Trop-2-expressing cell lines (SKBR3 cells in FIG. 56A; A431 cells in FIG. 56B) using 2M24/Trop-2 bispecific antibody.

Figure 57A:
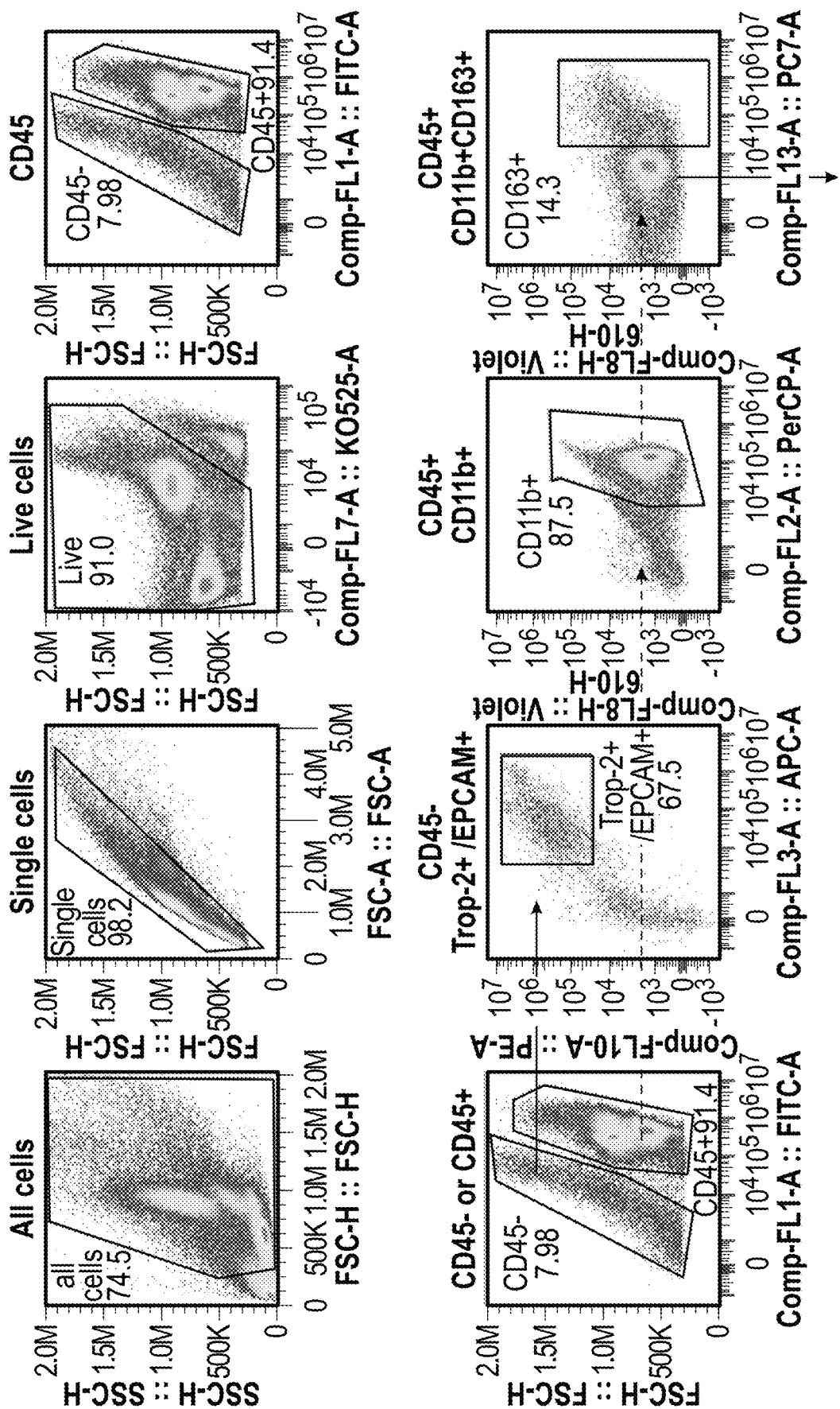
Figure 57B:
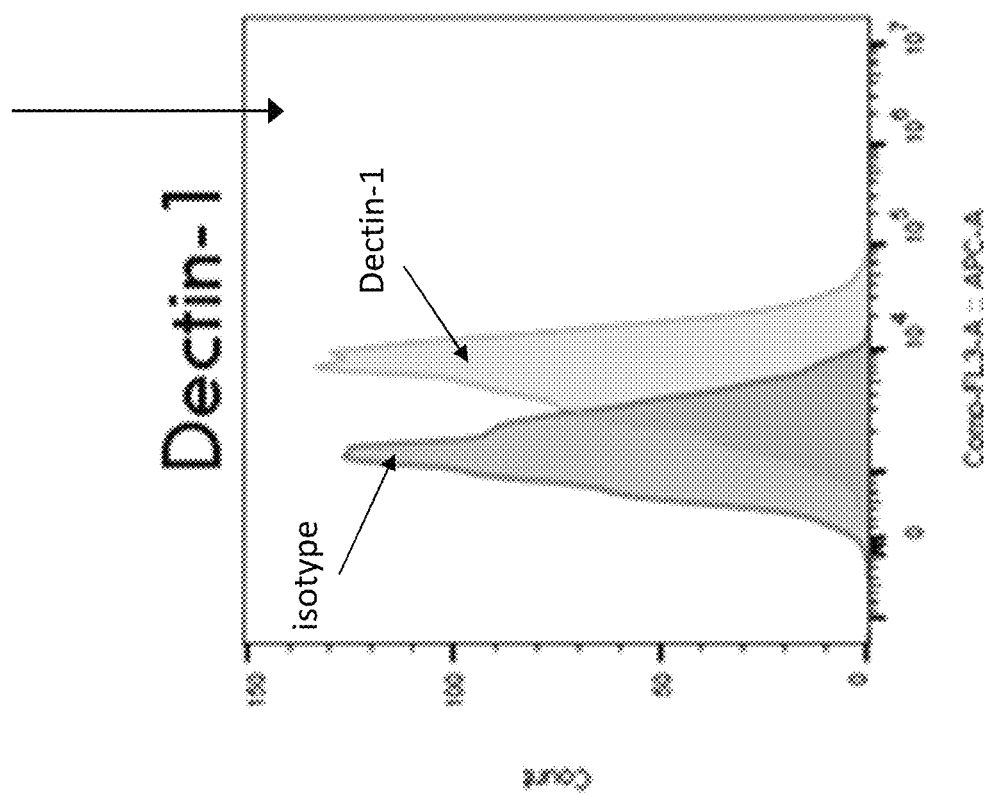

FIGS. 57A & 57B show Trop-2 and Dectin-1 expression in a lung cancer biopsy.

Figure 58:
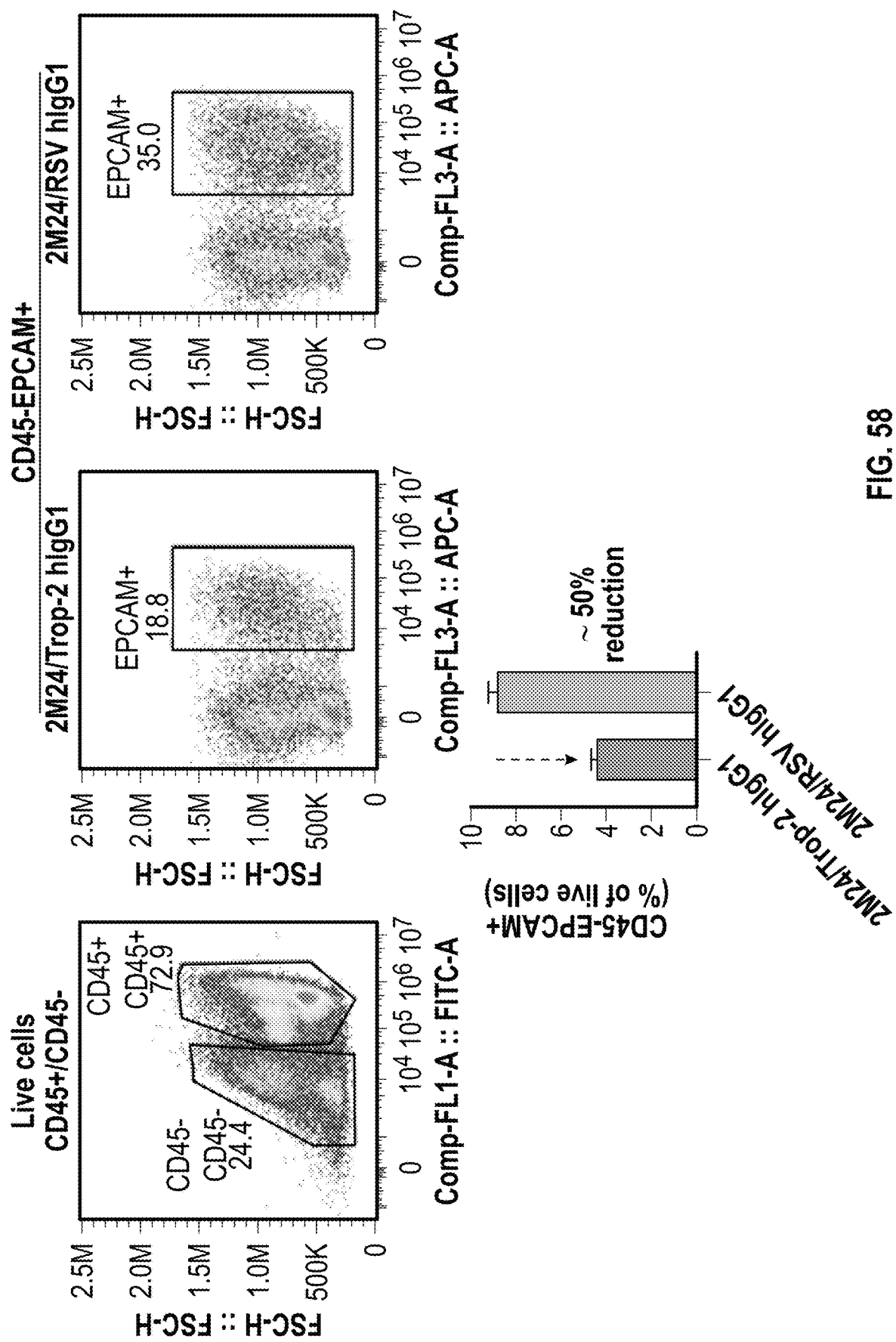

FIG. 58 shows depletion of Trop-2-positive cancer cells in a lung cancer biopsy.

Figure 59A:
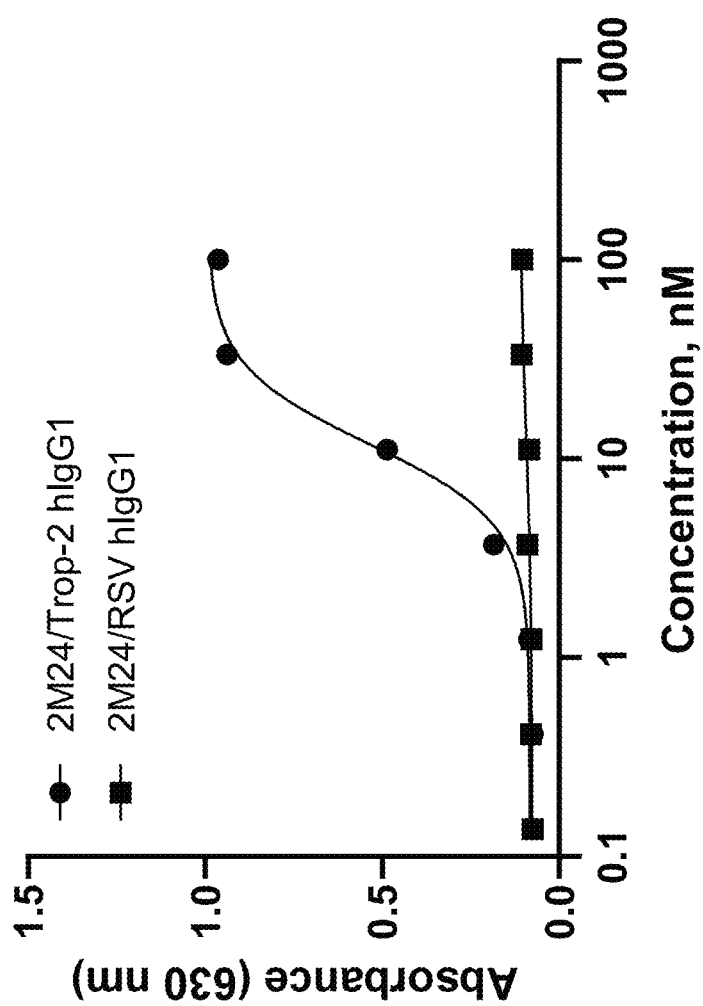

FIG. 59A shows activity of 2M24/Trop-2 bispecific antibody in an NFκB reporter assay.

Figure 59B:
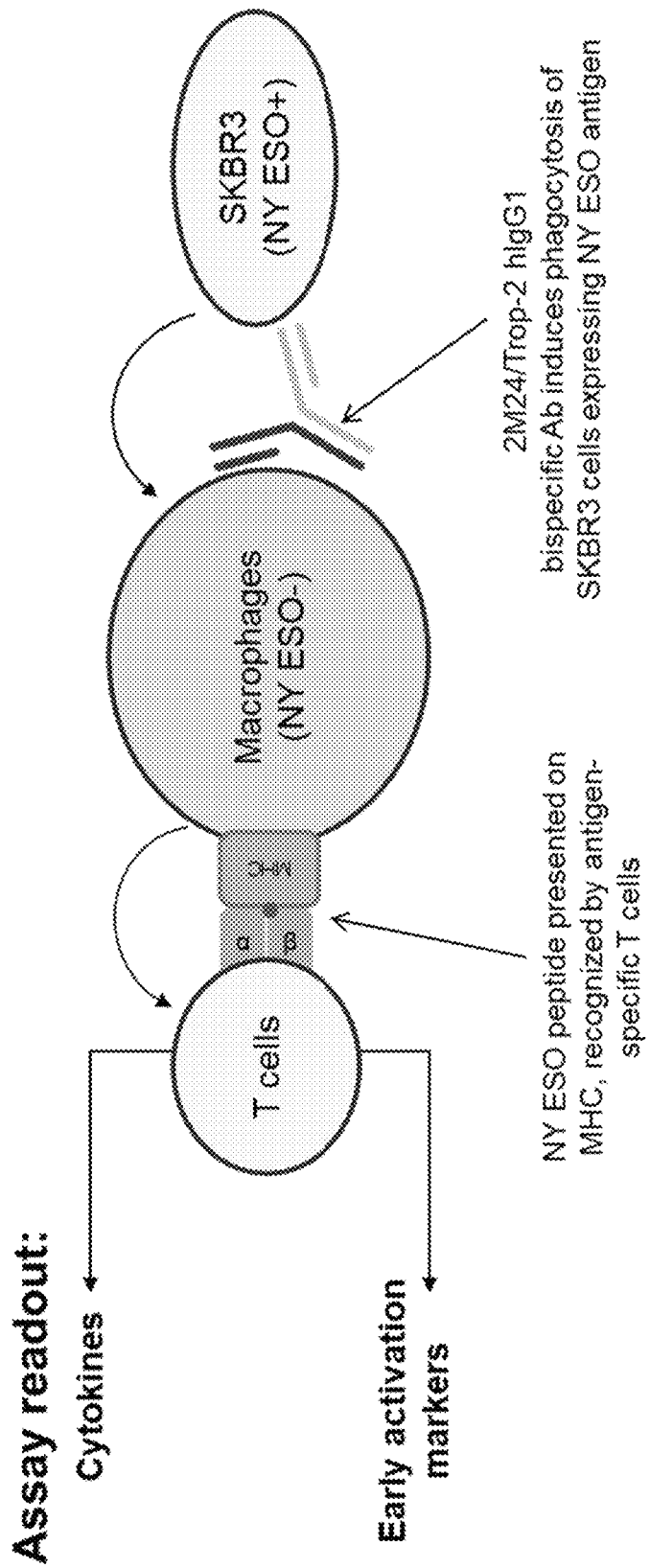
Figure 59C:
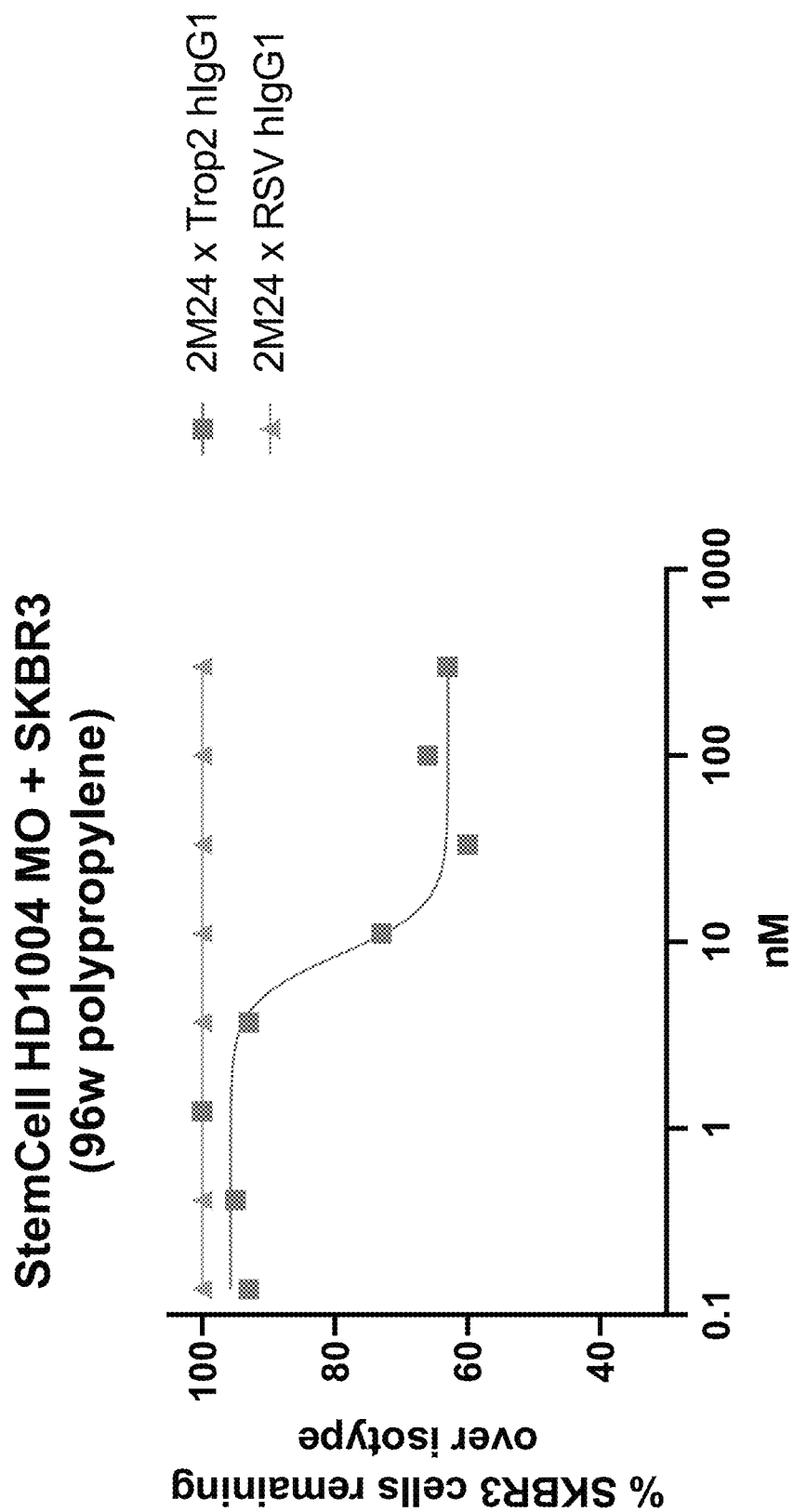
Figure 59E:
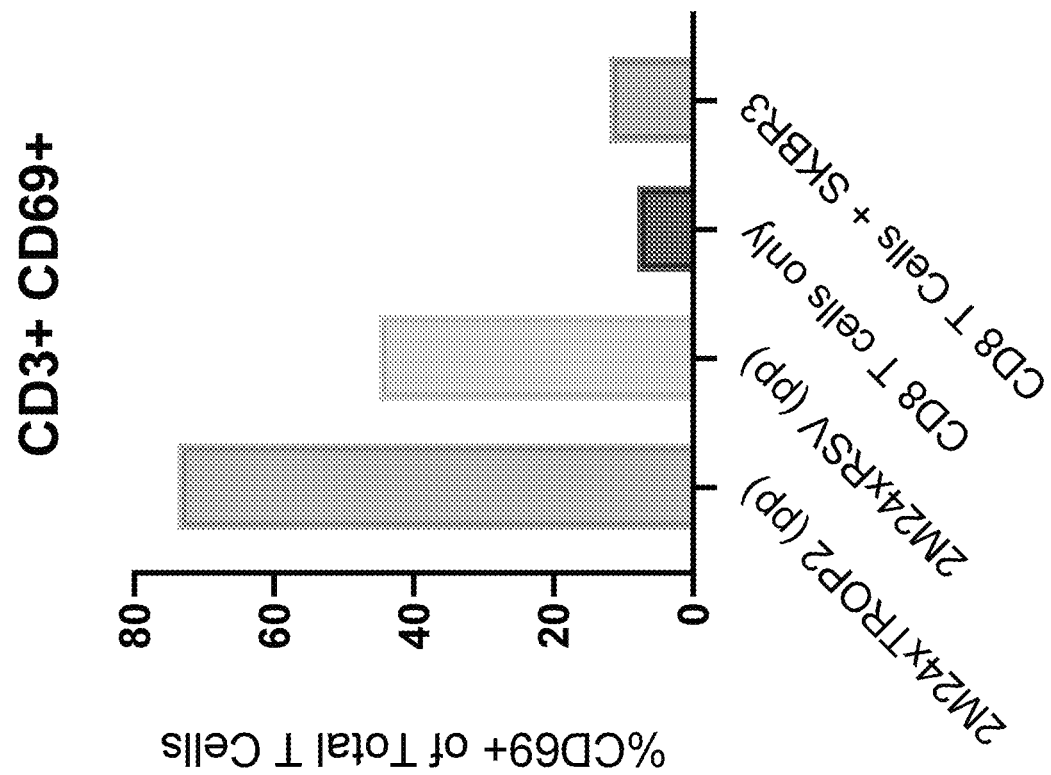
Figure 59D:
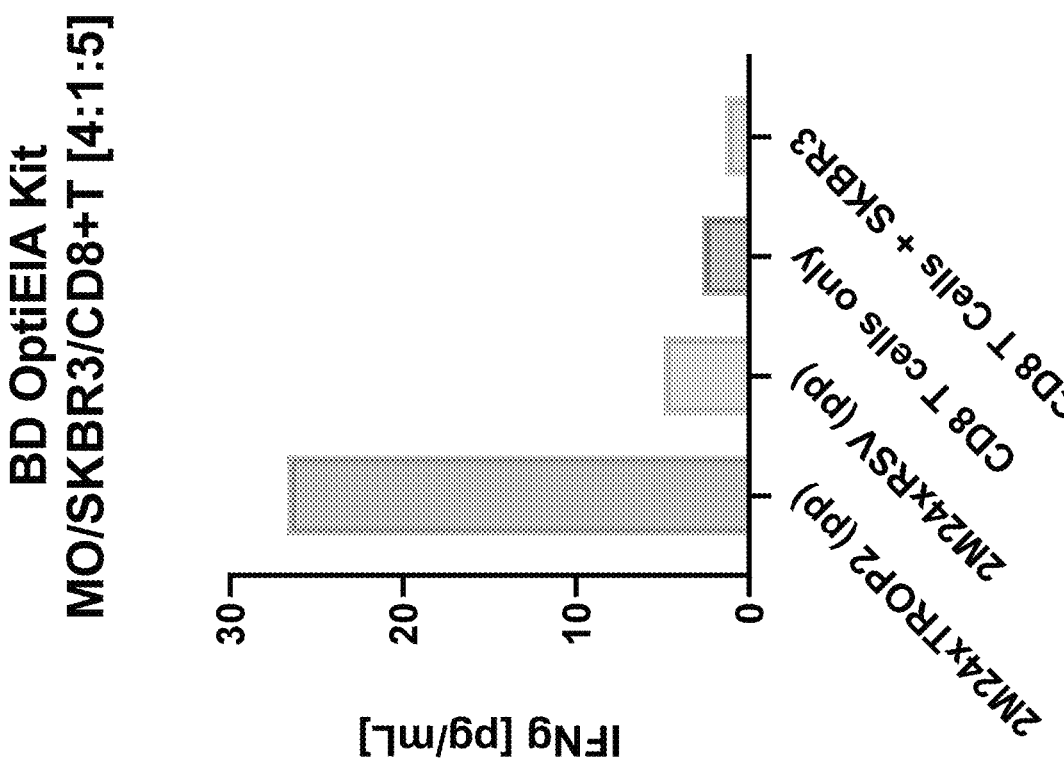

FIGS. 59B-59E show that 2M24/Trop-2 bispecific antibody promotes antigen presentation and T cell activation. FIG. 59B provides a schematic representation of the assay set up. In FIG. 59C, macrophages and SKBR3 breast cancer cells were co-incubated in the presence of 2M24/Trop-2 hIgG1 or control 2M24/RSV hIgG1 bispecific antibody. Phagocytosis or depletion of SKBR3 cells was assessed by flow cytometry by staining for EPCAM expression on SKBR3 cells. Data are reported as relative to the control bispecific 2M24/RSV. In FIG. 59D, IFN gamma levels in the supernatants were quantified using the BD OptiEIA Kit. In FIG. 59E, expression of CD69, an early activation marker, on T cells was assessed by flow cytometry. Data are reported as relative to total CD3+ T cells.

Figure 60A:
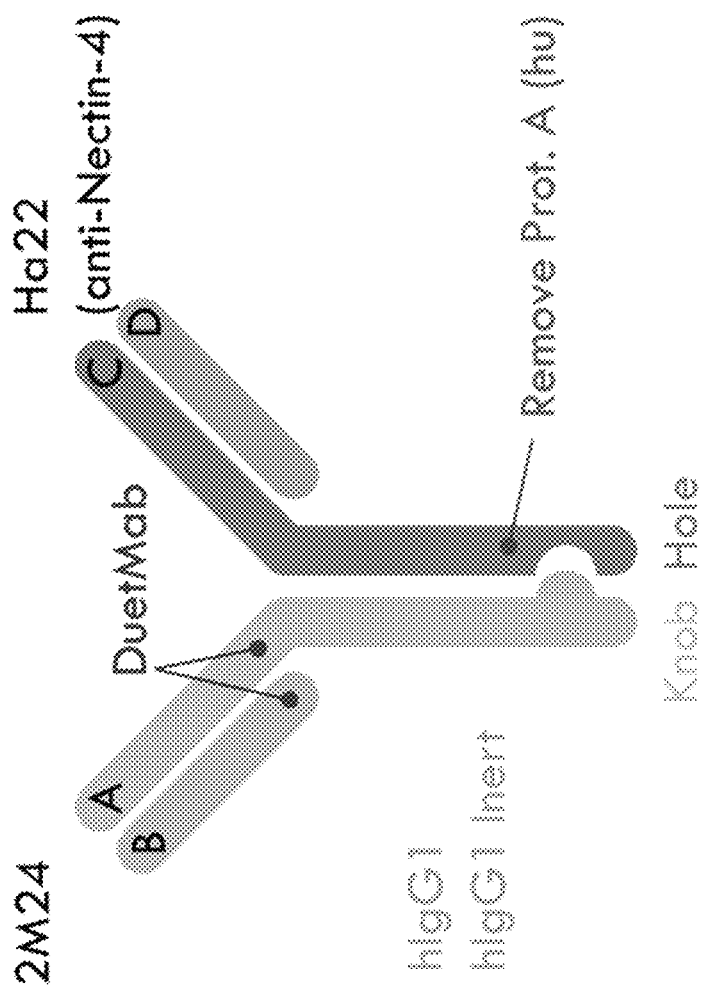
Figure 60B:
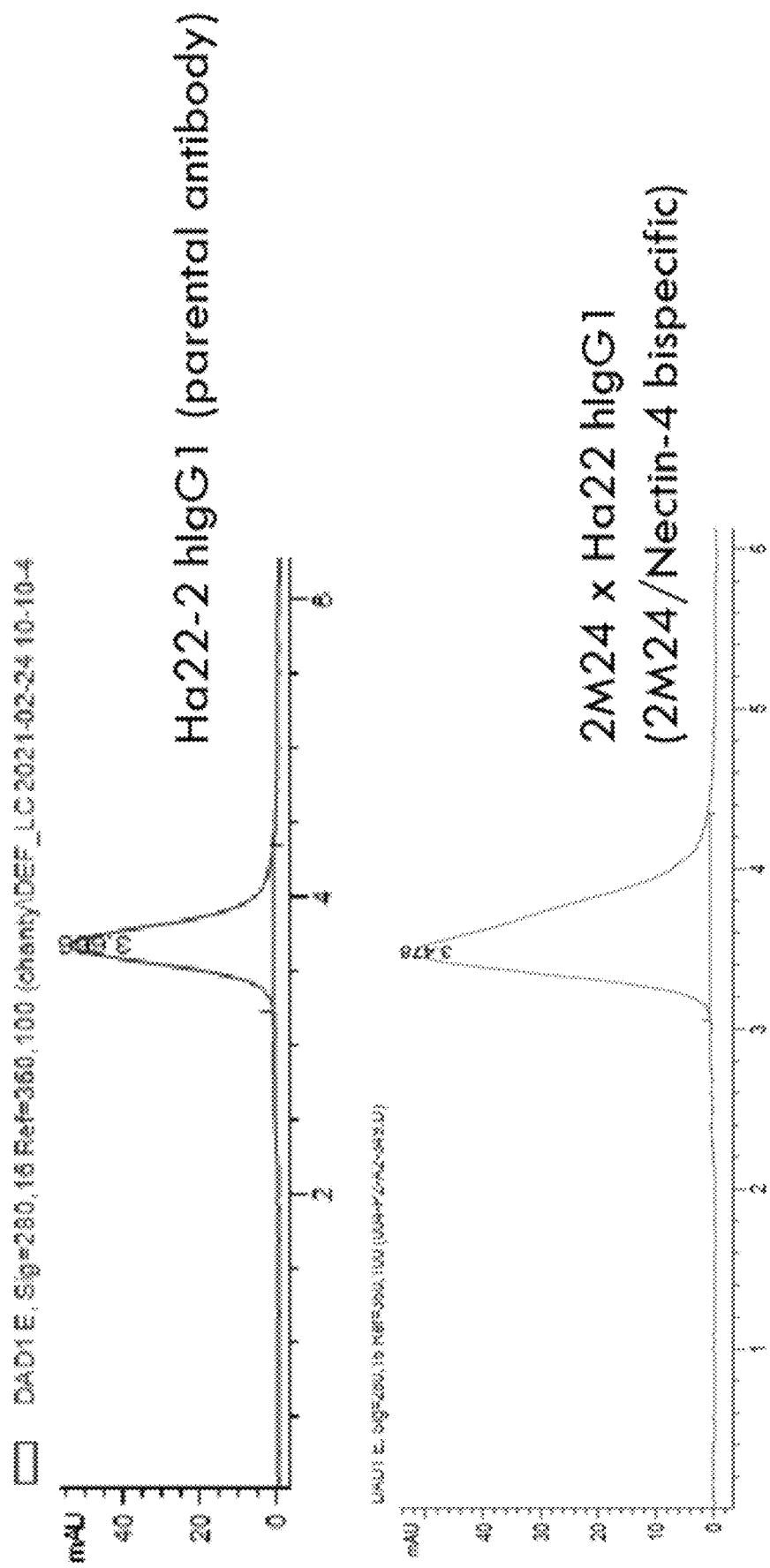

FIGS. 60A & 60B show design and production of a 2M24/Nectin-4 bispecific antibody. FIG. 60A shows a diagram of the bispecific molecule. FIG. 60B shows purification of the bispecific antibody using Protein A chromatography.

Figure 61A:
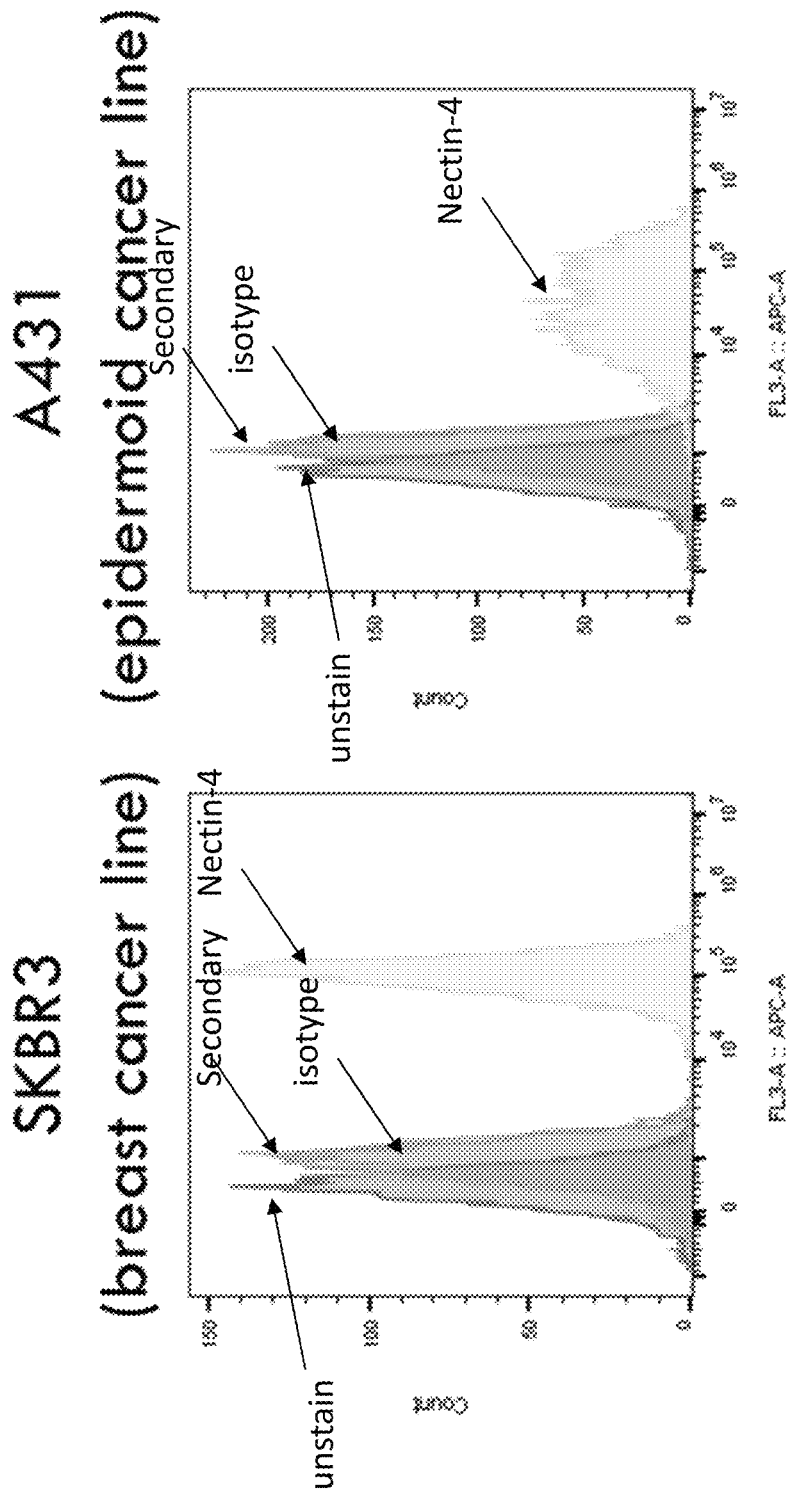
Figure 61B:
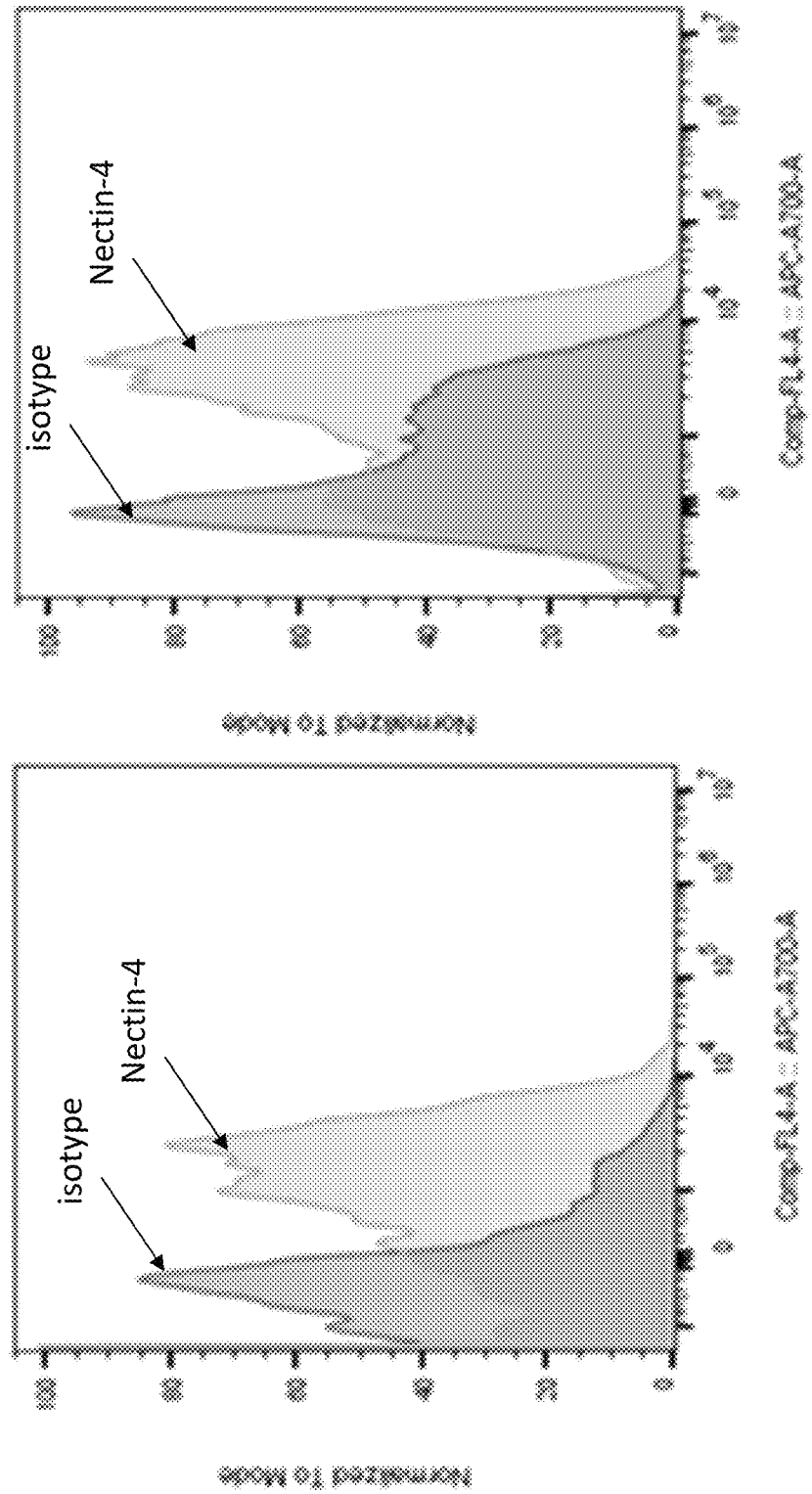

FIGS. 61A & 61B show Nectin-4 expression on cancer cell lines (FIG. 61A) and cancer cells from primary tumor biopsies (FIG. 61B).

Figure 62:
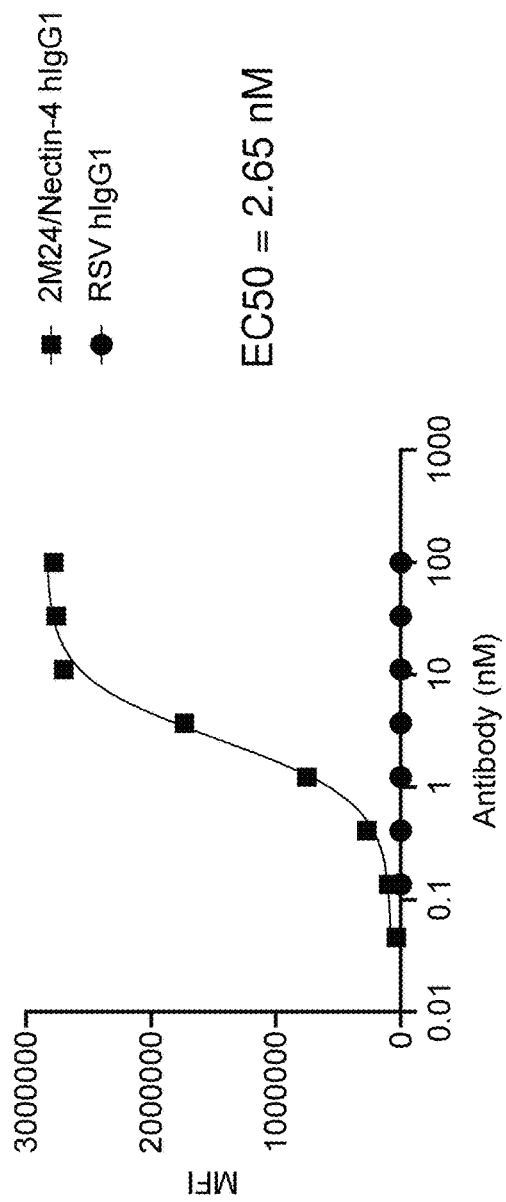
Figure 62:
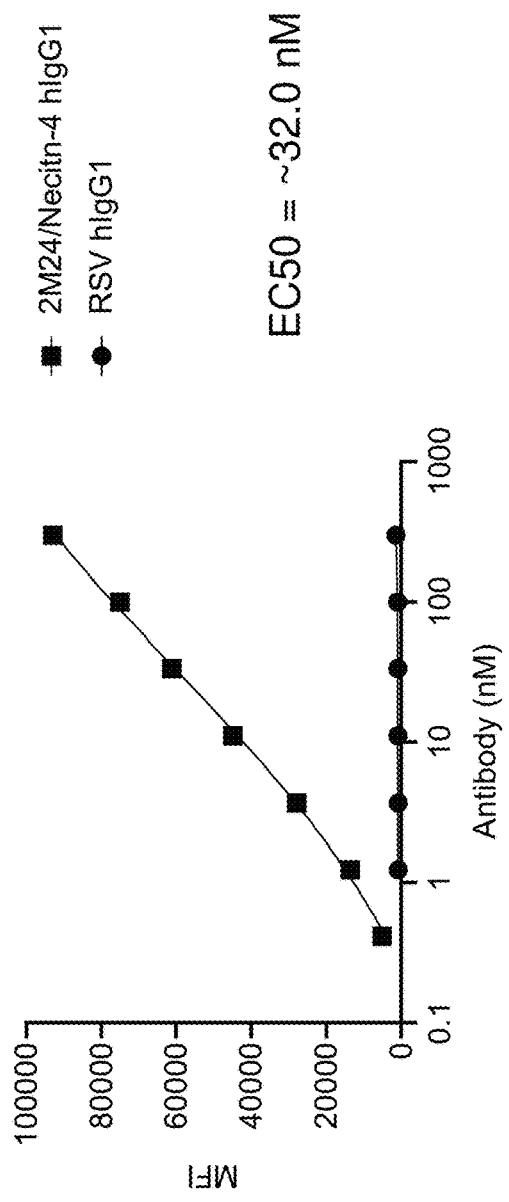

FIG. 62 shows binding of 2M24/Nectin-4 bispecific antibody to Dectin-1-expressing HEK cells (upper) or Nectin-4-expressing A431 cells (lower).

Figure 63:
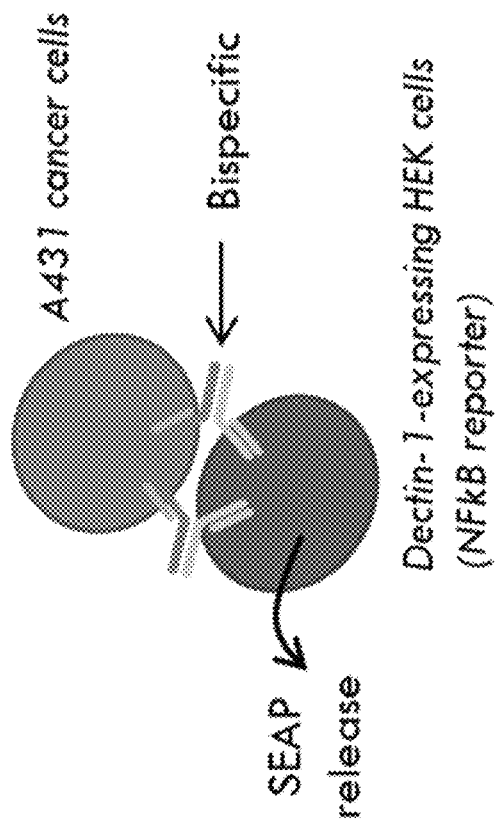
Figure 63:
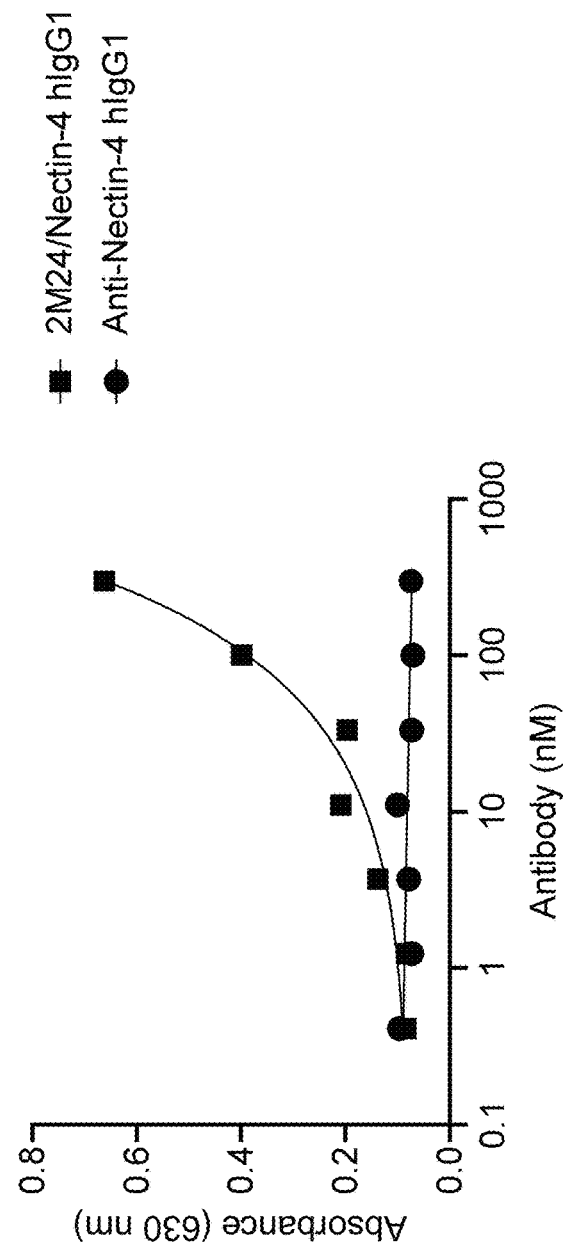

FIG. 63 shows stimulation of Dectin-1 in the NFκB reporter assay by 2M24/Nectin-4 bispecific antibody. Upper panel shows a diagram of the assay. Lower panel shows the results, as quantified based on SEAP levels in media.

Figure 64A:
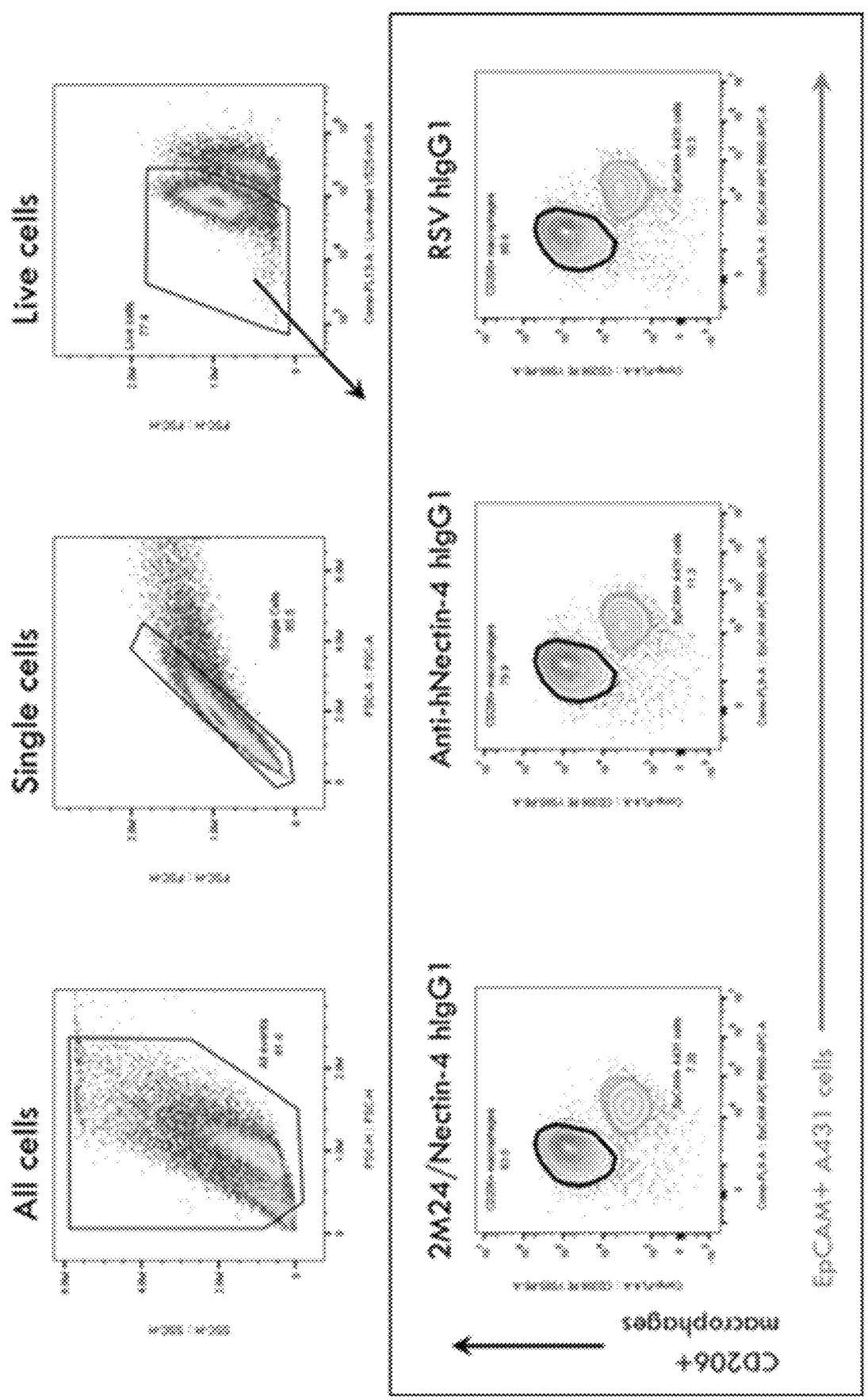
Figure 64B:
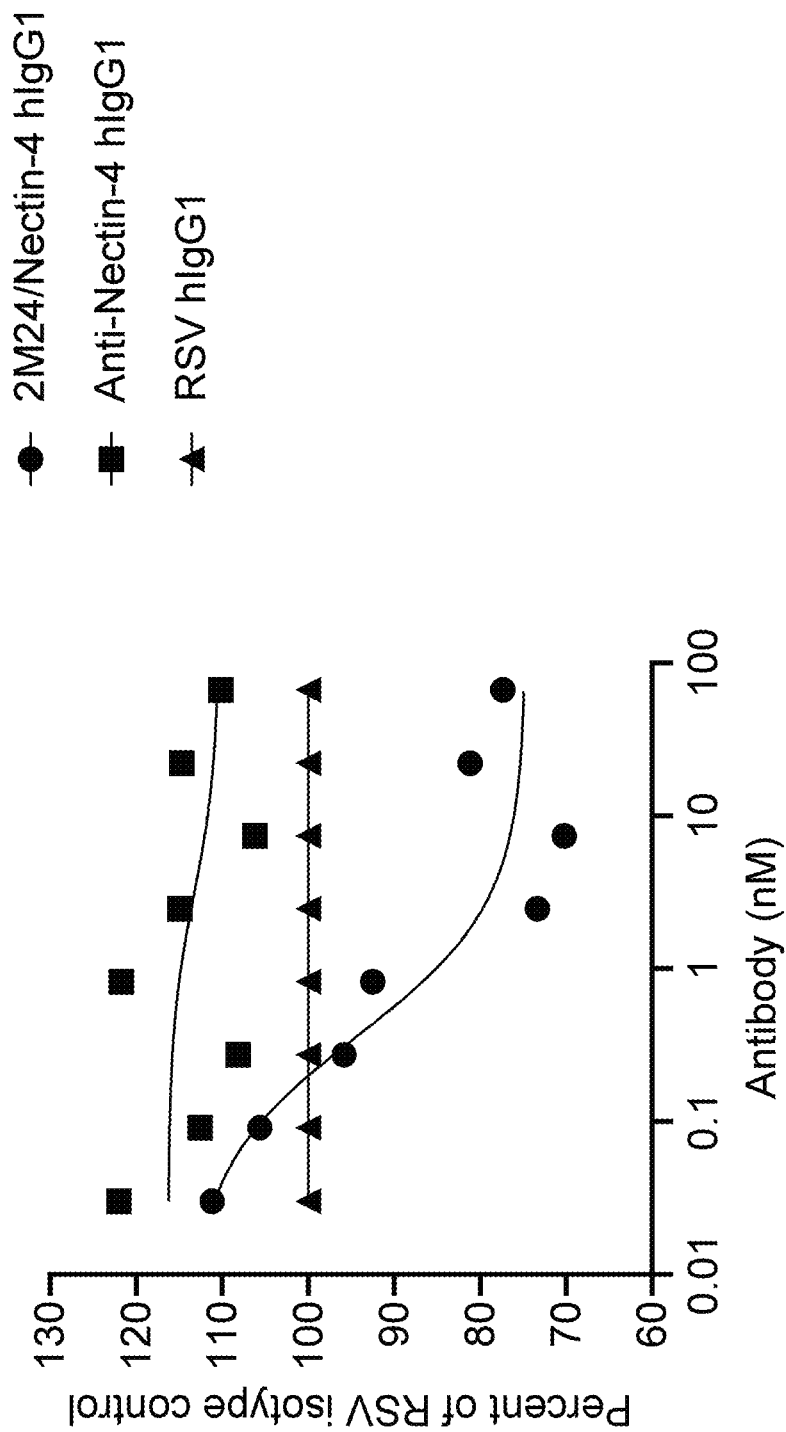

FIGS. 64A & 64B show depletion of Nectin-4-expressing cancer cells by the 2M24/Nectin-4 bispecific antibody. FIG. 64A shows detection of phagocytosis/depletion by flow cytometry. FIG. 64B shows depletion relative to RSV control.

Figure 65A:
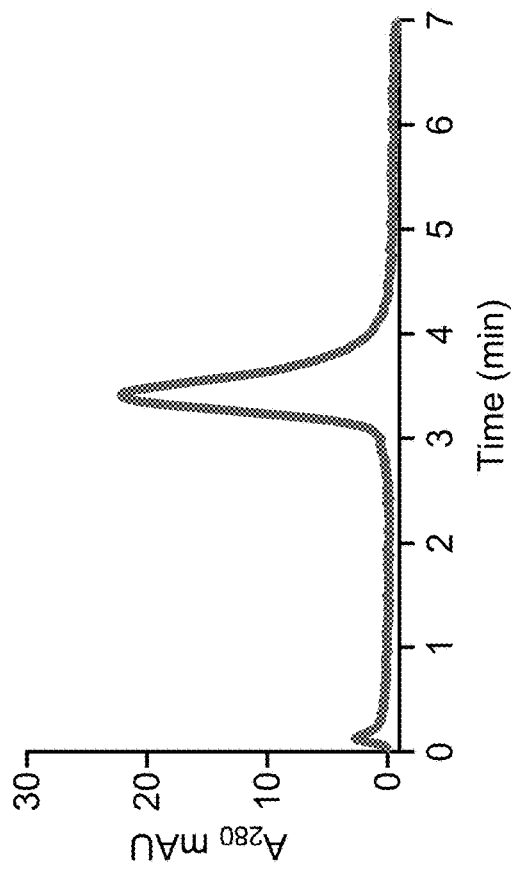
Figure 65A:
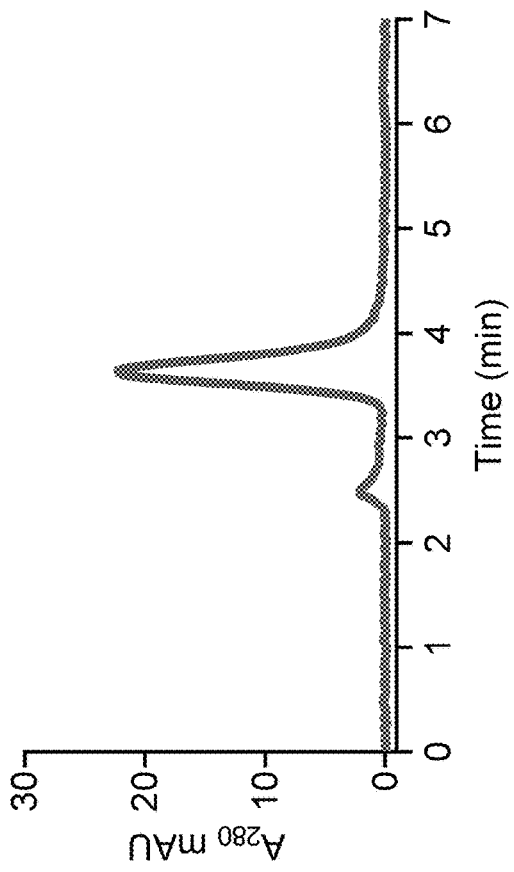
Figure 65B:
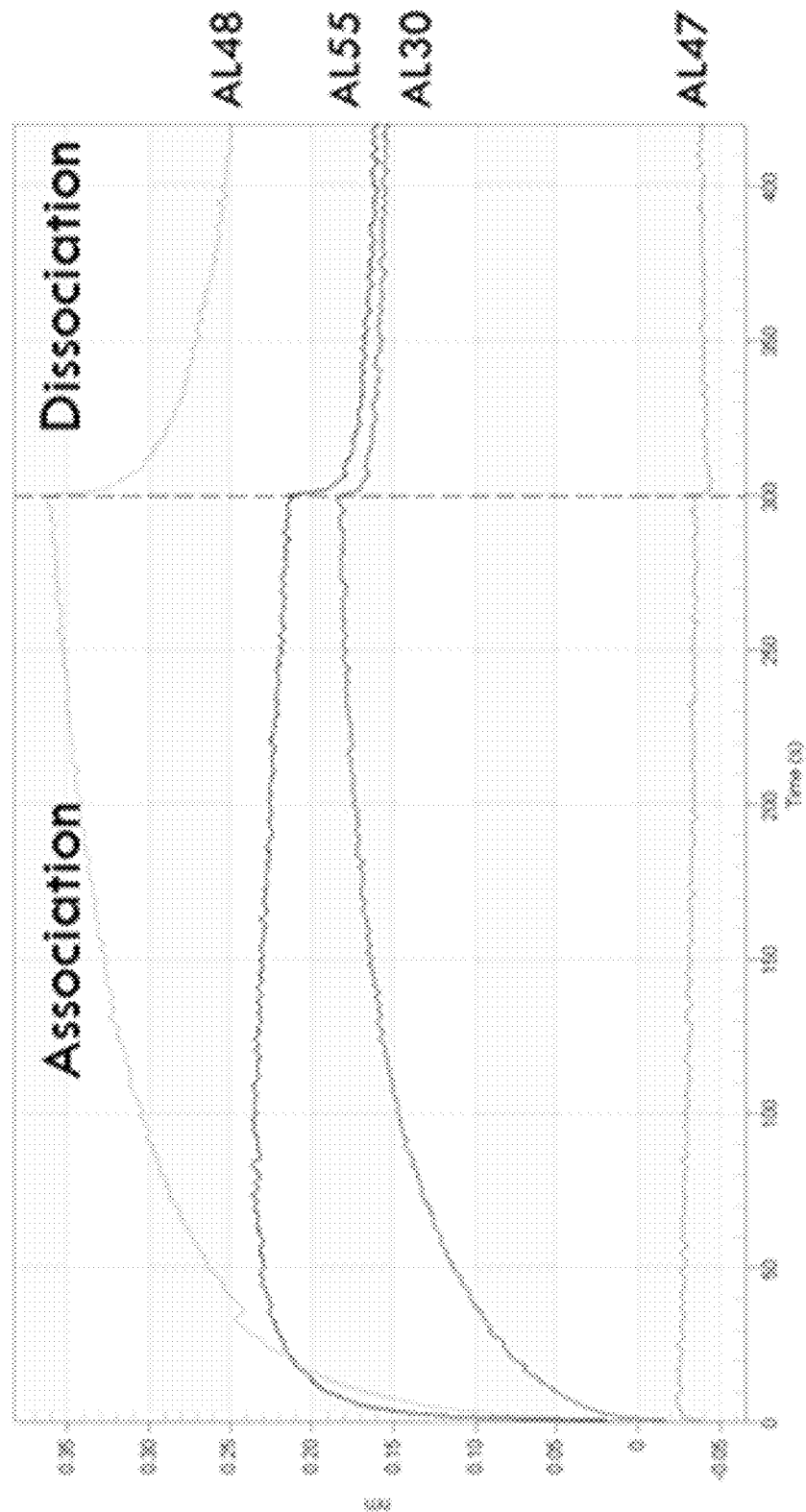
Figure 65C:
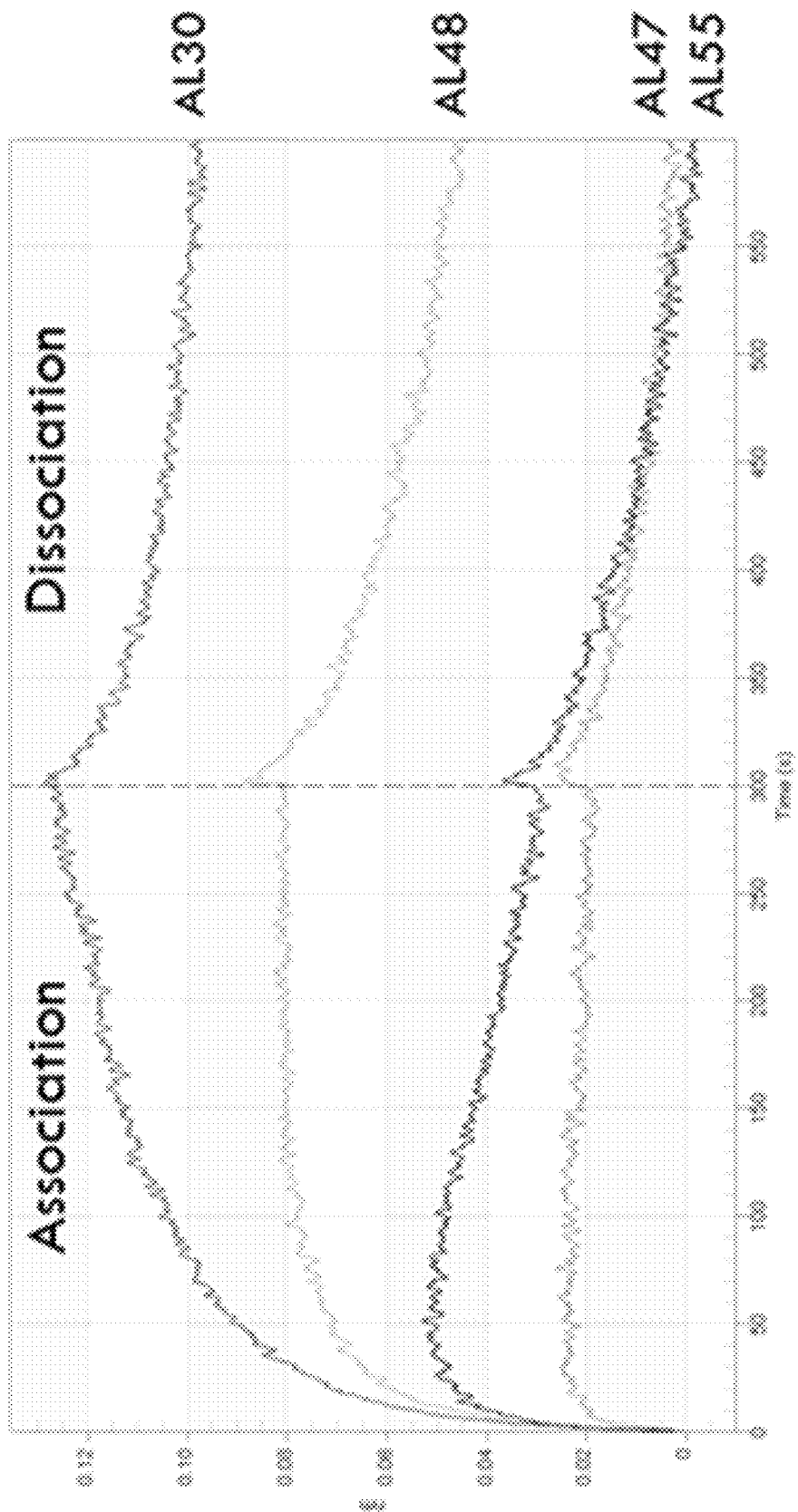

FIGS. 65A-65C show that 2M24/11-1F4 bispecific antibody binds to light chain amyloids. FIG. 65A shows purification of parental anti-amyloid antibody 11-1F4 (upper) and 2M24/11-1F4 bispecific antibody (lower) by SEC. FIGS. 65B & 65C show binding of 11-1F4 parental antibody (FIG. 65B) or 2M24/11-1F4 bispecific antibody (FIG. 65C) to recombinant light chain amyloids from different patients (AL30, AL47, AL48, and AL55) by Octet.

Figure 66:
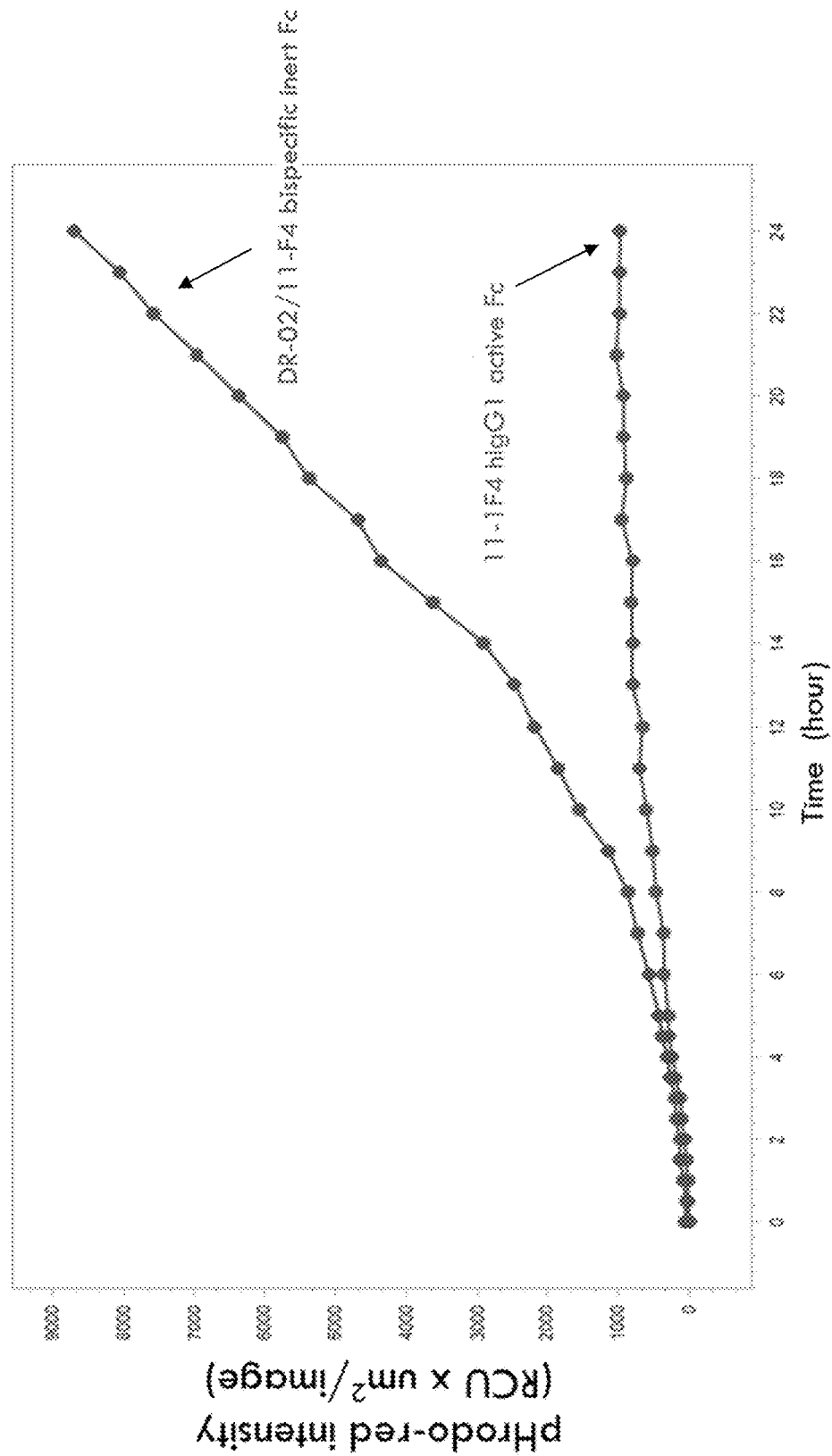

FIG. 66 shows phagocytosis of light chain amyloid fibrils by monocytes.

DETAILED DESCRIPTION

Several aspects are described below with reference to example applications for illustration. It should be understood that numerous specific details, relationships, and methods are set forth to provide a full understanding of the features described herein. One having ordinary skill in the relevant art, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

As used herein, the singular forms "a", "an", and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising". The term "comprising" as used herein is synonymous with "including" or "containing", and is inclusive or open-ended.

Any reference to "or" herein is intended to encompass "and/or" unless otherwise stated. As used herein, the term "about" with reference to a number refers to that number plus or minus 10% of that number. The term "about" with reference to a range refers to that range minus 10% of its lowest value and plus 10% of its greatest value.

I. Antibodies and Multispecific Binding Proteins

In certain aspects, the present disclosure provides antigen binding domains, antibodies, and antibody fragments that bind to human Dectin-1, as well as multispecific (e.g., bispecific) binding molecules comprising the same.

In some embodiments, antibody and immunoglobulin are used interchangeably and herein are used in the broadest sense and encompass various antibody structures, including but not limited to monoclonal antibodies (e.g., full length or intact monoclonal antibodies), polyclonal antibodies, multispecific antibodies (e.g., bispecific antibodies), antibody fragments and single domain antibody (as described in greater detail herein), so long as they exhibit the desired antigen binding activity.

In some embodiments, antibodies (immunoglobulins) refer to a protein having a structure substantially similar to a native antibody structure, or a protein having heavy and light chain variable regions having structures substantially similar to native heavy and light chain variable region structures. Native antibodies refer to naturally occurring immunoglobulin molecules with varying structures. For example, native immunoglobulins of the IgG class are heterotetrameric glycoproteins of about 150,000 daltons, composed of two light chains and two heavy chains that are disulfide-bonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a constant light (CL) domain, also called a light chain constant region. The subunit structures and three-dimensional configurations of the different classes of immunoglobulins are well known and described generally, for example, in Abbas et al., 2000, Cellular and Mol, and Kindt et al., Kuby Immunology, 6th ed., W.H. Freeman and Co., page 91 (2007). Antibodies (immunoglobulins) are assigned to different classes, depending on the amino acid sequences of the heavy chain constant domains. There are five major classes of antibodies: α (IgA), δ (IgD), ε (IgE), γ (IgG), or μ (IgM), some of which may be further divided into subtypes, e.g., γ1 (IgG1), γ2 (IgG2), γ3 (IgG3), γ4 (IgG4), α1 (IgA1) and α2 (IgA2). The light chain of an immunoglobulin may be assigned to one of two types, called kappa (κ) and lambda (λ), based on the amino acid sequence of its constant domain. An immunoglobulin essentially consists of two Fab molecules and an Fc domain, linked via the immunoglobulin hinge region.

In some embodiments, an Fc, Fc region, or Fc domain refers to the C-terminal region of an antibody heavy chain that contains at least a portion of the constant region. The term includes native sequence Fc regions and variant Fc regions. An Fc can refer to the last two constant region immunoglobulin domains (e.g., CH2 and CH3) of IgA, IgD, and IgG, the last three constant region immunoglobulin domains of IgE and IgM, and optionally, all or a portion of the flexible hinge N-terminal to these domains. For IgA and IgM, Fc may include the J chain. An IgG Fc region comprises an IgG CH2 and an IgG CH3 domain and in some cases, inclusive of the hinge. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991. Human IgG Fc domains are of particular use in the present disclosure, and can be the Fc domain from human IgG1, IgG2 or IgG4.

Multiple definitions for the CDR sequences of antibody variable domains are known in the art; see, e.g., Kabat (*Sequences of Proteins of Immunological Interest*, Fifth Edition, NIH Publication 91-3242, Bethesda MD (1991), vols. 1-3) and Chothia. Unless otherwise specified, CDR sequences are described herein according to the definition of IMGT. See, e.g., imgt.org/IMGTScientificChart/Nomenclature/IMGT-FRCDRdefinition.

In some embodiments, an antigen binding domain, antibody, or antibody fragment that binds to human Dectin-1 comprises a heavy chain variable (VH) domain and a light chain variable (VL) domain, wherein the VH domain comprises a CDR-H1 comprising the sequence GYTFTDYY (SEQ ID NO:1), a CDR-H2 comprising the sequence INPNSGDT (SEQ ID NO:2), and a CDR-H3 comprising the sequence ARNSGSYSFGY (SEQ ID NO:3), and wherein the VL domain comprises a CDR-L1 comprising the sequence QGISSW (SEQ ID NO:4), a CDR-L2 comprising the sequence GAS (SEQ ID NO:5), and a CDR-L3 comprising the sequence QQAYSFPFT (SEQ ID NO:6). In some embodiments, an antigen binding domain, antibody, or antibody fragment that binds to human Dectin-1 comprises a heavy chain variable (VH) domain and a light chain variable (VL) domain, wherein the VH domain comprises a CDR-H1, CDR-H2, and CDR-H3 from the VH domain sequence QVQLVQSGAEVKKPGASVKVSCK-SSGYTFTDYYIHWVRQAPGQGLEWMGWINPNSGD TNYAQKFQGRITMTRDTSISTAYLELSRLRSDD-TAVFYCARNSGSYSFGYWGQGTLVTV SS (SEQ ID NO:7), and wherein the VL domain comprises a CDR-L1, CDR-L2, and CDR-L3 from the VL domain sequence DIQMTQSPSSVSASVGDRVTITCRASQGISS-WLAWYQQKPGKAPKLLIFGASSLQSGVPS RFSGSGSGTDFTLTVSSLQPEDFATYYCQQAY-SFPFTFGPGTKVDIE (SEQ ID NO:8).

As noted above, the Kabat definition for CDR sequences can also be used. In some embodiments, an antigen binding domain, antibody, or antibody fragment that binds to human Dectin-1 comprises a heavy chain variable (VH) domain and a light chain variable (VL) domain, wherein the VH domain comprises a CDR-H1 comprising the sequence DYYI (SEQ ID NO:88), a CDR-H2 comprising the sequence WINPNSGDTNYAQKFQG (SEQ ID NO:89), and a CDR-H3 comprising the sequence NSGSYSFGY (SEQ ID NO:90), and wherein the VL domain comprises a CDR-L1 comprising the sequence RASQGISSWLA (SEQ ID NO:91), a CDR-L2 comprising the sequence GASSLQS (SEQ ID NO:92), and a CDR-L3 comprising the sequence QQAYSFPFT (SEQ ID NO:6).

In some embodiments, an antigen binding domain, antibody, or antibody fragment that binds to human Dectin-1 comprises a VH domain comprising a sequence with at least 90%, at least 91%, at least 92%, at least 93%, at least 94%, at least 95%, at least 96%, at least 97%, at least 98%, or at least 99% identity to the amino acid sequence QVQLVQSGAEVKKPGASVKVSCKSSGYTFTDYYIHWVRQAPGQGLEWMGWINPNSGDTNYAQKFQGRITMTRDTSISTAYLELSRLRSDDTAVFYCARNSGSYSFGYWGQGTLVTV SS (SEQ ID NO:7); and/or a VL domain comprising a sequence with at least 90%, at least 91%, at least 92%, at least 93%, at least 94%, at least 95%, at least 96%, at least 97%, at least 98%, or at least 99% identity to the amino acid sequence DIQMTQSPSSVSASVGDRVTITCRASQGISSWLAWYQQKPGKAPKLLIFGASSLQSGVPSRFSGSGSGTDFTLTVSSLQPEDFATYYCQQAYSFPFTFGPGTKVDIE (SEQ ID NO:8). In some embodiments, an antigen binding domain, antibody, or antibody fragment that binds to human Dectin-1 comprises a VH domain comprising the sequence QVQLVQSGAEVKKPGASVKVSCKSSGYTFTDYYIHWVRQAPGQGLEWMGWINPNSGD TNYAQKFQGRITMTRDTSISTAYLELSRLRSDDTAVFYCARNSGSYSFGYWGQGTL VTV SS (SEQ ID NO:7); and/or a VL domain comprising the sequence DIQMTQSPSSVSASVGDRVTITCRASQGISSWLAWYQQKPGKAPKLLIFGASSLQSGVPSRFSGSGSGTDFTLTVSSLQPEDFATYYCQQAYSFPFTFGPGTKVDIE (SEQ ID NO:8). In some embodiments, an antigen binding domain, antibody, or antibody fragment that binds to human Dectin-1 comprises a VH domain comprising the sequence QVQLVQSGAEVKKPGASVKVSCKSSGYTFTDYYIHWVRQAPGQGLEWMGWINPNSGD TNYAQKFQGRITMTRDTSISTAYLELSRLRSDDTAVFYCARNSGSYSFGYWGQGTL VTV SS (SEQ ID NO:7); and a VL domain comprising the sequence DIQMTQSPSSVSASVGDRVTITCRASQGISSWLAWYQQKPGKAPKLLIFGASSLQSGVPSRFSGSGSGTDFTLTVSSLQPEDFATYYCQQAYSFPFTFGPGTKVDIE (SEQ ID NO:8).

In some embodiments, the antigen binding domain, antibody, or antibody fragment is humanized.

In some embodiments, the antibody that binds to human Dectin-1 comprises a heavy chain comprising the sequence QVQLVQSGAEVKKPGASVKVSCKSSGYTFTDYYIHWVRQAPGQGLEWMGWINPNSGD TNYAQKFQGRITMTRDTSISTAYLELSRLRSDDTAVFYCARNSGSYSFGYWGQGTLVTV SSASTKGPSVFPLAPCSRSTSESTAALGCLVKDYFPEPVTVSWNSGALTSGVHTFPAVLQ SSGLYSLSSVVTVPSSSLGTKTYTCNVDHKPSNTKVDKRVES KYGPPCPPCPAPEFLGGP SVFLFPPKPKDTLMISRTPEVTCVVVDVSQEDPEVQFNWYVDGVEVHNAKTKPREEQFN STYRVVSVLTVLHQDWLNGKEYKCKVSNKGLPSSIE KTISKAKGQPREPQVYTLPPSQEE MTKNQVSLTCLVKGFYPSDIAVEWESNGQPENNYKTTPPVLDSDGSFFLYSRLTVDKSR WQEGNVFSCSVMHEALHNHYTQKSLSLSPG (SEQ ID NO:11) and/or a light chain comprising the sequence DIQMTQSPSSVSASVGDRVTITCRASQGISSWLAWYQQKPGKAPKLLIFGASSLQSGVPSRFSGSGSGTDFTLTVSSLQPEDFATYYCQQAYSFPFTFGPGTKVDIERTVAAPSVFIFPPSD EQLKSGTASVVCLLNNFYPREAKVQWKVDNALQSGNSQESVTEQDSKDSTYSLSSTLTL SKADYEKHKVYACEVTHQGLSSPVTKSFNRGEC (SEQ ID NO:12). In some embodiments, the antibody that binds to human Dectin-1 comprises a heavy chain comprising the sequence QVQLVQSGAEVKKPGASVKVSCKSSGYTFTDYYIHWVRQAPGQGLEWMGWINPNSGD TNYAQKFQGRITMTRDTSISTAYLELSRLRSDDTAVFYCARNSGSYSFGYWGQGTLVTV SSASTKGPSVFPLAPCSRSTSESTAALGCLVKDYFPEPVTVSWNSGALTSGVHTFPAVLQ SSGLYSLSSVVTVPSSSLGTKTYTCNVDHKPSNTKVDKRVES KYGPPCPPCPAPEFLGGP SVFLFPPKPKDTLMISRTPEVTCVVVDVSQEDPEVQFNWYVDGVEVHNAKTKPREEQFN STYRVVSVLTVLHQDWLNGKEYKCKVSNKGLPSSIE KTISKAKGQPREPQVYTLPPSQEE MTKNQVSLTCLVKGFYPSDIAVEWESNGQPENNYKTTPPVLDSDGSFFLYSRLTVDKSR WQEGNVFSCSVMHEALHNHYTQKSLSLSPG (SEQ ID NO:11) and a light chain comprising the sequence DIQMTQSPSSVSASVGDRVTITCRASQGISSWLAWYQQKPGKAPKLLIFGASSLQSGVPSRFSGSGSGTDFTLTVSSLQPEDFATYYCQQAYSFPFTFGPGTKVDIERTVAAPSVFIFPPSD EQLKSGTASVVCLLNNFYPREAKVQWKVDNALQSGNSQESVTEQDSKDSTYSLSSTLTL SKADYEKHKVYACEVTHQGLSSPVTKSFNRGEC (SEQ ID NO:12).

In some embodiments, the antigen binding domain, antibody, or antibody fragment binds to human Dectin-1. In some embodiments, the antigen binding domain, antibody, or antibody fragment binds to human Dectin-1 expressed on the surface of a macrophage, monocyte, dendritic cell, or granulocyte. In some embodiments, the antigen binding domain, antibody, or antibody fragment binds to human Dectin-1 isoform A and/or human Dectin-1 isoform B. In some embodiments, human Dectin-1 isoform A comprises the amino acid sequence MEYHPDLENLDEDGYTQLHFDSQSNTRIAVVSEKGSCAASPPWRLIAVILGILCLVILVIA VVLGTMAIWRSNSGSNTLENGYFLSRNKENHSQPTQSSLEDSVTPTKAVKTTG VLSSPCP PNWIIYEKSCYLFSMSLNSWDGSKRQCWQLGSNLLKIDSSNELGFIVKQVSSQPDNSFWI GLSRPQTEVPWLWEDGSTFSSNLFQIRTTATQENPSPNCVWIHVSVIYDQLCSV PSYSICE KKFSM (SEQ ID NO:9). In some embodiments, human Dectin-1 isoform B comprises the amino acid sequence MEYHPDLENLDEDGYTQLHFDSQSNTRIAVVSEKGSCAASPPWRLIAVILGILCLVILVIA VVLGTMGVLSSPCPPNWIIYEKSCYLFSMSLNSWDGSKRQCWQLGSNLLKIDSSNELGFI VKQVSSQPDNSFWIGLSRPQTEVPWLWEDGSTFSSNLFQIRTTATQENPSPNCVWIHVSV IYDQLCSVPSYSICEKKFSM (SEQ ID NO:10). In some embodiments, the antigen binding domain, antibody, or antibody fragment binds to human Dectin-1 expressed on the surface of a cell with an EC50 of less than 5 nM, less than 2 nM, less than 1 nM, or less than 0.5 nM. In some embodiments, the antigen binding domain, antibody, or antibody fragment is capable of binding to human Dectin-1 and monkey Dectin-1, e.g., cynomolgus Dectin-1.

In some embodiments, the antigen binding domain, antibody, or antibody fragment competes for binding to human Dectin-1 with a reference antibody that comprises a heavy chain variable (VH) domain comprising a CDR-H1 comprising the sequence GYTFTDYY (SEQ ID NO:1), a CDR-H2 comprising the sequence INPNSGDT (SEQ ID NO:2), and a CDR-H3 comprising the sequence ARNSGSYSFGY (SEQ ID NO:3), and a light chain variable (VL) domain comprising a CDR-L1 comprising the sequence QGISSW (SEQ ID NO:4), a CDR-L2 comprising the sequence GAS (SEQ ID NO:5), and a CDR-L3 comprising the sequence QQAYSFPFT (SEQ ID NO:6). In some embodiments, the antigen binding domain, antibody, or antibody fragment competes for binding to human Dectin-1 with a reference antibody that comprises a heavy chain variable (VH) domain comprising a CDR-H1 comprising the sequence DYYI (SEQ ID NO:88), a CDR-H2 comprising the sequence WINPNSGDTNYAQKFQG (SEQ ID NO:89), and a CDR-H3 comprising the sequence NSGSYSFGY (SEQ ID NO:90), and a light chain variable (VL) domain comprising a CDR-L1 comprising the sequence RASQGISSWLA (SEQ ID NO:91), a CDR-L2 comprising the sequence GASSLQS (SEQ ID NO:92), and a CDR-L3 comprising the sequence QQAYSFPFT (SEQ ID NO:6). In some embodiments, the antigen binding domain, antibody, or antibody fragment competes for binding to human Dectin-1 with a reference antibody that comprises a heavy chain variable (VH) domain comprising the sequence QVQLVQSGAEVKKP-GASVKVSCKSSGYTFTDYYIHWVRQAPGQ-GLEWMGWINPNSGD TNYAQKFQGRITMTRDTSIS-TAYLELSRLRSDDTAVFYCARNSGSYSFGYWGQGT LVTV SS (SEQ ID NO:7) and a light chain variable (VL) domain comprising the sequence DIQMTQSPSSVSASVGDRVTITCRASQGISS-WLAWYQQKPGKAPKLLIFGASSLQSGVPS RFSGSGSGTDFTLTVSSLQPEDFATYYCQQAY-SFPFTFGPGTKVDIE (SEQ ID NO:8).

In some embodiments, the antigen binding domain, antibody, or antibody fragment binds the same epitope of human Dectin-1 as a reference antibody that comprises a heavy chain variable (VH) domain comprising a CDR-H1 comprising the sequence GYTFTDYY (SEQ ID NO:1), a CDR-H2 comprising the sequence INPNSGDT (SEQ ID NO:2), and a CDR-H3 comprising the sequence ARNSGSYSFGY (SEQ ID NO:3), and a light chain variable (VL) domain comprising a CDR-L1 comprising the sequence QGISSW (SEQ ID NO:4), a CDR-L2 comprising the sequence GAS (SEQ ID NO:5), and a CDR-L3 comprising the sequence QQAYSFPFT (SEQ ID NO:6). In some embodiments, the antigen binding domain, antibody, or antibody fragment binds the same epitope of human Dectin-1 as a reference antibody that comprises a heavy chain variable (VH) domain comprising a CDR-H1 comprising the sequence DYYI (SEQ ID NO:88), a CDR-H2 comprising the sequence WINPNSGDTNYAQKFQG (SEQ ID NO:89), and a CDR-H3 comprising the sequence NSGSYSFGY (SEQ ID NO:90), and a light chain variable (VL) domain comprising a CDR-L1 comprising the sequence RASQGISSWLA (SEQ ID NO:91), a CDR-L2 comprising the sequence GASSLQS (SEQ ID NO:92), and a CDR-L3 comprising the sequence QQAYSFPFT (SEQ ID NO:6). In some embodiments, the antigen binding domain, antibody, or antibody fragment binds the same epitope of human Dectin-1 as a reference antibody that comprises a heavy chain variable (VH) domain comprising the sequence QVQLVQSGAEVKKP-GASVKVSCKSSGYTFTDYYIHWVRQAPGQ-GLEWMGWINPNSGD TNYAQKFQGRITMTRDTSIS-TAYLELSRLRSDDTAVFYCARNSGSYSFGYWGQGT LVTV SS (SEQ ID NO:7) and a light chain variable (VL) domain comprising the sequence DIQMTQSPSSVSASVGDRVTITCRASQGISS-WLAWYQQKPGKAPKLLIFGASSLQSGVPS RFSGSGSGTDFTLTVSSLQPEDFATYYCQQAY-SFPFTFGPGTKVDIE (SEQ ID NO:8).

Examples of antibody fragments include, but are not limited to, Fab, Fab', F(ab')2, and Fv fragments, Fab'-SH, F(ab')2, diabodies, linear antibodies, single chain antibodies, NANOBODY® single domain antibodies, scFv fragments, VH, and multispecific (e.g., bispecific) antibodies/fragments formed from antibody fragments.

A "Fab" (fragment antigen binding) is a portion of an antibody that binds to antigens and includes the variable region and CH1 of the heavy chain linked to the light chain via an inter-chain disulfide bond.

In some embodiments, an antibody of the present disclosure comprises an Fc region. An antibody may be of any class or subclass, including IgG and subclasses thereof (IgG1, IgG2, IgG3, IgG4), IgM, IgE, IgA, and IgD. An immunoglobulin Fc region of the molecule that causes targeted phagocytosis may have important role in the process by engaging Fc receptors and inducing additional phagocytosis. In some embodiments, the molecule has a modified Fc region that has reduced ADCC activity as compared to a wild type human IgG1 (e.g., comprising one or more mutations reducing effector function as described herein).

In some embodiments, an antibody of the present disclosure comprises an Fc region wherein a carbohydrate structure attached to the Fc region has reduced fucose or lacks fucose, e.g., at least one or two of the heavy chains of the antibody is non-fucosylated. In some embodiments, provided herein is a composition comprising an antibody of the present disclosure that comprises an Fc region wherein a carbohydrate structure attached to the Fc region has reduced fucose or lacks fucose, e.g., at least one or two of the heavy chains of the antibody is non-fucosylated. In some embodiments, less than 50% of the N-glycoside-linked carbohydrate chains in the composition contain a fucose residue. In some embodiments, substantially none of the N-glycoside-linked carbohydrate chains contain a fucose residue. In some embodiments, an antibody with reduced fucose or lacking fucose has improved ADCC function.

In other embodiments, an antibody of the present disclosure IgG1 antibody) or composition comprising an antibody of the present disclosure (e.g., an IgG1 antibody) comprises wild-type glycosylation of the Fc region. In some embodiments, provided herein are fucosylated antibodies of the present disclosure (e.g., an IgG1 antibody) or compositions comprising a fucosylated antibody of the present disclosure (e.g., an IgG1 antibody).

Fucosylation or fucosylated antibodies can refer to the presence of fucose residues within the oligosaccharides attached to the peptide backbone of an antibody. Specifically, a fucosylated antibody comprises α (1,6)-linked fucose at the innermost N-acetylglucosamine (GlcNAc) residue in one or both of the N-linked oligosaccharides attached to the antibody Fc region, e.g., at position Asn 297 of the human IgG1 Fc region (EU numbering of Fc region residues). Asn297 may also be located about +3 amino acids upstream or downstream of position 297, i.e., between positions 294 and 300, due to minor sequence variations in immunoglobulins. Non-fucosylated or fucose-deficient antibodies have reduced fucose relative to the amount of fucose on the same antibody produced in a cell line. Antibody fucosylation can be measured, e.g., in an N-glycosidase F treated antibody composition assessed by matrix-assisted laser desorption-ionization time-of-flight mass spectrometry (MALDI TOF MS).

In some embodiments, the Fc region comprises one or more mutations that reduce or eliminate fucosylation, e.g., a substitution at Asn 297 of the human IgG1 Fc region (EU numbering of Fc region residues). Optionally, the Fc region further comprises one or more amino acid substitutions therein which further improve ADCC, for example, substitutions at positions 298, 333, and/or 334 of the Fc region (Eu numbering of residues). Examples of publications related to "defucosylated" or "fucose-deficient" antibodies include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; Okazaki et al. J. Mol. Biol. 336:1239-1249 (2004); Yamane-Ohnuki et al. Biotech. Bioeng. 87: 614 (2004).

In some embodiments, the afucosylated or non-fucosylated antibody is produced in a cell line with a genetic modification that results in an afucosylated or non-fucosylated antibody. Examples of cell lines producing afucosylated antibodies include Lec13 CHO cells deficient in protein fucosylation (Ripka et al. Arch. Biochem. Biophys. 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (Yamane-Ohnuki et al. Biotech. Bioeng. 87: 614 (2004)), cells overexpressing β1,4-N-acetylglucosaminyltransferase III (GnT-III) and Golgi μ-mannosidase II (ManII), and cells with a knockout in the mannosyl-glycoprotein 2-beta-N-acetylglucosaminyltranferase (MGAT1; see Byrne, G. et al. (2018) *PLoS Biol.* 16:e2005817).

In some embodiments, the afucosylated or non-fucosylated antibody is produced in a cell line treated with an inhibitor of glycoprocessing enzyme(s), such as kifunensine, which is an inhibitor of mannosidase I (see, e.g., Elbein, A. D. et al. (1990) *J. Biol. Chem.* 265:15599-15605). For example, cells can be centrifuged and resuspended in growth medium comprising kifunensine (e.g., at 250 μg/mL), then cultured and used for antibody production.

In certain aspects, the present disclosure provides multispecific (e.g., bispecific) antibodies and antibody fragments comprising a first antigen-binding domain that binds to a first target of interest and a second antigen-binding domain that binds to a second target of interest. In some embodiments, the present disclosure provides multispecific (e.g., bispecific) antibodies and antibody fragments comprising a first antigen-binding domain that binds to human Dectin-1 and a second antigen-binding domain that binds to a target of interest.

In some embodiments, multispecific (e.g., bispecific) antibodies and antibody fragments comprise a first antibody or antigen-binding fragment comprising the first antigen-binding domain and a second antibody or antigen-binding fragment comprising the second antigen-binding domain. In some embodiments, the first antibody or fragment is coupled to avidin, streptavidin, neutravidin, or a biotin-binding derivative thereof, and the second antibody or fragment is coupled to biotin or an avidin-binding derivative thereof. In some embodiments, the second antibody or fragment is coupled to avidin, streptavidin, neutravidin, or a biotin-binding derivative thereof, and the first antibody or fragment is coupled to biotin or an avidin-binding derivative thereof. In some embodiments, the first antibody or fragment is bound to the second antibody or fragment via an interaction between the avidin, streptavidin, neutravidin, or biotin-binding derivative thereof and the biotin or avidin-binding derivative thereof.

Exemplary avidins, streptavidins, neutravidins, or biotin-binding derivatives thereof are known in the art. In some embodiments, the streptavidin is monomeric streptavidin (mSA). Exemplary biotins or avidin-binding derivatives thereof are known in the art. In some embodiments, an antibody or antigen-binding fragment thereof of the present disclosure is biotinylated. Kits for biotinylating an antibody of interest are known in the art and commercially available. In some embodiments, mSA comprises the sequence EFASAEAGITGTWYNQHGSTFTVTAGADGNLTGQYENRAQGTGCQNSPYTLTGRYNGT KLEWRVEWNNSTENCHSRTEWRGQYQGGAEARINTQWNLTYEGG SGPATEQGQDTFT KVKPSAASGS (SEQ ID NO:14).

In some embodiments, an antibody that binds human Dectin-1 and is coupled to mSA via a linker comprises the sequence QVQLVQSGAEVKKPGASVKVSCK-SSGYTFTDYYIHWVRQAPGQGLEWMGWINPNSGD TNYAQKFQGRITMTRDTSISTAYLELSRLRSDD-TAVFYCARNSGSYSFGYWGQGTLVTV SSAS-TKGPSVFPLAPCSRSTSESTAALGCLVKDYF-PEPVTVSWNSGALTSGVHTFPAVLQ SSGLYS-LSSVVTVPSSSLGTKTYTCNVDHKPSNTKVDKRVES KYGPPCPPCPAPEFLGGP SVFLFPPKPKDTLMISRTPE-VTCVVVDVSQEDPE-VQFNWYVDGVEVHNAKTKPREEQFN STYRVVSVLTVLHQDWLNGKEYKCKVSNKGLPSSIE KTISKAKGQPREPQVYTLPPSQEE MTKNQVSLT-CLVKGFYPSDIAVEWESNGQPEN-NYKTTPPVLDSDGSFFLYSRLTVDKSR WQEGNVFSCSVMHEALHNHYTQKSLSL-SPGKGGGSGGGSGGGSEFASAEAGITGTWYN QHG-STFTVTAGADGNLTGQYENRAQGTGCQNSPYTLT-GRYNGTKLEWRVEWNNSTEN CHSRTEWRGQYQGGAEARINTQWNLTYEGGSG-PATEQGQDTFTKVKPSAASGS (SEQ ID NO:15). In some embodiments, an antibody fragment that binds human Dectin-1 and is coupled to mSA via a linker comprises the sequence (SEQ ID NO: 16)
QVQLVQSGAEVKKPGASVKVSCKSSGYTFTDYYIHWVRQAPGQGLEWMGW

INPNSGDTNYAQKFQGRITMTRDTSISTAYLELSRLRSDDTAVFYCARNS

GSYSFGYWGQGTLVTVSSASTKGPSVFPLAPCSRSTSESTAALGCLVKDY

FPEPVTVSWNSGALTSGVHTFPAVLQSSGLYSLSSVVTVPSSSLGTKTYT

CNVDHKPSNTKVDKRVGGGSGGGSGGGSEFASAEAGITGTWYNQHGSTFT

VTAGADGNLTGQYENRAQGTGCQNSPYTLTGRYNGTKLEWRVEWNNSTEN

CHSRTEWRGQYQGGAEARINTQWNLTYEGGSGPATEQGQDTFTKVKPSAA

SGS
or (SEQ ID NO: 17)
QVQLVQSGAEVKKPGASVKVSCKSSGYTFTDYYIHWVRQAPGQGLEWMGW

INPNSGDTNYAQKFQGRITMTRDTSISTAYLELSRLRSDDTAVFYCARNS

GSYSFGYWGQGTLVTVSSASTKGPSVFPLAPCSRSTSESTAALGCLVKDY

FPEPVTVSWNSGALTSGVHTFPAVLQSSGLYSLSSVVTVPSSSLGTKTYT

CNVDHKPSNTKVDKRVGGGSGGGSGGGSEFASAEAGITGTWYNQHGSTFT

VTAGADGNLTGQYENRAQGTGCQNSPYTLTGRYNGTKLEWRVEWNNSTEN

CHSRTEWRGQYQGGAEARINTQWNLTYEGGSGPATEQGQDTFTKVKPSAA

SGSAAAGASHHHHHH.

In some embodiments, one or both of the first and second antigen binding domain, antibody, or fragment is/are humanized.

In some embodiments, one or both of the first and second antigen binding domain, antibody, or fragment comprise(s) a tag, e.g., for affinity purification. In some embodiments, the tag is a polyhistidine tag.

In some embodiments, one or both of the first and second antibodies or fragments are Fab, Fab', F(ab')2, Fv, Fab'-SH, F(ab')2, single chain antibodies, NANOBODY® single domain antibodies, or scFv fragments. In some embodiments, one or both of the first and second antibodies or fragments further comprise an Fc domain. In some embodiments, the first antibody or fragment is a Fab fragment, and wherein the second antibody or fragment is a full-length antibody. In some embodiments, the first and the second antibodies or fragments are both full-length antibodies. In some embodiments, the first antibody or fragment is a Fab fragment coupled to monomeric streptavidin (mSA), and wherein the second antibody or fragment is a biotinylated full-length antibody. In some embodiments, the first antibody or fragment is a full-length antibody coupled to monomeric streptavidin (mSA), and wherein the second antibody or fragment is a biotinylated full-length antibody.

In some embodiments, an antibody or fragment is coupled to avidin, streptavidin, neutravidin, or a biotin-binding derivative thereof, or coupled to biotin or an avidin-binding derivative thereof, via a linker. Linkers for creating antibody fusion proteins are known in the art. In some embodiments, the linker comprises, consists of, or consists essentially of, glycine and/or serine residues. In some embodiments, the linker is 15-20 amino acids in length. In some embodiments, the linker comprises the sequence GGGSGGGSGGGS (SEQ ID NO:13). In some embodiments, the linker comprises one or more repeats of the sequence GGGGS (SEQ ID NO:26). In some embodiments, the linker comprises the sequence GGGGSGGGGSGGGGS (SEQ ID NO:27) or GGGGSGGGGSGGGGSGGGGS (SEQ ID NO:28). Additional linker sequences are described in Chen, X. et al. (2013) *Adv. Drug Deliv. Rev.* 65:1357-1369. In some embodiments (e.g., in a scFv of the present disclosure), the scFv comprises one type of linker between the VH and VL domains, and another type of linker connecting the VL domain to the rest of the half-antibody, e.g., to an Fc region. For example, in some embodiments, the linker between the VH and VL domains comprises glycine and/or serine residues, such as GGGSGGGSGGGS (SEQ ID NO:13), GGGGSGGGGSGGGGS (SEQ ID NO:27), GGGGSGGGGSGGGGSGGGGS (SEQ ID NO:28), or one or more repeats of the sequence GGGGS (SEQ ID NO:26); and/or the linker connecting the VL domain to the Fc region comprises EPKRSDKTHTCPPC (SEQ ID NO:29) or SATHTCPPC (SEQ ID NO:30). In some embodiments, the linker between the VH and VL domains comprises glycine and/or serine residues and is 15-20 amino acids in length.

In some embodiments, the first target of interest is human Dectin-1 (e.g., isoform(s) A and/or B). In some embodiments, the second target of interest is a disease-causing agent. In some embodiments, the second target of interest is human Dectin-1 (e.g., isoform(s) A and/or B). In some embodiments, the first target of interest is a disease-causing agent.

In certain aspects, the present disclosure provides multispecific (e.g., bispecific) antibodies and antibody fragments comprising at least one antigen binding domain that binds to human Dectin-1. Any of the antigen binding domains that bind to human Dectin-1 of the present disclosure may find use in a multispecific (e.g., bispecific) binding molecule, antibody, or antibody fragment. In some embodiments, the multispecific (e.g., bispecific) binding molecule, antibody, or antibody fragment further comprises at least one antigen binding domain that binds to a target of interest, e.g., as described herein. In some embodiments, the target of interest is a disease-causing agent.

In some embodiments, the multispecific (e.g., bispecific) binding molecule comprises a first antibody arm comprising a single chain variable fragment (scFv) comprising VH and VL domains of the present disclosure that bind to human Dectin-1 and a first Fc region, and a second antibody arm comprising an antibody heavy chain that comprises a VH domain in association with an antibody light chain that comprises a VL domain, and a second Fc region connected to the VH domain. In some embodiments, the scFv arm binds to Dectin-1, and the conventional antibody arm with VH and VL domains on separate polypeptides binds to a target of interest, e.g., as described herein, such as a disease-causing agent. In some embodiments, the first Fc region comprises one or more knob-forming mutations, and the second Fc region comprises one or more cognate hole-forming mutations, or wherein the second Fc region comprises one or more knob-forming mutations, and the first Fc region comprises one or more cognate hole-forming mutations. In some embodiments, the first antibody arm comprises a first linker between the VH and VL domains (e.g., of 15-20 amino acids in length), and a second linker between the VL domain and the first Fc region. In some embodiments, the first linker comprises one or more repeats of the sequence GGGGS (SEQ ID NO:26), e.g., the sequence GGGGSGGGGSGGGGS (SEQ ID NO:27) or GGGGSGGGGSGGGGSGGGGS (SEQ ID NO:28). In some embodiments, the second linker comprises the sequence EPKRSDKTHTCPPC (SEQ ID NO:29) or SATHTCPPC (SEQ ID NO:30). Additional linker sequences are described in Chen, X. et al. (2013) *Adv. Drug Deliv. Rev.* 65:1357-1369. A non-limiting example of this format is shown in FIG. 51.

In some embodiments, the disease-causing agent is a bacterial cell, fungal cell, virus, senescent cell, tumor cell, protein aggregate, LDL particle, mast cell, eosinophil, ILC2 cell, or inflammatory immune cell. In some embodiments, the target of interest is an antigen expressed on the surface of the bacterial cell, fungal cell, senescent cell, tumor cell, mast cell, eosinophil, ILC2 cell, or inflammatory immune cell. In some embodiments, the target of interest is a surface antigen of the virus. In some embodiments, the target of interest is a protein aggregate or monomer thereof, e.g., amyloid beta (such as in Alzheimer's disease), or lambda or kappa light chain amyloid (such as in light chain amyloidosis). In some embodiments, e.g., for oncology applications, the second target of interest is CD70, HER2, DLL3, NECTIN-4, TROP-2, Mesothelin, LIV-1, C-MET, FOLR1, CD20, CCR8, CD33, or EGFR, e.g., as expressed on the surface of a cancer cell.

In some embodiments, the target of interest is CD20, e.g., human CD20. In some embodiments, the antigen binding domain that binds CD20 comprises a CDR-H1, CDR-H2, and CDR-H3 sequence from the VH domain sequence QVQLQQPGAELVKPGASVKMSCKASGYTFTSYN-MHWVKQTPGRGLEWIGAIYPGNGD TSYN-QKFKGKATLTADKSSSTAYMQLSSLTSEDSAVYY-CARSTYYGGDWYFNVWGAG TTVTVSA (SEQ ID NO:24) and/or a CDR-L1, CDR-L2, and CDR-L3 sequence from the VL domain sequence QIVLSQSPAIL-SASPGEKVTMTCRASSSVSYIHWFQQKPGSSPKPWI-YATSNLASGVPVRF SGSGSGTSYSLTISRVEAE-DAATYYCQQWTSNPPTFGGGTKLEIK (SEQ ID NO:25). In some embodiments, the antigen binding domain that binds CD20 comprises a VH domain that comprises the sequence QVQLQQPGAELVKPGASVKMSCKASGYTFTSYNMHWVKQTPGRGLEWIGAIYPGNGDTSYNQKFKGKATLTADKSSSTAYMQLSSLTSEDSAVYYCARSTYYGGDWYFNVWGAG TTVTVSA (SEQ ID NO:24) and/or a VL domain that comprises the sequence QIVLSQSPAILSASPGEKVTMTCRASSSVSYIHWFQQKPGSSPKPWIYATSNLASGVPVRF SGSGSGTSYSLTISRVEAEDAATYYCQQWTSNPPTFGGGTKLEIK (SEQ ID NO:25). In some embodiments, the antigen binding domain that binds CD20 comprises the VH and VL domain sequences from rituximab. In some embodiments, the antigen binding domain that binds CD20 comprises the VH and VL domain sequences from obinutuzumab. In some embodiments, the antigen binding domain that binds CD20 comprises a VH domain that comprises the sequence of SEQ ID NO:46 and/or a VL domain that comprises the sequence of SEQ ID NO:47.

In some embodiments, provided herein is a multispecific (e.g., bispecific) binding molecule that comprises a first antibody arm comprising a single chain variable fragment (scFv) comprising VH and VL domains of the present disclosure that bind to human Dectin-1 and a first Fc region, and a second antibody arm comprising an antibody heavy chain that comprises a VH domain in association with an antibody light chain that comprises a VL domain and a second Fc region connected to the VH domain, wherein the VH and VL domains of the second antibody arm form an antigen binding domain that binds to a target of interest (e.g., a disease causing agent of the present disclosure). In some embodiments, the first Fc region comprises one or more knob-forming mutations, and the second Fc region comprises one or more cognate hole-forming mutations, or the second Fc region comprises one or more knob-forming mutations, and the first Fc region comprises one or more cognate hole-forming mutations. In some embodiments, the scFv comprises a first linker of the present disclosure between the VH and VL domains and a second linker of the present disclosure between the VL domain and the first Fc region. In some embodiments, the first antibody arm comprises the amino acid sequence of (SEQ ID NO: 31)
QVQLVQSGAEVKKPGASVKVSCKSSGYTFTDYYIHWVRQAPGQGLEWMGW

INPNSGDTNYAQKFQGRITMTRDTSISTAYLELSRLRSDDTAVFYCARNS

GSYSFGYWGQGTLVTVSSGGGGSGGGGSGGGGSGGGGSDIQMTQSPSSVS

ASVGDRVTITCRASQGISSWLAWYQQKPGKAPKLLIFGASSLQSGVPSRF

SGSGSGTDFTLTVSSLQPEDFATYYCQQAYSFPFTFGPGTKVDIEEPKRS

DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSREEMTKNQVSLWCLVK

GFYPSDIAVEWESNGQPENNYKTTPPVLDSDGSFFLYSKLTVDKSRWQQG

NVFSCSVMHEALHNHYTQKSLSLSPG.

In some embodiments, provided herein is a multispecific (e.g., bispecific) binding molecule that comprises a first antibody arm comprising a single chain variable fragment (scFv) comprising VH and VL domains of the present disclosure that bind to human Dectin-1 and a first Fc region, and a second antibody arm comprising an antibody heavy chain that comprises a VH domain in association with an antibody light chain that comprises a VL domain and a second Fc region connected to the VH domain, wherein the VH and VL domains of the second antibody arm form an antigen binding domain that binds to CD20 (e.g., human CD20). In some embodiments, the first Fc region comprises one or more knob-forming mutations, and the second Fc region comprises one or more cognate hole-forming mutations, or the second Fc region comprises one or more knob-forming mutations, and the first Fc region comprises one or more cognate hole-forming mutations. In some embodiments, the scFv comprises a first linker of the present disclosure between the VH and VL domains and a second linker of the present disclosure between the VL domain and the first Fc region. In some embodiments, the first antibody arm comprises the amino acid sequence of QVQLVQSGAEVKKPGASVKVSCKSSGYTFTDYYIHWVRQAPGQGLEWMGWINPNSGDTNYAQKFQGRITMTRDTSISTAYLELSRLRSDDTAVFYCARNSGSYSFGYWGQGTLVTVSSGGGGSGGGGSGGGGSGGGGSDIQMTQSPSSVSASVGDRVTITCRASQGISSWLAWYQ QKPGKAPKLLIFGASSLQSGVPSRFSGSGSGTDFTLTVSSLQPEDFATYYCQQAYSFPFTF GPGTKVDIEEPKRSDKTHTCPPCPAPELLGGPSVFLFPPKPKDTLMISRTPEVTCVVVDVS HEDPEVKFNWYVDGVEVHNAKTKPREEQYNSTYRVVSVLTVLHQDWLNGKEYKCKVS NKALPAPIEKTISKAKGQPREPQVYTLPPSREEMTKNQVSLWCLVKGFYPSDIAVEWESN GQPENNYKTTPPVLDSDGSFFLYSKLTVDKSRWQQGNVFSCSVMHEALHNHYTQKSLS LSPG (SEQ ID NO:31). In some embodiments, the second antibody arm comprises a VH domain comprising the sequence of SEQ ID NO:24 and a VL domain comprising the sequence of SEQ ID NO:25. In some embodiments, the second antibody arm comprises a second polypeptide comprising the sequence of QVQLQQPGAELVKPGASVKMSCKASGYTFTSYNMHWVKQTPGRGLEWIGAIYPGNGDTSYNQKFKGKATLTADKSSSTAYMQLSSLTSEDSAVYYCARSTYYGGDWYFNVWGAGTTVTVSAASTKGPSVFPLAPSSKSTSGGTAALGCLVKDYFPEPVTVSWNSGALTSGVHTF PAVLQSSGLYSLSSVVTVPSSSLGTQTYICNVNHKPSNTKVDKKVEPKSCDKTHTCPPCP APELLGGPSVFLFPPKPKDTLMISRTPEVTCVVVDVSHEDPEVKFNWYVDGVEVHNAKT KPREEQYNSTYRVVSVLTVLHQDWLNGKEYKCKVSNKALPAPIEKTISKAKGQPREPQV YTLPPSREEMTKNQVSLSCAVKGFYPSDIAVEWESNGQPENNYKTTPPVLDSDG SFFLVS KLTVDKSRWQQGNVFSCSVMHEALHNRFTQKSLSLSPG (SEQ ID NO:32) and a third polypeptide comprising the amino acid sequence of QIVLSQSPAILSASPGEKVTMTCRASSSVSYIHWFQQKPGSSPKPWIYATSNLASGVPVRF SGSGSGTSYSLTISRVEAEDAATYYCQQWTSNPPTFGGGTKLEIKRTVAAPSVFIF PPSDE QLKSGTASVVCLLNNFYPREAKVQWKVDNALQSGNSQESVTEQDSKDSTYSLSSTLTLS KADYEKHKVYACEVTHQGLSSPVTKSFNRGEC (SEQ ID NO:33).

In some embodiments, provided herein is a multispecific (e.g., bispecific) binding molecule that comprises a first antibody arm comprising a single chain variable fragment (scFv) comprising VH and VL domains of the present disclosure that bind to human Dectin-1 and a first Fc region, and a second antibody arm comprising an antibody heavy chain that comprises a VH domain in association with an antibody light chain that comprises a VL domain and a second Fc region connected to the VH domain, wherein the VH and VL domains of the second antibody arm form an antigen binding domain that binds to HER2 (e.g., human HER2). In some embodiments, the first Fc region comprises one or more knob-forming mutations, and the second Fc region comprises one or more cognate hole-forming mutations, or the second Fc region comprises one or more knob-forming mutations, and the first Fc region comprises one or more cognate hole-forming mutations. In some embodiments, the scFv comprises a first linker of the present disclosure between the VH and VL domains and a second linker of the present disclosure between the VL domain and the first Fc region. In some embodiments, the first antibody arm comprises the amino acid sequence of QVQLVQS-GAEVKKPGASVKVSCK-SSGYTFTDYYIHWVRQAPGQGLEWMGWINPNSGD TNYAQKFQGRITMTRDTSISTAYLELSRLRSDD-TAVFYCARNSGSYSFGYWGQGTLVTV SSGGGGSGGGGSGGGGSGGGGSDIQMTQSPSSVSAS VGDRVTITCRASQGISSWLAWYQ QKPGKAPKLLIF-GASSLQSGVPSRFSGSGSGTDFTLTVSSLQPEDFA-TYYCQQAYSFPFTF GPGTKVDIEEPKRSDKTH-TCPPCPAPELLGGPSVFLFPPKPKDTLMISRTPEVTCV VVDVS HEDPEVKFNWYVDGVEVHNAKTKPRE-EQYNSTYRVVSVLTVLHQDWLNGKEYKCKVS NKA-LPAPIEKTISKAKGQPREPQVYTLPPSREEMT-KNQVSLWCLVKGFYPSDIAVEWESN GQPENNYKTTPPVLDSDGSFFLYSK-LTVDKSRWQQGNVFSCSVMHEALHNHYTQKSLS LSPG (SEQ ID NO:31). In some embodiments, the second antibody arm comprises a VH domain comprising the sequence of EVQLVESGGGLVQPGGSLRLS-CAASGFNIKDTYIHWVRQAPGKGLEW-VARIYPTNGYTR YADSVKGRFTISADTSKNTAY-LQMNSLRAEDTAVYYCSRWGGDGFYAMDYWGQGT L VTVSS (SEQ ID NO:34) and a VL domain comprising the sequence of DIQMTQSPSSLSASVGDRVTIT-CRASQDVNTAVAWYQQKPGKAPKLLIYSASFLY-SGVPS RFSGSRSGTDFTLTISSLQPEDFA-TYYCQQHYTTPPTFGQGTKVEIK (SEQ ID NO:35). In some embodiments, the antigen binding domain that binds HER2 comprises the VH and VL domain sequences from trastuzumab.

In some embodiments, provided herein is a multispecific (e.g., bispecific) binding molecule that comprises a first antibody arm comprising a single chain variable fragment (scFv) comprising VH and VL domains of the present disclosure that bind to human Dectin-1 and a first Fc region, and a second antibody arm comprising an antibody heavy chain that comprises a VH domain in association with an antibody light chain that comprises a VL domain and a second Fc region connected to the VH domain, wherein the VH and VL domains of the second antibody arm form an antigen binding domain that binds to Trop-2 (e.g., human Trop-2). In some embodiments, the first Fc region comprises one or more knob-forming mutations, and the second Fc region comprises one or more cognate hole-forming mutations, or the second Fc region comprises one or more knob-forming mutations, and the first Fc region comprises one or more cognate hole-forming mutations. In some embodiments, the scFv comprises a first linker of the present disclosure between the VH and VL domains and a second linker of the present disclosure between the VL domain and the first Fc region. In some embodiments, the first antibody arm comprises the amino acid sequence of QVQLVQS-GAEVKKPGASVKVSCK-SSGYTFTDYYIHWVRQAPGQGLEWMGWINPNSGD TNYAQKFQGRITMTRDTSISTAYLELSRLRSDD-TAVFYCARNSGSYSFGYWGQGTLVTV SSGGGGSGGGGSGGGGSGGGGSDIQMTQSPSSVSA SVGDRVTITCRASQGISSWLAWYQ QKPGKAPKLLIF-GASSLQSGVPSRFSGSGSGTDFTLTVSSLQPEDFA-TYYCQQAYSFPFTF GPGTKVDIEEPKRSDKTH-TCPPCPAPELLGGPSVFLFPPKPKDTLMISRTPEVTCV VVDVS HEDPEVKFNWYVDGVEVHNAKTKPRE-EQYNSTYRVVSVLTVLHQDWLNGKEYKCKVS NKA-LPAPIEKTISKAKGQPREPQVYTLPPSREEMT-KNQVSLWCLVKGFYPSDIAVEWESN GQPENNYKTTPPVLDSDGSFFLYSK-LTVDKSRWQQGNVFSCSVMHEALHNHYTQKSLS LSPG (SEQ ID NO:31). In some embodiments, the second antibody arm comprises a VH domain comprising the sequence of QVQLQQSGSELKKPGASVKVSCK-ASGYTFTNYGMNWVKQAPGQGLKWMGWINTYTG EPTYTDDFKGRFAFSLDTSVSTAYLQISSLKADD-TAVYFCARGGFGSSYWYFDVWGQGS LVTVSS (SEQ ID NO:42) and a VL domain comprising the sequence of DIQLTQSPSSLSASVGDRVSITCKASQDVSIA-VAWYQQKPGKAPKLLIYSASYRYTGVPD RFSGSGSGTDFTLTISSLQPED-FAVYYCQQHYITPLTFGAGTKVEIK (SEQ ID NO:43). In some embodiments, the second antibody arm comprises a VH domain comprising the sequence of QIQLVQSG-PELKKPGETVKISCK-ASGYTFTNYGMNWVKQAPGKGLKWMGWINTKT-GEP TYAEEFKGRFAFSLETSASTAYLQINNLKKED-TATYFCGRGGYGSSYWYFDVWGAGTT VTVSS (SEQ ID NO:56) and a VL domain comprising the sequence of DIVMTQSHKFMSTSVGDRVSITCKASQDVSIA-VAWYQQKPGQSPKVLIYSASYRYTGVP DRFTGSGSGTDFTFTISRVQAED-LAVYYCQQHYITPLTFGAGTKLELK (SEQ ID NO:57). In some embodiments, the second antibody arm comprises a VH domain comprising the sequence of QVQLQQSG-PELVRPGTSVRISCKASGYTFTIYWLGWVKQRPGH-GLEWIGNIFPGSAYINY NEKFKGKATL-TADTSSSTAYMQLSSLTSEDSAVYFCAREGSNSGYW GQGTTLTVSS (SEQ ID NO:58) and a VL domain comprising the sequence of DIVMTQSPSSLSVSAGEKVTMTCKSSQSLLNSGNQQ-NYLAWYQQKPGQPPKWYGAST RESGVPDRFTGSGSGTDFTLTINSVQAED-LAVYYCQSDHIYPYTFGGGTKLEIK (SEQ ID NO:59). In some embodiments, the second antibody arm comprises a VH domain comprising the sequence of QVQLQESGPGLVKPSETLSLTCTVSGGSIS-SYGVHWIRQPPGKGLEWIGVIWTGGSTDYN SALMSRVTISVDTSKNQFSLKLSSVTAADTAVYY-CARDGDYDRYTMDYWGQGTLVTV SS (SEQ ID NO:66) and a VL domain comprising the sequence of DIVMTQSPDSLAVSLGERATINCRASKSVST-SGYSYMHWYQQKPGQPPKLLIYLASNLES GVPDRFSGSGSGTDFTLTISSLQAEDVAVYYCQHS-RELPYTFGQGTKLEIK (SEQ ID NO:67). In some embodiments, the antigen binding domain that binds Trop-2 comprises the VH and VL domain sequences from sacituzumab, AR47A6.4.2, h7E6, or Pr1E11.

In some embodiments, provided herein is a multispecific (e.g., bispecific) binding molecule that comprises a first antibody arm comprising a single chain variable fragment (scFv) comprising VH and VL domains of the present disclosure that bind to human Dectin-1 and a first Fc region, and a second antibody arm comprising an antibody heavy chain that comprises a VH domain in association with an antibody light chain that comprises a VL domain and a second Fc region connected to the VH domain, wherein the VH and VL domains of the second antibody arm form an antigen binding domain that binds to light chain amyloids (e.g., human light chain amyloids, e.g., human kappa light chain amyloids, human lambda light chain amyloids, or both human kappa and lambda light chain amyloids). In some embodiments, the first Fc region comprises one or more knob-forming mutations, and the second Fc region comprises one or more cognate hole-forming mutations, or the second Fc region comprises one or more knob-forming mutations, and the first Fc region comprises one or more cognate hole-forming mutations. In some embodiments, the scFv comprises a first linker of the present disclosure between the VH and VL domains and a second linker of the present disclosure between the VL domain and the first Fc region. In some embodiments, the first antibody arm comprises the amino acid sequence of QVQLVQSGAEVKKPGASVKVSCKSSGYTFTDYYIHWVRQAPGQGLEWMGWINPNSGDTNYAQKFQGRITMTRDTSISTAYLELSRLRSDDTAVFYCARNSGSYSFGYWGQGTLVTVSSGGGGSGGGGSGGGGSGGGGSDIQMTQSPSSVSASVGDRVTITCRASQGISSWLAWYQ KPKPGKAPKLLIFGASSLQSGVPSRFSGSGSGTDFTLTVSSLQPEDFATYYCQQAYSFPFTF GPGTKVDIEEPKRSDKTHTCPPCPAPELLGGPSVFLFPPKPKDTLMISRTPEVTCVVVDVS HEDPEVKFNWYVDGVEVHNAKTKPREEQYNSTYRVVSVLTVLHQDWLNGKEYKCKVS NKALPAPIEKTISKAKGQPREPQVYTLPPSREEMTKNQVSLWCLVKGFYPSDIAVEWESNGQPENNYKTTPPVLDSDGSFFLYSKLTVDKSRWQQGNVFSCSVMHEALHNHYTQKSLS LSPG (SEQ ID NO:31). In some embodiments, the second antibody arm comprises a VH domain comprising the sequence of QVQLKESGPGLVAPSQSLSITCTVSGFSLSSYGVSWVRQPPGKGLEWLGVIWGDGSTNY KPNLMSRLSISKDISKSQVLFKLNSLQTDDTATYYCVTLDYWGQ GTSVTVSS (SEQ ID NO:44) and a VL domain comprising the sequence of DVVMTQTPLSLPVSLGDQASISCRSSQSLVHRNGNTYLHWYLQKPGQSPKLLIYKVSNR FSGVPDRFSGSGSGTDFTLKISRVEAEDLGLYFCFQTTYVPNTFGGGTKLEIK (SEQ ID NO:45). In some embodiments, the second antibody arm comprises a VH domain comprising the sequence of EVQLVESGGRLVQPKGSLKLSCAASGFTFNTYAMYWIRQAPGKGLEWVARIRSKSNNY AIYYADSVKDRFTIFRDDSQSMLYLQMNNLKTEDTAMYYCVRPYSDSFA YWGQGTLVT VSA (SEQ ID NO:52) and a VL domain comprising the sequence of DVVMTQTPLSLPVSLGDQASISCRSSQSLVHSTGNTYLHWYLQKPGQSPKLLIYKVSNRF SGVPDRFSGSGSGTYFTLKISRVEAEDLGVYFCSQSTHVPFTFGGGTKLEIK (SEQ ID NO:53). In some embodiments, the second antibody arm comprises a VH domain comprising the sequence of EVQLVESGGRLVQPKGSLKLSCAASGFTFNTYAMYWIRQAPGKGLEWVARIRSKSNNY AIYYADSVKDRFTIFRDDSQSMLYLQMNNLKTEDTAMYYCVRPYSDSFA YWGQGTLVT VSA (SEQ ID NO:54) and a VL domain comprising the sequence of DVVMTQTPLSLPVSLGDQASISCRSSLSLVHSTGNTYLHWYLQKPGQSPKLLIYKVSNRF SGVPDRFSGSGSGTYFTLKISRVEAEDLGVYFCSQSTHVPFTFGGGTKLEIK (SEQ ID NO:55). In some embodiments, the antigen binding domain that binds light chain amyloid comprises the VH and VL domain sequences from antibody 11-1F4, 2A4, or 7D8.

In some embodiments, provided herein is a multispecific (e.g., bispecific) binding molecule that comprises a first antibody arm comprising a single chain variable fragment (scFv) comprising VH and VL domains of the present disclosure that bind to human Dectin-1 and a first Fc region, and a second antibody arm comprising an antibody heavy chain that comprises a VH domain in association with an antibody light chain that comprises a VL domain and a second Fc region connected to the VH domain, wherein the VH and VL domains of the second antibody arm form an antigen binding domain that binds to amyloid beta (e.g., human amyloid beta). In some embodiments, the first Fc region comprises one or more knob-forming mutations, and the second Fc region comprises one or more cognate hole-forming mutations, or the second Fc region comprises one or more knob-forming mutations, and the first Fc region comprises one or more cognate hole-forming mutations. In some embodiments, the scFv comprises a first linker of the present disclosure between the VH and VL domains and a second linker of the present disclosure between the VL domain and the first Fc region. In some embodiments, the first antibody arm comprises the amino acid sequence of QVQLVQSGAEVKKPGASVKVSCKSSGYTFTDYYIHWVRQAPGQGLEWMGWINPNSGDTNYAQKFQGRITMTRDTSISTAYLELSRLRSDDTAVFYCARNSGSYSFGYWGQGTLVTVSSGGGGSGGGGSGGGGSGGGGSDIQMTQSPSSVSASVGDRVTITCRASQGISSWLAWYQ KQKPGKAPKLLIFGASSLQSGVPSRFSGSGSGTDFTLTVSSLQPEDFATYYCQQAYSFPFTF GPGTKVDIEEPKRSDKTHTCPPCPAPELLGGPSVFLFPPKPKDTLMISRTPEVTCVVVDVS HEDPEVKFNWYVDGVEVHNAKTKPREEQYNSTYRVVSVLTVLHQDWLNGKEYKCKVS NKALPAPIEKTISKAKGQPREPQVYTLPPSREEMTKNQVSLWCLVKGFYPSDIAVEWESNGQPENNYKTTPPVLDSDGSFFLYSKLTVDKSRWQQGNVFSCSVMHEALHNHYTQKSLS LSPG (SEQ ID NO:31). In some embodiments, the second antibody arm comprises a VH domain comprising the sequence of QVQLVESGGGVVQPGRSLRLSCAASGFAFSSYGMHWVRQAPGKGLEWVAVIWFDGTK KYYTDSVKGRFTISRDNSKNTLYLQMNTLRAEDTAVYYCARDRGIGARRGPYYMD VW GKGTTVTVSS (SEQ ID NO:48) and a VL domain comprising the sequence of DIQMTQSPSSLSASVGDRVTITCRASQSISSYLNWYQQKPGKAPKLLIYAASSLQSGVPSR FSGSGSGTDFTLTISSLQPEDFATYYCQQSYSTPLTFGGGTKVEIK (SEQ ID NO:49). In some embodiments, the second antibody arm comprises a VH domain comprising the sequence of EVQLVESGGGLVQPGGSLRLSCSASGFTFSSFGMHWVRQAPGKGLEWVAYISSGSSTIY YGDTVKGRFTISRDNAKNSLFLQMSSLRAEDTAVYYCAREGGYYYGRSY YTMDYWGQ GTTVTVSS (SEQ ID NO:50) and a VL domain comprising the sequence of DVVMTQSPLSLPVTPGAPASISCRSSQSIVHSNGNTYLEWYLQKPGQSPKLLIYKVSNRFS GVPDRFSGSGSGTDFTLRISRVEAE-DVGIYYCFQGSHVPPTFGPGTKLEIK (SEQ ID NO:51). In some embodiments, the antigen binding domain that binds amyloid beta comprises the VH and VL domain sequences from aducanumab or lecanemab.

In some embodiments, provided herein is a multispecific (e.g., bispecific) binding molecule that comprises a first antibody arm comprising a single chain variable fragment (scFv) comprising VH and VL domains of the present disclosure that bind to human Dectin-1 and a first Fc region, and a second antibody arm comprising an antibody heavy chain that comprises a VH domain in association with an antibody light chain that comprises a VL domain and a second Fc region connected to the VH domain, wherein the VH and VL domains of the second antibody arm form an antigen binding domain that binds to CD70 (e.g., human CD70). In some embodiments, the first Fc region comprises one or more knob-forming mutations, and the second Fc region comprises one or more cognate hole-forming mutations, or the second Fc region comprises one or more knob-forming mutations, and the first Fc region comprises one or more cognate hole-forming mutations. In some embodiments, the scFv comprises a first linker of the present disclosure between the VH and VL domains and a second linker of the present disclosure between the VL domain and the first Fc region. In some embodiments, the first antibody arm comprises the amino acid sequence of QVQLVQS-GAEVKKPGASVKVSCK-SSGYTFTDYYIHWVRQAPGQGLEWMGWINPNSGD TNYAQKFQGRITMTRDTSISTAYLELSRLRSDD-TAVFYCARNSGSYSFGYWGQGTLVTV SSGGGGSGGGGSGGGGSGGGGSDIQMTQSPSSVSAS VGDRVTITCRASQGISSWLAWYQ QKPGKAPKLLIF-GASSLQSGVPSRFSGSGSGTDFTLTVSSLQPEDFA-TYYCQQAYSFPFTF GPGTKVDIEEPKRSDKTH-TCPPCPAPELLGGPSVFLFPPKPKDTLMISRTPEVTCV VVDVS HEDPEVKFNWYVDGVEVHNAKTKPRE-EQYNSTYRVVSVLTVLHQDWLNGKEYKCKVS NKA-LPAPIEKTISKAKGQPREPQVYTLPPSREEMT-KNQVSLWCLVKGFYPSDIAVEWESN GQPENNYKTTPPVLDSDGSFFLYSK-LTVDKSRWQQGNVFSCSVMHEALHNHYTQKSLS LSPG (SEQ ID NO:31). In some embodiments, the second antibody arm comprises a VH domain comprising the sequence of EVQLVESGGGLVQPGGSLRLS-CAASGFTFSVYYMNWVRQAPGK-GLEWVSDINNEGGTT YYADSVKGRFTISRDNSKNS-LYLQMNSLRAEDTAVYYCARDAGYSNHVPIFDSWG QGT LVTVSS (SEQ ID NO:38) and a VL domain comprising the sequence of QAVVTQEPSLTVSPGGTVTLTCGLKSGSVTSDNFPT WYQQTPGQAPRLLIYNTNTRHSG VPDRFSGSILGN-KAALTITGAQADDEAEYFCALFISNPS-VEFGGGTQLTVL (SEQ ID NO:39). In some embodiments, the antigen binding domain that binds CD70 comprises the VH and VL domain sequences from 4ID12.

In some embodiments, provided herein is a multispecific (e.g., bispecific) binding molecule that comprises a first antibody arm comprising a single chain variable fragment (scFv) comprising VH and VL domains of the present disclosure that bind to human Dectin-1 and a first Fc region, and a second antibody arm comprising an antibody heavy chain that comprises a VH domain in association with an antibody light chain that comprises a VL domain and a second Fc region connected to the VH domain, wherein the VH and VL domains of the second antibody arm form an antigen binding domain that binds to nectin-4 (e.g., human nectin-4). In some embodiments, the first Fc region comprises one or more knob-forming mutations, and the second Fc region comprises one or more cognate hole-forming mutations, or the second Fc region comprises one or more knob-forming mutations, and the first Fc region comprises one or more cognate hole-forming mutations. In some embodiments, the scFv comprises a first linker of the present disclosure between the VH and VL domains and a second linker of the present disclosure between the VL domain and the first Fc region. In some embodiments, the first antibody arm comprises the amino acid sequence of QVQLVQS-GAEVKKPGASVKVSCK-SSGYTFTDYYIHWVRQAPGQGLEWMGWINPNSGD TNYAQKFQGRITMTRDTSISTAYLELSRLRSDD-TAVFYCARNSGSYSFGYWGQGTLVTV SSGGGGSGGGGSGGGGSGGGGSDIQMTQSPSSVSAS VGDRVTITCRASQGISSWLAWYQ QKPGKAPKLLIF-GASSLQSGVPSRFSGSGSGTDFTLTVSSLQPEDFA-TYYCQQAYSFPFTF GPGTKVDIEEPKRSDKTH-TCPPCPAPELLGGPSVFLFPPKPKDTLMISRTPEVTCV VVDVS HEDPEVKFNWYVDGVEVHNAKTKPRE-EQYNSTYRVVSVLTVLHQDWLNGKEYKCKVS NKA-LPAPIEKTISKAKGQPREPQVYTLPPSREEMT-KNQVSLWCLVKGFYPSDIAVEWESN GQPENNYKTTPPVLDSDGSFFLYSK-LTVDKSRWQQGNVFSCSVMHEALHNHYTQKSLS LSPG (SEQ ID NO:31). In some embodiments, the second antibody arm comprises a VH domain comprising the sequence of EVQLVESGGGLVQPGGSLRLS-CAASGFTFSSYNMNWVRQAPGKGLEWVSYIS-SSSSTIY YADSVKGRFTISRDNAKNSLSLQMNSLRD-EDTAVYYCARAYYYGMDVWGQGTTVTVS S (SEQ ID NO:40) and a VL domain comprising the sequence of DIQMTQSPSSVSASVGDRVTITCRASQGIS-GWLAWYQQKPGKAPKFLIYAASTLQSGVPS RFSGSGSGTDFTLTISSLQPEDFA-TYYCQQANSFPPTFGGGTKVEIK (SEQ ID NO:41). In some embodiments, the second antibody arm comprises a VH domain comprising the sequence of QVQLKQSGPGLVQPSQSL-SITCTVSGFSLTNYGVHWVRQSPGKGLEW-LGVIWSGGSTDY NAAFISRL-SISKDTSKSQVFFKMNSLQADDTAIYYCARELIHAM DNWGQGTSVTVSS (SEQ ID NO:60) and a VL domain comprising the sequence of DIQMTQSPASLSVSVGETVTITCRASENIYSN-LAWYQQKQGNSPQLLVFAATNLADGVP SRFSGSGSGTQYSLKIN-SLQSEDFGTYYCQHFWGTPTFGGGTKLEIK (SEQ ID NO:61). In some embodiments, the antigen binding domain that binds nectin-4 comprises the VH and VL domain sequences from N41 or Ha22-2.

In some embodiments, provided herein is a multispecific (e.g., bispecific) binding molecule that comprises a first antibody arm comprising a single chain variable fragment (scFv) comprising VH and VL domains of the present disclosure that bind to human Dectin-1 and a first Fc region, and a second antibody arm comprising an antibody heavy chain that comprises a VH domain in association with an antibody light chain that comprises a VL domain and a second Fc region connected to the VH domain, wherein the VH and VL domains of the second antibody arm form an antigen binding domain that binds to EGFR (e.g., human EGFR). In some embodiments, the first Fc region comprises one or more knob-forming mutations, and the second Fc region comprises one or more cognate hole-forming mutations, or the second Fc region comprises one or more knob-forming mutations, and the first Fc region comprises one or more cognate hole-forming mutations. In some embodiments, the scFv comprises a first linker of the present disclosure between the VH and VL domains and a second linker of the present disclosure between the VL domain and the first Fc region. In some embodiments, the first antibody arm comprises the amino acid sequence of QVQLVQS-GAEVKKPGASVKVSCK-SSGYTFTDYYIHWVRQAPGQGLEWMGWINPNSGD TNYAQKFQGRITMTRDTSISTAYLELSRLRSDD-TAVFYCARNSGSYSFGYWGQGTLVTV SSGGGGSGGGGSGGGGSGGGGSDIQMTQSPSSVSA SVGDRVTITCRASQGISSWLAWYQ QKPGKAPKLLIF-GASSLQSGVPSRFSGSGSGTDFTLTVSSLQPEDFA-TYYCQQAYSFPFTF GPGTKVDIEEPKRSDKTH-TCPPCPAPELLGGPSVFLFPPKPKDTLMISRTPEVTCV VVDVS HEDPEVKFNWYVDGVEVHNAKTKPRE-EQYNSTYRVVSVLTVLHQDWLNGKEYKCKVS NKA-LPAPIEKTISKAKGQPREPQVYTLPPSREEMT-KNQVSLWCLVKGFYPSDIAVEWESN GQPENNYKTTPPVLDSDGSFFLYSK-LTVDKSRWQQGNVFSCSVMHEALHNHYTQKSLS LSPG (SEQ ID NO:31). In some embodiments, the second antibody arm comprises a VH domain comprising the sequence of QVQLKQSGPGLVQPSQSL-SITCTVSGFSLTNYGVHWVRQSPGKGLEW-LGVIWSGGNTD YNTPFTSRL-SINKDNSKSQVFFKMNSLQSNDTAIYYCARALTYYD YEFAYWGQGTLVTV SA (SEQ ID NO:62) and a VL domain comprising the sequence of DILLTQSPVILSVSPGERVSFSCRASQSIGT-NIHWYQQRTNGSPRLLIKYASESISGIPSRFS GSGSGTDFTLSINSVESEDI-ADYYCQQNNNWPTTFGAGTKLELK (SEQ ID NO:63). In some embodiments, the second antibody arm comprises a VH domain comprising the sequence of QVQLQESGPGLVKPSQTLSLTCTVSGGSIS-SGDYYWSWIRQPPGKGLEWIGYIYYSGSTD YNPSLKSRVTMSVDTSKNQFSLKVNSVTAADTAVYY-CARVSIFGVGTFDYWGQGTLVT VSS (SEQ ID NO:64) and a VL domain comprising the sequence of EIVMTQSPATLSLSPGERATLSCRASQSVSSY-LAWYQQKPGQAPRLLIYDASNRATGIPA RFSGSGSGTDFTLTISSLEPEDFAVYYCHQYG-STPLTFGGGTKAEIK (SEQ ID NO:65). In some embodiments, the antigen binding domain that binds EGFR comprises the VH and VL domain sequences from cetuximab or necitumumab.

In some embodiments, provided herein is a multispecific (e.g., bispecific) binding molecule that comprises a first antibody arm comprising a single chain variable fragment (scFv) comprising VH and VL domains of the present disclosure that bind to human Dectin-1 and a first Fc region, and a second antibody arm comprising an antibody heavy chain that comprises a VH domain in association with an antibody light chain that comprises a VL domain and a second Fc region connected to the VH domain, wherein the VH and VL domains of the second antibody arm form an antigen binding domain that binds to DLL3 (e.g., human DLL3). In some embodiments, the first Fc region comprises one or more knob-forming mutations, and the second Fc region comprises one or more cognate hole-forming mutations, or the second Fc region comprises one or more knob-forming mutations, and the first Fc region comprises one or more cognate hole-forming mutations. In some embodiments, the scFv comprises a first linker of the present disclosure between the VH and VL domains and a second linker of the present disclosure between the VL domain and the first Fc region. In some embodiments, the first antibody arm comprises the amino acid sequence of QVQLVQS-GAEVKKPGASVKVSCK-SSGYTFTDYYIHWVRQAPGQGLEWMGWINPNSGD TNYAQKFQGRITMTRDTSISTAYLELSRLRSDD-TAVFYCARNSGSYSFGYWGQGTLVTV SSGGGGSGGGGSGGGGSGGGGSDIQMTQSPSSVSAS VGDRVTITCRASQGISSWLAWYQ QKPGKAPKLLIF-GASSLQSGVPSRFSGSGSGTDFTLTVSSLQPEDFA-TYYCQQAYSFPFTF GPGTKVDIEEPKRSDKTH-TCPPCPAPELLGGPSVFLFPPKPKDTLMISRTPEVTCV VVDVS HEDPEVKFNWYVDGVEVHNAKTKPRE-EQYNSTYRVVSVLTVLHQDWLNGKEYKCKVS NKA-LPAPIEKTISKAKGQPREPQVYTLPPSREEMT-KNQVSLWCLVKGFYPSDIAVEWESN GQPENNYKTTPPVLDSDGSFFLYSK-LTVDKSRWQQGNVFSCSVMHEALHNHYTQKSLS LSPG (SEQ ID NO:31). In some embodiments, the second antibody arm comprises a VH domain comprising the sequence of QVQLVQSGAEVKKPGASVKVSCK-ASGYTFTNYGMNWVRQAPGQGLEWMGWINTYTG EPTYADDFKGRVTMTTDTSTSTAYMELRSLRSDD-TAVYYCARIGDSSPSDYWGQGTLV TVSS (SEQ ID NO:68) and a VL domain comprising the sequence of EIVMTQSPATLSVSPGERATLSCK-ASQSVSNDVVWYQQKPGQAPRLLIYYASNRYTGIPA RFSGSGSGTEFTLTISSLQSEDFAVYYCQQDYT-SPWTFGQGTKLEIK (SEQ ID NO:69). In some embodiments, the second antibody arm comprises a VH domain comprising the sequence of QVQLQESGPGLVKP-SETLSLTCTVSGGSISSYYWSWIRQPPGKGLEWI-GYVYYSGTTNYN PSLKSRVTISVDTSKNQFSLKLSSVTAADTAVYYCA-SIAVTGFYFDYWGQGTLVTVSS (SEQ ID NO:70) and a VL domain comprising the sequence of EIVLTQSPGTLSL-SPGERVTLSCRASQRVNN-NYLAWYQQRPGQAPRLLIYGASSRATGIP DRFSGSGSGTDFTLTISRLEPEDFAVYYCQQYDR-SPLTFGGGTKLEIK (SEQ ID NO:71). In some embodiments, the antigen binding domain that binds DLL3 comprises the VH and VL domain sequences from rovalpituzumab or DLL3-4.

In some embodiments, provided herein is a multispecific (e.g., bispecific) binding molecule that comprises a first antibody arm comprising a single chain variable fragment (scFv) comprising VH and VL domains of the present disclosure that bind to human Dectin-1 and a first Fc region, and a second antibody arm comprising an antibody heavy chain that comprises a VH domain in association with an antibody light chain that comprises a VL domain and a second Fc region connected to the VH domain, wherein the VH and VL domains of the second antibody arm form an antigen binding domain that binds to mesothelin (e.g., human mesothelin). In some embodiments, the first Fc region comprises one or more knob-forming mutations, and the second Fc region comprises one or more cognate hole-forming mutations, or the second Fc region comprises one or more knob-forming mutations, and the first Fc region comprises one or more cognate hole-forming mutations. In some embodiments, the scFv comprises a first linker of the present disclosure between the VH and VL domains and a second linker of the present disclosure between the VL domain and the first Fc region. In some embodiments, the first antibody arm comprises the amino acid sequence of QVQLVQS-GAEVKKPGASVKVSCK-SSGYTFTDYYIHWVRQAPGQGLEWMGWINPNSGD TNYAQKFQGRITMTRDTSISTAYLELSRLRSDD-TAVFYCARNSGSYSFGYWGQGTLVTV SSGGGGSGGGGSGGGGSGGGGSDIQMTQSPSSVSAS VGDRVTITCRASQGISSWLAWYQ QKPGKAPKLLIF-GASSLQSGVPSRFSGSGSGTDFTLTVSSLQPEDFA-TYYCQQAYSFPFTF GPGTKVDIEEPKRSDKTH-TCPPCPAPELLGGPSVFLFPPKPKDTLMISRTPEVTCV VVDVS HEDPEVKFNWYVDGVEVHNAKTKPRE-EQYNSTYRVVSVLTVLHQDWLNGKEYKCKVS NKA-LPAPIEKTISKAKGQPREPQVYTLPPSREEMT-KNQVSLWCLVKGFYPSDIAVEWESN GQPENNYKTTPPVLDSDGSFFLYSK-LTVDKSRWQQGNVFSCSVMHEALHNHYTQKSLS LSPG (SEQ ID NO:31). In some embodiments, the second antibody arm comprises a VH domain comprising the sequence of QVQLQQSGPELEKPGASVKISCK-ASGYSFTGYTMNWVKQSHGKSLEWIGLITPYNGASS YNQKFRGKATLTVDKSSSTAYMDLLSLTSED-SAVYFCARGGYDGRGFDYWGSGTPVTV SS (SEQ ID NO:72) and a VL domain comprising the sequence of DIELTQSPAIM-SASPGEKVTMTCSASSSVSYMHWYQQKSGTSPKR-WIYDTSKLASGVPG RFSGSGSGNSYSLTISSVEAED-DATYYCQQWSKHPLTFGSGTKVEIK (SEQ ID NO:73). In some embodiments, the antigen binding domain that binds mesothelin comprises the VH and VL domain sequences from amatuximab.

In some embodiments, provided herein is a multispecific (e.g., bispecific) binding molecule that comprises a first antibody arm comprising a single chain variable fragment (scFv) comprising VH and VL domains of the present disclosure that bind to human Dectin-1 and a first Fc region, and a second antibody arm comprising an antibody heavy chain that comprises a VH domain in association with an antibody light chain that comprises a VL domain and a second Fc region connected to the VH domain, wherein the VH and VL domains of the second antibody arm form an antigen binding domain that binds to CD33 (e.g., human CD33). In some embodiments, the first Fc region comprises one or more knob-forming mutations, and the second Fc region comprises one or more cognate hole-forming mutations, or the second Fc region comprises one or more knob-forming mutations, and the first Fc region comprises one or more cognate hole-forming mutations. In some embodiments, the scFv comprises a first linker of the present disclosure between the VH and VL domains and a second linker of the present disclosure between the VL domain and the first Fc region. In some embodiments, the first antibody arm comprises the amino acid sequence of QVQLVQS-GAEVKKPGASVKVSCK-SSGYTFTDYYIHWVRQAPGQGLEWMGWINPNSGD TNYAQKFQGRITMTRDTSISTAYLELSRLRSDD-TAVFYCARNSGSYSFGYWGQGTLVTV SSGGGGSGGGGSGGGGSGGGGSDIQMTQSPSSVSAS VGDRVTITCRASQGISSWLAWYQ QKPGKAPKLLIF-GASSLQSGVPSRFSGSGSGTDFTLTVSSLQPEDFA-TYYCQQAYSFPFTF GPGTKVDIEEPKRSDKTH-TCPPCPAPELLGGPSVFLFPPKPKDTLMISRTPEVTCV VVDVS HEDPEVKFNWYVDGVEVHNAKTKPRE-EQYNSTYRVVSVLTVLHQDWLNGKEYKCKVS NKA-LPAPIEKTISKAKGQPREPQVYTLPPSREEMT-KNQVSLWCLVKGFYPSDIAVEWESN GQPENNYKTTPPVLDSDGSFFLYSK-LTVDKSRWQQGNVFSCSVMHEALHNHYTQKSLS LSPG (SEQ ID NO:31). In some embodiments, the second antibody arm comprises a VH domain comprising the sequence of EVQLVQSGAEVKKPGSSVKVSCK-ASGYTITDSNIHWVRQAPGQSLEWIGYIYPYNGGTD YNQKFKNRATLTVDNPTNTAYMELSSLRSED-TAFYYCVNGNPWLAYWGQGTLVTVSS (SEQ ID NO:74) and a VL domain comprising the sequence of DIQLTQSPSTLSASVGDRVTITCRASESLDNY-GIRFLTWFQQKPGKAPKLLMYAASNQGS GVPSRFSGSGSGTEFTLTISSLQPDDFA-TYYCQQTKEVPWSFGQGTKVEVK (SEQ ID NO:75). In some embodiments, the antigen binding domain that binds CD33 comprises the VH and VL domain sequences from gemtuzumab.

In some embodiments, provided herein is a multispecific (e.g., bispecific) binding molecule that comprises a first antibody arm comprising a single chain variable fragment (scFv) comprising VH and VL domains of the present disclosure that bind to human Dectin-1 and a first Fc region, and a second antibody arm comprising an antibody heavy chain that comprises a VH domain in association with an antibody light chain that comprises a VL domain and a second Fc region connected to the VH domain, wherein the VH and VL domains of the second antibody arm form an antigen binding domain that binds to CCR8 (e.g., human CCR8). In some embodiments, the first Fc region comprises one or more knob-forming mutations, and the second Fc region comprises one or more cognate hole-forming mutations, or the second Fc region comprises one or more knob-forming mutations, and the first Fc region comprises one or more cognate hole-forming mutations. In some embodiments, the scFv comprises a first linker of the present disclosure between the VH and VL domains and a second linker of the present disclosure between the VL domain and the first Fc region. In some embodiments, the first antibody arm comprises the amino acid sequence of QVQLVQS-GAEVKKPGASVKVSCK-SSGYTFTDYYIHWVRQAPGQGLEWMGWINPNSGD TNYAQKFQGRITMTRDTSISTAYLELSRLRSDD-TAVFYCARNSGSYSFGYWGQGTLVTV SSGGGGSGGGGSGGGGSGGGGSDIQMTQSPSSVSA SVGDRVTITCRASQGISSWLAWYQ QKPGKAPKLLIF-GASSLQSGVPSRFSGSGSGTDFTLTVSSLQPEDFA-TYYCQQAYSFPFTF GPGTKVDIEEPKRSDKTH-TCPPCPAPELLGGPSVFLFPPKPKDTLMISRTPEVTC VVVDVS HEDPEVKFNWYVDGVEVHNAKTKPRE-EQYNSTYRVVSVLTVLHQDWLNGKEYKCKVS NKA-LPAPIEKTISKAKGQPREPQVYTLPPSREEMT-KNQVSLWCLVKGFYPSDIAVEWESN GQPENNYKTTPPVLDSDGSFFLYSK-LTVDKSRWQQGNVFSCSVMHEALHNHYTQKSLS LSPG (SEQ ID NO:31). In some embodiments, the second antibody arm comprises a VH domain comprising the sequence of EVQLVESGGRLVQPKGSLKLS-CAASGFAFNTYALYWIRQAPGKGLEWVARIR-SKSNNY ATYYADSVKDRFTISRDDSQSM-LYLQMNNLKTEDTAMYYCVRARFYYSDYGYAMDY WGQGTSVTVSS (SEQ ID NO:76) and a VL domain comprising the sequence of DIVMTQAAPSVPVTPGESV-SISCRSSKSLLHSNGNTYLYW-FLQRPGQSPQLLIYRMSNLA SGVPDRFSGSGSGTAFTLRISRVEAEDVGVYYCMQH-LEYPLTFGAGTKLELK (SEQ ID NO:77). In some embodiments, the antigen binding domain that binds CCR8 comprises the VH and VL domain sequences from 10A11.

In some embodiments, provided herein is a multispecific (e.g., bispecific) binding molecule that comprises a first antibody arm comprising a single chain variable fragment (scFv) comprising VH and VL domains of the present disclosure that bind to human Dectin-1 and a first Fc region, and a second antibody arm comprising an antibody heavy chain that comprises a VH domain in association with an antibody light chain that comprises a VL domain and a second Fc region connected to the VH domain, wherein the VH and VL domains of the second antibody arm form an antigen binding domain that binds to CTLA4 (e.g., human CTLA4). In some embodiments, the first Fc region comprises one or more knob-forming mutations, and the second Fc region comprises one or more cognate hole-forming mutations, or the second Fc region comprises one or more knob-forming mutations, and the first Fc region comprises one or more cognate hole-forming mutations. In some embodiments, the scFv comprises a first linker of the present disclosure between the VH and VL domains and a second linker of the present disclosure between the VL domain and the first Fc region. In some embodiments, the first antibody arm comprises the amino acid sequence of QVQLVQS-GAEVKKPGASVKVSCK-SSGYTFTDYYIHWVRQAPGQGLEWMGWINPNSGD TNYAQKFQGRITMTRDTSISTAYLELSRLRSDD-TAVFYCARNSGSYSFGYWGQGTLVTV SSGGGGSGGGGSGGGGSGGGGSDIQMTQSPSSVSA SVGDRVTITCRASQGISSWLAWYQ QKPGKAPKLLIF-GASSLQSGVPSRFSGSGSGTDFTLTVSSLQPEDFA-TYYCQQAYSFPFTF GPGTKVDIEEPKRSDKTH-TCPPCPAPELLGGPSVFLFPPKPKDTLMISRTPEVTC VVVDVS HEDPEVKFNWYVDGVEVHNAKTKPRE-EQYNSTYRVVSVLTVLHQDWLNGKEYKCKVS NKA-LPAPIEKTISKAKGQPREPQVYTLPPSREEMT-KNQVSLWCLVKGFYPSDIAVEWESN GQPENNYKTTPPVLDSDGSFFLYSK-LTVDKSRWQQGNVFSCSVMHEALHNHYTQKSLS LSPG (SEQ ID NO:31). In some embodiments, the second antibody arm comprises a VH domain comprising the sequence of QVQLVESGGGVVQPGRSLRLS-CAASGFTFSSYTMHWVRQAPGKGLEWVTFI-SYDGNNK YYADSVKGRFTISRDNSKNTLYLQMNSL-RAEDTAIYYCARTGWLGPFDYWGQGTLVTV SS (SEQ ID NO:78) and a VL domain comprising the sequence of EIVLTQSPGTLSLSPGERATLSCRASQSVGSSY-LAWYQQKPGQAPRLLIYGAFSRATGIPD RFSGSGSGTDFTLTISRLEPED-FAVYYCQQYGSSPWTFGQGTKVEIK (SEQ ID NO:79). In some embodiments, the antigen binding domain that binds CTLA4 comprises the VH and VL domain sequences from ipilimumab.

In some embodiments, provided herein is a multispecific (e.g., bispecific) binding molecule that comprises a first antibody arm comprising a single chain variable fragment (scFv) comprising VH and VL domains of the present disclosure that bind to human Dectin-1 and a first Fc region, and a second antibody arm comprising an antibody heavy chain that comprises a VH domain in association with an antibody light chain that comprises a VL domain and a second Fc region connected to the VH domain, wherein the VH and VL domains of the second antibody arm form an antigen binding domain that binds to cMET (e.g., human cMET). In some embodiments, the first Fc region comprises one or more knob-forming mutations, and the second Fc region comprises one or more cognate hole-forming mutations, or the second Fc region comprises one or more knob-forming mutations, and the first Fc region comprises one or more cognate hole-forming mutations. In some embodiments, the scFv comprises a first linker of the present disclosure between the VH and VL domains and a second linker of the present disclosure between the VL domain and the first Fc region. In some embodiments, the first antibody arm comprises the amino acid sequence of QVQLVQS-GAEVKKPGASVKVSCK-SSGYTFTDYYIHWVRQAPGQGLEWMGWINPNSGD TNYAQKFQGRITMTRDTSISTAYLELSRLRSDD-TAVFYCARNSGSYSFGYWGQGTLVTV SSGGGGSGGGGSGGGGSGGGGSDIQMTQSPSSVSA SVGDRVTITCRASQGISSWLAWYQ QKPGKAPKLLIF-GASSLQSGVPSRFSGSGSGTDFTLTVSSLQPEDFA-TYYCQQAYSFPFTF GPGTKVDIEEPKRSDKTH-TCPPCPAPELLGGPSVFLFPPKPKDTLMISRTPEVTCV VVDVS HEDPEVKFNWYVDGVEVHNAKTKPRE-EQYNSTYRVVSVLTVLHQDWLNGKEYKCKVS NKA-LPAPIEKTISKAKGQPREPQVYTLPPSREEMT-KNQVSLWCLVKGFYPSDIAVEWESN GQPENNYKTTPPVLDSDGSFFLYSK-LTVDKSRWQQGNVFSCSVMHEALHNHYTQKSLS LSPG (SEQ ID NO:31). In some embodiments, the second antibody arm comprises a VH domain comprising the sequence of EVQLVESGGGLVQPGGSLRLS-CAASGYTFTSYWLHWVRQAPGKGLEWVG-MIDPSNSDT RFNPNFKDRFTISADTSKNTAY-LQMNSLRAEDTAVYYCATYRSYVTPLDYWGQGTL VT VSS (SEQ ID NO:80) and a VL domain comprising the sequence of DIQMTQSPSSLSASVGDRVTITCKSSQSL-LYTSSQKNYLAWYQQKPGKAPKLLIYWASTR ESGVPSRFSGSGSGTDFTLTISSLQPEDFA-TYYCQQYYAYPWTFGQGTKVEIK (SEQ ID NO:81). In some embodiments, the antigen binding domain that binds cMET comprises the VH and VL domain sequences from onartuzumab.

In some embodiments, provided herein is a multispecific (e.g., bispecific) binding molecule that comprises a first antibody arm comprising a single chain variable fragment (scFv) comprising VH and VL domains of the present disclosure that bind to human Dectin-1 and a first Fc region, and a second antibody arm comprising an antibody heavy chain that comprises a VH domain in association with an antibody light chain that comprises a VL domain and a second Fc region connected to the VH domain, wherein the VH and VL domains of the second antibody arm form an antigen binding domain that binds to LIV-1 (e.g., human LIV-1). In some embodiments, the first Fc region comprises one or more knob-forming mutations, and the second Fc region comprises one or more cognate hole-forming mutations, or the second Fc region comprises one or more knob-forming mutations, and the first Fc region comprises one or more cognate hole-forming mutations. In some embodiments, the scFv comprises a first linker of the present disclosure between the VH and VL domains and a second linker of the present disclosure between the VL domain and the first Fc region. In some embodiments, the first antibody arm comprises the amino acid sequence of QVQLVQS-GAEVKKPGASVKVSCK-SSGYTFTDYYIHWVRQAPGQGLEWMGWINPNSGD TNYAQKFQGRITMTRDTSISTAYLELSRLRSDD-TAVFYCARNSGSYSFGYWGQGTLVTV SSGGGGSGGGGSGGGGSGGGGSDIQMTQSPSSVSAS VGDRVTITCRASQGISSWLAWYQ QKPGKAPKLLIF-GASSLQSGVPSRFSGSGSGTDFTLTVSSLQPEDFA-TYYCQQAYSFPFTF GPGTKVDIEEPKRSDKTH-TCPPCPAPELLGGPSVFLFPPKPKDTLMISRTPEVTCV VVDVS HEDPEVKFNWYVDGVEVHNAKTKPRE-EQYNSTYRVVSVLTVLHQDWLNGKEYKCKVS NKA-LPAPIEKTISKAKGQPREPQVYTLPPSREEMT- KNQVSLWCLVKGFYPSDIAVEWESN
GQPENNYKTTPPVLDSDGSFFLYSK-
LTVDKSRWQQGNVFSCSVMHEALHNHYTQKSLS
LSPG (SEQ ID NO:31). In some embodiments, the second antibody arm comprises a VH domain comprising the sequence of QVQLVQSGAEVKKPGASVKVSCK-
ASGYTIEDYYMHWVRQAPGQGLEWMGWIDPENG
DTEYAPTFQGRVTMTRDTSINTAYMELSRLRSDD-
TAVYYCARHDAHYGTWFAYWGQG TLVTVSS (SEQ ID NO:82) and a VL domain comprising the sequence of DVVMTQSPLSLPVTLGQPASISCRSSQSIIRNDGN-
TYLEWYQQRPGQSPRRLIYRVSNRFS
GVPDRFSGSGSGTDFTLKISRVEAE-
DVGVYYCFQGSHVPYTFGGGTKVEIK (SEQ ID NO:83). In some embodiments, the antigen binding domain that binds LIV-1 comprises the VH and VL domain sequences from hLIV14.

In some embodiments, provided herein is a multispecific (e.g., bispecific) binding molecule that comprises a first antibody arm comprising a single chain variable fragment (scFv) comprising VH and VL domains of the present disclosure that bind to human Dectin-1 and a first Fc region, and a second antibody arm comprising an antibody heavy chain that comprises a VH domain in association with an antibody light chain that comprises a VL domain and a second Fc region connected to the VH domain, wherein the VH and VL domains of the second antibody arm form an antigen binding domain that binds to ROR-1 (e.g., human ROR-1). In some embodiments, the first Fc region comprises one or more knob-forming mutations, and the second Fc region comprises one or more cognate hole-forming mutations, or the second Fc region comprises one or more knob-forming mutations, and the first Fc region comprises one or more cognate hole-forming mutations. In some embodiments, the scFv comprises a first linker of the present disclosure between the VH and VL domains and a second linker of the present disclosure between the VL domain and the first Fc region. In some embodiments, the first antibody arm comprises the amino acid sequence of QVQLVQS-
GAEVKKPGASVKVSCK-
SSGYTFTDYYIHWVRQAPGQGLEWMGWINPNSGD
TNYAQKFQGRITMTRDTSISTAYLELSRLRSDD-
TAVFYCARNSGSYSFGYWGQGTLVTV
SSGGGGSGGGGSGGGGSGGGGSDIQMTQSPSSVSA
SVGDRVTITCRASQGISSWLAWYQ QKPGKAPKLLIF-
GASSLQSGVPSRFSGSGSGTDFTLTVSSLQPEDFA-
TYYCQQAYSFPFTF GPGTKVDIEEPKRSDKTH-
TCPPCPAPELLGGPSVFLFPPKPKDTLMISRTPEVTCV
VVDVS HEDPEVKFNWYVDGVEVHNAKTKPRE-
EQYNSTYRVVSVLTVLHQDWLNGKEYKCKVS NKA-
LPAPIEKTISKAKGQPREPQVYTLPPSREEMT-
KNQVSLWCLVKGFYPSDIAVEWESN
GQPENNYKTTPPVLDSDGSFFLYSK-
LTVDKSRWQQGNVFSCSVMHEALHNHYTQKSLS
LSPG (SEQ ID NO:31). In some embodiments, the second antibody arm comprises a VH domain comprising the sequence of QVQLQESGPGLVKPSQTLSLTCTVSG-
YAFTAYNIHWVRQAPGQGLEWMGSFDPYDGGS
SYNQKFKDRLTISKDTSKNQVVLTMTNMDPVD-
TATYYCARGWYYFDYWGHGTLVTVS S (SEQ ID NO:84) and a VL domain comprising the sequence of DIVMTQTPLSLPVTPGEPASISCRASKSISKY-
LAWYQQKPGQAPRLLIYSGSTLQSGIPPRF
SGSGYGTDFTLTINNIESEDAAYYFCQQHDESPY-
TFGEGTKVEIK (SEQ ID NO:85). In some embodiments, the antigen binding domain that binds ROR-1 comprises the VH and VL domain sequences from Ab1.

In some embodiments, provided herein is a multispecific (e.g., bispecific) binding molecule that comprises a first antibody arm comprising a single chain variable fragment (scFv) comprising VH and VL domains of the present disclosure that bind to human Dectin-1 and a first Fc region, and a second antibody arm comprising an antibody heavy chain that comprises a VH domain in association with an antibody light chain that comprises a VL domain and a second Fc region connected to the VH domain, wherein the VH and VL domains of the second antibody arm form an antigen binding domain that binds to serum amyloid P (SAP), e.g., human SAP. In some embodiments, the first Fc region comprises one or more knob-forming mutations, and the second Fc region comprises one or more cognate hole-forming mutations, or the second Fc region comprises one or more knob-forming mutations, and the first Fc region comprises one or more cognate hole-forming mutations. In some embodiments, the scFv comprises a first linker of the present disclosure between the VH and VL domains and a second linker of the present disclosure between the VL domain and the first Fc region. In some embodiments, the first antibody arm comprises the amino acid sequence of QVQLVQS-
GAEVKKPGASVKVSCK-
SSGYTFTDYYIHWVRQAPGQGLEWMGWINPNSGD
TNYAQKFQGRITMTRDTSISTAYLELSRLRSDD-
TAVFYCARNSGSYSFGYWGQGTLVTV
SSGGGGSGGGGSGGGGSGGGGSDIQMTQSPSSVSA
SVGDRVTITCRASQGISSWLAWYQ QKPGKAPKLLIF-
GASSLQSGVPSRFSGSGSGTDFTLTVSSLQPEDFA-
TYYCQQAYSFPFTF GPGTKVDIEEPKRSDKTH-
TCPPCPAPELLGGPSVFLFPPKPKDTLMISRTPEVTCV
VVDVS HEDPEVKFNWYVDGVEVHNAKTKPRE-
EQYNSTYRVVSVLTVLHQDWLNGKEYKCKVS NKA-
LPAPIEKTISKAKGQPREPQVYTLPPSREEMT-
KNQVSLWCLVKGFYPSDIAVEWESN
GQPENNYKTTPPVLDSDGSFFLYSK-
LTVDKSRWQQGNVFSCSVMHEALHNHYTQKSLS
LSPG (SEQ ID NO:31). In some embodiments, the second antibody arm comprises a VH domain comprising the sequence of QVQLVQSGAEVKKPGSSVKVSCK-
ASGFTFATYNMHWVRQAPGQGLEWMGYIYPGDG
NANYNQQFKGRVTITADKSTSTAYMELSSLRSED-
TAVYYCARGDFDYDGGYYFDSWG QGTLVTVSS (SEQ ID NO:86) and a VL domain comprising the sequence of DIQMTQSPSSLSASVGDRVTITCRASENIYSY-
LAWYQQKPGKAPKLLIHNAKTLAEGVPS
RFSGSGSGTDFTLTISSLQPEDFA-
TYYCQHHYGAPLTFGQGTKLEIK (SEQ ID NO:87). In some embodiments, the antigen binding domain that binds SAP comprises the VH and VL domain sequences from dezamizumab.

Multispecific antibodies have binding specificities for at least two different epitopes, usually from different antigens. Multispecific or bispecific antibodies can be prepared as full-length antibodies or antibody fragments (e.g., F(ab')$_2$ bispecific antibodies).

To enable the targeted removal of a disease-causing agent via phagocytosis, an antigen-binding domain of the present disclosure may be selected from IgGs, intrabodies, peptibodies, NANOBODY® single domain antibodies, single domain antibodies, SMTPs, and multispecific antibodies (e.g., bispecific antibodies, diabodies, triabodies, tetrabodies, tandem di-scFV, tandem tri-scFv, ADAPTIR).

Methods for making bispecific antibodies are known in the art. One well-established approach for making bispecific antibodies is the "knobs-into-holes" or "protuberance-into-cavity" approach. See e.g., U.S. Pat. No. 5,731,168. Two immunoglobulin polypeptides (e.g., heavy chain polypeptides) each comprise an interface; an interface of one immunoglobulin polypeptide interacts with a corresponding or cognate interface on the other immunoglobulin polypeptide, thereby allowing the two immunoglobulin polypeptides to associate. In some embodiments, interfaces may be engineered such that a "knob" or "protuberance" located in the interface of one immunoglobulin polypeptide corresponds with a cognate "hole" or "cavity" located in the interface of the other immunoglobulin polypeptide. In some embodiments, a knob may be constructed by replacing a small amino acid side chain with a larger side chain. In some embodiments, a hole may be constructed by replacing a large amino acid side chain with a smaller side chain. Knobs or holes may exist in the original interface, or they may be introduced synthetically. Polynucleotides encoding modified immunoglobulin polypeptides with one or more corresponding knob- or hole-forming mutations may be expressed and purified using standard recombinant techniques and cell systems known in the art. See, e.g., U.S. Pat. Nos. 5,731,168; 5,807,706; 5,821,333; 7,642,228; 7,695,936; 8,216,805; 8,679,785; 8,844,834; U.S. Pub. No. 2013/0089553; Spiess et al., Nature Biotechnology 31: 753-758, 2013; and Ridgway and Carter (1996) Protein Eng. 9:617-621. Modified immunoglobulin polypeptides may be produced using prokaryotic host cells, such as *E. coli*, or eukaryotic host cells, such as mammalian cells (e.g., CHO cells) or yeast cells. Corresponding knob- and hole-bearing immunoglobulin polypeptides may be expressed in host cells in co-culture and purified together as a heteromultimer, or they may be expressed in single cultures, separately purified, and assembled in vitro. Exemplary cognate knob and hole mutations are provided below (numbering according to EU index). EU numbering as used herein is known in the art; see, e.g., IMGT resources at imgt.org/IMGTScientificChart/Numbering/Hu_IGHGnber and imgt.org/IMGTScientific-Chart/Numbering/Hu_IGKCnber. As used herein, an "antibody arm" may refer to the pairing between an antibody heavy chain and an antibody light chain, wherein the variable domains of the heavy and light chains form an antigen binding site that binds a target antigen.

Multispecific (e.g., bispecific) antibodies also include cross-linked or "heteroconjugate" antibodies. Techniques for generating bispecific antibodies from antibody fragments have also been described in the literature. For example, bispecific antibodies can be prepared using chemical linkage. In some embodiments, a bispecific antibody comprises a first IgG antibody comprising the first antigen binding domain covalently linked to a second IgG antibody comprising the second antigen binding domain.

In some embodiments, multispecific (e.g., bispecific) antibodies further comprise one or more mutations on only one of the antibody arms to reduce binding affinity for Protein A. See, e.g., Ollier, R. et al. (2019) *MAbs* 11:1464-1478 and AU2018204314. In some embodiments, the multispecific or bispecific antibody comprises two antibody light chains and two antibody heavy chains, wherein only one of the antibody heavy chains comprises amino acid substitutions H435R and Y436F, according to EU numbering.

In some embodiments, the monospecific or multispecific (e.g., bispecific) antibodies further comprise one or more mutations to reduce effector function, e.g., to reduce or eliminate binding of the Fc region to an Fc receptor. In some embodiments, the antibody comprises two antibody Fc regions, wherein the antibody Fc regions comprise an amino acid substitution at one or more of positions 234, 235, or 237, according to EU numbering. In some embodiments, the antibody comprises two antibody Fc regions, wherein the antibody Fc regions comprise L234A, L235E, and G237A substitutions, according to EU numbering.

In some embodiments, the monospecific or multispecific (e.g., bispecific) antibodies comprise two antibody heavy chains and two antibody light chains, wherein the VH domain of the first antibody heavy chain forms an antigen binding domain with the VL domain of the first antibody light chain, wherein the VH domain of the second antibody heavy chain forms an antigen binding domain with the VL domain of the second antibody light chain, wherein the first antibody heavy chain comprises F126C, C220V, and T366W substitutions, wherein the first antibody light chain comprises S121C and C214V substitutions, and wherein the second antibody heavy chain comprises T366S, L368A,

| Fc region 1 | Y407T | Y407A | F405A | T394S | T366S L368A Y407V | T394W Y407T | T394W Y407A | T366W T394S |
|---|---|---|---|---|---|---|---|---|
| Fc region 2 | T366Y | T366W | T394W | F405W | T366W | T366Y F405A | T366W F405W | F405W Y407A |

According to a different approach, antibody variable domains with the desired binding specificities (antibody-antigen combining sites) are fused to immunoglobulin constant domain sequences.

In some embodiments, multispecific (e.g., bispecific) antibodies further comprise one or more mutations on only one of the antibody arms to improve heavy chain/light chain pairing. For example, amino acid substitutions can be used to replace a native disulfide bond in the CH1-CL interface of one antibody arm with an engineered disulfide bond. See, e.g., Mazor, Y. et al. (2015) *MAbs* 7:377-389 and EP3452089A2. In some embodiments, the multispecific or bispecific antibody comprises two antibody light chains and two antibody heavy chains, wherein only one of the antibody heavy chains comprises amino acid substitutions F126C and C220V, and only the corresponding or cognate light chain comprises amino acid substitutions S121C and C214V, according to EU numbering.

Y407V, H435R, and Y436F substitutions, according to EU numbering. In some embodiments, the first and second antibody heavy chains further comprise L234A, L235E, and G237A substitutions, according to EU numbering. In some embodiments, the first and second antibody heavy chains comprise human IgG1 Fc domains.

In some embodiments, provided herein is a polynucleotide encoding the antibody or multispecific binding molecule of any one of the above embodiments. In some embodiments, provided herein is a vector (e.g., an expression vector) comprising the polynucleotide of any one of the above embodiments. In some embodiments, provided herein is a host cell (e.g., an isolated host cell or cell line) comprising the polynucleotide or vector of any one of the above embodiments. In some embodiments, provided herein is a pharmaceutical composition comprising the antibody or multispecific binding molecule of any one of the above embodiments and a pharmaceutically acceptable carrier.

Any of these may find use in the methods of production and/or treatment disclosed herein.

In some embodiments, provided herein is a method of producing an antibody or multispecific binding molecule, comprising culturing the host cell of any one of the above embodiments under conditions suitable for production of the antibody or multispecific binding molecule. In some embodiments, the method further comprises recovering the antibody or multispecific binding molecule. The antibodies or multispecific binding molecules may be produced using standard recombinant techniques, as described herein, and/or as exemplified infra.

Antibodies and antibody fragments may be produced using recombinant methods. For example, nucleic acid encoding the antibody/fragment can be isolated and inserted into a replicable vector for further cloning or for expression. DNA encoding the antibody/fragment may be readily isolated and sequenced using conventional procedures (e.g., via oligonucleotide probes capable of binding specifically to genes encoding the heavy and light chains of the antibody/fragment). Many vectors are known in the art; vector components generally include, but are not limited to, one or more of the following: a signal sequence, an origin of replication, one or more marker genes, an enhancer element, a promoter, and a transcription termination sequence. Suitable host cells for cloning or expressing the DNA in the vectors herein are the prokaryote, yeast, or higher eukaryote cells. When using recombinant techniques, the antibody/fragment can be produced intracellularly, in the periplasmic space, or directly secreted into the medium. If the antibody/fragment is produced intracellularly, the particulate debris, either host cells or lysed fragments, are removed, for example, by centrifugation or ultrafiltration. Where the antibody/fragment is secreted into the medium, supernatants from such expression systems are generally first concentrated using a commercially available protein concentration filter.

In some embodiments, an antibody or multispecific binding molecule of the present disclosure is part of a pharmaceutical composition, e.g., including the antibody and one or more pharmaceutically acceptable carriers. Pharmaceutical compositions and formulations as described herein can be prepared by mixing the active ingredients (such as a fusion protein) having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives; low molecular weight (less than about 10 residues) polypeptides; proteins, such as serum albumin, gelatin, or immunoglobulins; hydrophilic polymers such as polyvinylpyrrolidone; amino acids; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Certain aspects of the present disclosure relate to kits or articles of manufacture comprising any of the antibodies or multispecific binding molecules disclosed herein. In some embodiments, the article of manufacture comprises a container and a label or package insert on or associated with the container. In some embodiments, the kit or article of manufacture further comprises instructions for using the antibody or multispecific binding molecule according to any of the methods disclosed herein, e.g., for treating a disease or disorder such as cancer.

Suitable containers include, for example, bottles, vials, syringes, etc. The containers may be formed from a variety of materials such as glass or plastic. The container holds a composition that is effective for treating the condition and may have a sterile access port (for example the container may be an intravenous solution bag or a vial having a stopper pierceable by a hypodermic injection needle). At least one active agent in the composition is an antibody or multispecific binding molecule as described herein. The label or package insert indicates that the composition is used for treating the particular condition. The label or package insert will further comprise instructions for administering the antibody or multispecific binding molecule composition to the subject. Articles of manufacture and kits comprising combinatorial therapies described herein are also contemplated.

II. Methods of Production and Identification

In certain aspects, the present disclosure provides methods of producing or generating multispecific (e.g., bispecific) antibodies and antibody fragments. In some embodiments, the methods comprise providing a first antibody or antigen-binding fragment thereof comprising a first antigen-binding domain that binds to a first target of interest; providing a second antibody or antigen-binding fragment thereof comprising a second antigen-binding domain that binds to a second target of interest; and contacting the first antibody or fragment with the second antibody or fragment under conditions suitable for binding between the first antibody or fragment and the second antibody or fragment via an interaction between the avidin, streptavidin, neutravidin, or biotin-binding derivative thereof and the biotin or avidin-binding derivative thereof, thereby generating a multispecific binding molecule. In some embodiments, the first antibody or fragment is coupled to avidin, streptavidin, neutravidin, or a biotin-binding derivative thereof, and the second antibody or fragment is coupled to biotin or an avidin-binding derivative thereof. In some embodiments, the second antibody or fragment is coupled to avidin, streptavidin, neutravidin, or a biotin-binding derivative thereof, and the first antibody or fragment is coupled to biotin or an avidin-binding derivative thereof. Any of the antigen binding domains, antibodies, and antibody fragments of the present disclosure (e.g., as described supra in section I) may be produced or generated using the methods of producing or generating multispecific (e.g., bispecific) antibodies and antibody fragments disclosed herein. Advantageously, this platform provides a modular format for generation of a variety of multispecific (e.g., bispecific) binding molecules in which distinct antigen binding domains, antibodies, and/or antibody fragments are coupled together via a high affinity avidin:biotin interaction.

In certain aspects, the present disclosure provides methods of identifying a multispecific (e.g., bispecific) binding molecule that binds a first and a second target of interest. In some embodiments, the methods comprise providing a first antibody or antigen-binding fragment thereof comprising a first antigen-binding domain that binds to a first target of interest; providing a second antibody or antigen-binding fragment thereof comprising a second antigen-binding domain that binds to a second target of interest; contacting the first antibody or fragment with the second antibody or fragment under conditions suitable for binding between the first antibody or fragment and the second antibody or fragment via an interaction between the avidin, streptavidin, neutravidin, or biotin-binding derivative thereof and the biotin or avidin-binding derivative thereof, thereby generating a multispecific binding molecule; and measuring binding between the multispecific binding molecule and at least one of the first and the second target of interest. In some embodiments, the first antibody or fragment is coupled to avidin, streptavidin, neutravidin, or a biotin-binding derivative thereof, and the second antibody or fragment is coupled to biotin or an avidin-binding derivative thereof. In some embodiments, the second antibody or fragment is coupled to avidin, streptavidin, neutravidin, or a biotin-binding derivative thereof, and the first antibody or fragment is coupled to biotin or an avidin-binding derivative thereof. Advantageously, this platform allows for screening a variety of antigen-binding domains for binding a target of interest in a multispecific (e.g., bispecific) format.

In some embodiments, the first target of interest is human Dectin-1 (e.g., isoform(s) A and/or B). In some embodiments, the second target of interest is a disease-causing agent. In some embodiments, the second target of interest is human Dectin-1 (e.g., isoform(s) A and/or B). In some embodiments, the first target of interest is a disease-causing agent.

Any of the antigen binding domains, antibodies, and antibody fragments of the present disclosure (e.g., as described supra in section I) may find use in the methods of identifying multispecific (e.g., bispecific) antibodies and antibody fragments disclosed herein. In some embodiments, the antigen binding domains, antibodies, and antibody fragments bind to human Dectin-1. For example, in some embodiments, the antibody or fragment binds human Dectin-1 and is coupled to mSA via a linker. In some embodiments, the antibody or fragment comprises a sequence selected from the group consisting of SEQ ID NOs:15-17.

Assays for measuring binding between the multispecific binding molecule and at least one of the first and the second target of interest are known in the art. In some embodiments, binding between the multispecific binding molecule and a purified antigen is measured, e.g., as with an ELISA or SPR binding assay. In some embodiments, binding between the multispecific binding molecule and a cell expressing the antigen on its surface is measured, e.g., as with a flow cytometry-based binding assay. In some embodiments, binding between the multispecific binding molecule and a bead or other solid substrate coated with the antigen is measured. In some embodiments, a functional assay is used to detect an interaction between two or more cells (each expressing a surface antigen bound by an antigen binding domain of the multispecific binding molecule) brought together by binding the multispecific binding molecule, e.g., by measuring cytokine production, cell death/phagocytosis, etc.

III. Methods of Use

In certain aspects, the present disclosure provides methods of treating a disease or disorder, comprising administering an effective amount of an antibody, antibody fragment, multispecific (e.g., bispecific) binding molecule, or composition of the present disclosure to an individual in need thereof. In some embodiments, the individual is a human.

Any of the antigen binding domains, antibodies, and antibody fragments of the present disclosure (e.g., as described supra in section I) may find use in the methods of treatment and uses disclosed herein, as well as the compositions (e.g., pharmaceutical compositions) related thereto. For example, in some embodiments, the methods include using a multispecific (e.g., bispecific) binding molecule of the present disclosure with a first antigen binding domain that binds to human Dectin-1, and a second antigen binding domain that binds to a disease-causing agent. In some embodiments, the disease-causing agent is a bacterial cell, fungal cell, virus, senescent cell, tumor cell, protein aggregate (e.g., amyloid beta, or lambda or kappa light chain amyloids), LDL particle, mast cell, eosinophil, ILC2 cell, or inflammatory immune cell. In some embodiments, the target of interest is an antigen expressed on the surface of the bacterial cell, fungal cell, senescent cell, tumor cell, mast cell, eosinophil, ILC2 cell, or inflammatory immune cell. In some embodiments, the target of interest is a surface antigen of the virus. In some embodiments, the target of interest is CD70, HER2, DLL3, NECTIN-4, TROP-2, Mesothelin, LIV-1, C-MET, FOLR1, CD20, CCR8, CD33, or EGFR. Binding of the molecule that mediates targeted removal of a disease-causing agent via phagocytosis could be with and without avidity i.e., with and without inducing dimerization of the phagocytosis receptor such as Dectin-1 or the target antigen present on the agent.

In some embodiments, the disease or disorder is cancer, a bacterial infection, a fungal infection, a viral infection, a mast cell disease or disorder, systemic mastocytosis, amyloidosis, or an aging-related disease or disorder. There are variety of accumulated and not cleared aberrant host cells such as tumor, lymphoma, dead, necrotic, apoptotic, dying, infected, damaged cells that are associated with diseases. In addition, diverse cell products such as aggregated proteins (β-amyloid plaque, Tau aggregates, or antibody lambda or kappa light chain amyloids), lipoprotein particles, could cause a disease upon increased accumulation. Disease-causing cell may have glycoprotein, surface protein, or glycolipid typical of aberrant cells associated with a disease, disorder, or other undesirable condition. Besides the host generated agents, variety of foreign pathogens such as infectious microbes (e.g., viruses, fungus and bacteria) and the microbe generated products and debris (e.g., viral particle envelopes, endotoxin) may not be well cleared in patients. In some embodiments, the virus is an influenza virus. In some embodiments, the virus is SARS-CoV-2.

The above listed abnormalities may cause illnesses such as cancer, Alzheimer disease, fibrosis, Parkinson disease, Huntington disease, HIV, Hepatitis A, B or C, sepsis etc. Many of these disorders or diseases are characterized by an accumulation of disease-causing agents in different organs in human subjects. In addition to the beneficial removal of a disease-causing agent via phagocytosis, the molecule may induce production of inflammatory mediators to alter the disease microenvironment such as in tumors, cancers and lymphomas. Without wishing to be bound to theory, it is thought that the molecule that performs targeted phagocytosis may demonstrate clear benefits for patients such as Alzheimer disease, Parkinson disease, cancer, infectious diseases (viral, bacterial, fungal, protozoan infections), inflammatory, or immune diseases (e.g., autoimmune diseases, inflammatory bowel diseases, multiple sclerosis), degenerative disease (e.g., joint and cartilage) Rheumatoid arthritis, Felty's syndrome, aggressive NK leukemia, IBM, IBD etc. In addition, targeted phagocytosis antibody treatment may have better activity of depleting cells in tissues over ADCC that relies on NK cells. The treatment may have a selective activity for removal of a particular disease-causing agent over a therapy that targets myeloid cells and improves phagocytosis in general. For example, targets of interest for treatment of cancer include, without limitation, CD70, HER2, DLL3, NECTIN-4, TROP-2, Mesothelin, LIV-1, C-MET, FOLR1, CD20, CCR8, CD33, and EGFR.

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

EXAMPLES

Example 1: Functional Characterization of 2M24 Anti-Dectin-1 Antibody

This example describes the production of monoclonal antibodies specific for human Dectin-1. This example also describes the characterization of a novel anti-human Dectin-1 antibody.

Materials and Methods

Production of Anti-Dectin-1 Antibodies

Four-week-old, ATX-Gx transgenic mice were immunized subcutaneously with recombinant human Dectin-1 isoform B for five weeks, with one boost of antigen per week. Antibody titers in mouse serum were assessed during pre- and post-boosts via ELISA and flow cytometry. The mice with the highest serum antibody titer were selected to supply B cells for the generation of hybridomas.

Prior to cell fusion, mice were administered with one additional boost of recombinant human Dectin-1 isoform B. Mice were sacrificed and the spleens were harvested. Spleen cells and SP2/0-Ag14 myeloma cells were mixed, in which fusion was then induced by 37 C incubation and in the presence of polyethylene glycol (PEG) or electroporation. The cells were then harvested and plated into 96 well plates with limited dilution to achieve one cell per well. The cells were subsequently treated with hypoxanthine, aminopterin and thymidine (HAT) medium and selected for over 2 weeks in culture.

To identify candidates specific towards Dectin-1, the hybridoma supernatants were screened by flow cytometry on cells overexpressing Dectin-1 and human primary monocytes. Cynomolgus monkey Dectin-1 cross-reactivity was assessed by antibody binding to cynomolgus monkey primary monocytes using flow cytometry.

Healthy Donor Samples

Fresh healthy donor buffy coats were obtained from Stanford Blood Center Peripheral blood mononuclear cells were isolated via ficoll paque (GE Healthcare, Chicago, IL) separation and cryopreserved in Bambanker cell freezing media (Bulldog Bio, Portsmouth, NH). Briefly, buffy coats were diluted in phosphate buffered saline (in 1:1 ratio), followed by layering of the diluted buffy coat in ficoll and centrifugation at 760 g. The PBMC layer was isolated and washed in PBS prior to downstream analysis Peripheral blood leukocytes were isolated through red blood cell lysis Cryopreserved cynomolgus monkey PBMC were obtained from Human Cells Biosciences.

Primary Cells and Cell Culture

Human monocytes were isolated from healthy donor PBMCs according to the manufacturer's instructions of the pan monocyte isolation kit (Miltenyi Biotec, Inc., Auburn, CA) For macrophage and dendritic cells differentiation, monocytes were cultured in RPMI with 10 Human Serum (Millipore Sigma) in the presence of 50 ng/ml MCSF (Peprotech, Rocky Hill, NJ) for 6 days to fully differentiate into macrophages or in the presence of 50 ng/ml GMCSF and 50 ng/ml IL-4 (Peprotech, Rocky Hill, NJ) for 6 days to fully differentiate into dendritic cells. The medium with cytokines was refreshed every 3 days.

HEK Blue hDectin-1-a cells and HEK Blue hDectin-1-b cells (Invivogen, San Diego, CA) were maintained in DMEM/10% FBS supplemented with mormocin and puromycin according to manufacturer's instructions. Freestyle 293F cells were transiently transfected according to the manufacturer's suggestion (Thermo Fisher, Waltham, MA) Briefly, viable cell density and percent viability was determined Cells were diluted to a final density of $11\times10^6$ viable cells/mL with Freestyle 293 Expression Medium. Freestyle Max Reagent was diluted with OptiPro SFM Medium, mixed and incubated at room temperature for 5 minutes. The diluted Freestyle Max Reagent was added to plasmid DNA diluted with OptiPro SFM Medium and mixed. The Freestyle Max Reagent/plasmid DNA complexes were incubated at room temperature for 10-20 minutes. The complexes were slowly transferred to the cells, swirling the culture flask gently during the addition, and the cells were then incubated in a 37° C. incubator with 80% relative humidity and 8% CO2 on an orbital shaker.

Binding of Dectin-1 Antibodies to Dectin-1 Expressing Cells

Dectin-1 expressing cells (HEK Blue hDectin-1-a, HEK Blue hDectin-1-b, HEK293F hDectin-1 a FL, human monocytes or cyno monocytes) were plated at $1\times10^5$-$2\times10^5$ cells per well in non-tissue culture treated, 96 well V bottom plates. Additionally, human monocytes were incubated in human FcgR blocking antibody (Biolegend, San Diego, CA) for 10 minutes at room temperature to reduce binding of the antibodies to the Fc receptor. The cells were subsequently stained with the eFluor 506 viability dye (ThermoFisher, Waltham, MA) in a 1:1000 dilution for 30 minutes on ice, followed by a wash step in FACS buffer (PBS with 2% fetal bovine serum). Primary Dectin-1 antibodies or isotypes were used at a titration of 300, 100, 33.3, 11.1, 3.7, 1.23, 0.41, and 0.14 nM and incubated on ice for 30 minutes, followed by another wash step in FACS buffer.

For detection of mouse primary antibodies, the cells were incubated with a fluorescently labeled AF647 anti-mouse Fc-specific secondary antibody (Jackson Immuno). For detection of human IgG4 primary antibody, the cells were incubated for 30 minutes on ice with an Alexa Fluor 647 anti-human Fc-specific secondary antibody (Jackson Immuno) (detection in HEK cells) or a FITC anti-human IgG4 antibody (Sigma) (detection in primary monocytes). Data acquisition was performed using a CytoFlex flow cytometer (Beckman Coulter, Atlanta, GA) and analyzed using Graphpad Prism 8.4.

Dectin-1 Antibody Blocking of Laminarin

HEK Blue hDectin-1a cells were plated at $1\times10^5$ cells per well in non-tissue culture treated, 96 well V bottom plates. Primary anti-Dectin-1 antibodies were used at a titration of 300, 100, 33.3, 11.1, 3.7, 1.23, 0.41, 0.14, 0.05, 0.015 and 0.005 nM and incubated on ice for 30 minutes in the presence of 8 μg/ml biotin laminarin Following a wash step in FACS buffer, binding of biotin laminarin on the HEK cells was detected using streptavidin-AF647 for 30 minutes on ice. For analysis, 4000 cell events were acquired in a CytoFlex flow cytometer (Beckman Coulter, Atlanta, GA) and analyzed using Graphpad Prism 8.4.

Labelling of Polystyrene Beads with pHrodo and Conjugation to Antibodies

Polystyrene beads of different sizes coated with goat anti-mouse IgG (or biotin) (Spherotech, Lake Forest, IL) were washed with PBS/Tween20 0.05% twice. pHrodo Red, succinimidyl ester (pHrodo Red, SE) (ThermoFisher, Waltham, MA) was added to the beads at 10 µM and allowed to incubate for 60 minutes at room temperature with shaking. The beads were then washed with PBS/BSA 0.1% to remove excess pHrodo Red.

After pHrodo labeling, the antibody was conjugated to the beads according to the manufacturer's recommendations. Briefly, based on the binding capacity of the beads to antibody, an 5× excess of antibody was added to the beads and allowed to incubate at room temperature for 60 minutes with shaking. The beads were then washed with PBS/BSA 0.1% to remove unbound antibody. To assess the quality of the beads, pHrodo red activation was assessed in low pH buffer by flow cytometry. Antibody bound on the beads was assessed using a fluorescently labeled AF647 anti-mouse Fc specific or a FITC anti-human IgG4 antibody secondary antibody.

Antibody-Dependent Targeted Phagocytosis of Phrodo Labeled Beads

For phagocytosis experiments, 50,000 HEK cells overexpressing Dectin-1 or primary cells (macrophages or dendritic cells) were seeded in a 96-well plate in RPMI with 10 ultra-low IgG FBS. pHrodo-labelled beads conjugated to anti-Dectin-1 antibodies or isotypes were added at a desired ratio ranging from 1:1 to 1:3 cells beads, and the plates were briefly spun down.

In some experiments cell tracker Calcein AM (Thermo Fisher, Waltham, MA) was added to label the cells. Phagocytosis was monitored in an IncuCyte S3 live imaging system (Germany) by taking images at desired time points and analyzed using the IncuCyte S3 software. Phagocytosis was quantified as the overlap of bright red fluorescence (engulfed beads) with Calcein AM positive cells or integrated red intensity of bright red fluorescence.

SEAP Reporter Assay in HEK Cells Overexpressing Dectin-1 with Anti Dectin-1 Antibodies Anti-Dectin-1 monoclonal antibodies 2M24 (VH and VL domains comprising SEQ ID NO:7 and 8, respectively) or 15E2 and control isotypes were immobilized by coating onto the surfaces of wells of untreated 96-well, U bottomed polypropylene microtiter plates. For coating, 10, 2, 1, 0.5 and 0.1 µg of the anti-Dectin-1 antibody diluted in 50 µl sterile PBS was added to each well. Plates were left overnight in a class II laminar flow cabinet with the lids removed to allow the solutions to evaporate. Coated plates were washed twice with 200 µl sterile PBS to remove salt crystals and unbound antibody. HEK Blue hDectin-1-a cells were then cultured on the plates in RPMI with 10% ultra-low IgG FBS (VWR) for 22 hours and alkaline phosphatase levels were assessed in the supernatant at OD 630 nm using QUANTI Blue Solution (Invivogen, San Diego, CA) per manufacturer's instructions.

To determine HEK cells SEAP secretion induced by anti-Dectin-1 antibody conjugated beads, streptavidin-2M24 (hIgG4) was conjugated to biotin polystyrene beads of 3, 10 and 16 µm in size (Spherotech, Lake Forest, IL) by incubating the beads with the antibody for 30 minutes in room temperature and washing twice with PBS to remove the unbound antibody. Anti-Dectin-1 antibody-conjugated beads were mixed with $1 \times 10^5$ HEK Blue hDectin-1-a cells at a ratio of 1:3 cells:bead in RPM1 with 10% ultra-low IgG FBS for 22 hours, followed by evaluation of alkaline phosphatase secretion at OD 630 nm in the supernatant as described above.

Cytokine Secretion

Anti-Dectin-1 monoclonal antibodies 2M24 or 15E2 clones and control isotypes were immobilized by coating 10 ug onto the surfaces of wells of untreated 96-well, U bottomed polypropylene microtiter plates as described above. Freshly isolated monocytes or peripheral blood mononuclear cells were then cultured on the plates with the immobilized antibodies in RPM1 with 10% ultra-low IgG FBS at 200,000 cell/per well for 24 hours. In other wells the cells were treated with 10 µg/ml of Dectin-1 antibodies in solution instead of immobilized antibodies. TNFa, IL-6 and IFNg in the supernatant were assessed using the U-PLEX Assay Platform (Meso Scale Discovery) and their levels were expressed as fold change of Dectin-1 antibody-induced cytokine secretion versus the isotype control. As a positive control, cells were stimulated with zymosan at 25 µg/ml.

Results

To generate Dectin-1 antibodies, four-week-old, ATX-Gx Alloy transgenic mice were immunized subcutaneously with recombinant Dectin-1 isoform B protein, with one boost of antigen per week. The antibodies generated from this immunization have a human variable domain and a mouse constant domain.

Figure 1A:
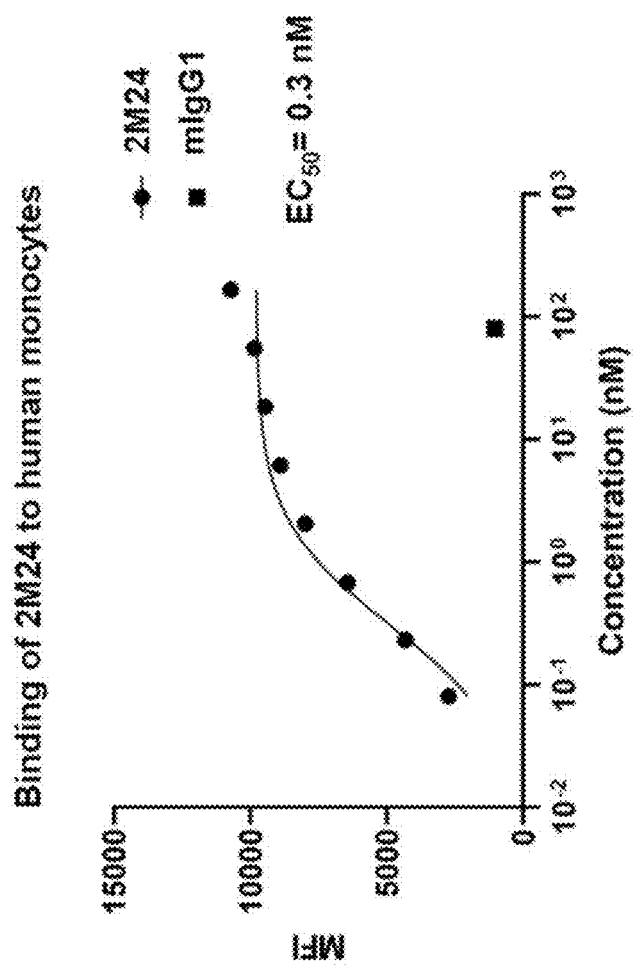

From the 56 candidate anti-Dectin-1 antibody clones generated in this study, the 2M24 clone was the only one that showed binding to both Dectin-1 isoforms A and B in HEK cells as well as to monocytes. As shown in FIG. 1A, the 2M24 anti-Dectin-1 antibody clone demonstrated high affinity to Dectin-1 expressing human monocytes. In contrast, other clones bound only to Dectin-1 isoform A (e.g., 2M08, 2M12, 2M38) or showed no binding at all (2M49). Moreover, the affinity to Dectin-1 of 2M24 was superior to the affinity presented by other clones and the commercial Dectin-1 antibodies (15E2, 259931, GE2). FIG. 1C shows a comparison of the binding to human monocytes and HEK cells overexpressing Dectin-1 between 2M24 clone and other Dectin-1 clones identified from the Alloy transgenic mice immunization, as well as commercial Dectin-1 clones.

Figure 1B:
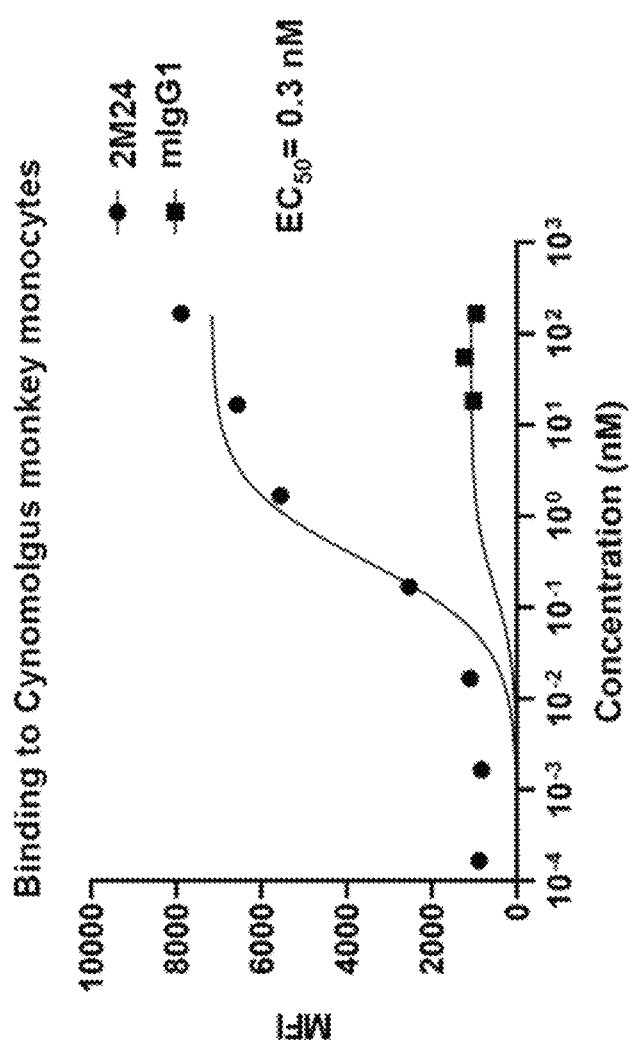

The 2M24 antibody was also assessed for its cross-reactivity to cynomolgus Dectin-1. The binding was assessed by flow cytometry analysis of cynomolgus monkey monocytes derived from PBMCs. As shown in FIG. 1B, anti-human Dectin-1 clone 2M24 antibody demonstrated cross-reactivity and high affinity to cynomolgus monkey Dectin-1 expressed on monocytes. The 2M24 anti-Dectin-1 antibody was superior to commercial antibodies tested in terms of affinity, exhibiting an EC50 of 0.3 nM. The agonistic 15E2 and the 255931 commercial antibodies exhibited EC50 of 14 nM and 16 nM, respectively, in cynomolgus monkey monocytes. FIG. 1C shows a comparison of binding to cynomolgus monkey monocytes between 2M24 clone and the commercial clones 15E2 and 259931.

Figure 2A:
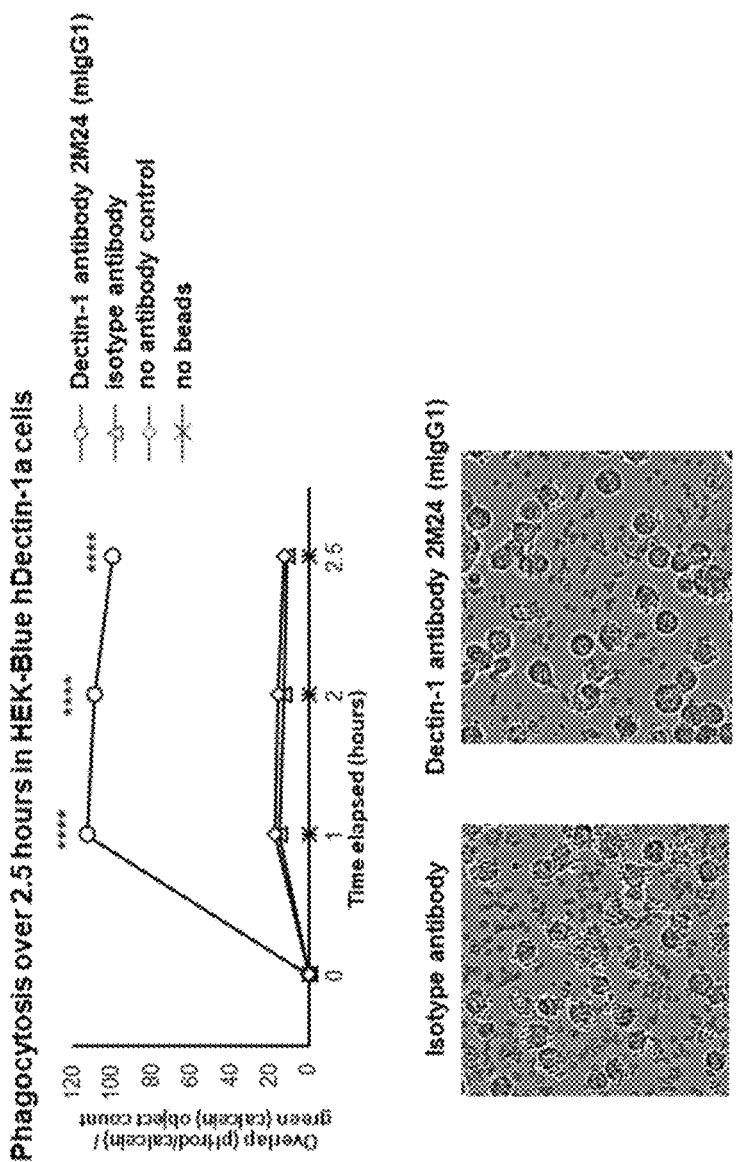
FIGS. 2A-2B show the phagocytosis of pHrodo-labeled polystyrene anti-mouse Fc IgG beads conjugated with anti- Dectin-1 antibody 2M24 or isotype control antibody by HEK-Blue hDectin-1a cells and human monocytes. Polystyrene anti-mouse Fc IgG beads (~3.4 μm) were labeled with a pH-sensitive fluorescent dye (pHrodo Red) and conjugated with Dectin-1 antibody 2M24 or isotype control. The beads were then incubated with cultured HEK-Blue hDectin-1a cells or human monocytes at a ratio of 1:2 (cells:beads). HEK-Blue hDectin-1a cells were labeled with the cell-permeant dye Calcein AM. The phagocytosis of the beads was monitored by IncuCyte live cell imaging. Phagocytosis was quantified using the IncuCyte analysis software and expressed as overlap of red object count (pHrodo) to calcein-positive cells.
Figure 2B:
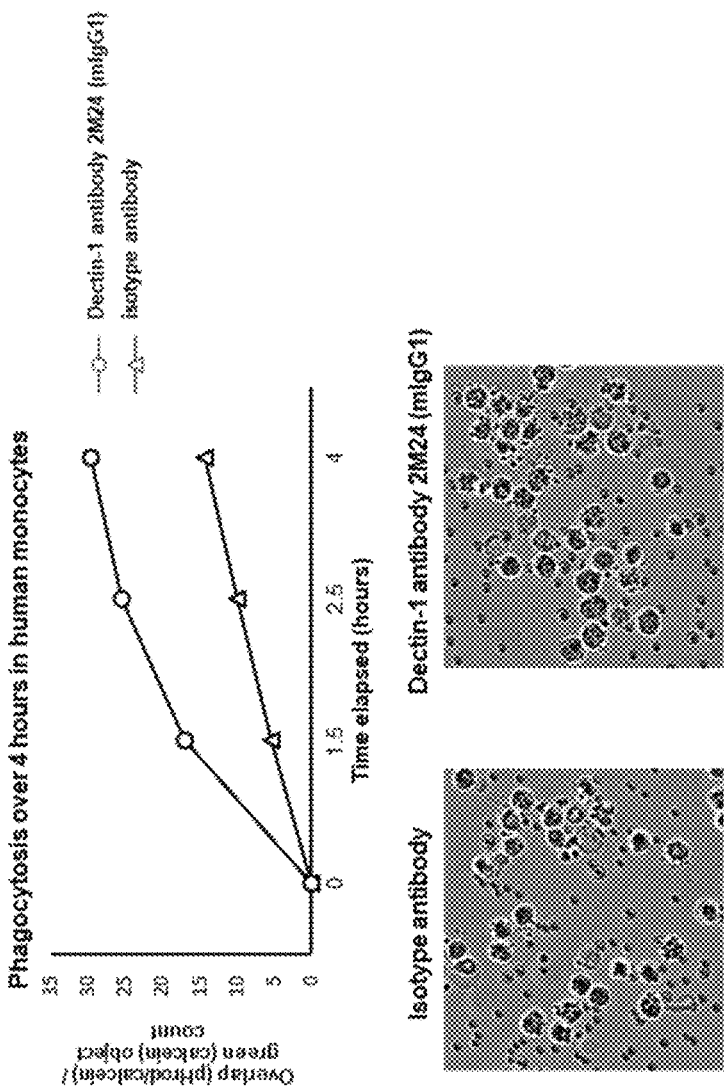

To assess the functionality of the 2M24 Dectin-1 antibody in promoting phagocytosis, polystyrene beads were coated with the 2M24 antibody and mixed with HEK-Blue hDectin-1a cells or primary human monocytes. The 2M24 antibody efficiently induced the phagocytosis of the beads. As shown in FIGS. 2A-2B, the 2M24 anti-Dectin-1 antibody coupled to polystyrene beads promoted phagocytosis in both HEK-Blue hDectin-1a cells and human primary monocytes.

Figures 3A, 3B:
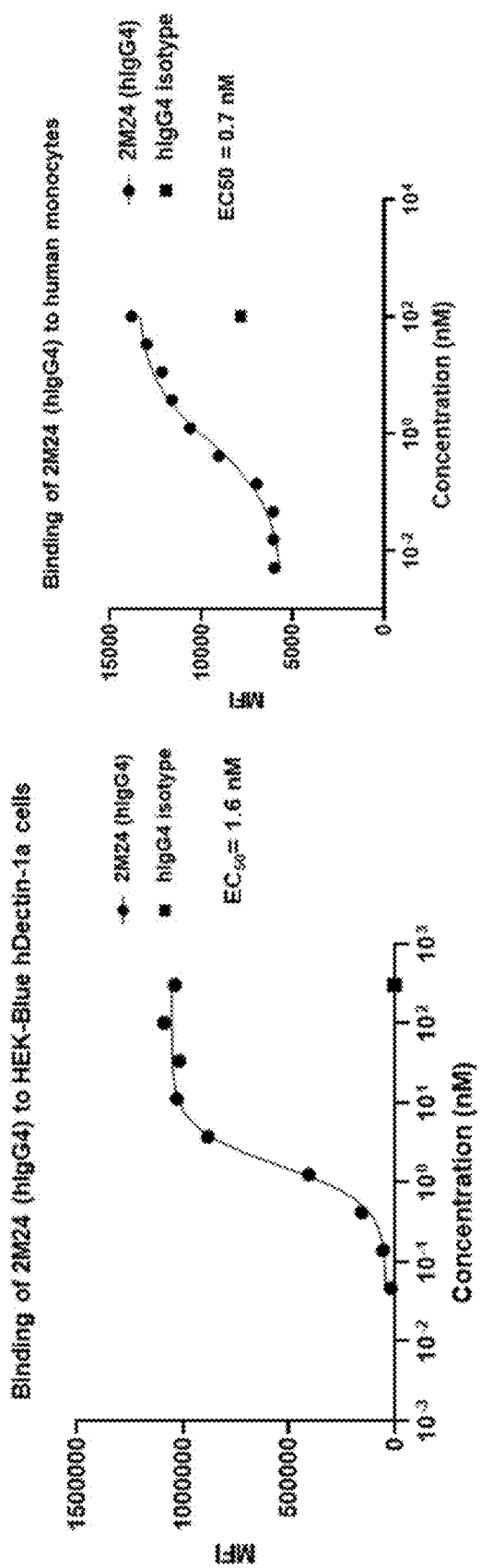
FIGS. 3A-3B show the binding of the fully human 2M24 anti-Dectin-1 antibody (hIgG4) or isotype control antibody in HEK-Blue hDectin-1a cells and primary human monocytes.

From the mIgG1 2M24 clone, a fully human 2M24 antibody of the IgG4 isotype was developed. This antibody has human constant and variable regions. The functionality of the hIgG4 2M24 was then assessed for binding to two Dectin-1 expressing cell types, HEK-Blue hDectin-1a cells and human monocytes. As shown in FIGS. 3A-3B, the fully human 2M24 showed high affinity binding to Dectin-1 in transfected HEK cells (EC50=1.6 nM) and human monocytes (EC50=0.7 nM).

Figure 4:
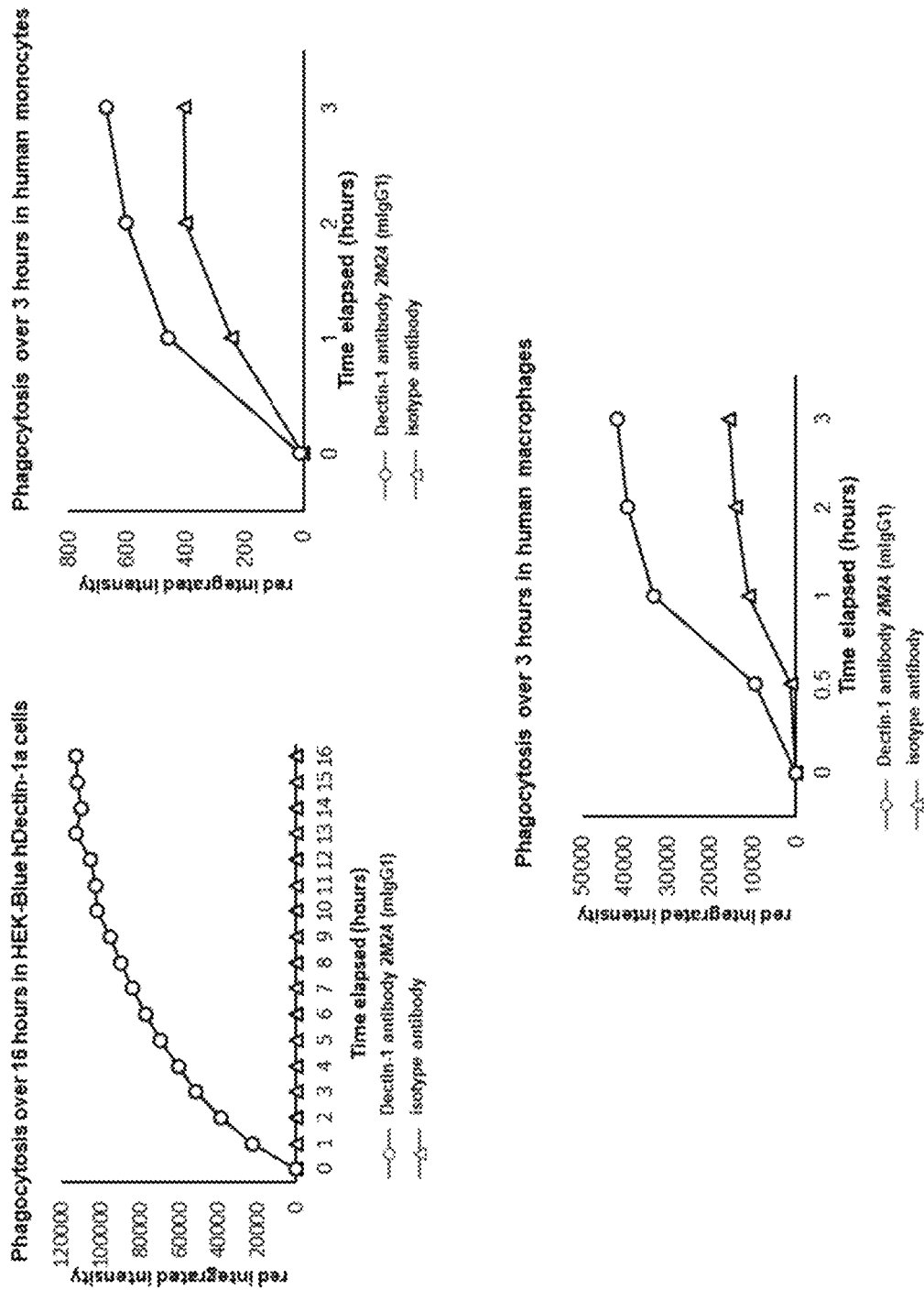
FIG. 4 shows the targeted phagocytosis of pHrodo-labeled polystyrene biotin beads conjugated with the fully human 2M24 anti-Dectin-1 antibody (hIgG4) or isotype control antibody by Dectin-1 expressing cells. Polystyrene biotin beads were labeled with pHrodo Red and conjugated via streptavidin to anti-Dectin-1 antibody 2M24 or an isotype control. The conjugated beads were mixed with cells at a ratio of 1:3, and phagocytosis of the beads was monitored by IncuCyte live cell imaging. The phagocytosis of phrodo-biotin beads conjugated to streptavidin 2M24 anti-Dectin-1 hIgG4 antibody is shown for HEK-Blue hDectin-1a cells (top left), human monocytes (top right) and human macrophages (bottom). The fully human 2M24 anti-Dectin-1 antibody (hIgG4) promoted phagocytosis in Dectin-1 expressing cells.

Next, the hIgG4 2M24 antibody was tested for its ability to promote phagocytosis of beads in Dectin-1 expressing cells. As shown in FIG. 4, the hIgG4 2M24 antibody exhibited efficient phagocytic ability in HEK cells overexpressing Dectin-1, human monocytes, and human macrophages. Thus, the fully human IgG4 2M24 antibody can promote phagocytosis in Dectin-1 expressing cells.

Figure 5A:
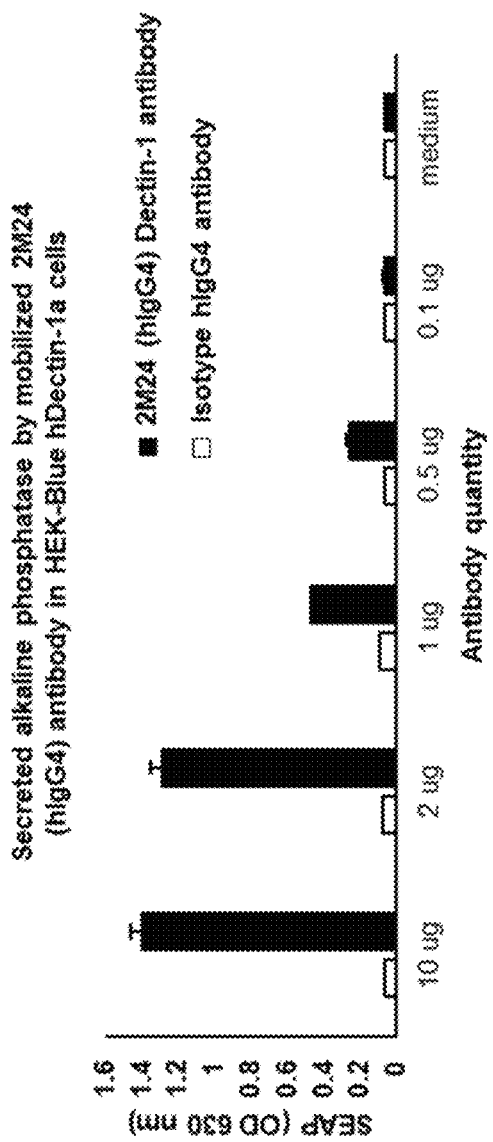
FIGS. 5A-5B show the results of a secreted alkaline phosphatase reporter assay of Dectin-1 in HEK-Blue hDectin-1a cells.
Figure 5B:
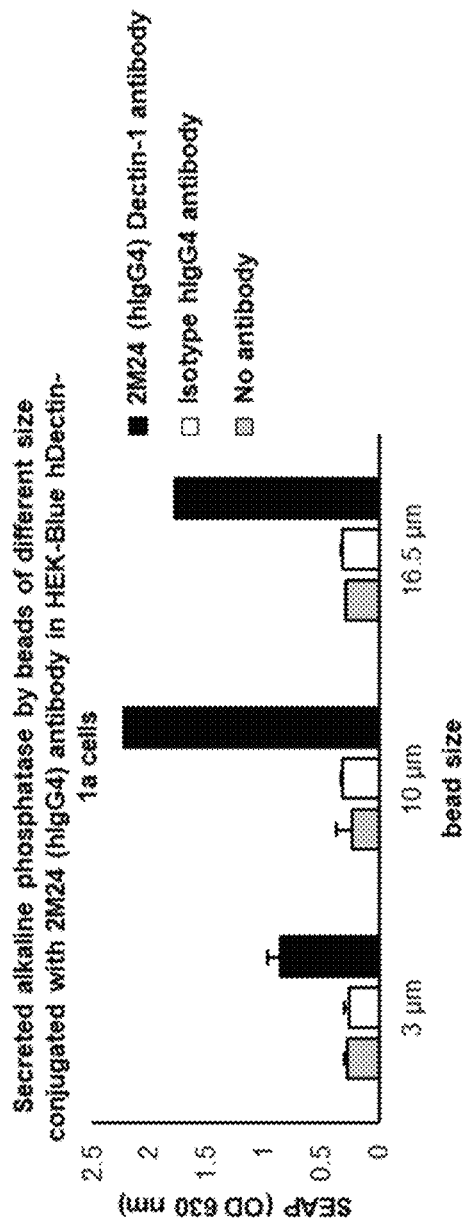

The fully human 2M24 (hIgG4) anti-Dectin-1 antibody was also tested for its ability to promote signaling through Dectin-1. Activation of Dectin-1 signaling by the antibodies can be assessed with a secreted alkaline phosphatase assay using HEK-Blue hDectin-1a cells. The HEK-Blue hDectin-1a cells have been engineered to express Dectin-1 isoform A and genes involved in the Dectin-1/NF-κB/SEAP signaling pathway and thus express a secreted alkaline phosphatase (SEAP) in response to stimulation by Dectin-1 ligands. As shown in FIGS. 5A-5B, the 2M24 (hIgG4) anti-Dectin-1 antibody induced alkaline phosphatase secretion in HEK-Blue hDectin-1a cells both in immobilized form and conjugated to beads. These observations support the idea that the 2M24 (hIgG4) antibody promotes SEAP secretion by engaging Dectin-1 on the surface of the cells, indicating clustering of the receptor and an agonistic activity by this antibody. Moreover, efficient clustering signaling of Dectin-1 can be promoted by beads conjugated to 2M24 (hIgG4). Signaling was better induced with bigger beads, reflecting better clustering of the receptor. This supports that clustering of Dectin-1 promoted by a bispecific antibody comprising the anti-Dectin-1 antibody, which targets a phagocyte, and an antibody targeting another cell, such as a cancer cell, could promote clustering and signaling by Dectin-1 on the phagocyte.

Figure 6A:
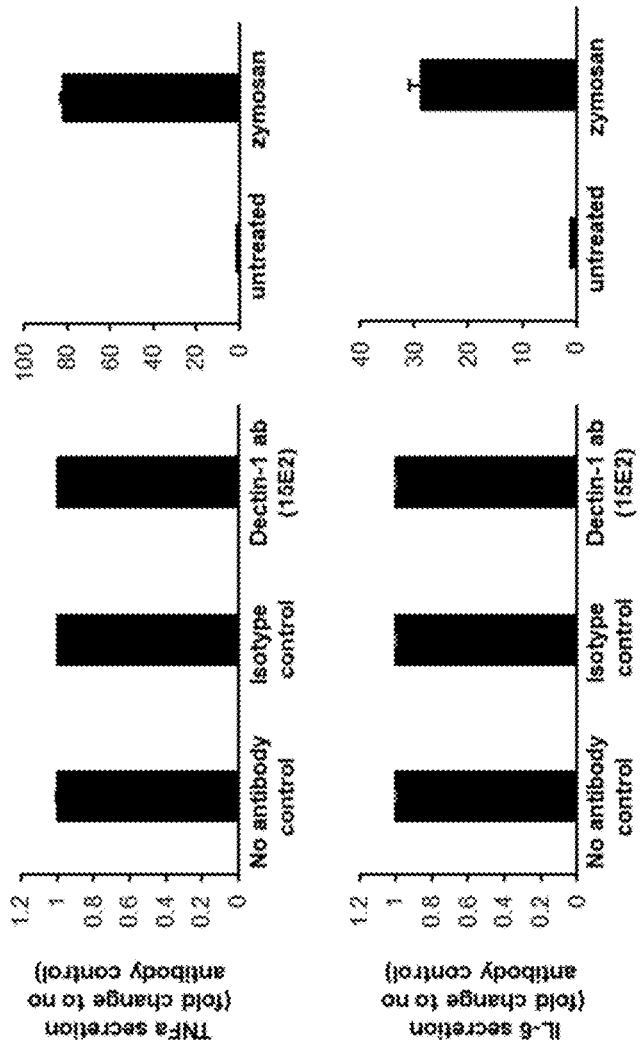
FIGS. 6A-6B show the cytokine secretion by human primary macrophages stimulated with anti-Dectin-1 (15E2) antibody in solution. Primary human macrophages and primary monocytes were stimulated with 10 μg/ml of the 15E2 anti-Dectin-1 antibody or isotype antibody in solution for 24 hours, and secretion of TNFa and IL6 was assessed by ELISA analysis of the supernatant. Zymosan was used as positive controls for cytokine secretion. Bars represent mean±s.d.; n=2 replicates
Figure 6B:
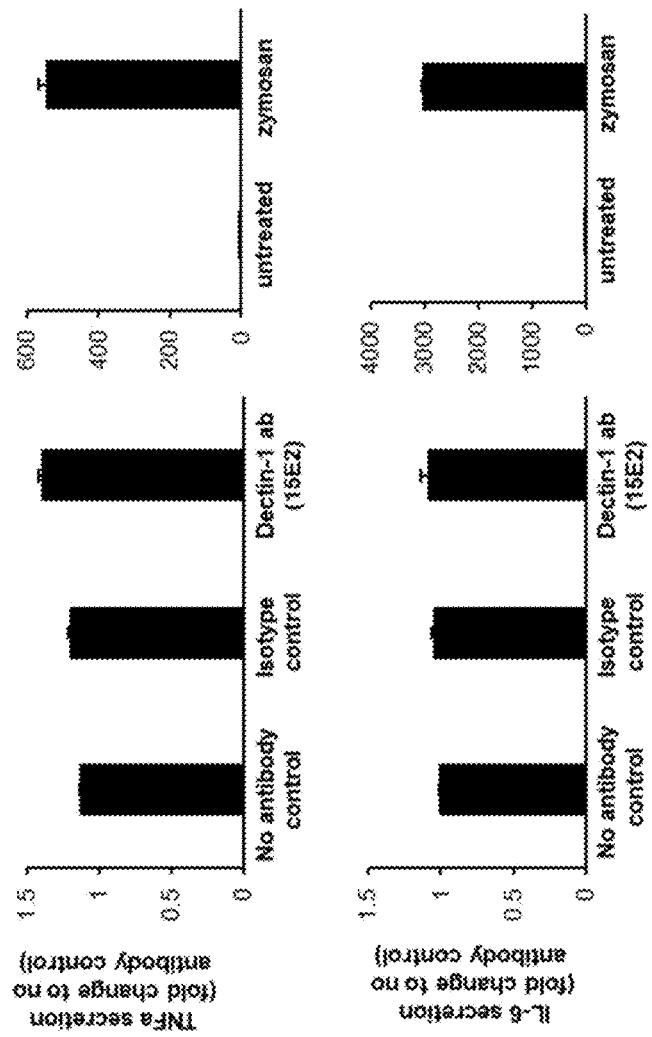

Natural ligands of Dectin-1 cluster the receptor and signal downstream of Dectin-1/Syk/NFkB to induce inflammatory gene expression. To assess if engagement of Dectin-1 antibody in solution can trigger cytokine secretion, monocytes or macrophages were treated with 10 ug/ml of a commercial anti-Dectin-1 antibody. As shown in FIGS. 6A-6B, the 15E2 commercial anti-Dectin-1 antibody did not induce cytokine secretion in primary human macrophages and monocytes, indicating that there was insufficient clustering of the Dectin-1 receptor. This data supports that free Dectin-1 antibody in solution does not induce immuno stimulation, due to lack of sufficient Dectin-1 clustering.

Figure 7A:
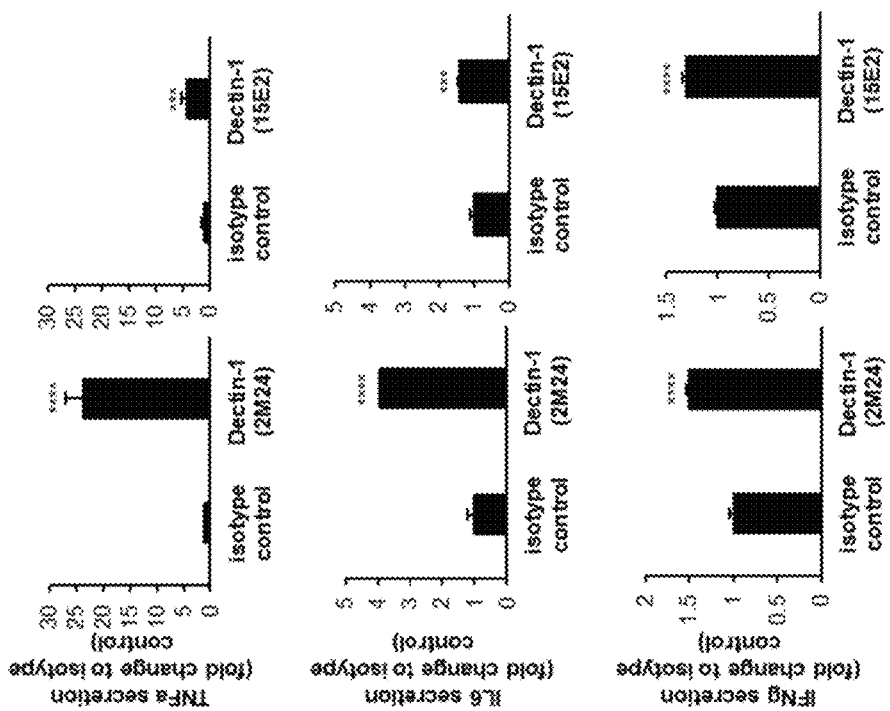
FIGS. 7A-7B show the cytokine secretion by human primary monocytes and PBMCs stimulated with immobilized 2M24 or 15E2 anti-Dectin-1 antibody. The anti-Dectin-1 antibodies or isotype control antibodies were immobilized overnight in U-bottomed polypropylene microtiter plates at 10 μg per well, followed by culture of human monocytes or human PBMCs for 24 hours. The secretion of TNFa, IL6 and IFNg was evaluated by ELISA analysis of the supernatant.
Figure 7B:
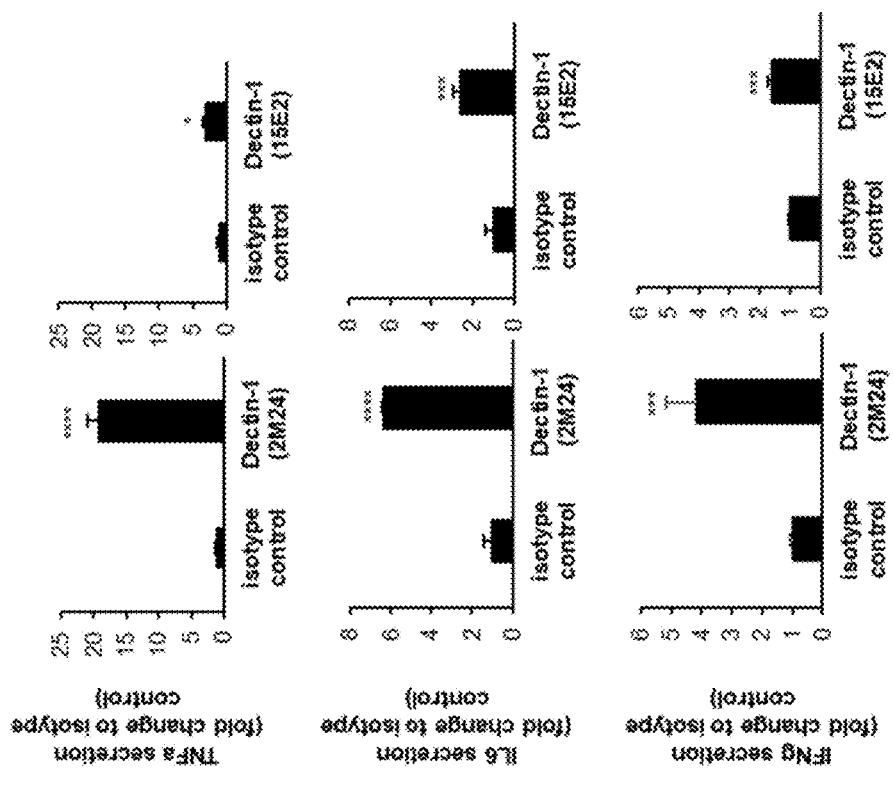

To assess if cytokine secretion could be induced by the 2M24 (hIgG4) anti-Dectin-1 antibody, the antibody was immobilized on beads and cultured with monocytes or PBMCs. As shown in FIGS. 7A-7B, the 2M24 anti-Dectin-1 antibody induced cytokine secretion in primary human monocytes and PBMCs. The 2M24 antibody not only promoted cytokine secretion, but also exhibited superior immuno stimulation as compared to that promoted by the 15E2 anti-Dectin-1 agonistic antibody. Of the cytokines measured in this experiment, TNFa and IL6 are secreted by monocytes that express Dectin-1. In contrast, IFNg is mainly secreted by T-cells that exist in PBMCs. Because T-cells do not express Dectin-1, they are not activated directly by the anti-Dectin-1 antibodies, but rather from cytokines secreted by the monocytes in the PBMCs that are stimulated by the Dectin-1 antibodies. The differential effect of Dectin-1 antibodies on IFNg was therefore more prominent in PBMCs than in pure monocytes.

Figure 8:
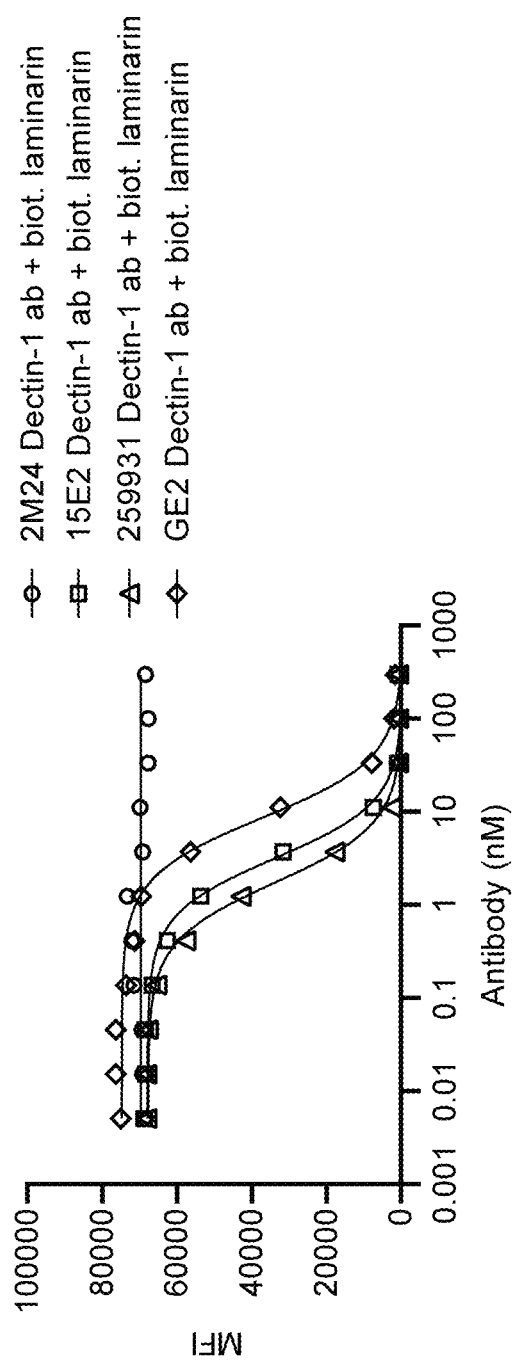
FIG. 8 shows the results of a competition assay performed using the 12M4 anti-Dectin-1 antibody clone and natural ligands for Dectin-1. HEK-Blue hDectin-1a cells were incubated in a ⅓ serial dose titration of 2M24 (hIgG4) anti-Dectin-1 antibody or the 15E2, 259931, GE2 anti-Dectin-1 commercial antibodies starting at 300 nM and in the presence of 8 ug/ml of biotin-laminarin for 30 minutes on ice. Binding of laminarin to Dectin-1 was assessed by flow cytometry using Streptavidin-Alexa fluor 647. The 2M24 (hIgG4) anti-Dectin-1 antibody did not compete with natural ligand for binding to Dectin-1.

Finally, the activation of Dectin-1 by natural ligands in the presence of anti-Dectin-1 antibody was tested. HEK-Blue hDectin-1a cells were incubated in a ⅓ serial dose titration of 2M24 (hIgG4) Dectin-1 antibody or the 15E2, 259931, GE2 anti-Dectin-1 commercial antibodies starting at 300 nM in the presence of 8 ug/ml of biotinylated laminarin. As shown in FIG. 8, binding of the 2M24 (hIgG4) antibody to Dectin-1 did not block the binding of laminarin, a natural ligand of Dectin-1. Thus, engaging Dectin-1 with the 2M24 anti-Dectin-1 antibody does not block clearance of pathogens and is unlikely to increase susceptibility to potential fungal infections.

In conclusion, the 2M24 anti-Dectin-1 antibody can induce phagocytosis by Dectin-1 expressing cells and can induce activation of Dectin-1 signaling without competing with the natural ligands for Dectin-1. The properties of the 2M24 and 15E2 antibodies are summarized in FIG. 9.

Example 2: Bispecific Anti-Dectin-1 Antibodies

This example describes the generation and characterization of bispecific antibodies comprising a Dectin-1-binding arm and a second arm that binds specific tumor antigens.

Materials and Methods

Generation of Bispecifics

Antibodies were differentially labeled with MTA or FOL reagent following manufacturer's guidelines (AAT Bioquest). Labeled antibodies were mixed and incubated to allow for covalent assembly via MTA and FOL interaction. The following antibodies were used for bioin: streptavidin-induced bispecific antibodies:

```
Anti-Dectin-1 15E2 antibody heavy chain:
mSA fusion
                                    (SEQ ID NO: 18)
QWQLQQSGAELARPGASWKMSCKASGYTFTTYTMHWWKQRPGQGLEWIGY

INPSSGYTNYNQKFKDKATLTADKSSSTASMQLSSLTSEDSAWYYCARER

AVLVPYAMDYWGQGTSVTVSSASTKGPSVFPLAPCSRSTSESTAALGCLV

KDYFPEPVTVSWNSGALTSGVHTFPAVLQSSGLYSLSSVVTVPSSSLGTK

TYTCNVDHKPSNTKVDKRVGGGSGGGSGGGSEFASAEAGITGTWYNQHGS

TFTVTAGADGNLTGQYENRAQGTGCQNSPYTLTGRYNGTKLEWRVEWNNS

TENCHSRTEWRGQYQGGAEARINTQWNLTYEGGSGPATEQGQDTFTKVKP

SAASGSAAAGASHHHHHH

Anti-Dectin-1 15E2 antibody light chain
                                    (SEQ ID NO: 19)
QIVLTQSPAVMSASPGEKWTITCTASSSLSYMHWFQQKPGTSPKLWLYST

SILASGVPTRFSGSGSGTSYSLTISRMEAEDAATYYCQQRSSSPFTFGSG

TKLEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC

Avi-tagged anti-CD20 Fab heavy chain (CH1 domain
based on hIgG4 sequence)
                                    (SEQ ID NO: 20)
QVQLQQPGAELVKPGASVKMSCKASGYTFTSYNMHWVKQTPGRGLEWIGA

IYPGNGDTSYNQKFKGKATLTADKSSSTAYMQLSSLTSEDSAVYYCARST
```

-continued

YYGGDWYFNVWGAGTTVTVSAASTKGPSVFPLAPCSRSTSESTAALGCLV

KDYFPEPVTVSWNSGALTSGVHTFPAVLQSSGLYSLSSVVTVPSSSLGTK

TYTCNVDHKPSNTKVDKRVAAAGASHHHHHHGSGLNDIFEAQKIEWHE

Anti-CD20 Fab light chain
(SEQ ID NO: 21)
QIVLSQSPAILSASPGEKVTMTCRASSSVSYIHWFQQKPGSSPKPWIYAT

SNLASGVPVRFSGSGSGTSYSLTISRVEAEDAATYYCQQWTSNPPTFGGG

TKLEIKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC

Avi-tagged anti-HER2 Fab heavy chain (CH1 domain
based on hIgG4 sequence)
(SEQ ID NO: 22)
EVQLVESGGGLVQPGGSLRLSCAASGFNIKDTYIHWVRQAPGKGLEWVAR

IYPTNGYTRYADSVKGRFTISADTSKNTAYLQMNSLRAEDTAVYYCSRWG

GDGFYAMDYWGQGTLVTVSSASTKGPSVFPLAPCSRSTSESTAALGCLVK

DYFPEPVTVSWNSGALTSGVHTFPAVLQSSGLYSLSSVVTVPSSSLGTKT

YTCNVDHKPSNTKVDKRVAAAGASHHHHHHGSGLNDIFEAQKIEWHE

Anti-HER2 Fab light chain
(SEQ ID NO: 23)
DIQMTQSPSSLSASVGDRVTITCRASQDVNTAVAWYQQKPGKAPKLLIYS

ASFLYSGVPSRFSGSRSGTDFTLTISSLQPEDFATYYCQQHYTTPPTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC

Cell Coupling Assay

Dectin-1-expressing cells were labelled with calcein green, and target cells were labelled with calcein reds. The cells were incubated in the presence of a bispecific or an isotype control antibody, then analyzed by flow cytometry. Coupling of the cells was indicated by a double positive signal (green+red+). Coupling efficiency was quantified as the percentage of total target cells that forms doublets with Dectin-1-expressing cells.

Five million effector (Dectin-1 expressing cells) or target cells (cells expressing the target of interest, e.g., CD20 positive Raji cells or HER2 positive SKBR3 cells) were differentially labeled with either calcein green (0.5 nM) or calcein red/pHrodo-red (0.5 nM). Cells were thoroughly washed with PBS and kept on ice. Effector and target cells were then co-cultured at a 3:1 ratio (effector:target) in the presence of 2M24 bispecific antibody or isotype control and incubated for 30 minutes at 37° C. Following incubation, samples were gently resuspended and analyzed by flow cytometry. PMT voltages were adjusted accordingly, and cells were gated based on FITC and/or PE fluorescence corresponding to calcein green or red fluorescence. Coupling efficiency is reported as the number of PE-positive cells (target cells) in the doublet population, divided by the total number of PE-positive target cells in the reaction.

SEAP Reporter Assay in HEK Cells Overexpressing Dectin-1 with Anti Dectin-1 Antibodies To determine HEK cell SEAP secretion induced by Raji cells (expressing CD20), Raji cells were coated with a 2M24/anti-hCD20 or a hIgG4/anti-CD20 bispecific for 30 minutes on ice, followed by washing twice with PBS to remove the unbound bispecific. The bispecific-coated Raji cells were mixed with $1\times10^5$ HEK Blue hDectin-1-a cells at a ratio of 1:2 (HEK cells Raji cells) in RPM1 with 10% ultra-low IgG FBS. After 22 hours, alkaline phosphatase secretion in the supernatant was evaluated at OD 630 nm as described in Example 2.

Results

Figure 10A:
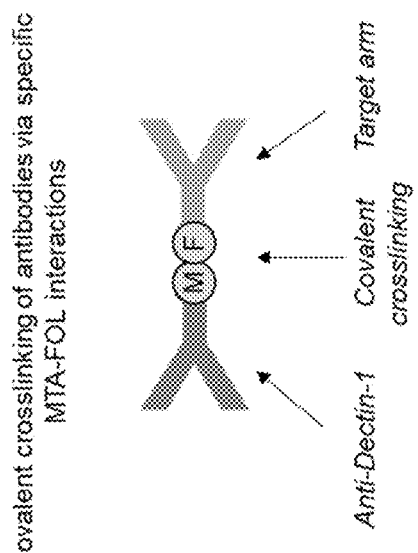
FIGS. 10A-10B show a schematic illustration of bispecific antibody generation by click chemistry.
Figure 10B:
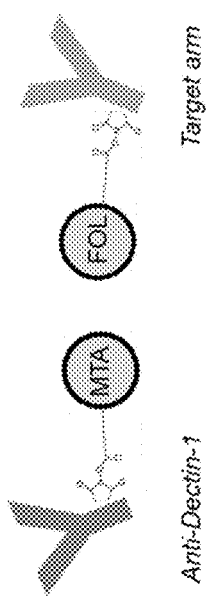
Figure 11A:
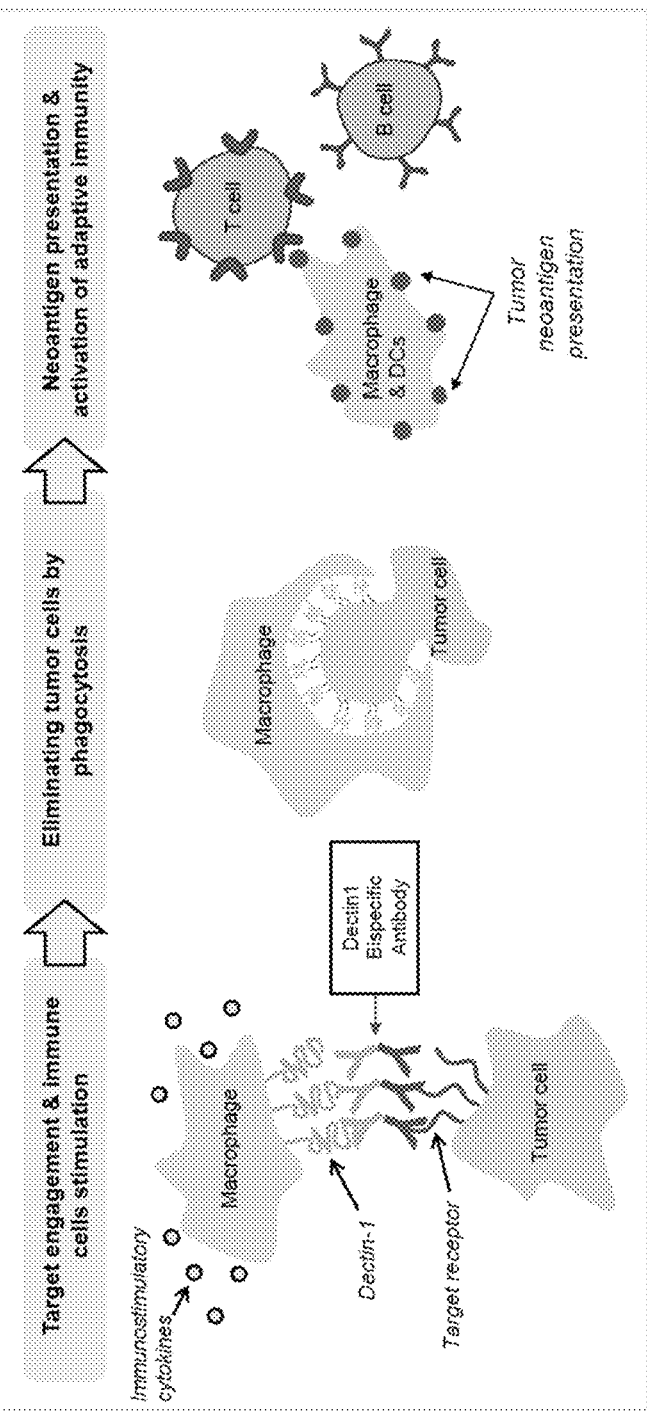
FIG. 11A illustrates the potential modes of activity deployed by anti-Dectin-1 agonistic bispecific antibodies to eliminate target cancer cells. These include immune stimulation, phagocytosis, neo-antigen presentation and activation of T and B lymphocytes of the adaptive immune system.
Figure 11B:
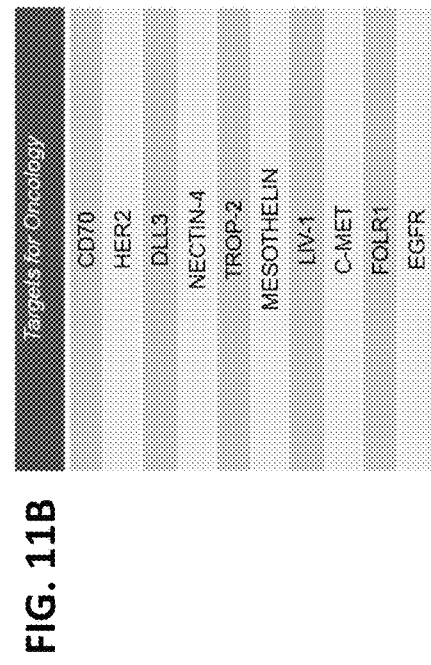
FIG. 11B shows a list of potential targets for cancer cell depletion.

Dectin-1 agonist bispecific antibodies can exploit various modes of activity (e.g., immune activation, phagocytosis, neoantigen presentation and adaptive immunity activation) for the targeted depletion of cancer cells (FIGS. 11A-11B). As a proof-of-concept to engage a Dectin-1 antibody (15E2 or 2M24) and a target antibody, a click-chemistry approach was used to develop bispecifics comprising an anti-Dectin-1-targeting arm and a second arm targeting a protein of interest. This approach enabled the generation of bispecifics for various assays. A schematic of this approach is shown in FIGS. 10A-10B. As binding of Dectin-1 by Dectin-1-specific antibodies can induce phagocytosis of targets (see Example 1 and Example 2), the bispecific antibodies were evaluated for their ability to promote phagocytosis of specific target cells. First, the bispecifics were evaluated for their ability to eliminate CD70-expressing cancer cells by phagocytosis. CD70 is a type II transmembrane glycoprotein that belongs to the tumor necrosis factor (TNF) superfamily CD70 is expressed at low levels in normal tissues, but is highly overexpressed in various diseases, including acute myeloid leukemia (AML), renal cell carcinoma, rheumatoid arthritis and lupus.

Figure 12A:
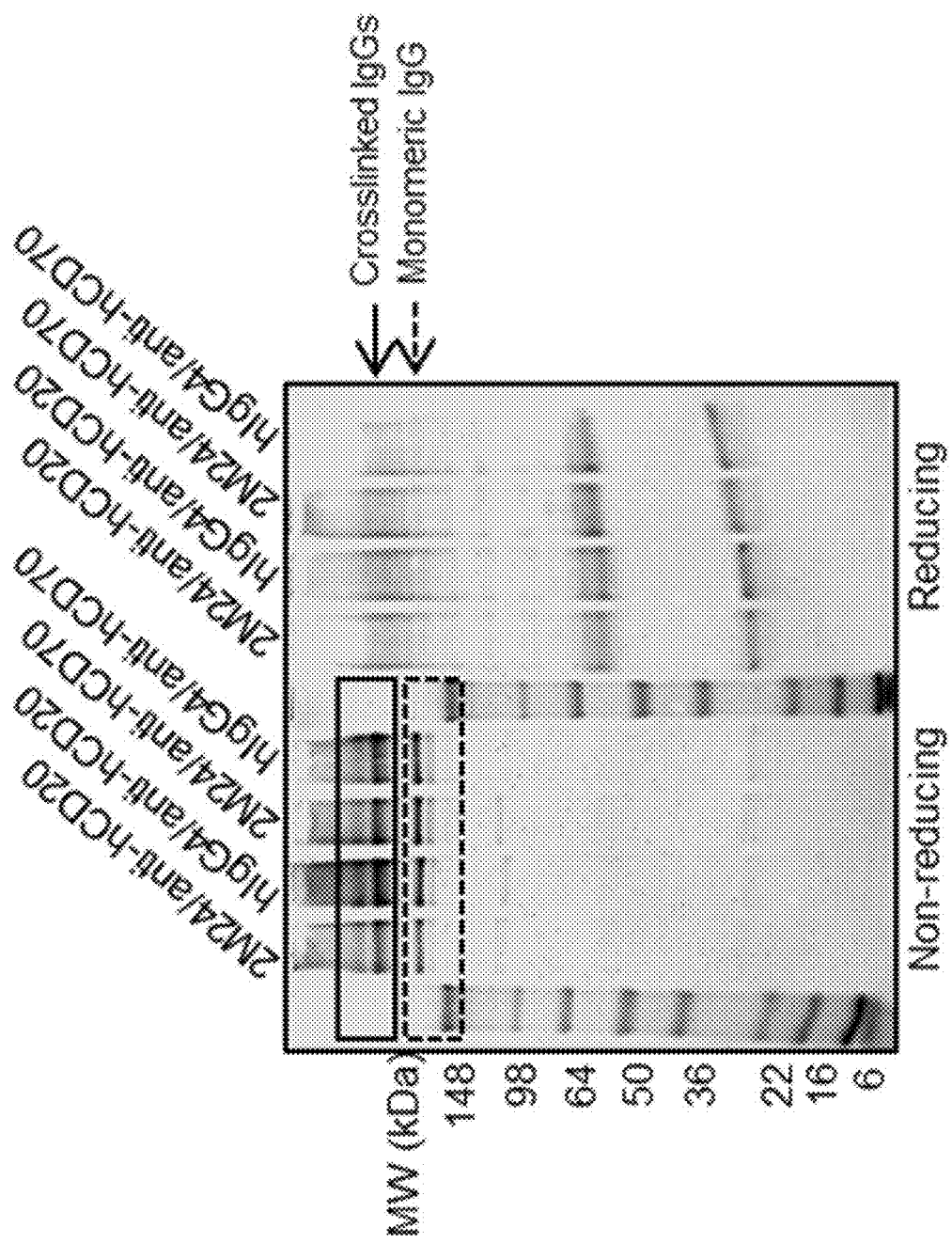
FIGS. 12A-12B show the characterization of click chemistry-conjugated bispecifics comprising anti-Dectin-1 (clone 2M24) and anti-hCD70 arms.
Figure 12B:
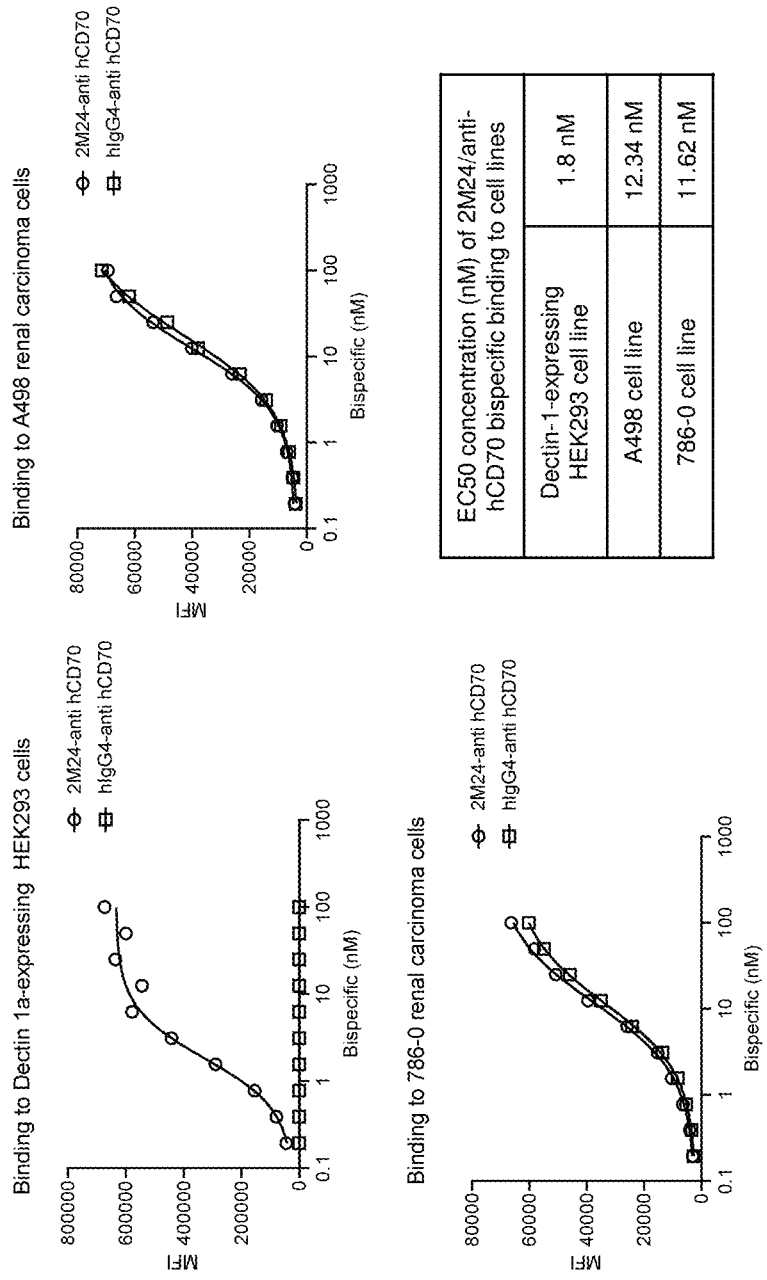

Using click chemistry, a bispecific molecule comprising a Dectin-1-targeting arm (anti-Dectin-1; clone 2M24) and a CD70-targeting arm (anti-hCD70; clone 113-16) was generated. The purity of the bispecific (2M24/anti-hCD70) antibody was assessed by SDS-PAGE analysis (FIG. 12A), while binding was assessed by flow cytometry analysis (FIG. 12B). As shown in FIG. 12B, binding studies on cells revealed that 2M24/anti-hCD70 bound to the HEK293 cell line expressing Dectin-1 with an EC50 of 1.8 nM and bound to CD70-positive renal carcinoma cell lines with an EC50 of 12.34 nM (A498 cells) or 11.62 nM (786-0 cells). The bispecific was then evaluated for its ability to induce cell coupling. As shown in FIG. 13, the 2M24/anti-hCD70 bispecific induced coupling of Dectin-1-expressing HEK293 cells and CD70-expressing renal carcinoma cells, resulting in cell doublets of HEK293 cells (labeled with calcein green) and A498 cells (labeled with calcein red).

Next, targeting of CD20-expressing cells with a bispecific was evaluated. CD20 is a transmembrane protein present on virtually all B cells from the stage at which they become committed to B-cell development until it is downregulated when they differentiate into antibody-secreting plasma cells and is considered a pan-B-cell antigenic marker. As shown in FIGS. 14A-14B, a 2M24/anti-hCD20 bispecific induced coupling of Dectin-1-expressing cells (both Dectin-1-expressing HEK293 cells and human MO macrophages) with CD20-expressing B cells (Raji cell line). This cell-to-cell coupling mediated by the bispecific could induce synapse formation between effector and target cell that may alter cytokine signaling, activate phagocytosis and ultimately target antigen presentation.

To test for induction of signaling resulting from stimulation with bispecific antibodies that bind Dectin-1, a secreted alkaline phosphatase assay was performed. As shown in FIG. 15, Raji cells coated with an anti-Dectin-1/anti-CD20 bispecific induced alkaline phosphatase secretion in HEK-Blue hDectin-1a cells. Thus, using a bispecific antibody to connect a target cell with a cell expressing Dectin-1 (such as phagocyte) can promote signaling by the Dectin-1 expressing cell. In the case of phagocytes, signaling may result in the production of cytokines and immunostimulation.

Previously, it was demonstrated that Dectin-1 expression in HEK 293 cells is necessary and sufficient to induce phagocytosis of various size beads coated with anti-Dectin-1 targeting antibody (see Example 1 and Example 2). To demonstrate phagocytosis of live target cells, a bispecific comprising an Dectin-1-targeting arm and a CD20-targeting arm was developed. In a co-culture assay of HEK 293 cells and CD20-expressing Raji cells, phagocytosis in cells treated with anti-Dectin-1/anti-hCD20 bispecific was observed, in contrast to isotype control bispecifics (FIG. 16). Furthermore, pre-incubation of cells with Latrunculin A, an inhibitor of phagocytosis that blocks actin polymerization, blocked phagocytosis of cells treated with anti-Dectin-1/anti-hCD20 bispecific. These findings indicate that Dectin-1 expression is sufficient to induce phagocytosis, and that co-targeting Dectin-1 and a target of interest with an Dectin-1-agonistic bispecific is sufficient to induce phagocytosis of a target cell.

A proof-of-concept experiment was performed for co-targeting Dectin-1-expressing cells and HER2-positive breast cancer cells using an anti-Dectin-1/anti-HER2 bispecific antibody. Approximately 20% to 25% of invasive breast cancers exhibit overexpression of the human epidermal growth factor receptor HER2 tyrosine kinase receptor. As shown in FIG. 17, anti-Dectin-1 (15E2)/anti-HER2 bispecific induced coupling of Dectin-1- and HER2-expressing cells. This interaction is thought to promote synapse formation between effector and target cells, as Dectin-1 clustering induces cytokine secretion by effector cells, triggers phagocytosis of target cells, and leads to neo-antigen presentation and activation of adaptive immune cells (B and T cells).

Finally, an anti-Dectin-1 (2M24)/anti-hCD94 bispecific was also evaluated. Large granular lymphocyte (LGL) leukemia is a rare chronic lymphoproliferative disease of T cell and natural killer (NK) cell lineage. CD94/NKG2 is a family of C-type lectin receptors which are expressed predominantly on the surface of NK cells and a subset of CD8+T-lymphocytes. As shown in FIG. 18, an anti-Dectin-1 (2M24)/anti-hCD94 bispecific induced coupling of Dectin-1-expressing cells and CD94-expressing cells. Thus, bispecific antibodies that bind Dectin-1 can mediate coupling of Dectin-1-expressing cells with a variety of target cells.

Example 3: Generation of Bispecific Anti-Dectin-1 Antibodies Using Streptavidin-Biotin This example describes the biochemical and functional characterization of bispecific antibodies that bind Dectin-1 generated using streptavidin-biotin conjugation.

Materials and Methods
Generation of Bispecifics mSA was genetically fused to either Fab 2M24 or full length 2M24. Chimeric fusions were incubated with biotinylated target antibodies to generate a bispecific comprising a Dectin-1-binding arm and a second arm binding a target receptor or protein of interest. Full-length 2M24 sequence fused to mSA:

```
Full-length 2M24 sequence fused to mSA:
                                      (SEQ ID NO: 15)
QVQLVQSGAEVKKPGASVKVSCKSSGYTFTDYYIHWVRQAPGQGLEWMGW
INPNSGDTNYAQKFQGRITMTRDTSISTAYLELSRLRSDDTAVFYCARNS
GSYSFGYWGQGTLVTVSSASTKGPSVFPLAPCSRSTSESTAALGCLVKDY
FPEPVTVSWNSGALTSGVHTFPAVLQSSGLYSLSSVVTVPSSSLGTKTYT
CNVDHKPSNTKVDKRVESKYGPPCPPCPAPEFLGGPSVFLFPPKPKDTLM
ISRTPEVTCVVVDVSQEDPEVQFNWYVDGVEVHNAKTKPREEQFNSTYRV
VSVLTVLHQDWLNGKEYKCKVSNKGLPSSIEKTISKAKGQPREPQVYTLP
PSQEEMTKNQVSLTCLVKGFYPSDIAVEWESNGQPENNYKTTPPVLDSDG
SFFLYSRLTVDKSRWQEGNVFSCSVMHEALHNHYTQKSLSLSPGKGGGSG
GGSGGGSEFASAEAGITGTWYNQHGSTFTVTAGADGNLTGQYENRAQGTG
CQNSPYTLTGRYNGTKLEWRVEWNNSTENCHSRTEWRGQYQGGAEARINT
QWNLTYEGGSGPATEQGQDTFTKVKPSAASGS Fab 2M24 sequence fused to mSA:
                                      (SEQ ID NO: 17)
QVQLVQSGAEVKKPGASVKVSCKSSGYTFTDYYIHWVRQAPGQGLEWMGW
INPNSGDTNYAQKFQGRITMTRDTSISTAYLELSRLRSDDTAVFYCARNS
GSYSFGYWGQGTLVTVSSASTKGPSVFPLAPCSRSTSESTAALGCLVKDY
FPEPVTVSWNSGALTSGVHTFPAVLQSSGLYSLSSVVTVPSSSLGTKTYT
CNVDHKPSNTKVDKRVGGGSGGGSGGGSEFASAEAGITGTWYNQHGSTFT
VTAGADGNLTGQYENRAQGTGCQNSPYTLTGRYNGTKLEWRVEWNNSTEN
CHSRTEWRGQYQGGAEARINTQWNLTYEGGSGPATEQGQDTFTKVKPSAA
SGSAAAGASHHHHHH
```

Antibody-Dependent Targeted Phagocytosis of Phrodo-Labeled Beads

Antibody-dependent targeted phagocytosis of Phrodo-labeled beads was performed as described in Example 2. To monitor phagocytosis by flow cytometry, HEK cells overexpressing Dectin-1 were incubated with biotin beads conjugated to Fab 2M24-mSA for 30 minutes on ice or at 37° C. for 30 minutes, followed by washing with PBS twice. Phagocytosis was assessed by detecting activated Phrodo red within the HEK cell/beads duplet population by flow cytometry in the PE channel using a CytoFlex flow cytometer (Beckman Coulter, Atlanta, GA).

Results

To enable the efficient generation of bispecific antibodies, a novel strategy was developed which utilizes the high affinity interaction of streptavidin and biotin. A monomeric streptavidin (mSA) construct was fused to the Fc-domain of 2M24, or CH1 domain of Fab 2M24. The recombinant fusion proteins were incubated with various biotinylated antibodies of interest to assemble the bispecifics. A schematic of this strategy is shown in FIGS. 19A-19B.

This fusion technology enables the high-throughput generation and screening of bispecific antibodies. To test this approach, a Fab 2M24-mSA fusion protein was generated and purified. As shown in FIGS. 20A-20C, the Fab 2M24-mSA fusion showed high affinity binding (EC50=1.45 nM) to Dectin-1 expressing cells. This Fab 2M24-mSA fusion protein can be combined with various biotinylated antibodies against targets of interests. Moreover, the Fab 2M24-mSA fusion also induced binding and phagocytosis of beads by Dectin-1-expressing HEK 293 cells (FIGS. 21A-21B), indicating that the Fab version of the 2M24 antibody can efficiently promote phagocytosis in cells expressing Dectin-1.

Using the anti-Dectin-1-streptavidin fusion, bispecifics against various targets (e.g., CD20, CD19, CD70, amyloid B (1-42)) were developed. As shown in FIGS. 22A-22D, these bispecifics showed high homogeneity based on HPLC analysis. These data demonstrate robust feasibility of this technology for bispecific antibody generation.

Next, the anti-Dectin-1 bispecifics generated using the Fab 2M24-mSA fusion protein were evaluated for their ability to induce cell coupling. As shown in FIG. 23, the Fab 2M24-mSA/biotin anti-hCD20 bispecific induced coupling of Dectin-1-expressing HEK293 cells and CD20-expressing B cells (Raji cell line). This interaction can promote Dectin-1 clustering, which induces cytokine secretion by effector cells, triggers phagocytosis of target cells, and leads to neo-antigen presentation and activation of adaptive immune cells (B and T-cells).

Example 4: Targeted Phagocytosis of Amyloid Deposits Using Anti-Dectin-1 Bispecific Antibodies This example describes the use of bispecific antibodies that bind Dectin-1 in the targeted delivery of pathogen antigens to phagocytic cells.

Dectin-1-induced targeted phagocytosis can be used to mediate amyloid clearance by antigen presenting (e.g., monocytes, macrophages, dendritic cells, and neutrophils), and maximize depletion of circulating amyloid precursors (free light chains) and deposited amyloid fibrils. The targeted phagocytosis relies on the bispecific antibody targeting of Dectin-1 (by 2M24) and AL amyloids (by an amyloid-reactive antibody or serum amyloid protein P antibody).

To test this approach, recruitment or presence of antigen presenting cells to sites of amyloid deposits is first demonstrated Immune cell populations in freshly isolated, amyloid-laden tissues from AL amyloidosis patients are phenotyped. Frequency of antigen presenting cells (e.g., macrophages, monocytes, neutrophils, and dendritic cells) is determined. Dectin-1 expression on APCs in AL amyloidosis patient tissues is assessed.

Then, bispecific antibodies comprising a Dectin-1 binding arm (e.g., clone 2M24) and amyloid-binding arm (based on external antibodies) are developed. For proof-of-concept studies, phagocytosis of AL amyloid fibrils by circulating monocytes, monocyte-derived macrophages (in vitro differentiated) or patient-derived macrophages (in situ) is demonstrated with Dectin-1 bispecific antibodies prepared with external antibodies (FIG. 24). An antibody discovery campaign to identify high affinity binders to amyloid fibrils or amyloid precursors is initiated, from which the resulting antibodies are used to further develop Dectin-1 bispecific antibodies to target amyloid deposits.

Example 5: Targeted Phagocytosis of Mast Cells Using Anti-Dectin-1 Bispecific Antibodies This example describes the use of bispecific antibodies that bind Dectin-1 in the targeted delivery of pathogen antigens to phagocytic cells.
Materials and Methods
Bead Phagocytosis Assay Large (~16.5 µm) polystyrene anti-mouse Fc IgG beads were labeled with a pH-sensitive fluorescent dye (pHrodo red) and conjugated with an anti-Dectin-1 antibody or isotype control. For the phagocytosis assay, the beads were incubated with cultured dendritic cells at a ratio of 1:3 (cells:beads). Bead phagocytosis was monitored by IncuCyte live cell imaging. Phagocytosis was quantified using the IncuCyte analysis software and expressed as total integrated intensity (total sum fluorescent intensity) of red objects (pHrodo fluorescence) in the image.

Mastocytosis is characterized by a pathological accumulation of mast cells in one or more organs. Given the tissue-resident nature of mast cells, and difficulty in accessing these cells therapeutically, tissue-resident macrophages can be engaged and enlisted to deplete and reduce pathological levels of mast cells. As described in Example 1, engagement of Dectin-1 can promote phagocytosis of particles with similar size to cells, including mast cells. Thus, for the targeted depletion of mast cells, the Dectin-1 induced targeted phagocytosis platform can be applied.

First, bispecific antibodies with a macrophage-targeting arm (via Dectin-1 binding) and a mast cell-targeting arm (via mast cell surface antigen) are developed, as depicted in FIG. 25A. Potential mast cell surface antigens/receptors that can be used as lead candidates for bispecific development are summarized in FIG. 25B. These bispecific antibodies are then evaluated for their ability to bind and target mast cells for phagocytosis by Dectin-1 expressing cells and deplete patient mast cells in situ. Phagocytosis of in vitro-differentiated mast cells or mast cell lines by monocyte-derived macrophages (in vitro differentiated) or patient-derived macrophages (in situ) is demonstrated using Dectin-1 bispecific antibodies.

The presence or recruitment of antigen presenting cells (e.g., macrophages, monocytes, neutrophils, and dendritic cells) is demonstrated in patient tissues/organs with high number of mast cells Immune cell populations are phenotyped in fresh tissues isolated from mastocytosis patients. Dectin-1 expression is assessed on APCs. Binding of external antibodies is assessed on donor mast cells.

Given the large size of mast cells, we assessed if Dectin-1 can promote phagocytosis of large entities by conjugating anti-Dectin-1 antibody to large beads (~16.5 um), which are similar in size to large cells. Since macrophages are large phagocytic cells and can ingest large targets, the phagocytosis assay for large beads was performed using macrophages differentiated from monocytes in the presence of MCSF for 6 days. As shown in FIG. 26, anti-Dectin-1 antibody promoted the directed phagocytosis of large beads in cultured human macrophages. Anti-Dectin-1-conjugated beads were more readily engulfed by the macrophages compared to isotype control-conjugated beads. These data support that targeting Dectin-1 enables targeting of large cells, such as mast cells (size: 16-20 µm), for phagocytosis.

Example 6: Targeted Depletion of Microbes Using Anti-Dectin-1 Bispecific Antibodies This example describes the use of bispecific antibodies that bind Dectin-1 in the targeted phagocytosis of microbes.
Materials and Methods
Binding to H3N2 Flu Virus by ELISA To assess the binding of the anti-Dectin-1/a-hemagglutinin bispecific antibody to the H3N2 flu virus, H3N2 flu particles at 2.5, 5, and 10 ug/mL were coated overnight on high binding 96-well plates. The plates were washed twice with PBS, blocked with 3% BSA in PBS/Tween-20 0.05% for 1 hour at RT, followed by more washes with PBS/Tween-20 0.05%. Primary antibodies, including anti-Dectin-1 (15E2), anti-hemagglutinin (12CA5), anti-Dectin-1/anti-hemagglutinin bispecific, and isotype controls were incubated at 20 nM for 1 hour at RT. The plates were then washed with PBS/Tween-20 0.05% twice, and a secondary anti-mouse Fcg:HRP at 1:5000 was incubated for 1 hour at RT. Finally, the plates were washed, incubated with TMB substrate for 30 minutes, and the reaction was stopped with 2N $H_2SO_4$. The plates were read at 450 nm on a plate reader.

Innate immune cells play a vital role in recognition and elimination of microbial pathogens. To aid phagocytes in attacking bacteria, viruses, or fungal pathogens, a bispecific comprising a Dectin-1-targeting arm which binds antigen presenting cells (macrophages, monocytes, dendritic cells, and neutrophils) and a second arm targeting an antigen expressed on the surface of pathogens can be used for Dectin-1-induced targeted depletion (FIG. 27). The targeted phagocytosis of pathogens enables effector cells to efficiently recognize a target pathogen and secrete cytokines and proteases that can directly kill the bound pathogen Furthermore, the bispecific antibody can mediate Dectin-1 clustering, induced targeted-phagocytosis of the bound target. Finally, following degradation of the target, target antigens are presented and modulates the adaptive immune response which further enables the host organism to fight off the pathogen.

As a proof-of-principle, high affinity antibodies against pathogen-specific surface antigens of interest are identified and used to generate bispecific antibodies comprising a Dectin-1-binding arm (anti-Dectin-1 antibody 2M24) and a pathogen-targeting arm. The anti-Dectin-1/anti-pathogen bispecific antibodies are tested for target binding, cytokine secretion by phagocytes following target engagement, target phagocytosis and degradation of the pathogen, and target antigen presentation. Moreover, high affinity antibodies are developed to validate the pathogen targets and are used to subsequently develop Dectin-1 bispecific antibodies from lead candidates.

To test for the targeted delivery of pathogen to phagocytic cells antigens, a bispecific antibody with a Dectin-1-binding arm and a second arm that binds Hematogglutinin from influenza H3N2 virus was generated. The anti-Dectin-1/anti-Hemagglutinin bispecific antibody was then tested for binding using both ELISA and flow cytometry. As shown in FIGS. 28A-28B, the anti-Dectin-1/anti-Hemagglutinin bispecific antibody bound efficiently to both the H3N2 flu virus and to HEK cells expressing Dectin-1. This antibody format could be used to target the flu virus or an antigen of the flu virus to antigen presenting cells (e.g., dendritic cells, macrophages).

Example 7: Targeted Delivery of Antigens for Vaccine Development

This example describes the targeted delivery of viral antigens to phagocytic cells.
Materials and Methods
Bead Phagocytosis Assay Small (~3.4 μm) polystyrene anti-mouse Fc IgG beads were labeled with a pH-sensitive fluorescent dye (pHrodo red) and conjugated with an anti-Dectin-1 antibody or isotype control. For the phagocytosis assay, the beads were incubated with cultured dendritic cells at a ratio of 1:3 (cells:beads). Bead phagocytosis was monitored by IncuCyte live cell imaging. Phagocytosis was quantified using the IncuCyte analysis software and expressed as total integrated intensity (total sum fluorescent intensity) of red objects (pHrodo fluorescence) in the image.
Labelling of Polystyrene Beads with pHrodo and Conjugation to Antibodies Labelling of polystyrene beads with pHrodo and conjugation to antibodies was performed as described earlier.

To coat polystyrene beads with the SARS-Cov-2 spike protein 51, goat anti Rabbit IgG (Fc) beads (Spherotech) were labeled with pHrodo Red and conjugated to a rabbit anti-Flag antibody (Cell Signaling) as described above. Flag-tagged Spike protein (Genscript) was then coupled to pHrodo/anti-Flag beads, and unbound Spike protein was washed off with PBS.
Antibody-Dependent Targeted Phagocytosis of Phrodo Labeled Beads For phagocytosis of SARS-CoV-2 spike protein coated beads, the beads were pre-incubated with anti-Dectin-1/anti-SARS-CoV-2 spike protein bispecific (anti-SARS-CoV-2 spike protein antibody was purchase from Genscript) for 60 minutes in RT and unbound antibody was washed off. The beads were then mixed with HEK cells.
Results Dendritic cells are specialized antigen-presenting cells. Targeting an antigen expressed on a disease-causing agent (cancer cell, pathogen, or protein-aggregate) or the agent itself to dendritic cells through Dectin-1 can potentially elicit a protective immune response directed against the antigen and the disease-causing agent from which it was derived. This response will involve T cell activation and expansion, cytokine secretion and B cell activation. Thus, a Dectin-1 antibody-targeted vaccine could be designed to deliver antigens to dendritic cells and promote the recognition and elimination the disease-causing agent (e.g., cancer cells or pathogen). Target antigen could be fused to an anti-Dectin-1 antibody for delivery to APCs (FIG. 29A), or anti-Dectin-1 bispecific antibody could be used to target delivery of a disease-causing agent to APCs (FIG. 29B).

To determine if phagocytosis in human dendritic cells can be promoted by antibody engagement of Dectin-1, purified monocytes (CD14+) from human PBMC were differentiated to Dendritic cells in the presence of IL4/GMCSF. After 6 days the dendritic cells were incubated with pHrodo-labeled polystyrene beads conjugated with the 15E2 anti-Dectin-1 antibody or an isotype control. As shown in FIG. 30, anti-Dectin-1 antibodies promoted directed phagocytosis of beads in cultured monocyte-derived dendritic cells. Significantly more phagocytosis of anti-Dectin-1-conjugated beads than of isotype-conjugated beads was observed, as evidenced by the bright red phrodo particles within the cells. Dendritic cells are specialized antigen-presenting cells. Targeting an antigen on a disease-causing agent (e.g., a cancer cell, pathogen, or protein aggregate), or the agent itself, to dendritic cells through Dectin-1 can potentially elicit a protective immune response directed against the antigen and the disease-causing agent from which it was derived. This response can involve T cell activation and expansion, cytokine secretion, and B cell activation. Therefore, a Dectin-1 antibody-targeted vaccine can be designed to deliver antigens to dendritic cells and promote the recognition and elimination of a disease-causing agent (e.g., a cancer cell or pathogen).

Targeting of a different virus, SARS-CoV-2, using Dectin-1 agonist bispecific antibodies was also evaluated. A bispecific antibody was generated using click chemistry to target Dectin-1 and the spike 51 protein of SARS-CoV-2. The spike protein was coated onto beads, and the beads were then engulfed in the presence of the anti-Dectin-1/anti-SARC-CoV-2 spike 51 bispecific (FIG. 31A). The anti-Dectin-1/anti-SARS-CoV-2 spike 51 bispecific induced coupling between Dectin-1 expressing HEK 293 cells and the spike coated beads (FIG. 31B), as well as promoted phagocytosis of the spike-coated beads by the Dectin-1-expressing cells (FIG. 31C). Based on these results, the anti-Dectin-1/ anti-SARS-CoV-2 spike 51 bispecific could mediate targeted delivery of SARS-CoV-2 Spike protein to macrophages.

Conclusions

Bispecific antibody comprising a Dectin-1-binding arm and a second arm that binds an antigen from a pathogen, such as influenza virus or SARS-CoV-2 as described in this example, can promote engulfment of the target pathogen, and presentation of the antigens followed by activation and expansion of T cells and antibody production by B cells. The adaptive immune response can promote elimination of the virus and virus-infected cells. Dectin-1 antibody-targeted vaccine approach has the potential to work against other pathogens of bacterial or viral origin.

Various anti-Dectin-1 (e.g., 2M24)/antigen-specific bispecific antibodies are developed and demonstrated to efficiently bind to APCs. Internalization of the targeted antigen from APCs is assessed. Methods to assess antigen presentation of the targeted antigen on the surface of dendritic cells are developed. Activation of CD4+ and CD8+ T cells (T cell expansion and cytokine secretion) is assessed from dendritic cells that have received antigen through Dectin-1. B cell activation and antibody production against the antigen are assessed. Mice are vaccinated, and adaptive immune response is assessed in vivo, along with protection against the disease caused by the pathogen/malignant cells.

Example 8: Bispecific Design for Development of a Human Bispecific Antibody Targeting Dectin-1 and a Disease Target or Antigen To enable the assembly and efficient production of highly purified and active bispecifics, design principles were adopted based on previously reported strategies including "knobs-into-holes" (Ridgway, 1996; U.S. Pat. No. 8,679,785B2), DuetMab (Mazor, 2015; patent EP3452089A2), single-step Protein A and G avidity purification methods (Ollier, 2019; AU2018204314B2), and mutations to eliminate FcR binding (patent WO 2016/081746 A2). Assembly of complete bispecific involves expression of 4 individual subunits, e.g., cloned into expression vectors such as pFUSE. A diagram of an exemplary anti-Dectin-1 bispecific antibody is shown in FIG. 32A.

As shown in Table 1, bispecific antibodies using this design were constructed for proof-of-concept studies. These bispecific antibodies have one arm that targets hDectin-1 and a second arm that targets hCD20, hHER2, hCD70, or a protein on RSV. The bispecific antibodies described in Table 1 were generated by expressing all 4 chains and purifying to 95% purity and homogeneity. All bispecifics were found to bind their respective targets.

TABLE 1

Bispecific antibodies targeting human Dectin-1 and antigen expressed on cancer cells/disease targets.

| Name | Target 1 | Target 2 |
|---|---|---|
| 2M24/CD20 hIgG1 (fucosylated or afucosylated) | hDectin-1 (variable domain from clone 2M24) | hCD20 (variable domain based on Rituximab antibody) |
| 2M24/HER2 hIgG1 (fucosylated or afucosylated) | hDectin-1 (variable domain from clone 2M24) | hHER2 (variable domain based on Trastuzumab antibody) |
| 2M24/CD70 hIgG1 (fucosylated or afucosylated) | hDectin-1 (variable domain from clone 2M24) | hCD70 (variable domain based on Cusatuzumab antibody) |
| 2M24/RSV hIgG1 (fucosylated or afucosylated) | hDectin-1 (variable domain from clone 2M24) | This bispecific is used as an isotype control antibody for POC studies. The second arm binds a protein on respiratory syncytial virus (RSV). |

Variable domains for the antibody arm opposite anti-Dectin-1 in Table 1 were as follows.

CD20 VH:
(SEQ ID NO: 24)
QVQLQQPGAELVKPGASVKMSCKASGYTFTSYNMHWVKQTPGRGLEWIGA

IYPGNGDTSYNQKFKGKATLTADKSSSTAYMQLSSLTSEDSAVYYCARST

YYGGDWYFNVWGAGTTVTVSA

CD20 VL:
(SEQ ID NO: 25)
QIVLSQSPAILSASPGEKVTMTCRASSSVSYIHWFQQKPGSSPKPWIYAT

SNLASGVPVRFSGSGSGTSYSLTISRVEAEDAATYYCQQWTSNPPTFGGG

TKLEIK

HER2 VH:
(SEQ ID NO: 34)
EVQLVESGGGLVQPGGSLRLSCAASGFNIKDTYIHWVRQAPGKGLEWVAR

IYPTNGYTRYADSVKGRFTISADTSKNTAYLQMNSLRAEDTAVYYCSRWG

GDGFYAMDYWGQGTLVTVSS

HER2 VL:
(SEQ ID NO: 35)
DIQMTQSPSSLSASVGDRVTITCRASQDVNTAVAWYQQKPGKAPKLLIYS

ASFLYSGVPSRFSGSRSGTDFTLTISSLQPEDFATYYCQQHYTTPPTFGQ

GTKVEIK

CD70 VH:
(SEQ ID NO: 38)
EVQLVESGGGLVQPGGSLRLSCAASGFTFSVYYMNWVRQAPGKGLEWVSD

INNEGGTTYYADSVKGRFTISRDNSKNSLYLQMNSLRAEDTAVYYCARDA

GYSNHVPIFDSWGQGTLVTVSS

CD70 VL:
(SEQ ID NO: 39)
QAVVTQEPSLTVSPGGTVTLTCGLKSGSVTSDNFPTWYQQTPGQAPRLLI

YNTNTRHSGVPDRFSGSILGNKAALTITGAQADDEAEYFCALFISNPSVE

FGGGTQLTVL

RSV VH:
(SEQ ID NO: 36)
QVTLRESGPALVKPTQTLTLTCTFSGFSLSTSGMSVGWIRQPPGKALEWL

ADIWWDDKKDYNPSLKSRLTISKDTSANQVVLKVTNMDPADTATYYCARS

MITNWYFDVWGAGTTVTVSS

-continued

RSV VL:

(SEQ ID NO: 37)
DIQMTQSPSTLSASVGDRVTITCKCQLSVGYMHWYQQKPGKAPKLLIYDT

SKLASGVPSRFSGSGSGTAFTLTISSLQPDDFATYYCFQGSGYPFTFGGG

TKLEIK.

These hDectin-1 bispecific antibodies engage 3 targets: Dectin-1 on myeloid cells, an antigen on a target cell or disease-causing agent, and Fc receptors on myeloid and NK cells, eliciting robust immune stimulation and phagocytosis (FIG. 32B). In particular, bispecific antibodies with a non-fucosylated, active hIgG1 Fc domain allow the bispecific antibody to recruit myeloid cells (e.g., monocytes, macrophages, and dendritic cells) and natural killer (NK) cells to eliminate disease-causing target cells, such as tumor cells expressing specific antigens. In the context of cancer, and without wishing to be bound to theory, dual engagement of Dectin-1 and Fcγ receptors on myeloid and NK cells is thought to elicit a strong immune response that ultimately eliminates cancer cells via the following actions: (1) bispecific antibody-induced cross-linking of Dectin-1 and Fcγ receptors leads to ITAM-dependent activation of downstream inflammatory pathways and release of immunomodulatory cytokines and cytotoxic proteins (proteases, perforin) which modulates the tumor microenvironment and may directly kill targeted cells; (2) bispecific antibody-induced clustering of Dectin-1 and Fcγ receptors triggers phagocytosis and elimination of targeted cancer cells by monocytes, macrophages and dendritic cells; and (3) phagocytosed antigens are presented by macrophages and DCs, a process that triggers a T cell immune response aimed at eliminating cancer cells.

The 2M24/CD20 and 2M24/RSV bispecific antibodies described in Table 1 were tested for binding to cells expressing human Dectin-1 or CD20. 2M24/RSV was used in all assays as an isotype control for the target binding arm. The bispecific variants tested here contained mutations in the hIgG1 Fc domain (hIgG1 inert) that eliminate Fc binding to Fc receptors (L234A, L235E, and G237A, according to EU numbering). Binding of 2M24/CD20 or 2M24/RSV bispecific to HEK293 cells stably expressing human Dectin-1 was assessed by flow cytometry (FIG. 33A). 2M24/CD20 and 2M24/RSV hIgG1 inert bispecific antibodies were able to bind cells expressing human Dectin-1 with similar affinities (cell-based binding EC50 values of 1.4 and 1.7 nM, respectively). Thus, 2M24/CD20 or 2M24/RSV bispecific antibodies displayed high affinity binding to Dectin-1-expressing HEK293 cells.

Binding of Rituximab, 2M24/CD20, or 2M24/RSV hIgG1 active or inert bispecific antibodies was also assessed using the CD20-expressing B cell lymphoma Raji cell line (FIG. 33B). 2M24/CD20 bispecific (active or inert hIgG1 isotypes) antibodies were able to bind to CD20-expressing Raji cells, but with at least 10-fold reduced affinity compared to Rituximab. Without wishing to be bound to theory, it is thought that the difference in CD20 binding affinity between 2M24/CD20 bispecific and Rituximab is likely mediated by the loss of avidity (monovalent versus bivalent binding) in the bispecific antibody.

Next, the ability of 2M24/CD20 bispecific antibody to induce coupling of cells expressing hDectin-1 and cells expressing hCD20 was assayed. Dectin-1-expressing HEK293 cells (effector) and CD20-expressing Raji cells (target) were differentially labeled with calcein green (effector) or calcein red (target) dyes. Labeled cells were co-cultured and treated with hIgG1 inert 2M24/CD20 or 2M24/RSV (control) bispecific antibody to induce effector:target coupling. Successful coupling of effector:target cells was indicated by the double-positive staining (Calcein green+, calcein red+, square box; FIG. 34A). Coupling efficiency (quantified as the percentage of total target cells that binds or couples to effector cells) was assayed using dose titration of bispecific antibody in co-cultures of effector:target cells (FIG. 34B).

These results indicate that 2M24/CD20 bispecific antibody can couple Dectin-1-expressing 'effector' cells and CD20-expressing 'target' cells with a potent EC50 of 0.17 nM. Despite the low affinity binding of 2M24/CD20 bispecific to CD20 on Raji cells (FIG. 33B), the 2M24/CD20 was highly efficient at coupling. These findings suggest that 2M24/CD20 binding affinity is enhanced by the high expression of Dectin-1 or CD20 on both effector and target cells (avidity), thereby promoting efficient coupling of the two cells. Based on these findings, it is thought that 2M24/CD20 bispecific antibody could effectively engage Dectin-1-expressing monocytes, macrophages or dendritic cells with target disease cells, such as B cell lymphoma, which express high levels of CD20. Effector: target engagement is the first step in the MOA of 2M24 bispecific antibodies.

Human IgG1 active isotype binds Fcγ receptors on NK cells or monocytes. Therefore, it was assessed whether the hIgG1 active isotype of 2M24/CD20 can trigger monocyte killing by NK cells (via antibody dependent-cellular cytotoxicity, ADCC) or other monocytes (Fratricide or antibody-dependent cellular phagocytosis, ADCP). In this scenario, the active hIgG1 domain of 2M24/CD20 engages the Fcγ receptors on NK cells or monocytes, and Dectin-1 receptor on monocytes, thereby inducing Fcγ-mediated activation and depletion of target. PBMCs from two healthy donors—donor 76 (FIG. 35A) and donor 77 (FIG. 35B) were treated with increasing concentrations of 2M24/CD20 bispecifics (hIgG1 active or inert isotypes) and rituximab for 24 h, and subsequently analyzed by flow cytometry to quantify the levels of live, CD14+ monocytes remaining (as a % of isotype controls). No decrease in the number of monocytes was found in either donor, indicating that 2M24/CD20 active IgG1 did not induce monocyte depletion. Without wishing to be bound to theory, it is thought that 2M24/CD20 hIgG1 (active isotype) should not affect the levels of monocytes and thus poses minimal risk of infection.

Based on the proposed MOA of 2M24/CD20 bispecific antibody (described in FIG. 32B), B cell depletion by 2M24/CD20 hIgG1 (active isotype) bispecific antibody or Rituximab was assessed in order to compare B cell depletion. PBMCs from two healthy donors—donors 83 (FIG. 36A) and 84 (FIG. 36B)—were treated with increasing concentrations of the indicated antibodies for 24 hours, and subsequently analyzed by flow cytometry to quantify the levels of remaining live, CD19+ B cells (reported as a % of B cells in isotype control-treated PBMCs). Thus, in two healthy donors, high concentrations of 2M24/CD20 bispecific antibody induced superior B cell depletion (~80% reduction) compared to Rituximab (~40% reduction), despite the bivalent binding nature of Rituximab and ~10-fold difference in binding affinity (as shown in FIG. 33B). The unique mechanism of action of 2M24/CD20 active IgG1, which involves binding to Dectin-1 on myeloid cells, Fcγ receptors on NK cells and monocytes, and CD20 on target B cells (FIG. 32B), leads to an overall superior depletion of B cells compared to Rituximab. These data support the concept that Dectin-1 induced immune stimulation via 2M24/CD20 bispecific enhances depletion of the target cells.

Ability of 2M24/CD20 hIgG1 (active isotype) bispecific antibody or Rituximab (hIgG1) to downregulate CD19 expression on B cells in a process known as shaving or trogocytosis was assessed. Expression of CD19+ on B cells from two healthy donors—donor 83 (FIG. 37A) and donor 84 (FIG. 37B)—was quantified by flow cytometry following a 24-hour incubation with increasing concentration of 2M24/CD20 hIgG1 (active isotype) bispecific antibody, Rituximab, or isotype controls. The mean fluorescent intensity (MFI) for CD19 staining using anti-CD19 (BV605 conjugated) was used to evaluate the effect of 2M24/CD20 bispecific and Rituximab on CD19 expression on B cells. In PBMCs from donor 83, the EC50 with respect to CD19 expression was 0.014 nM for rituximab and 0.080 nM for 2M24/CD20 hIgG1 bispecific (FIG. 37A). In PBMCs from donor 84, the EC50 with respect to CD19 expression was 0.013 nM for rituximab and 0.090 nM for 2M24/CD20 hIgG1 bispecific (FIG. 37B). Both 2M24/CD20 active IgG1 bispecific Ab and Rituximab led to downregulation of CD19 expression on B cells. Interestingly, Rituximab demonstrated at least five-fold more potent shaving compared to 2M24/CD20 bispecific Ab. Downregulation of target CD20 on B cells was previously reported as a mechanism by which malignant B cells escape Rituximab-mediated depletion (Beum, P. V. et al. (2006) J. Immunol. 176:2600-2609). These findings therefore suggest that 2M24/CD20 active IgG1 bispecific may be superior in depleting B-cells as compared to Rituximab due to reduced shaving potential.

Immune stimulation triggered by 2M24/CD20 active IgG1 bispecific antibody led to secretion of a unique repertoire of cytokines compared to Rituximab (FIG. 38). ELISA-based (mesoscale discovery) quantification of cytokines was undertaken in supernatants isolated from healthy donor PBMCs treated with 2M24/CD20 active hIgG1 bispecific, Rituximab, or isotype controls. PBMCs were stimulated with antibodies overnight, and supernatants were subsequently analyzed by MSD. Cytokines tested were IFNγ, IL-12p70, IL-6, TNFα, IL-1β, IL-4, IL-13, IL-10, and IL-8. The results indicated that 2M24/CD20 active IgG1 triggered higher level and distinct cytokine activation in PBMCs compared to Rituximab. Furthermore, engagement of Dectin-1 and Fc receptor alone by the 2M24/RSV bispecific does not induce cytokine release, excluding the possibility of systemic cytokine activation. These findings highlight a unique MOA that distinguishes 2M24/CD20 active IgG1 bispecific antibody from Rituximab. Without wishing to be bound to theory, these findings further indicate that 2M24/CD20 could trigger release of Th1 and Th2-type of responses and promote immune stimulation of tumor microenvironment.

2M24/CD20 hIgG1 (active isotype) bispecific antibody was also found to induce superior B-cell depletion and lower CD19 shaving compared to Rituximab in co-cultures of human macrophages and GFP-expressing Raji B cells. Co-cultures of human macrophages and Raji-GFP cells (3:1 ratio) were analyzed by flow cytometry in the presence of 2M24/CD20 hIgG1 (active isotype) bispecific, 2M24/RSV control, fucosylated Rituximab or isotype hIgG1 control (FIG. 39A). Co-cultures were incubated at 37° C. for 24 hours and then stained with a PE a-CD206 Ab to label macrophages and a BV-605 a-CD19 antibody to label Raji cells. The number of the remaining live/Raji-GFP+ cells was assessed in the end of the experiment. The primary antibodies were used in a serial dose titration. CD19 was assessed on Raji-GFP cells after 24 hours (FIG. 39B), with B-cell receptor shown as the reduction in the CD19 MFI in the presence of a-Dectin-1/a-hCD20 bispecific or Rituximab. The EC50 with respect to CD19 expression was 0.020 nM for rituximab and 0.95 nM for 2M24/CD20 hIgG1 bispecific. These results demonstrate enhanced B-cell depletion (Fcγ receptor mediated) by the 2M24/CD20 bispecific antibody compared to Rituximab. Rituximab reduced the B-cell receptor CD19 surface levels more potently than the a-Dectin-1/a-hCD20 bispecific antibody. Similarly, B-cell receptor shaving has been observed for CD20 by Rituximab, and the reduction of the CD20 limits the effectiveness of Rituximab to deplete B-cell. Without wishing to be bound to theory, it is thought that these data indicate that the superiority of the 2M24/CD20 hIgG1 (active isotype) bispecific to deplete B-cells is due to the lower B-cell receptor shaving compared to Rituximab. This highlights a differential mechanism of cell depletion by 2M24/CD20 hIgG1 (active isotype) bispecific.

B-cell depletion was also analyzed in single cell suspensions from kidney cancer tissue biopsies. Single cell suspensions from two Kidney cancer tissue biopsies were analyzed by flow cytometry in the presence of 2M24/CD20 hIgG1 (active or inert) bispecific antibody, 2M24/RSV hIgG1 controls, fucosylated Rituximab, and respective isotype controls. Kidney cancer tissue biopsies were dissociated to single cell suspensions and treated with primary antibodies (2 µg/ml) for 24 hours at 37° C. Immune cell populations were analyzed by flow cytometry (FIGS. 40A & 40B). The number of the remaining live B cells was assessed by an anti-CD19 antibody and expressed as percentage of the CD45+ immune cell population (FIG. 40C). 2M24/CD20 active IgG1 bispecific antibody induced superior tissue B cell depletion as compared to Rituximab in single cell suspension of kidney cancer biopsies. The 2M24/CD20 hIgG1 (active isotype) bispecific antibody reduced B cells in the two kidney cancer donor biopsies by 44% and 46% (respectively), whereas Rituximab induced a B cell reduction of 33% and 18%, respectively (FIG. 40C). The data support the functionality of the 2M24/CD20 hIgG1 (active isotype) bispecific to deplete cells in cancer tissues via Dectin-1 induced immune stimulation and Fcγ receptor engagement. Without wishing to be bound to theory, it is thought that, since Dectin-1 is predominantly expressed on tumor associated macrophages (TAMs) in the above-described biopsies, 2M24/CD20 hIgG1 (active isotype) bispecific antibody may engage TAMs to enhance the target cell depletion.

Cytokine secretion by cultured macrophages and single cell suspension of kidney cancer biopsies stimulated with immobilized anti-Dectin-1 antibody (clone 2M24) or 2M24/CD20 bispecific antibody was tested. The anti-Dectin-1 antibody (clone 2M24), isotype control or the 2M24/CD20 bispecific antibody were immobilized overnight in U-bottomed polypropylene microtiter plates at 10 ug per well, followed by culture of human monocyte-derived macrophages (FIGS. 41A & 41B) or single cell suspension from kidney cancer biopsy (FIG. 41C). The cells were cultured for 24 hours and evaluation of TNFα secretion in the supernatant was assessed by ELISA. As a positive control, cells were stimulated with zymosan. Anti-Dectin 1 antibody (clone 2M24) was found to induce Dectin 1-clustering and TNFα secretion from human macrophages. These data provide evidence that the parental anti-Dectin-1 antibody (clone 2M24) can promote immune-stimulation in primary macrophage cultures as well as in single cell homogenate of cancer biopsies. Since Dectin-1 is expressed in myeloid cells, tumor associated macrophages in the cancer biopsies are expected to produce cytokines in response to the anti-Dectin-1 antibody stimulation. This promotes the transition of the tumor associated macrophages from anti-inflammatory to pro-inflammatory with strong anti-tumoral effects. Moreover, monovalent binding of the 2M24/CD20 bispecific antibody to Dectin-1 was sufficient to promote Dectin-1 clustering and immune-stimulation on macrophages.

Immune stimulation by immobilized anti-Dectin-1 antibody in single cell suspensions from kidney cancer biopsies were also analyzed (FIG. 42). Single-cell suspensions from kidney cancer biopsies were treated with immobilized anti-Dectin-1 antibody (clone 2M24) or isotype control hIgG4 antibody for 24 h. Supernatants were analyzed by ELISA for the release of various cytokines, including IFNγ, IL-6, TNFα, IL-23, IL-12p70, IL-10, and IL-13. These results show that activation of Dectin-1 on myeloid cells (in this example, Dectin-1 is expressed predominantly by tumor-associated macrophages, TAMs), elicited the release of specific repertoire of cytokines that are either directly downstream of Dectin-1 signaling pathway, or indirectly through activation of other immune cells. Without wishing to be bound to theory, it is thought that Dectin-1 engagement by 2M24 bispecific antibody promotes immune stimulation that could modulate the tumor microenvironment to support the elimination of target-expressing cancer cells.

Example 9: Characterization of a Bispecific Antibody Targeting Dectin-1 and CD20

This Example describes the further characterization of a bispecific antibody targeting human Dectin-1 and human CD20. The anti-Dectin-1 arm included the variable domains of 2M24, and the anti-CD20 arm included the variable domains of Rituximab (see SEQ ID Nos:24 and 25 for VH and VL domains, respectively).

Materials and Methods
CD16 Expression on NK Cells
Human PBMCs from a healthy donor were treated with a serial dilution of 2M24/CD20 hIgG1 KIF, Rituximab KIF, and isotype control RSV hIgG1 KIF antibodies. After 24 hours of treatment, PBMCs were stained with antibodies against lineage-specific markers for flow cytometry analysis. CD16 expression on CD56+ NK cells was quantified and compared to expression levels in the isotype control treated group.

CD19 Expression on B Cells
Human PBMCs from a healthy donor were treated with 0.1 nM of 2M24/CD20 hIgG1 KIF, Rituximab KIF, and isotype control RSV hIgG1 KIF antibodies. After 24 hours of treatment, PBMCs were stained with antibodies against lineage-specific markers for flow cytometry analysis. CD19 expression (MFI) on B cells was quantified.

B Cell Depletion in PBMCs
Human PBMCs from a healthy donor were treated with a serial dilution of the indicated antibodies. After 24 hours of treatment, PBMCs were stained with antibodies against lineage-specific markers for flow cytometry analysis. B cells were quantified relative to an untreated control group (indicated by the dotted line in FIG. 45).

B Cell Depletion in Kidney Cancer Biopsies
Single-cell suspension was generated from kidney cancer biopsy and the cells were treated with 2M24/CD20 hIgG1, 2M24/RSV hIgG1, Rituximab hIgG1, and isotype control RSV hIgG1 antibodies. After 24 hours of treatment, the cells were stained with antibodies against lineage-specific markers for flow cytometry analysis. B cells were quantified as the percentage of CD19+ cells within the CD45+ immune cell population.

Results
First, the effect of the 2M24/CD20 bispecific on CD16 expression was examined in human NK cells. CD16 is required for ADCC activity by NK cells, therefore the loss of CD16 expression can decrease the cytotoxic potential of NK cells. Rituximab induced potent and robust shedding of CD16 on NK cells compared to 2M24/CD20 hIgG1 KIF (FIG. 43). In contrast, CD16 levels on NK cells were better maintained after 2M24/CD20 bispecific antibody treatment compared to rituximab treatment. Without wishing to be bound to theory, it is thought that 2M24/CD20 bispecific has the potential to better preserve NK cell cytotoxic potential.

Next, the effect of the 2M24/CD20 bispecific on CD19 expression was examined in human B cells. Preserving target antigen expression is critical for therapeutic activity of monoclonal antibodies. B cell antigens such as CD20, CD19, and BCMA are validated immuno-oncology targets. CD19 is known to be downregulated via shaving/shedding following binding of anti-CD19 antibodies. Using CD20-targeting antibodies, a bystander effect was observed where CD19 expression was reduced upon treatment with Rituximab, but not with the 2M24/CD20 hIgG1 KIF bispecific (FIG. 44). CD19 levels on B cells were better maintained by 2M24/CD20 bispecific antibody compared to rituximab. Without wishing to be bound to theory, it is thought that, therapeutically, 2M24/CD20 bispecific may exhibit prolonged activity due to minimal impact on target antigen expression.

To compare rituximab with the anti-CD20 antibody obinutuzumab, 2M24 bispecific antibodies against CD20 were generated using the variable domain sequences from either Rituximab or Obinutuzumab. Obinutuzumab variable domain sequences were as follows. VH:

VH:
(SEQ ID NO: 46)
QVQLVQSGAEVKKPGSSVKVSCKASGYAFSYSWINWVRQAPGQGLEWMGR

IFPGDGDTDYNGKFKGRVTITADKSTSTAYMELSSLRSEDTAVYYCARNV

FDGYWLVYWGQGTLVTVSS;

VL:
(SEQ ID NO: 47)
DIVMTQTPLSLPVTPGEPASISCRSSKSLLHSNGITYLYWYLQKPGQSPQ

LLIYQMSNLVSGVPDRFSGSGSGTDFTLKISRVEAEDVGVYYCAQNLELP

YTFGGGTKVEIK.

In an ADCC/ADCP assay, 2M24/CD20 (derived from Rituximab sequence) demonstrated almost complete depletion of B cells, superior to that of 2M24/CD20 (derived from obinutuzumab) or parental bivalent antibodies and isotype control (FIG. 45). These data support utilization of the rituximab sequence for 2M24/CD20 bispecific development

Example 10: Characterization of a Bispecific Antibody Targeting Dectin-1 and CD20 in an Exploratory Study in Non-Human Primates This Example describes the results of an exploratory study on the safety and efficacy of the bispecific antibody targeting human Dectin-1 and human CD20 described in Example 9 in cynomolgus monkeys.

Materials and Methods

Three groups of Cynomolgus monkeys (1 male and 1 female per group) were treated with a single dose (5 mg/kg) of test articles: A) 2M24/CD20 hIgG1 KIF, B) 2M24/CD20 hIgG1 inert, and C) Rituximab hIgG1 KIF. Blood was collected at the indicated time points. Abbreviations for test articles (2M24/CD20 KIF, 2M24/CD20 inert, RTX KIF).

B cell levels were assessed by flow cytometry. Depletion was quantified by the number of CD19+ B cells remaining in samples post-dose compared to the levels before test-articles were administered. Bone marrow and lymph node aspirates were collected at the indicated time points, and B cell levels were assessed by flow cytometry. Depletion was quantified by the number of CD19+ B cells remaining in samples post-dose (Day 7) compared to the levels before test-articles were administered (Day −7).

For PBMC assay, PBMCs from a healthy Cyno were treated with a serial dilution of 2M24/CD20 hIgG1 KIF, Rituximab KIF, and isotype control RSV hIgG1 KIF antibodies. After 24 hours of treatment, PBMCs were stained with antibodies against lineage-specific markers for flow cytometry analysis. B cell depletion was quantified relative to the isotype control group.

Results

This exploratory study was designed to examine the safety and efficacy of 2M24/CD20 bispecific antibody in non-human primates. The study design is shown in FIG. 46. Cynomolgus monkeys were divided into three treatment groups comprising 2 animals (1 male, 1 female) per group. Each group was administered a specific test article at a single dose of 5 mg/kg. The test articles included: 1) 2M24/CD20 hIgG1 KIF, 2) 2M24/CD20 hIgG1 inert, and 3) Rituximab hIgG1 KIF. Animals were monitored daily, and samples such as whole blood, bone marrow, lymph node, and colorectal tissues were collected as indicated. The study was planned for 8 weeks.

As shown in FIG. 47 (upper), 2M24/CD20 hIgG1 KIF bispecific antibody depleted B cells in vivo in Cynomolgus monkeys. Nearly complete and sustained B cell depletion (~98%) was observed in both animals treated with a single dose (5 mg/kg) of 2M24/CD20 hIgG1 KIF. In the Rituximab group (FIG. 48), one animal showed complete depletion, whereas the second showed robust yet incomplete depletion (~87%). Partial B cell depletion was observed for one animal in the 2M24/CD20 hIgG1 inert group (FIG. 47 lower), whereas the second animal showed no depletion at Day 7. 2M24/CD20 hIgG1 KIF bispecific antibody was well-tolerated in cynomolgus monkeys.

2M24/CD20 hIgG1 KIF bispecific also depleted bone marrow (FIG. 49A) and lymph node (FIG. 49B) B cells in vivo in Cynomolgus monkey. A single dose (5 mg/kg) of 2M24/CD20 hIgG1 KIF induced robust B cell depletion in the bone marrow (~87-88%) and partial depletion in the lymph node (60-78%) in both animals. In the Rituximab group, B cell depletion was also observed in both tissues. Partial B cell depletion was observed in the 2M24/CD20 hIgG1 inert group, except for animal CB764A with minimal B cell depletion in the lymph node.

2M24/CD20 hIgG1 KIF bispecific antibody also induced robust depletion of Cyno B cells ex vivo (FIG. 50). 2M24/CD20 hIgG1 KIF induced robust depletion of B cells compared to Rituximab hIgG1 KIF. The maximum depletion achieved by Rituximab was ~30% of B cells, whereas 2M24/CD20 hIgG1 KIF bispecific demonstrated maximum depletion at ~50%.

Example 11: Purification and Functional Characterization of the 2M24/CD20 Bispecific Antibody in scFv Format This Example describes the production, purification, and characterization of a 2M24/CD20 bispecific antibody in which the Dectin-1 targeting arm (based on 2M24 variable domains) was an scFv fused to a human IgG1 Fc domain with knob-forming mutations, and the CD20 targeting arm was based on rituximab hIgG1 with hole-forming mutations. A diagram of the molecule is shown in FIG. 51. Knob-forming mutation on Dectin-1 targeting arm was T366W; hole-forming mutations on CD20 targeting arm were T366S, L368A, and Y407V. Without wishing to be bound by theory, it is thought that this format provides a universal platform for generating anti-Dectin-1 bispecific antibodies with simpler manufacturing requirements (e.g., as compared to bispecific antibodies having an anti-Dectin-1 arm with multiple polypeptide chains).

2M24 scFv/CD20 hIgG1 was expressed in Hek293 cells by transfecting 3 plasmids (2M24 scFv hIgG1 plasmid, CD20 heavy chain, and CD20 light chain). Supernatant was harvested after four days of expression and purified via Protein A. Aggregates were removed with size exclusion chromatography. As shown in FIG. 52A, the 2M24 scFv/CD20 hIgG1 bispecific antibody purified as a homogenous molecule on SEC.

Next, co-cultures of CD20-expressing Raji cells and the Dectin-1-expressing HEK reporter assay were treated with increasing concentration of 2M24 scFv/CD20 hIgG1 bispecific. Reporter activation was assessed by measuring SEAP levels (based on absorbance at 630 nm) in media. The bispecific molecule promoted targeted immune stimulation, as assessed by this NFkB reporter assay (FIG. 52B).

To examine B cell depletion, human PBMCs from a healthy donor were treated with a serial dilution of the indicated antibodies. After 24 hours of treatment, PBMCs were stained with antibodies against lineage-specific markers for flow cytometry analysis. B cells were quantified relative to an untreated control group (indicated by the dotted line in FIG. 52C). The results demonstrated that the 2M24 scFv/CD20 hIgG1 bispecific antibody, similar to the 2M24/CD20 hIgG1 KIF molecule, was able to deplete human B cells (FIG. 52C).

Example 12: Development and Characterization of an Anti-Dectin-1/Anti-Trop-2 Bispecific Antibody Trop-2 is a 323 aa type I membrane protein involved in calcium signal transduction, embryonic and fetal development, tight junction formation, and integrin-dependent signaling. Mutations in Trop-2 are associated with gelatinous drop-like corneal dystrophy, characterized by corneal amyloidosis and blindness. Trop-2 is overexpressed in various epithelial cancers, promoting cell proliferation, invasion and neovascularization. High expression correlates with poor prognosis and survival in many cancers (notably in TNBC breast and NSCLC lung cancer). Sacituzumab govitecan (Trodelvy®), a Trop-2-directed ADC, is the only therapeutic that is approved for the treatment of patients with metastatic TNBC. FDA-accelerated approval in 2020.

Therefore, Trop-2 is an oncology target that is clinically validated. However, there is an unmet need: Trodelvy® achieved a 33% response rate in a heavily pretreated population of patients with metastatic TNBC. Adverse reactions such as neutropenia, diarrhea, and vomiting are associated with Trodelvy toxin (SN-38) conjugate.

In contrast, an anti-Dectin-1-targeted approach has the potential to restrict anti-tumor activity to the disease microenvironment Immune modulation and phagocytosis activities of 2M24 are tightly regulated by the presence of cancer cells. While Trodelvy® has a single mode of action (toxin conjugate delivery to induce target cell killing), the anti-Dectin-1-targeted approach utilizes multiple modes of action (targeted immune stimulation, phagocytosis, and antigen presentation) to eliminate cancer cells and promote lasting immunity.

This Example describes the development and characterization of an anti-Dectin-1 (2M24)/anti-Trop-2 bispecific antibody. Variable domains used for anti-Trop-2 were as follows.

VH:
(SEQ ID NO: 42)
QVQLQQSGSELKKPGASVKVSCKASGYTFTNYGMNWVKQAPGQGLKWMGW

INTYTGEPTYTDDFKGRFAFSLDTSVSTAYLQISSLKADDTAVYFCARGG

FGSSYWYPDVWGQGSLVTVSS;

VL:
(SEQ ID NO: 43)
DIQLTQSPSSLSASVGDRVSITCKASQDVSIAVAWYQQKPGKAPKLLIYS

ASYRYTGVPDRFSGSGSGTDFTLTISSLQPEDFAVYYCQQHYITPLTFGA

GTKVEIK.

2M24/Trop-2 bispecific antibody was purified by size exclusion chromatography, and purified antibody was analyzed by SDS-PAGE under non-reducing (NR) or reducing (R) conditions (FIG. 53A). 2M24/Trop2 bispecific antibody purified as a monodispersed molecule. 2M24/Trop2 bispecific antibody was found to bind with high affinity to Dectin-1-expressing HEK cells (FIG. 53B) and moderate affinity to Trop-2-expressing A431 cancer cell line (FIG. 53C).

To evaluate the level of Trop-2 expression on different cancer cells, cancer cell lines (A431 and SKBR3) were stained with anti-human PE Trop-2 or isotype control antibodies to evaluate Trop-2 expression. Receptor copy number was assessed by comparing the fluorescence intensity of fluorochrome-labeled microspheres with known amounts of the fluorophore to the fluorescence intensity of the labeled cells by flow cytometry. Trop-2 was found to be highly expressed on the cancer cell lines A431 and SKBR3, with receptor copy numbers of 8.4 million and 1.1 million, respectively (FIG. 54). These results demonstrate that Trop-2 polypeptide is highly expressed on cancer cells. High expression on cancer cells makes Trop-2 an attractive antigen for the targeted-killing of cancer cells by a 2M24/Trop-2 bispecific antibody.

Next, binding of the 2M24/Trop-2 bispecific antibody to Trop-2-expressing cell lines was examined Cancer cell lines (HeLa, SiHa, BxPC-3, and Capan-2) were incubated with serial dilutions of the 2M24/Trop-2 hIgG1 bispecific antibody or an isotype control antibody as a single concentration (300 nM). The secondary antibody (AF647 goat Anti-Human) was used for detection by flow cytometry. Binding EC50 was determined using four-parameter logistic (4PL) non-linear regression. The results demonstrated that 2M24/Trop-2 bispecific antibody binds with variable sub-micromolar affinity to different Trop-2-expressing cell lines (FIGS. 55A-55D).

2M24/Trop-2 bispecific antibody was assayed for ability to deplete Trop-2 expressing cell lines. Macrophages were generated by monocytes cultured with MCSF for 6 days. After differentiation, macrophages were co-cultured with Trop-2-expressing cancer cell lines, SKBR3 or A431, for 24 hours in the presence of 10 ug/ml 2M24/Trop-2 hIgG1 or 2M24/RSV hIgG1. To detect macrophages, PE-CD206 antibody was used. The cancer cells were detected either by pre-staining with Calcein AM (FIG. 56A, SKBR3 cells) or using an APC-EPCAM antibody (FIG. 56B, A431 cells). Phagocytosis was assessed by flow cytometry as double positive PE-CD206+Calcein+ cells in the single cell gate for SKBR3 cells (FIG. 56A) or remaining EPCAM+ cells for A431 cells (FIG. 56B). The results demonstrated that 2M24/Trop-2 bispecific antibody induced robust depletion of both cancer cell lines that express Trop-2. 2M24/Trop-2 bispecific antibody induced phagocytosis of Trop-2 expressing cell lines by macrophages. The cancer cell reduction was 56% for SKBR3 (FIG. 56A) and 87% for A431 cancer cells (FIG. 56B). The data provide strong evidence that the 2M24/Trop-2 bispecific antibody can direct the macrophages to eliminate cancer cells that express Trop-2.

Trop-2 expression in non-immune cells and Dectin-1 expression in tumor associated macrophages was assessed in a single-cell suspension of lung cancer biopsy tissue. Trop-2 was evaluated in CD45− cancer cells using a PE Trop-2 antibody. Expression of EPCAM was also confirmed in the same population. Expression of Dectin-1 was confirmed in tumor associated macrophages gated as CD45+CD11b+ CD163+ cells after excluding B-cell, T-cells and NK-cells (FIGS. 57A & 57B). Dectin-1 is expressed in tumor associated macrophages and Trop-2 is expressed in cancer cells of lung cancer biopsy.

To examine whether 2M24/Trop-2 bispecific antibody was able to induce depletion of Trop-2-expressing cancer cells from lung cancer biopsy tissue, a single-cell suspension was generated from lung cancer biopsy, and the cells were treated with 2M24/Trop-2 hIgG1 or 2M24/RSV hIgG1 antibodies. After 24 hours of treatment, the cancer cells were quantified by staining with FITC CD45 and APC EPCAM antibodies for flow cytometry analysis. Cancer cell reduction was expressed as the percentage of CD45-EPCAM+ cells within the live cell population. The results demonstrated that 2M24/Trop-2 bispecific depleted Trop-2-expressing cancer cells in the lung cancer biopsy (FIG. 58). 2M24/Trop-2 bispecific antibody induced a 50% reduction of cancer cells expressing Trop-2 in the lung cancer biopsy. The data indicate that the 2M24/Trop-2 bispecific antibody can induce the phagocytosis and elimination of cancer cells by the tumor associated macrophages within the lung cancer tissue.

To assess Dectin-1 signaling as stimulated by 2M24/Trop-2 bispecific antibody, NFκB reporter HEK cells expressing Dectin-1 were incubated with A431 cancer cells in the presence of serial titration of the 2M24/Trop-2 bispecific or 2M24/RSV antibodies. 2M24/Trop-2 bispecific engaged the two cell lines, promoting Dectin-1 receptor clustering and downstream activation of NFkB. Upon activation, SEAP is released into the media and used as a readout for Dectin-1 activation. Media levels of SEAP were quantified using a spectrophotometer. 2M24/Trop-2 bispecific antibody induced robust stimulation of Dectin-1 and downstream NFκB activity (FIG. 59). These data indicate that the 2M24/Trop-2 bispecific promotes Dectin-1 signaling in effector cells in the presence of Trop-2 expressing cells. Therefore, the 2M24/Trop-2 bispecific antibody has the potential to drive Dectin-1 mediated immune stimulation by monocytes and macrophages that express high levels of Dectin-1.

Next, effects of 2M24/Trop-2 bispecific antibody on antigen presentation and T cell activation were examined. In this assay, as shown in FIG. 59B, monocyte-derived macrophages were co-cultured with SKBR3 breast cancer cells in the presence of 2M24/Trop-2 bispecific antibody. Macrophages are NY ESO-negative, while SKBR3 cells are NY ESO-positive. Bispecific antibody promoted phagocytosis and degradation of SKBR3 cells, and subsequent loading of the ESO peptide on MHC Class I or II on the surface of macrophages. Antigen-specific (ESO-reactive) T cells were then added to the co-culture assay where the TCR recognizes the ESO/MHC complex. This interaction triggered T cell activation, resulting in the release of cytokines (e.g., IFNγ) and expression of early activation markers such as CD69. This assay enables direct assessment of 2M24/Trop-2 bispecific-dependent phagocytosis and presentation of target cell antigens. The results are shown in FIGS. 59C-59E. Macrophages and SKBR3 breast cancer cells were co-incubated in the presence of 2M24/Trop-2 hIgG1 or control 2M24/RSV hIgG1 bispecific antibody. Phagocytosis or depletion of SKBR3 cells was assessed by flow cytometry by staining for EPCAM expression on SKBR3 cells (FIG. 59C). T cell activation is measured by the release of IFN gamma and expression of CD69. IFN gamma levels in the supernatants were quantified (FIG. 59D), and expression of CD69, an early activation marker, on T cells was assessed by flow cytometry (FIG. 59E). These data demonstrated that 2M24/Trop-2 bispecific antibody promotes antigen-presentation and T cell activation. The bispecific antibody 2M24/Trop-2 hIgG1 induced T cell activation by promoting phagocytosis of target cell or antigen by macrophages, and subsequent presentation of neoantigen (ESO-peptide) on MHC Class I on the surface of macrophages. These findings demonstrate that bispecific antibodies targeting Dectin-1 on antigen presenting cells (APCs) are sufficient to activate T cells.

Example 13: Development and Characterization of an Anti-Dectin-1/Anti-Nectin-4 Bispecific Antibody Nectin-4, or PVRL4, belongs to the nectin subfamily of immunoglobulin-like adhesion molecules that participate in Ca(2+)-independent cell-cell adhesion. It consists of three conserved immunoglobulin-like domains (V, C, C) in its extracellular region. Nectin-4 is mainly expressed during fetal development (embryo and placenta) and expression decreases with age.

Nectin-4 overexpression has been reported in many types of cancer. Its re-expression during tumor development makes it a tumor-associated antigen with the possibility of developing a targeted therapy. Silencing Nectin-4 inhibits tumor growth, cell proliferation and migration (Deng et al (2019) *Cancer Cell Int.* 19:106; Nishiwada et al (2015) *J. Exp. Clin. Cancer Res.* 34:30). Nectin-4 interacts with ErbB2 and its trastuzumab-resistant splice variants, enhancing their activation and DNA synthesis. (Kedashiro et al (2019) *Sci. Rep.* 9:18997). Nectin-4 is cleaved by ADAM-17, and circulating Nectin-4 is detected in breast cancer (Fabre-Lafay et al. (2005) *J. Biol. Chem.* 280:19543-19550; Fabre-Lafay et al. (2007) *BMC Cancer* 7:73).

Enfortumab vedotin (ASG-22ME) is a first-in-class antibody-drug conjugate (ADC) directed against Nectin-4. Enfortumab vedotin monoclonal antibody binds to Nectin-4 expressing cells followed by the internalization and release of the anti-tumor agent monomethyl auristatin E (MMAE) into the cell, which result in cell cycle arrest and apoptosis. Enfortumab vedotin (Padcev) was approved for treatment of urothelial cancer in patients who have previously received PD-1 or PD-L1 inhibitor and a platinum-containing chemotherapy, based on NCT03219333 trial in December 2019.

In summary, Nectin-4 is a clinically validated target with an approved ADC. Nectin-4 is minimally expressed in normal tissues, but highly expressed in bladder, breast, cervical, pancreatic, lung, and esophageal cancers, among others. Nectin-4-positive solid tumor types have elevated levels of tumor-associated macrophages (TAMs). Dectin-1 expression on TAMs has been confirmed by single cell RNA sequencing and flow cytometry. As such, and without wishing to be bound to theory, it is thought that targeting Nectin-4 with a Dectin-1 bispecific antibody has the potential to treat Nectin-4-positive cancers by mechanisms including: (1) dual engagement of Nectin-4 on tumor cells and Dectin-1 on TAMs; (2) induction of phagocytosis and depletion of Nectin-4-expressing tumor cells by macrophages; (3) re-programming the immune-suppressive environment by inducing cytokine release through Dectin-1 clustering on TAMs; and/or (4) presenting tumor neoantigens, activating adaptive immune cells like T and B cells, and promoting durable anti-tumor immunity through engagement of professional antigen-presenting cells in the tumor microenvironment.

The bispecific 2M24/Nectin-4 antibody is shown in FIG. 60A, which uses the 2M24 anti-Dectin-1 variable domains and the Ha22 anti-Nectin-4 variable domains

```
(VH:
                                        (SEQ ID NO: 40)
EVQLVESGGGLVQPGGSLRLSCAASGFTFSSYNMNWVRQAPGKGLEWVSY

ISSSSSTIYYADSVKGRFTISRDNAKNSLSLQMNSLRDEDTAVYYCARAY

YYGMDVWGQGTTVTVSS;

VL:
                                        (SEQ ID NO: 41))
DIQMTQSPSSVSASVGDRVTITCRASQGISGWLAWYQQKPGKAPKFLIYA

ASTLQSGVPSRFSGSGSGTDFTLTISSLQPEDFATYYCQQANSFPPTFGG

GTKVEIK.
```

DuetMab mutations on the heavy chain included F126C and C220V; mutations on the light chain included S121C and C214V. It was produced by transfecting 4 plasmids (2M24 heavy chain, 2M24 light chain, Nectin-4 heavy chain, and Nectin-4 light chain) into HEK293 cells. Supernatant was harvested after four days of expression and purified via Protein A (FIG. 60B).

Nectin-4 expression was assessed in cancer cell lines SKBR3 and A431 (FIG. 61A), and in single-cell suspension of prostate or ovarian cancer biopsies (FIG. 61B). Nectin-4 was detected using an anti-Nectin-4 mIgG2b antibody and an Alexa Fluor-647-conjugated secondary antibody. An isotype mIgG2b antibody was used as a negative control for background staining. Nectin-4 expression was observed in cancer cell lines as well as cancer cells in the tumor biopsy tissues.

Binding of 2M24/Nectin-4 bispecific antibody to cells that express Dectin-1 or Nectin-4 was analyzed. Cell lines expressing Dectin-1 (HEK cells) or Nectin-4 (A431 cells) were incubated with serial dilutions of the 2M24/Nectin-4 hIgG1 bispecific antibody or RSV hIgG1 (isotype control) to assess target binding. The secondary antibody (AF647 goat Anti-human IgG) was used for detection by flow cytometry. Binding EC50 values were determined using four parameter logistic (4PL) non-linear regression. The results demonstrated that 2M24/Nectin-4 bispecific antibody bound with high affinity to Dectin-1 and low affinity to Nectin-4 (FIG. 62).

Activity of the 2M24/Nectin-4 bispecific antibody was measured using an NFkB reporter assay. Schematic representation of assay setup is shown in FIG. 63 (upper). NFkB reporter HEK cells expressing Dectin-1 were incubated with A431 cancer cells in the presence of serial titration of the 2M24/Nectin-4 bispecific or bivalent anti-Nectin-4 antibody. 2M24/Nectin-4 bispecific engages the two cell lines, promoting Dectin-1 receptor clustering and downstream activation of NFkB. Upon activation, SEAP was released into the media and used as a readout for Dectin-1 activation. Media levels of SEAP were quantified using a spectrophotometer (FIG. 63, lower). The results demonstrated robust stimulation of Dectin-1 and downstream NFkB activity by the 2M24/Nectin-4 bispecific antibody.

2M24/Nectin-4 bispecific antibody was analyzed for depletion of Nectin-4-expressing cancer cells. Macrophages were generated by monocytes cultured with MCSF for 6 days. After differentiation, macrophages were co-cultured with the Nectin-4-expressing cancer cell line A431 for 24 hours in the presence of 2M24/Nectin-4 bispecific, anti-Nectin-4 bivalent parental antibody, or RSV hIgG1 (isotype control). To detect macrophages (FIG. 64A), a PE-CD206 antibody was used. The cancer cells were detected using an APC-EPCAM antibody. Phagocytosis or depletion was assessed by quantifying the remaining EPCAM-positive cells. Data were reported as relative to the RSV control (FIG. 64B). 2M24/Nectin-4 bispecific antibody was able to deplete Nectin-4-expressing cancer cell lines via targeted phagocytosis by macrophages. Thus, this bispecific molecule has the potential for targeted depletion of Nectin-4-positive cancers.

Example 14: Development and Characterization of an Anti-Dectin-1 Bispecific Antibody Targeting Light Chain Amyloids Light chain amyloidosis (AL) is caused by the expansion of an indolent B cell clone that produces an immunoglobulin light chain λ in 75-80% of cases and κ light chains in the remaining cases (Dispenzieri, A. and G. Merlini (2016). *Cancer Treat Res* 169: 273-318). High concentrations of misfolded light chain proteins are secreted into circulation and deposit in various organs. Amyloid deposition leads to irreversible organ failure and death if remains untreated. Greater than 4000 new AL cases are diagnosed annually in the U.S. 10-15% of multiple myeloma patients develop AL.

There is an unmet need for AL treatments. Myeloid cells such as tissue resident macrophages are involved in tissue amyloid clearance (Wall et al. (2012) *PLoS ONE* 7:e52686). Patients with hereditary transthyretin amyloidosis (ATTR) have impaired phagocytosis activity by myeloid cells (Suenaga et al. (2016) *PLoS ONE* 11:e0163944). Targeted phagocytosis of light chain amyloids via the Dectin-1 receptor on myeloid cells, like macrophages, monocytes and dendritic cells, is an attractive approach for amyloid clearance from tissues. The targeted myeloid engager bispecific strategy could enable Dectin-1 dependent, Fc-independent phagocytosis. Without wishing to be bound to theory, it is hypothesized that this approach may potentially overcome the limitations of current monoclonal antibody strategies that rely primarily on Fc-mediated signaling for amyloid clearance.

A bispecific antibody targeting Dectin-1 and light chain amyloids was constructed using the 2M24 anti-Dectin-1 and 11-1F4 anti-amyloid variable domains. 11-1F4 variable domains were as follows.

```
VH:
                                        (SEQ ID NO: 44)
QVQLKESGPGLVAPSQSLSITCTVSGFSLSSYGVSWVRQPPGKGLEWLGV

IWGDGSTNYKPNLMSRLSISKDISKSQVLFKLNSLQTDDTATYYCVTLDY

WGQGTSVTVSS;

VL:
                                        (SEQ ID NO: 45)
DVVMTQTPLSLPVSLGDQASISCRSSQSLVHRNGNTYLHWYLQKPGQSPK

LLIYKVSNRFSGVPDRFSGSGSGTDFTLKISRVEAEDLGLYFCFQTTYVP

NTFGGGTKLEIK.
```

The bispecific molecule was purified, and binding activity assayed. The parental bivalent antibody 11-1F4 hIgG1 (FIG. 65A, upper) and bispecific antibody 2M24/11-1F4 hIgG1 (FIG. 65A, lower) were purified in PBS by size exclusion chromatography. Purified antibodies were then evaluated for binding to recombinant light chain amyloids from different patients (AL30, AL47, AL48, and AL55) by Octet (FIG. 65B for 11-1F4 hIgG1 and FIG. 65C for 2M24/11-1F4 hIgG1). These results demonstrate that 2M24/11-1F4 bispecific antibody bound to light chain amyloids in vitro.

The ability of 2M24/11-1F4 bispecific antibody to induce phagocytosis of light chain amyloids was also examined Monocytes were freshly isolated from healthy donor PBMCs and co-cultured with pHrodo-labeled light chain amyloids in the presence of either 2M24/11-1F4 hIgG1 inert bispecific antibody or the parental bivalent 11-1F4 hIgG1 antibody. Phagocytosis of light chain amyloids was monitored by the change in pHrodo fluorescence in the low-pH environment of phagosomes. Change in pHrodo activity over 24 hours was monitored in real-time using an Incucyte. The results demonstrated that 2M24/11-1F4 bispecific antibody induced robust phagocytosis of light chain amyloid fibrils compared to the control 11-1F4 hIgG1 antibody (FIG. 66). In this study, an Fc inactive or effectorless 2M24/11-1F4 demonstrated robust amyloid clearance activity, indicating that Dectin-1 binding was sufficient to promote phagocytosis. The 11-1F4 hIgG1 antibody contains an active Fc domain, however minimal clearance activity was observed. These findings suggest that targeting the phagocytic receptor Dectin-1 is an attractive approach treating light chain amyloidosis.

Example 15: Development and Characterization of an Anti-Dectin-1 Bispecific Antibody Targeting Amyloid Beta in Alzheimer's Disease (AD)

AD is the most common cause of dementia worldwide. It accounts for about 80% of all diagnosed cases (Weller and Budson, (2018) *F1000Res* 7). In the United States, AD claims more lives than prostate and breast cancer combined (Patterson, C. (2018). World Alzheimer Report 2018. The State of the Art of Dementia Research: New Frontiers. London, UK Alzheimer's Disease International. Available at alz.co.uk/research/world-report-2018). AD is categorized into two forms: sporadic and familial Ninety-nine percent of AD cases are sporadic, i.e., the exact cause of onset is unknown (Wang, J., Gu, B. J., Masters, C. L., and Wang, Y.-J. (2017). *Nat. Rev. Neurol.* 13, 612-623). Sporadic AD (SAD) or late-onset AD (LOAD) is most likely driven by genetic and environmental factors (Bondi, M. W., Edmonds, E. C., and Salmon, D. P. (2017). *J. Int. Neuropsychol. Soc.* 23, 818-831). The major genetic factor for SAD is the apolipoprotein E (APOE) gene. Other targets identified by GWAS studies include triggering receptor expressed in myeloid cells 2 (TREM2), complement C3b/C4b receptor 1 (CR1), CR1 (complement C3b/C4b receptor 1), CD33, and ABCA7 (Hansen, D. V., et al. (2018). *J Cell Biol* 217(2): 459-472). Many of these genes are expressed on microglial cells, suggesting a critical role of these cells AD etiology (Hansen, D. V., et al. (2018). *J Cell Biol* 217(2): 459-472). TREM2 is a microglial cell surface receptor central to phagocytosis, chemotaxis, survival, and proliferation of microglia (Carmona, S., Zahs, K., Wu, E., Dakin, K., Bras, J., and Guerreiro, R. (2018). *Lancet Neurol.* 17, 721-730). The TREM2 loss-of-function mutation R47H results in a two- to four-fold increase in the risk of AD like the risk associated with inheriting one copy of the e4 variant of APOE (Gratuze, M., Leyns, C. E. G., and Holtzman, D. M. (2018). *Mol. Neurodegener.* 13:66).

Most risk genes for Alzheimer's are highly expressed by microglia, suggesting that microglial dysfunction is associated with AD development and progression (Hansen, 2018). For instance, loss-of-function variants of the microglial phagocytic receptor TREM2 impairs clearance of amyloid β deposits and is linked to enhanced risk of dementia. The Dectin-1 phagocytic receptor is expressed on microglial cells and is not known to be a risk gene for AD. Therefore, without wishing to be bound to theory, it is thought that targeting Dectin-1 on microglial cells could induce targeted phagocytosis and clearance of amyloid beta in AD patients. Targeting Dectin-1 may bypass loss-of-function variants of microglial genes such as TREM2. Unlike current monoclonal antibody approaches such as aducanumab that rely on Fc receptors on microglial cells to execute phagocytosis (Sevigny, J., et al. (2016). *Nature* 537(7618): 50-56), this approach targets a conserved microbial pathway to induce phagocytosis and immune stimulation.

Bispecific antibodies were generated with one arm targeting Dectin-1 and the other arm targeting amyloid beta (based on the variable domain sequences of aducanumab or lecanemab). Aducanumab variable domain sequences are as follows.

VH:
(SEQ ID NO: 48)
QVQLVESGGGVVQPGRSLRLSCAASGFAFSSYGMHWVRQAPGKGLEWVAV

IWFDGTKKYYTDSVKGRFTISRDNSKNTLYLQMNTLRAEDTAVYYCARDR

GIGARRGPYYMDVWGKGTTVTVSS;

VL:
(SEQ ID NO: 49)
DIQMTQSPSSLSASVGDRVTITCRASQSISSYLNWYQQKPGKAPKLLIYA

ASSLQSGVPSRFSGSGSGTDFTLTISSLQPEDFATYYCQQSYSTPLTFGG

GTKVEIK.

Lecanemab variable domain sequences are as follows.

VH:
(SEQ ID NO: 50)
EVQLVESGGGLVQPGGSLRLSCSASGFTFSSFGMHWVRQAPGKGLEWVAY

ISSGSSTIYYGDTVKGRFTISRDNAKNSLFLQMSSLRAEDTAVYYCAREG

GYYYGRSYYTMDYWGQGTTVTVSS;

VL:
(SEQ ID NO: 51)
DVVMTQSPLSLPVTPGAPASISCRSSQSIVHSNGNTYLEWYLQKPGQSPK

LLIYKVSNRFSGVPDRFSGSGSGTDFTLRISRVEAEDVGIYYCFQGSHVP

PTFGPGTKLEIK.

Although the present disclosure has been described in some detail by way of illustration and example for purposes of clarity of understanding, the descriptions and examples should not be construed as limiting the scope of the present disclosure. The disclosures of all patent and scientific literature cited herein are expressly incorporated in the entirety by reference.

What is claimed is:

1. An antibody or antigen-binding fragment thereof that binds to human Dectin-1, wherein the antibody or fragment comprises a heavy chain variable (VH) domain and a light chain variable (VL) domain, wherein the VH domain comprises a CDR-H1 comprising the sequence GYTFTDYY (SEQ ID NO:1), a CDR-H2 comprising the sequence INPNSGDT (SEQ ID NO:2), and a CDR-H3 comprising the sequence ARNSGSYSFGY (SEQ ID NO:3), and wherein the VL domain comprises a CDR-L1 comprising the sequence QGISSW (SEQ ID NO:4), a CDR-L2 comprising the sequence GAS (SEQ ID NO:5), and a CDR-L3 comprising the sequence QQAYSFPFT (SEQ ID NO:6).

2. An antibody or antigen-binding fragment thereof that binds to human Dectin-1, wherein the antibody or fragment comprises a heavy chain variable (VH) domain and a light chain variable (VL) domain, wherein the VH domain comprises a CDR-H1, CDR-H2, and CDR-H3 from the VH domain sequence QVQLVQSGAEVKKPGASVKVSCK-SSGYTFTDYYIHWVRQAPGQGLEWMGWINPNSGD TNYAQKFQGRITMTRDTSISTAYLELSRLRSDD-TAVFYCARNSGSYSFGYWGQGTLVTV SS (SEQ ID NO:7), and wherein the VL domain comprises a CDR-L1, CDR-L2, and CDR-L3 from the VL domain sequence DIQMTQSPSSVSASVGDRVTITCRASQGISS-WLAWYQQKPGKAPKLLIFGASSLQSGVPS RFSGSGSGTDFTLTVSSLQPEDFATYYCQQAY-SFPFTFGPGTKVDIE (SEQ ID NO:8).

3. The antibody of claim 2, wherein the VH domain comprises a CDR-H1 comprising the sequence DYYI (SEQ ID NO:88), a CDR-H2 comprising the sequence WINPNSGDTNYAQKFQG (SEQ ID NO:89), and a CDR-H3 comprising the sequence NSGSYSFGY (SEQ ID NO:90), and wherein the VL domain comprises a CDR-L1 comprising the sequence RASQGISSWLA (SEQ ID NO:91), a CDR-L2 comprising the sequence GASSLQS (SEQ ID NO:92), and a CDR-L3 comprising the sequence QQAYSFPFT (SEQ ID NO:6).

4. The antibody of claim 1, wherein the VH domain comprises a sequence with at least 90% identity to the sequence QVQLVQSGAEVKKPGASVKVSCK-SSGYTFTDYYIHWVRQAPGQGLEWMGWINPNSGD TNYAQKFQGRITMTRDTSISTAYLELSRLRSDD-TAVFYCARNSGSYSFGYWGQGTLVTV SS (SEQ ID NO:7); and wherein the VL domain comprises a sequence with at least 90% identity to the sequence DIQMTQSPSSVSASVGDRVTITCRASQGISS-WLAWYQQKPGKAPKLLIFGASSLQSGVPS RFSGSGSGTDFTLTVSSLQPEDFATYYCQQAY-SFPFTFGPGTKVDIE (SEQ ID NO:8).

5. The antibody of claim 4, wherein the VH domain comprises the sequence QVQLVQSGAEVKKP-GASVKVSCKSSGYTFTDYYIHWVRQAPGQ-GLEWMGWINPNSGD TNYAQKFQGRITMTRDTSIS-TAYLELSRLRSDDTAVFYCARNSGSYSFGYWGQGTL VTV SS (SEQ ID NO:7); and wherein the VL domain comprises the sequence DIQMTQSPSSVSASVGDRVTIT-CRASQGISSWLAWYQQKPGKAPKLLIF-GASSLQSGVPS RFSGSGSGTDFTLTVSSLQPEDFA-TYYCQQAYSFPFTFGPGTKVDIE (SEQ ID NO:8).

6. The antibody of claim 1, wherein the antibody or fragment is a human antibody or fragment.

7. The antibody of claim 1, wherein the antibody or fragment binds to human Dectin-1 expressed on the surface of a macrophage, monocyte, dendritic cell, and/or granulocyte.

8. The antibody of claim 1, wherein the antigen-binding fragment is a Fab, Fab', F(ab')2, Fv, Fab'-SH, F(ab')2, single chain antibody, or scFv fragment.

9. The antibody of claim 1, wherein the antibody further comprises an Fc region.

10. The antibody of claim 1, wherein the antibody or fragment is a multispecific antibody or fragment.

11. The antibody of claim 10, wherein the antibody or fragment is a bispecific antibody, fragment, or diabody comprising a first antigen binding domain comprising the VH and VL domains that bind to human Dectin-1 and a second antigen binding domain comprising second VH and VL domains that bind to a target of interest.

12. The antibody of claim 11, wherein the bispecific antibody comprises:
   (a) a first IgG antibody comprising the first antigen binding domain covalently linked to a second IgG antibody comprising the second antigen binding domain;
   (b) a first antibody arm comprising a first antibody heavy chain that comprises the VH domain of the first antigen binding domain and a first Fc region, and a second antibody arm comprising a second antibody heavy chain that comprises the VH domain of the second antigen binding domain and a second Fc region, wherein the first Fc region comprises one or more knob-forming mutations, and the second Fc region comprises one or more cognate hole-forming mutations; or
   (c) a first antibody arm comprising a first antibody heavy chain that comprises the VH domain of the first antigen binding domain and a first Fc region, and a second antibody arm comprising a second antibody heavy chain that comprises the VH domain of the second antigen binding domain and a second Fc region, wherein the first Fc region comprises one or more hole-forming mutations, and the second Fc region comprises one or more cognate knob-forming mutations.

13. The antibody of claim 11, wherein the bispecific antibody comprises a first antibody arm comprising a single chain variable fragment (scFv) comprising the VH and VL domains that bind to human Dectin-1 and a first Fc region, and a second antibody arm comprising an antibody heavy chain that comprises the VH domain of the second antigen binding domain in association with an antibody light chain that comprises the VL domain of the second antigen binding domain and a second Fc region connected to the VH domain of the second antigen binding domain.

14. The antibody of claim 13, wherein the first Fc region comprises one or more knob-forming mutations, and the second Fc region comprises one or more cognate hole-forming mutations, or wherein the second Fc region comprises one or more knob-forming mutations, and the first Fc region comprises one or more cognate hole-forming mutations.

15. The antibody of claim 13, wherein the first antibody arm comprises a first linker between the VH and VL domains, and a second linker between the VL domain and the first Fc region.

16. The antibody of claim 15, wherein the first linker comprises one or more repeats of the sequence GGGGS (SEQ ID NO:26).

17. The antibody of claim 16, wherein the first linker comprises the sequence GGGGSGGGGSGGGGS (SEQ ID NO:27) or GGGGSGGGGSGGGGSGGGGS (SEQ ID NO:28).

18. The antibody of claim 15, wherein the second linker comprises the sequence EPKRSDKTHTCPPC (SEQ ID NO:29) or SATHTCPPC (SEQ ID NO:30).

19. The antibody of claim 11, wherein the bispecific antibody comprises:
(a) a first IgG antibody comprising the first antigen binding domain coupled to biotin or an avidin-binding derivative thereof, and a second IgG antibody comprising the second antigen binding domain coupled to avidin, streptavidin, neutravidin, or a biotin-binding derivative thereof, wherein the biotin or avidin-binding derivative thereof is bound to the avidin, streptavidin, neutravidin, or biotin-binding derivative thereof; or
(b) a first IgG antibody comprising the first antigen binding domain coupled to avidin, streptavidin, neutravidin, or a biotin-binding derivative thereof, and a second IgG antibody comprising the second antigen binding domain coupled to biotin or an avidin-binding derivative thereof, wherein the biotin or avidin-binding derivative thereof is bound to the avidin, streptavidin, neutravidin, or biotin-binding derivative thereof.

20. The antibody of claim 11, wherein the target of interest is a disease-causing agent.

21. The antibody of claim 20, wherein the disease-causing agent is a bacterial cell, fungal cell, virus, senescent cell, tumor cell, protein aggregate, LDL particle, mast cell, eosinophil, ILC2 cell, or inflammatory immune cell.

22. The antibody of claim 21, wherein the target of interest is an antigen expressed on the surface of the bacterial cell, fungal cell, senescent cell, tumor cell, mast cell, eosinophil, ILC2 cell, or inflammatory immune cell.

23. The antibody of claim 21, wherein the target of interest is a surface antigen of the virus.

24. The antibody of claim 20, wherein the target of interest is an antigen expressed on the surface of a cancer cell.

25. The antibody of claim 9, wherein the antibody comprises two antibody heavy chains comprising human IgG1 Fc domains, and wherein each of the human IgG1 Fc domains comprises an amino acid substitution at one or more of positions 234, 235, and 237, according to EU numbering.

26. The antibody of claim 25, wherein each of the antibody heavy chains comprises L234A, L235E, and G237A substitutions, according to EU numbering.

27. The antibody of claim 11, wherein the antibody comprises two antibody heavy chains, and wherein only one of the antibody heavy chains comprises H435R and Y436F substitutions, according to EU numbering.

28. The antibody of claim 11, wherein the antibody comprises two arms, wherein only one of the two antibody arms comprises a heavy chain comprising F126C and C220V substitutions and a light chain comprising S121C and C214V substitutions, according to EU numbering.

29. The antibody of claim 11, wherein the bispecific antibody comprises two antibody heavy chains and two antibody light chains, wherein the VH domain of the first antibody heavy chain forms an antigen binding domain with the VL domain of the first antibody light chain, wherein the VH domain of the second antibody heavy chain forms an antigen binding domain with the VL domain of the second antibody light chain, wherein the first antibody heavy chain comprises F126C, C220V, and T366W substitutions, wherein the first antibody light chain comprises S121C and C214V substitutions, and wherein the second antibody heavy chain comprises T366S, L368A, Y407V, H435R, and Y436F substitutions, according to EU numbering.

30. The antibody of claim 29, wherein the first and second antibody heavy chains further comprise L234A, L235E, and G237A substitutions, according to EU numbering.

31. The antibody of claim 11, wherein the bispecific antibody comprises a first and a second antibody heavy chain, wherein the first and second antibody heavy chains comprise human IgG1 Fc domains.

32. The antibody of claim 11, wherein the bispecific antibody comprises a first and a second antibody heavy chain, wherein at least one or two of the first and second antibody heavy chains is/are non-fucosylated.

33. A multispecific binding molecule, comprising:
(a) a first antibody or antigen-binding fragment thereof comprising a first antigen-binding domain, wherein the first antigen-binding domain binds to human Dectin-1, wherein the first antigen-binding domain comprises a heavy chain variable (VH) domain and a light chain variable (VL) domain, wherein the VH domain comprises a CDR-H1 comprising the sequence GYTFTDYY (SEQ ID NO:1), a CDR-H2 comprising the sequence INPNSGDT (SEQ ID NO:2), and a CDR-H3 comprising the sequence ARNSGSYSFGY (SEQ ID NO:3), and wherein the VL domain comprises a CDR-L1 comprising the sequence QGISSW (SEQ ID NO:4), a CDR-L2 comprising the sequence GAS (SEQ ID NO:5), and a CDR-L3 comprising the sequence QQAYSFPFT (SEQ ID NO:6); and
(b) a second antibody or antigen-binding fragment thereof comprising a second antigen-binding domain, wherein the second antigen binding domain binds to a target of interest.

34. The multispecific binding molecule of claim 33, wherein the target of interest is a disease-causing agent.

35. The multispecific binding molecule of claim 34, wherein the disease-causing agent is a bacterial cell, fungal cell, virus, senescent cell, tumor cell, protein aggregate, LDL particle, mast cell, eosinophil, ILC2 cell, or inflammatory immune cell.

36. The multispecific binding molecule of claim 35, wherein the target of interest is an antigen expressed on the surface of the bacterial cell, fungal cell, senescent cell, tumor cell, mast cell, eosinophil, ILC2 cell, or inflammatory immune cell.

37. The multispecific binding molecule of claim 35, wherein the target of interest is a surface antigen of the virus.

38. The multispecific binding molecule of claim 34, wherein the target of interest is an antigen expressed on the surface of a cancer cell.

39. The multispecific binding molecule of claim 33, wherein the VH domain comprises a sequence with at least 90% identity to the sequence QVQLVQSGAEVKKP-GASVKVSCKSSGYTFTDYYIHWVRQAPGQ-GLEWMGWINPNSGD TNYAQKFQGRITMTRDTSIS-TAYLELSRLRSDDTAVFYCARNSGSYSFGYWGQGT \LVTV SS (SEQ ID NO:7); and wherein the VL domain comprises a sequence with at least 90% identity to the sequence DIQMTQSPSSVSASVGDRVTITCRASQGISS-WLAWYQQKPGKAPKLLIFGASSLQSGVPS RFSGSGSGTDFTLTVSSLQPEDFATYYCQQAY-SFPFTFGPGTKVDIE (SEQ ID NO:8).

40. The multispecific binding molecule of claim 39, wherein the VH domain comprises the sequence QVQLVQSGAEVKKPGASVKVSCK-SSGYTFTDYYIHWVRQAPGQGLEWMGWINPNSGD TNYAQKFQGRITMTRDTSISTAYLELSRLRSDD-TAVFYCARNSGSYSFGYWGQGTLVTV SS (SEQ ID NO:7); and wherein the VL domain comprises the sequence DIQMTQSPSSVSASVGDRVTITCRASQGISS-WLAWYQQKPGKAPKLLIFGASSLQSGVPS RFSGSGSGTDFTLTVSSLQPEDFATYYCQQAY-SFPFTFGPGTKVDIE (SEQ ID NO:8).

41. The multispecific binding molecule of claim 33, wherein:
   (a) the first antibody or fragment is coupled to avidin, streptavidin, neutravidin, or a biotin-binding derivative thereof, and the second antibody or fragment is coupled to biotin or an avidin-binding derivative thereof, wherein the first antibody or fragment is bound to the second antibody or fragment via an interaction between the avidin, streptavidin, neutravidin, or biotin-binding derivative thereof and the biotin or avidin-binding derivative thereof;
   (b) the second antibody or fragment is coupled to avidin, streptavidin, neutravidin, or a biotin-binding derivative thereof, and the first antibody or fragment is coupled to biotin or an avidin-binding derivative thereof, wherein the first antibody or fragment is bound to the second antibody or fragment via an interaction between the avidin, streptavidin, neutravidin, or biotin-binding derivative thereof and the biotin or avidin-binding derivative thereof; or
   (c) the multispecific binding molecule comprises a first IgG antibody comprising the first antigen binding domain covalently linked to a second IgG antibody comprising the second antigen binding domain.

42. The multispecific binding molecule of claim 33, wherein the multispecific binding molecule comprises a first antibody arm comprising a single chain variable fragment (scFv) comprising the VH and VL domains that bind to human Dectin-1 and a first Fc region, and a second antibody arm comprising an antibody heavy chain that comprises the VH domain of the second antigen binding domain in association with an antibody light chain that comprises the VL domain of the second antigen binding domain and a second Fc region connected to the VH domain of the second antigen binding domain.

43. The multispecific binding molecule of claim 42, wherein the first Fc region comprises one or more knob-forming mutations, and the second Fc region comprises one or more cognate hole-forming mutations, or wherein the second Fc region comprises one or more knob-forming mutations, and the first Fc region comprises one or more cognate hole-forming mutations.

44. The multispecific binding molecule of claim 42, wherein the first antibody arm comprises a first linker between the VH and VL domains of the first antibody arm, and a second linker between the VL domain of the first antibody arm and the first Fc region.

45. The multispecific binding molecule of claim 44, wherein the first linker comprises one or more repeats of the sequence GGGGS (SEQ ID NO:26).

46. The multispecific binding molecule of claim 45, wherein the first linker comprises the sequence GGGGSGGGGSGGGGS (SEQ ID NO:27) or GGGGSGGGGSGGGGSGGGGS (SEQ ID NO:28).

47. The multispecific binding molecule of claim 44, wherein the second linker comprises the sequence EPKRSDKTHTCPPC (SEQ ID NO:29) or SATHTCPPC (SEQ ID NO:30).

48. The multispecific binding molecule of claim 33, wherein the multispecific binding molecule comprises a first antibody arm comprising a first antibody heavy chain that comprises the VH domain of the first antigen binding domain and a first Fc region and a first antibody light chain comprising the VL domain of the first antigen binding domain, and a second antibody arm comprising a second antibody heavy chain that comprises the VH domain of the second antigen binding domain and a second Fc region and a second antibody light chain comprising the VL domain of the second antigen binding domain, wherein:
   (a) the first Fc region comprises one or more knob-forming mutations, and the second Fc region comprises one or more cognate hole-forming mutations; or
   (b) the first Fc region comprises one or more hole-forming mutations, and the second Fc region comprises one or more cognate knob-forming mutations.

49. The multispecific binding molecule of claim 43, wherein:
   (a) the first Fc region comprises a T366W substitution, and wherein the second Fc region comprises T366S, L368A, and Y407V substitutions, according to EU numbering; or
   (b) wherein the first Fc region comprises T366S, L368A, and Y407V substitutions, and wherein the second Fc region comprises a T366W substitution, according to EU numbering.

50. The multispecific binding molecule of claim 42, wherein the first and/or the second Fc region is a human IgG1 Fc region that comprises an amino acid substitution at one or more of positions 234, 235, and 237, according to EU numbering.

51. The multispecific binding molecule of claim 50, wherein each of the first and second Fc regions comprises L234A, L235E, and G237A substitutions, according to EU numbering.

52. The multispecific binding molecule of claim 48, wherein only one of the Fc regions comprises H435R and Y436F substitutions, according to EU numbering.

53. The multispecific binding molecule of claim 48, wherein only one of the antibody arms comprises a heavy chain comprising F126C and C220V substitutions and a light chain comprising S121C and C214V substitutions, according to EU numbering.

54. The multispecific binding molecule of claim 33, wherein the multispecific binding molecule comprises a first antibody heavy chain and a first antibody light chain and a second antibody heavy chain and a second antibody light chain, wherein the VH domain of the first antibody heavy chain forms a first antigen binding domain with the VL domain of the first antibody light chain, wherein the VH domain of the second antibody heavy chain forms a second antigen binding domain with the VL domain of the second antibody light chain, wherein the first antibody heavy chain comprises F126C, C220V, and T366W substitutions, wherein the first antibody light chain comprises S121C and C214V substitutions, and wherein the second antibody heavy chain comprises T366S, L368A, Y407V, H435R, and Y436F substitutions, according to EU numbering.

55. The multispecific binding molecule of claim 54, wherein the first and second antibody heavy chains further comprise L234A, L235E, and G237A substitutions, according to EU numbering.

56. The multispecific binding molecule of claim 48, wherein the first and second antibody heavy chains comprise human IgG1 Fc domains.

57. The multispecific binding molecule of claim 48, wherein at least one or two of the first and second antibody heavy chains is/are non-fucosylated.

58. The multispecific binding molecule of claim 33, wherein one or both of the first and second antibodies or fragments are humanized antibodies or fragments.

59. The multispecific binding molecule of claim 33, wherein:
(a) one or both of the first and second antibodies or fragments are Fab, Fab', F(ab')2, Fv, Fab'-SH, F(ab')2, single chain antibodies, or scFv fragments;
(b) one or both of the first and second antibodies further comprise an Fc domain;
(c) the first antibody or fragment is a Fab fragment, and the second antibody comprises an antibody heavy chain and an antibody light chain;
(d) the first and the second antibodies or fragments are both full-length antibodies;
(e) the first antibody or fragment is a Fab fragment coupled to monomeric streptavidin (mSA), and the second antibody is a biotinylated antibody that comprises an antibody heavy chain and an antibody light chain; or
(f) the first antibody or fragment is a full-length antibody coupled to monomeric streptavidin (mSA), and the second antibody or fragment is a biotinylated full-length antibody.

60. A multispecific binding molecule comprising a first arm comprising a first antigen-binding domain and a second arm comprising a second antigen-binding domain; wherein the first antigen-binding domain binds to human Dectin-1 and the second antigen-binding domain binds to a target of interest; and wherein the first arm comprises a polypeptide chain comprising the sequence (SEQ ID NO: 31)
QVQLVQSGAEVKKPGASVKVSCKSSGYTFTDYYIHWVRQAPGQGLEWMGW

INPNSGDTNYAQKFQGRITMTRDTSISTAYLELSRLRSDDTAVFYCARNS

GSYSFGYWGQGTLVTVSSGGGGSGGGGSGGGGSGGGGSDIQMTQSPSSVS

ASVGDRVTITCRASQGISSWLAWYQQKPGKAPKLLIFGASSLQSGVPSRF

SGSGSGTDFTLTVSSLQPEDFATYYCQQAYSFPFTFGPGTKVDIEEPKRS

DKTHTCPPCPAPELLGGPSVFLFPPKPKDTLMISRTPEVTCVVVDVSHED

PEVKFNWYVDGVEVHNAKTKPREEQYNSTYRVVSVLTVLHQDWLNGKEYK

CKVSNKALPAPIEKTISKAKGQPREPQVYTLPPSREEMTKNQVSLWCLVK

GFYPSDIAVEWESNGQPENNYKTTPPVLDSDGSFFLYSKLTVDKSRWQQG

NVFSCSVMHEALHNHYTQKSLSLSPG.

61. A polynucleotide encoding the antibody of claim 1.

62. A vector comprising the polynucleotide of claim 61.

63. An isolated host cell comprising the polynucleotide of claim 61.

64. The isolated host cell of claim 63, wherein the host cell is a mammalian, yeast, insect, plant, or prokaryotic cell.

65. The isolated host cell of claim 64, wherein the mammalian cell is a Chinese hamster ovary (CHO) cell.

66. The isolated host cell of claim 64, wherein the host cell:
(a) comprises an alpha1,6-fucosyltransferase (Fut8) or alpha-1,3-mannosyl-glycoprotein 2-beta-N-acetylglucosaminyltranferase (MGAT1) knockout; or
(b) overexpresses β1,4-N-acetylglucosaminyltransferase III (GnT-III).

67. The isolated host cell of claim 66, wherein the host cell overexpresses GnT-III and further overexpresses Golgi μ-mannosidase II (ManII).

68. A method of producing an antibody, comprising culturing the host cell of claim 63 under conditions suitable for production of the antibody.

69. The method of claim 68, wherein, prior to production of the antibody, the host cell is treated with kifunensine.

70. An antibody or antigen-binding fragment thereof that binds to human Dectin-1 produced by the method of claim 68.

71. A pharmaceutical composition comprising the antibody of claim 1 and a pharmaceutically acceptable carrier.

72. A method of treating a disease or disorder, wherein the disease or disorder is cancer, a bacterial infection, a fungal infection, a viral infection, a mast cell disease or disorder, systemic mastocytosis, amyloidosis, or an aging-related disease or disorder, comprising administering an effective amount of the composition of claim 71 to an individual in need thereof.

73. The method of claim 72, wherein a first target of interest is human Dectin-1, and wherein a second target of interest is a disease-causing agent.

74. The method of claim 73, wherein the disease-causing agent is a bacterial cell, fungal cell, virus, senescent cell, tumor cell, protein aggregate, LDL particle, mast cell, eosinophil, ILC2 cell, or inflammatory immune cell.

75. The method of claim 74, wherein the target of interest is an antigen expressed on the surface of the virus, bacterial cell, fungal cell, senescent cell, tumor cell, mast cell, eosinophil, ILC2 cell, or inflammatory immune cell.

76. The method of claim 72, wherein a target of interest is an antigen expressed on the surface of a cancer cell.

77. The method of claim 72, wherein the individual is a human.

78. A multispecific binding molecule, comprising:
(a) a first antibody or antigen-binding fragment thereof comprising a first antigen-binding domain, wherein the first antigen-binding domain binds to human Dectin-1, wherein the first antigen-binding domain comprises a heavy chain variable (VH) domain and a light chain variable (VL) domain, wherein the VH domain comprises a CDR-H1, CDR-H2, and CDR-H3 from the VH domain sequence QVQLVQSGAEVKKP-GASVKVSCKSSGYTFTDYYIHWVRQAPGQ-GLEWMGWIN PNSGDTNYAQKFQGRITMTRDT-SISTAYLELSRLRSDDTAVFYCARNSGSYSFGY WGQGTLVTVSS (SEQ ID NO:7), and wherein the VL domain comprises a CDR-L1, CDR-L2, and CDR-L3 from the VL domain sequence DIQMTQSPSSVSASVGDRVTITCRASQGISS-WLAWYQQKPGKAPKLLIFGASSLQ SGVPSRFSGSGSGTDFTLTVSSLQPEDFA-TYYCQQAYSFPFTFGPGTKVDIE (SEQ ID NO:8); and (b) a second antibody or antigen-binding fragment thereof comprising a second antigen-binding domain, wherein the second antigen binding domain binds to a target of interest.

79. The multispecific binding molecule of claim 78, wherein the VH domain comprises a CDR-H1 comprising the sequence DYYI (SEQ ID NO:88), a CDR-H2 comprising the sequence WINPNSGDTNYAQKFQG (SEQ ID NO:89), and a CDR-H3 comprising the sequence NSGSYS-FGY (SEQ ID NO:90), and wherein the VL domain comprises a CDR-L1 comprising the sequence RASQGISSWLA (SEQ ID NO:91), a CDR-L2 comprising the sequence GASSLQS (SEQ ID NO:92), and a CDR-L3 comprising the sequence QQAYSFPFT (SEQ ID NO:6).

80. A polynucleotide encoding the antibody of claim 5.

81. A vector comprising the polynucleotide of claim 80.

82. An isolated host cell comprising the polynucleotide of claim 80.

83. A method of producing an antibody, comprising culturing the host cell of claim 82 under conditions suitable for production of the antibody.

84. A pharmaceutical composition comprising the antibody of claim 5 and a pharmaceutically acceptable carrier.

85. A method of treating a disease or disorder, wherein the disease or disorder is cancer, a bacterial infection, a fungal infection, a viral infection, a mast cell disease or disorder, systemic mastocytosis, amyloidosis, or an aging-related disease or disorder, comprising administering an effective amount of the composition of claim 84 to an individual in need thereof.

86. A polynucleotide encoding the multispecific binding molecule of claim 33.

87. A vector comprising the polynucleotide of claim 86.

88. An isolated host cell comprising the polynucleotide of claim 86.

89. A method of producing a multispecific binding molecule, comprising culturing the host cell of claim 88 under conditions suitable for production of the multispecific binding molecule.

90. A pharmaceutical composition comprising the multispecific binding molecule of claim 33 and a pharmaceutically acceptable carrier.

91. A method of treating a disease or disorder, wherein the disease or disorder is cancer, a bacterial infection, a fungal infection, a viral infection, a mast cell disease or disorder, systemic mastocytosis, amyloidosis, or an aging-related disease or disorder, comprising administering an effective amount of the composition of claim 90 to an individual in need thereof.

92. A polynucleotide encoding the multispecific binding molecule of claim 40.

93. A vector comprising the polynucleotide of claim 92.

94. An isolated host cell comprising the polynucleotide of claim 92.

95. A method of producing a multispecific binding molecule, comprising culturing the host cell of claim 94 under conditions suitable for production of the multispecific binding molecule.

96. A pharmaceutical composition comprising the multispecific binding molecule of claim 40 and a pharmaceutically acceptable carrier.

97. A method of treating a disease or disorder, wherein the disease or disorder is cancer, a bacterial infection, a fungal infection, a viral infection, a mast cell disease or disorder, systemic mastocytosis, amyloidosis, or an aging-related disease or disorder, comprising administering an effective amount of the composition of claim 96 to an individual in need thereof.

* * * * *